(12) United States Patent
Sloma et al.

(10) Patent No.: US 7,811,806 B2
(45) Date of Patent: Oct. 12, 2010

(54) METHODS FOR PRODUCING HYALURONAN IN A RECOMBINANT HOST CELL

(75) Inventors: Alan Sloma, Davis, CA (US); Regine Behr, Roseville, CA (US); William Widner, Davis, CA (US); Maria Tang, Fairfield, CA (US); David Sternberg, Davis, CA (US); Stephen Brown, Davis, CA (US)

(73) Assignee: Novozymes, Inc., Davis, CA (US)

( * ) Notice: Subject to any disclaimer, the term of this patent is extended or adjusted under 35 U.S.C. 154(b) by 562 days.

(21) Appl. No.: 10/326,185

(22) Filed: Dec. 20, 2002

(65) Prior Publication Data

US 2003/0175902 A1 Sep. 18, 2003

Related U.S. Application Data

(60) Provisional application No. 60/342,644, filed on Dec. 21, 2001.

(51) Int. Cl.
*C12N 1/20* (2006.01)
*C12N 15/74* (2006.01)
*C12N 15/00* (2006.01)
*C12P 21/06* (2006.01)
*C12P 19/04* (2006.01)
*C12P 19/26* (2006.01)

(52) U.S. Cl. ............... 435/252.31; 435/471; 435/320.1; 435/69.1; 435/101; 435/84

(58) Field of Classification Search ............... 435/4, 435/6, 69.1, 41, 101, 183, 193, 200, 232, 435/252.3, 252.31, 320.1; 536/23.2, 23.4; 530/23.7, 350

See application file for complete search history.

(56) References Cited

U.S. PATENT DOCUMENTS

| | | | |
|---|---|---|---|
| 4,801,539 A | 1/1989 | Akasaka et al. | |
| 6,255,076 B1 * | 7/2001 | Widner et al. | 435/69.1 |
| 6,455,304 B1 | 9/2002 | Weigel et al. | |
| 6,833,264 B1 | 12/2004 | Weigek et al. | |
| 6,951,743 B2 * | 10/2005 | DeAngelis et al. | 435/84 |
| 2003/0092118 A1 | 5/2003 | DeAngelis et al. | |

FOREIGN PATENT DOCUMENTS

| WO | WO 99/23227 | 5/1999 |
|---|---|---|
| WO | WO 99/51265 | 10/1999 |
| WO | WO 00/27437 | 5/2000 |

OTHER PUBLICATIONS

Weigel et al. (US 6833264 filing date Oct. 31, 1997, see enclosed sequence alignment).*
Wang et al. (Gen Bank Accession No. ACA50306, Mar. 2001, see enclosed sequence alignment).*
Moriya et al. (GenBank Acc No. D26185, 1999, see enclosed sequence alignment).*
Varoon et al. (GenBank Acc. No. L12272, 1993, see enclosed sequence alignment).*
Soldo et al. (GenBank Acc. No. AF015609, 1999 see enclosed sequence alignment).*
Widner et al., Development of marker-free strains of *Bacillus subtilis* capable of secreting high levels of industrial enzymes. J. Industrial Microbiol. & Biotechnol., 2000, vol. 25: 204-212.*
Broun et al., Catalytic plasticity of fatty acid modification enzymes underlying chemical diversity of plant lipids. Science, 1998, vol. 282: 1315-1317.*
Devos et al., Practical limits of function prediction: Proteins: Structure, function, and Genetics, 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Dougherty et al., Molecular characterization of hasA from operon required for hyaluronic acid synthesis in Group A strerptococci., J. Biol. Sci., Jan. 1994, vol. 269, No. 1, pp. 169-175.
Ferrett, J., et al., Complete genome sequence of an M1 strain of S.pyogenes. Apr. 2001, PNAS, vol. 98, No. 8, pp. 4658-4663.
Kumari, K., et al., Molecular cloning, expression and characterization of the authethentic hyaluronan synthase from group C S.equisimilis., Dec. 1997, J. Biol. Chem., vol. 272, No. 51, pp. 32539-32546.
Torvard C. Laurent and J. Robert E. Fraser, "Proteoglycans and hyaluronan in morphogenesis and differentiation", FASEB J. 6: pp. 2397-2404, and Toole B.P., 1991.
Elizabeth D. Hay, Cell Biology of Extracellular Matrix, pp. 305-341, Plenum, New York, 1991.
DeAngelis, P.L., "Hyaluronan synthases: fasinating glycosyltransferases from vertebrates, bacterial pathogens, and algal viruses", Cell. Mol. Life Sci. 56: pp. 670-682, 1999.

* cited by examiner

*Primary Examiner*—Ganapathirama Raghu
(74) *Attorney, Agent, or Firm*—Robert L. Starnes

(57) ABSTRACT

The present invention relates to methods for producing a hyaluronic acid, comprising: (a) cultivating a *Bacillus* host cell under conditions suitable for production of the hyaluronic acid, wherein the *Bacillus* host cell comprises a nucleic acid construct comprising a hyaluronan synthase encoding sequence operably linked to a promoter sequence foreign to the hyaluronan synthase encoding sequence; and (b) recovering the hyaluronic acid from the cultivation medium. The present invention also relates to an isolated nucleic acid sequence encoding a hyaluronan synthase operon comprising a hyaluronan synthase gene and a UDP-glucose 6-dehydrogenase gene, and optionally one or more genes selected from the group consisting of a UDP-glucose pyrophosphorylase gene, UDP-N-acetylglucosamine pyrophosphorylase gene, and glucose-6-phosphate isomerase gene. The present invention also relates to isolated nucleic acid sequences encoding a UDP-glucose 6-dehydrogenase, UDP-glucose pyrophosphorylase, and UDP-N-acetylglucosamine pyrophosphorylase.

20 Claims, 45 Drawing Sheets

SEQUENCE LISTING

```
<160> NUMBER OF SEQ ID NOS: 108

<210> SEQ ID NO 1
<211> LENGTH: 1251
<212> TYPE: DNA
<213> ORGANISM: Streptococcus equisimilis
<220> FEATURE:
<221> NAME/KEY: CDS
<222> LOCATION: (1)..(1251)
<223> OTHER INFORMATION:

<400> SEQUENCE: 1 atg aga aca tta aaa aac ctc ata act gtt gtg gcc ttt agt att ttt        48
Met Arg Thr Leu Lys Asn Leu Ile Thr Val Val Ala Phe Ser Ile Phe
1               5                   10                  15 tgg gta ctg ttg att tac gtc aat gtt tat ctc ttt ggt gct aaa gga        96
Trp Val Leu Leu Ile Tyr Val Asn Val Tyr Leu Phe Gly Ala Lys Gly
            20                  25                  30 agc ttg tca att tat ggc ttt ttg ctg ata gct tac cta tta gtc aaa       144
Ser Leu Ser Ile Tyr Gly Phe Leu Leu Ile Ala Tyr Leu Leu Val Lys
        35                  40                  45 atg tcc tta tcc ttt ttt tac aag cca ttt aag gga agg gct ggg caa       192
Met Ser Leu Ser Phe Phe Tyr Lys Pro Phe Lys Gly Arg Ala Gly Gln
    50                  55                  60 tat aag gtt gca gcc att att ccc tct tat aac gaa gat gct gag tca       240
Tyr Lys Val Ala Ala Ile Ile Pro Ser Tyr Asn Glu Asp Ala Glu Ser
65                  70                  75                  80 ttg cta gag acc tta aaa agt gtt cag cag caa acc tat ccc cta gca       288
Leu Leu Glu Thr Leu Lys Ser Val Gln Gln Gln Thr Tyr Pro Leu Ala
                85                  90                  95 gaa att tat gtt gtt gac gat gga agt gct gat gag aca ggt att aag       336
Glu Ile Tyr Val Val Asp Asp Gly Ser Ala Asp Glu Thr Gly Ile Lys
            100                 105                 110 cgc att gaa gac tat gtg cgt gac act ggt gac cta tca agc aat gtc       384
Arg Ile Glu Asp Tyr Val Arg Asp Thr Gly Asp Leu Ser Ser Asn Val
```

```
                115                 120                 125
att gtt cac cgg tca gaa aaa aat caa gga aag cgt cat gca cag gcc    432
Ile Val His Arg Ser Glu Lys Asn Gln Gly Lys Arg His Ala Gln Ala
    130                 135                 140 tgg gcc ttt gaa aga tca gac gct gat gtc ttt ttg acc gtt gac tca    480
Trp Ala Phe Glu Arg Ser Asp Ala Asp Val Phe Leu Thr Val Asp Ser
145                 150                 155                 160 gat act tat atc tac cct gat gct tta gag gag ttg tta aaa acc ttt    528
Asp Thr Tyr Ile Tyr Pro Asp Ala Leu Glu Glu Leu Leu Lys Thr Phe
                165                 170                 175 aat gac cca act gtt ttt gct gcg acg ggt cac ctt aat gtc aga aat    576
Asn Asp Pro Thr Val Phe Ala Ala Thr Gly His Leu Asn Val Arg Asn
            180                 185                 190 aga caa acc aat ctc tta aca cgc ttg aca gat att cgc tat gat aat    624
Arg Gln Thr Asn Leu Leu Thr Arg Leu Thr Asp Ile Arg Tyr Asp Asn
        195                 200                 205 gct ttt ggc gtt gaa cga gct gcc caa tcc gtt aca ggt aat att ctc    672
Ala Phe Gly Val Glu Arg Ala Ala Gln Ser Val Thr Gly Asn Ile Leu
    210                 215                 220 gtt tgc tca ggc ccg ctt agc gtt tac aga cgc gag gtg gtt gtt cct    720
Val Cys Ser Gly Pro Leu Ser Val Tyr Arg Arg Glu Val Val Val Pro
225                 230                 235                 240 aac ata gat aga tac atc aac cag acc ttc ctg ggt att cct gta agt    768
Asn Ile Asp Arg Tyr Ile Asn Gln Thr Phe Leu Gly Ile Pro Val Ser
                245                 250                 255 atc ggt gat gac agg tgc ttg acc aac tat gca act gat tta gga aag    816
Ile Gly Asp Asp Arg Cys Leu Thr Asn Tyr Ala Thr Asp Leu Gly Lys
            260                 265                 270 act gtt tat caa tcc act gct aaa tgt att aca gat gtt cct gac aag    864
Thr Val Tyr Gln Ser Thr Ala Lys Cys Ile Thr Asp Val Pro Asp Lys
        275                 280                 285 atg tct act tac ttg aag cag caa aac cgc tgg aac aag tcc ttc ttt    912
Met Ser Thr Tyr Leu Lys Gln Gln Asn Arg Trp Asn Lys Ser Phe Phe
    290                 295                 300 aga gag tcc att att tct gtt aag aaa atc atg aac aat cct ttt gta    960
Arg Glu Ser Ile Ile Ser Val Lys Lys Ile Met Asn Asn Pro Phe Val
305                 310                 315                 320 gcc cta tgg acc ata ctt gag gtg tct atg ttt atg atg ctt gtt tat   1008
Ala Leu Trp Thr Ile Leu Glu Val Ser Met Phe Met Met Leu Val Tyr
                325                 330                 335 tct gtg gtg gat ttc ttt gta gac aat gtc aga gaa ttt gat tgg ctc   1056
Ser Val Val Asp Phe Phe Val Asp Asn Val Arg Glu Phe Asp Trp Leu
            340                 345                 350 agg gtt ttg gcc ttt ctg gtg att atc ttc att gtt gct ctt tgt cgt   1104
Arg Val Leu Ala Phe Leu Val Ile Ile Phe Ile Val Ala Leu Cys Arg
        355                 360                 365 aat att cac tat atg ctt aag cac ccg ctg tcc ttc ttg tta tct ccg   1152
Asn Ile His Tyr Met Leu Lys His Pro Leu Ser Phe Leu Leu Ser Pro
    370                 375                 380 ttt tat ggg gta ctg cat ttg ttt gtc cta cag ccc ttg aaa ttg tat   1200
Phe Tyr Gly Val Leu His Leu Phe Val Leu Gln Pro Leu Lys Leu Tyr
385                 390                 395                 400 tct ctt ttt act att aga aat gct gac tgg gga aca cgt aaa aaa tta   1248
Ser Leu Phe Thr Ile Arg Asn Ala Asp Trp Gly Thr Arg Lys Lys Leu
                405                 410                 415 tta                                                                1251
Leu

<210> SEQ ID NO 2
```

<211> LENGTH: 417
<212> TYPE: PRT
<213> ORGANISM: Streptococcus equisimilis

<400> SEQUENCE: 2

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Asp Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
370                 375                 380

Phe Tyr Gly Val Leu His Leu Phe Val Leu Gln Pro Leu Lys Leu Tyr
```

|   |   |   |   |   |   |   |   |   |   |   |   |   |   |
|---|---|---|---|---|---|---|---|---|---|---|---|---|---|
| | | 385 | | | 390 | | | 395 | | | 400 | | |
| Ser | Leu | Phe | Thr | Ile | Arg | Asn | Ala | Asp | Trp | Gly | Thr | Arg | Lys | Lys | Leu |
| | | | | 405 | | | | 410 | | | | 415 | |

Leu

<210> SEQ ID NO 3
<211> LENGTH: 49
<212> TYPE: DNA
<213> ORGANISM: Streptococcus equisimilis

<400> SEQUENCE: 3
gagctctata aaatgagga gggaaccgaa tgagaacatt aaaaaacct        49

<210> SEQ ID NO 4
<211> LENGTH: 48
<212> TYPE: DNA
<213> ORGANISM: Streptococcus equisimilis

<400> SEQUENCE: 4
gttaacgaat tcagctatgt aggtaccta taataatttt ttacgtgt         48

<210> SEQ ID NO 5
<211> LENGTH: 20
<212> TYPE: DNA
<213> ORGANISM: Streptococcus equisimilis

<400> SEQUENCE: 5
gttgacgatg gaagtgctga                                       20

<210> SEQ ID NO 6
<211> LENGTH: 20
<212> TYPE: DNA
<213> ORGANISM: Streptococcus equisimilis

<400> SEQUENCE: 6
atccgttaca ggtaatatcc                                       20

<210> SEQ ID NO 7
<211> LENGTH: 20
<212> TYPE: DNA
<213> ORGANISM: Streptococcus equisimilis

<400> SEQUENCE: 7
tccttttgta gccctatgga                                       20

<210> SEQ ID NO 8
<211> LENGTH: 20
<212> TYPE: DNA
<213> ORGANISM: Streptococcus equisimilis

<400> SEQUENCE: 8
tcagcacttc catcgtcaac                                       20

<210> SEQ ID NO 9
<211> LENGTH: 20
<212> TYPE: DNA
<213> ORGANISM: Streptococcus equisimilis

<400> SEQUENCE: 9
ggatattacc tgtaacggat                                       20

<210> SEQ ID NO 10

-continued

```
<211> LENGTH: 20
<212> TYPE: DNA
<213> ORGANISM: Streptococcus equisimilis

<400> SEQUENCE: 10
tccatagggc tacaaaagga                                                    20

<210> SEQ ID NO 11
<211> LENGTH: 1383
<212> TYPE: DNA
<213> ORGANISM: Bacillus subtilis
<220> FEATURE:
<221> NAME/KEY: CDS
<222> LOCATION: (1)..(1383)
<223> OTHER INFORMATION:

<400> SEQUENCE: 11 gtg aaa aaa ata gct gtc att gga aca ggt tat gta gga ctc gta tca        48
Val Lys Lys Ile Ala Val Ile Gly Thr Gly Tyr Val Gly Leu Val Ser
1               5                   10                  15 ggc act tgc ttt gcg gag atc ggc aat aaa gtt gtt tgc tgt gat atc        96
Gly Thr Cys Phe Ala Glu Ile Gly Asn Lys Val Val Cys Cys Asp Ile
            20                  25                  30 gat gaa tca aaa atc aga agc ctg aaa aat ggg gta atc cca atc tat       144
Asp Glu Ser Lys Ile Arg Ser Leu Lys Asn Gly Val Ile Pro Ile Tyr
        35                  40                  45 gaa cca ggg ctt gca gac tta gtt gaa aaa aat gtg ctg gat cag cgc       192
Glu Pro Gly Leu Ala Asp Leu Val Glu Lys Asn Val Leu Asp Gln Arg
    50                  55                  60 ctg acc ttt acg aac gat atc ccg tct gcc att cgg gcc tca gat att       240
Leu Thr Phe Thr Asn Asp Ile Pro Ser Ala Ile Arg Ala Ser Asp Ile
65                  70                  75                  80 att tat att gca gtc gga acg cct atg tcc aaa aca ggt gaa gct gat       288
Ile Tyr Ile Ala Val Gly Thr Pro Met Ser Lys Thr Gly Glu Ala Asp
                85                  90                  95 tta acg tac gtc aaa gcg gcg gcg aaa aca atc ggt gag cat ctt aac       336
Leu Thr Tyr Val Lys Ala Ala Ala Lys Thr Ile Gly Glu His Leu Asn
            100                 105                 110 ggc tac aaa gtg atc gta aat aaa agc aca gtc ccg gtt gga aca ggg       384
Gly Tyr Lys Val Ile Val Asn Lys Ser Thr Val Pro Val Gly Thr Gly
        115                 120                 125 aaa ctg gtg caa tct atc gtt caa aaa gcc tca aag ggg aga tac tca       432
Lys Leu Val Gln Ser Ile Val Gln Lys Ala Ser Lys Gly Arg Tyr Ser
    130                 135                 140 ttt gat gtt gta tct aac cct gaa ttc ctt cgg gaa ggg tca gcg att       480
Phe Asp Val Val Ser Asn Pro Glu Phe Leu Arg Glu Gly Ser Ala Ile
145                 150                 155                 160 cat gac acg atg aat atg gag cgt gcc gtg att ggt tca aca agt cat       528
His Asp Thr Met Asn Met Glu Arg Ala Val Ile Gly Ser Thr Ser His
                165                 170                 175 aaa gcc gct gcc atc att gag gaa ctt cat cag cca ttc cat gct cct       576
Lys Ala Ala Ala Ile Ile Glu Glu Leu His Gln Pro Phe His Ala Pro
            180                 185                 190 gtc att aaa aca aac cta gaa agt gca gaa atg att aaa tac gcc gcg       624
Val Ile Lys Thr Asn Leu Glu Ser Ala Glu Met Ile Lys Tyr Ala Ala
        195                 200                 205 aat gca ttt ctg gcg aca aag att tcc ttt atc aac gat atc gca aac       672
Asn Ala Phe Leu Ala Thr Lys Ile Ser Phe Ile Asn Asp Ile Ala Asn
    210                 215                 220 att tgt gag cga gtc ggc gca gac gtt tca aaa gtt gct gat ggt gtt       720
Ile Cys Glu Arg Val Gly Ala Asp Val Ser Lys Val Ala Asp Gly Val
225                 230                 235                 240
```

```
ggt ctt gac agc cgt atc ggc aga aag ttc ctt aaa gct ggt att gga        768
Gly Leu Asp Ser Arg Ile Gly Arg Lys Phe Leu Lys Ala Gly Ile Gly
                245                 250                 255 ttc ggc ggt tca tgt ttt cca aag gat aca acc gcg ctg ctt caa atc        816
Phe Gly Gly Ser Cys Phe Pro Lys Asp Thr Thr Ala Leu Leu Gln Ile
            260                 265                 270 gca aaa tcg gca ggc tat cca ttc aag ctc atc gaa gct gtc att gaa        864
Ala Lys Ser Ala Gly Tyr Pro Phe Lys Leu Ile Glu Ala Val Ile Glu
        275                 280                 285 acg aac gaa aag cag cgt gtt cat att gta gat aaa ctt ttg act gtt        912
Thr Asn Glu Lys Gln Arg Val His Ile Val Asp Lys Leu Leu Thr Val
    290                 295                 300 atg gga agc gtc aaa ggg aga acc att tca gtc ctg gga tta gcc ttc        960
Met Gly Ser Val Lys Gly Arg Thr Ile Ser Val Leu Gly Leu Ala Phe
305                 310                 315                 320 aaa ccg aat acg aac gat gtg aga tcc gct cca gcg ctt gat att atc       1008
Lys Pro Asn Thr Asn Asp Val Arg Ser Ala Pro Ala Leu Asp Ile Ile
                325                 330                 335 cca atg ctg cag cag ctg ggc gcc cat gta aaa gca tac gat ccg att       1056
Pro Met Leu Gln Gln Leu Gly Ala His Val Lys Ala Tyr Asp Pro Ile
            340                 345                 350 gct att cct gaa gct tca gcg atc ctt ggc gaa cag gtc gag tat tac       1104
Ala Ile Pro Glu Ala Ser Ala Ile Leu Gly Glu Gln Val Glu Tyr Tyr
        355                 360                 365 aca gat gtg tat gct gcg atg gaa gac act gat gca tgc ctg att tta       1152
Thr Asp Val Tyr Ala Ala Met Glu Asp Thr Asp Ala Cys Leu Ile Leu
    370                 375                 380 acg gat tgg ccg gaa gtg aaa gaa atg gag ctt gta aaa gtg aaa acc       1200
Thr Asp Trp Pro Glu Val Lys Glu Met Glu Leu Val Lys Val Lys Thr
385                 390                 395                 400 ctc tta aaa cag cca gtc atc att gac ggc aga aat tta ttt tca ctt       1248
Leu Leu Lys Gln Pro Val Ile Ile Asp Gly Arg Asn Leu Phe Ser Leu
                405                 410                 415 gaa gag atg cag gca gcc gga tac att tat cac tct atc ggc cgt ccc       1296
Glu Glu Met Gln Ala Ala Gly Tyr Ile Tyr His Ser Ile Gly Arg Pro
            420                 425                 430 gct gtt cgg gga acg gaa ccc tct gac aag tat ttt ccg ggc ttg ccg       1344
Ala Val Arg Gly Thr Glu Pro Ser Asp Lys Tyr Phe Pro Gly Leu Pro
        435                 440                 445 ctt gaa gaa ttg gct aaa gac ttg gga agc gtc aat tta                   1383
Leu Glu Glu Leu Ala Lys Asp Leu Gly Ser Val Asn Leu
    450                 455                 460

<210> SEQ ID NO 12
<211> LENGTH: 461
<212> TYPE: PRT
<213> ORGANISM: Bacillus subtilis

<400> SEQUENCE: 12

Val Lys Lys Ile Ala Val Ile Gly Thr Gly Tyr Val Gly Leu Val Ser
1               5                   10                  15

Gly Thr Cys Phe Ala Glu Ile Gly Asn Lys Val Cys Cys Asp Ile
            20                  25                  30

Asp Glu Ser Lys Ile Arg Ser Leu Lys Asn Gly Val Ile Pro Ile Tyr
        35                  40                  45

Glu Pro Gly Leu Ala Asp Leu Val Glu Lys Asn Val Leu Asp Gln Arg
    50                  55                  60

Leu Thr Phe Thr Asn Asp Ile Pro Ser Ala Ile Arg Ala Ser Asp Ile
65                  70                  75                  80
```

```
Ile Tyr Ile Ala Val Gly Thr Pro Met Ser Lys Thr Gly Glu Ala Asp
                85                  90                  95

Leu Thr Tyr Val Lys Ala Ala Lys Thr Ile Gly Glu His Leu Asn
            100                 105                 110

Gly Tyr Lys Val Ile Val Asn Lys Ser Thr Val Pro Val Gly Thr Gly
            115                 120                 125

Lys Leu Val Gln Ser Ile Val Gln Lys Ala Ser Lys Gly Arg Tyr Ser
130                 135                 140

Phe Asp Val Val Ser Asn Pro Glu Phe Leu Arg Glu Gly Ser Ala Ile
145                 150                 155                 160

His Asp Thr Met Asn Met Glu Arg Ala Val Ile Gly Ser Thr Ser His
                165                 170                 175

Lys Ala Ala Ala Ile Ile Glu Glu Leu His Gln Pro Phe His Ala Pro
                180                 185                 190

Val Ile Lys Thr Asn Leu Glu Ser Ala Glu Met Ile Lys Tyr Ala Ala
            195                 200                 205

Asn Ala Phe Leu Ala Thr Lys Ile Ser Phe Ile Asn Asp Ile Ala Asn
    210                 215                 220

Ile Cys Glu Arg Val Gly Ala Asp Val Ser Lys Val Ala Asp Gly Val
225                 230                 235                 240

Gly Leu Asp Ser Arg Ile Gly Arg Lys Phe Leu Lys Ala Gly Ile Gly
                245                 250                 255

Phe Gly Gly Ser Cys Phe Pro Lys Asp Thr Thr Ala Leu Leu Gln Ile
                260                 265                 270

Ala Lys Ser Ala Gly Tyr Pro Phe Lys Leu Ile Glu Ala Val Ile Glu
            275                 280                 285

Thr Asn Glu Lys Gln Arg Val His Ile Val Asp Lys Leu Leu Thr Val
            290                 295                 300

Met Gly Ser Val Lys Gly Arg Thr Ile Ser Val Leu Gly Leu Ala Phe
305                 310                 315                 320

Lys Pro Asn Thr Asn Asp Val Arg Ser Ala Pro Ala Leu Asp Ile Ile
                325                 330                 335

Pro Met Leu Gln Gln Leu Gly Ala His Val Lys Ala Tyr Asp Pro Ile
                340                 345                 350

Ala Ile Pro Glu Ala Ser Ala Ile Leu Gly Glu Gln Val Glu Tyr Tyr
            355                 360                 365

Thr Asp Val Tyr Ala Ala Met Glu Asp Thr Asp Ala Cys Leu Ile Leu
370                 375                 380

Thr Asp Trp Pro Glu Val Lys Glu Met Glu Leu Val Lys Val Lys Thr
385                 390                 395                 400

Leu Leu Lys Gln Pro Val Ile Ile Asp Gly Arg Asn Leu Phe Ser Leu
                405                 410                 415

Glu Glu Met Gln Ala Ala Gly Tyr Ile Tyr His Ser Ile Gly Arg Pro
            420                 425                 430

Ala Val Arg Gly Thr Glu Pro Ser Asp Lys Tyr Phe Pro Gly Leu Pro
            435                 440                 445

Leu Glu Glu Leu Ala Lys Asp Leu Gly Ser Val Asn Leu
450                 455                 460

<210> SEQ ID NO 13
<211> LENGTH: 26
<212> TYPE: DNA
<213> ORGANISM: Bacillus subtilis
```

<400> SEQUENCE: 13
ggtaccgaca ctgcgaccat tataaa                                        26

<210> SEQ ID NO 14
<211> LENGTH: 49
<212> TYPE: DNA
<213> ORGANISM: Bacillus subtilis

<400> SEQUENCE: 14
gttaacgaat tccagctatg tatctagaca gcttcaacca agtaacact              49

<210> SEQ ID NO 15
<211> LENGTH: 20
<212> TYPE: DNA
<213> ORGANISM: Bacillus subtilis

<400> SEQUENCE: 15
agcatcttaa cggctacaaa                                               20

<210> SEQ ID NO 16
<211> LENGTH: 20
<212> TYPE: DNA
<213> ORGANISM: Bacillus subtilis

<400> SEQUENCE: 16
tgtgagcgag tcggcgcaga                                               20

<210> SEQ ID NO 17
<211> LENGTH: 20
<212> TYPE: DNA
<213> ORGANISM: Bacillus subtilis

<400> SEQUENCE: 17
gggcgcccat gtaaaagcat                                               20

<210> SEQ ID NO 18
<211> LENGTH: 20
<212> TYPE: DNA
<213> ORGANISM: Bacillus subtilis

<400> SEQUENCE: 18
tttgtagccg ttaagatgct                                               20

<210> SEQ ID NO 19
<211> LENGTH: 20
<212> TYPE: DNA
<213> ORGANISM: Bacillus subtilis

<400> SEQUENCE: 19
tctgcgccga ctcgctcaca                                               20

<210> SEQ ID NO 20
<211> LENGTH: 20
<212> TYPE: DNA
<213> ORGANISM: Bacillus subtilis

<400> SEQUENCE: 20
atgcttttac atgggcgccc                                               20

<210> SEQ ID NO 21
<211> LENGTH: 876
<212> TYPE: DNA
<213> ORGANISM: Bacillus subtilis
<220> FEATURE:
<221> NAME/KEY: CDS
<222> LOCATION: (1)..(876)
<223> OTHER INFORMATION:

<400> SEQUENCE: 21

| | | | | | | | | | | | | | | | | |
|---|---|---|---|---|---|---|---|---|---|---|---|---|---|---|---|---|
| atg | aaa | aaa | gta | cgt | aaa | gcc | ata | att | cca | gca | gca | ggc | tta | gga | aca | 48 |
| Met | Lys | Lys | Val | Arg | Lys | Ala | Ile | Ile | Pro | Ala | Ala | Gly | Leu | Gly | Thr | |
| 1 | | | 5 | | | | | 10 | | | | | 15 | | | |
| cgt | ttt | ctt | ccg | gct | acg | aaa | gca | atg | ccg | aaa | gaa | atg | ctt | cct | atc | 96 |
| Arg | Phe | Leu | Pro | Ala | Thr | Lys | Ala | Met | Pro | Lys | Glu | Met | Leu | Pro | Ile | |
| | | | 20 | | | | 25 | | | | | 30 | | | | |
| gtt | gat | aaa | cct | acc | att | caa | tac | ata | att | gaa | gaa | gct | gtt | gaa | gcc | 144 |
| Val | Asp | Lys | Pro | Thr | Ile | Gln | Tyr | Ile | Ile | Glu | Glu | Ala | Val | Glu | Ala | |
| | | 35 | | | | 40 | | | | | 45 | | | | | |
| ggt | att | gaa | gat | att | att | atc | gta | aca | gga | aaa | agc | aag | cgt | gcg | att | 192 |
| Gly | Ile | Glu | Asp | Ile | Ile | Ile | Val | Thr | Gly | Lys | Ser | Lys | Arg | Ala | Ile | |
| 50 | | | | | 55 | | | | | 60 | | | | | | |
| gag | gat | cat | ttt | gat | tac | tct | cct | gag | ctt | gaa | aga | aac | cta | gaa | gaa | 240 |
| Glu | Asp | His | Phe | Asp | Tyr | Ser | Pro | Glu | Leu | Glu | Arg | Asn | Leu | Glu | Glu | |
| 65 | | | | 70 | | | | | 75 | | | | | 80 | | |
| aaa | gga | aaa | act | gag | ctg | ctt | gaa | aaa | gtg | aaa | aag | gct | tct | aac | ctg | 288 |
| Lys | Gly | Lys | Thr | Glu | Leu | Leu | Glu | Lys | Val | Lys | Lys | Ala | Ser | Asn | Leu | |
| | | | | 85 | | | | | 90 | | | | | 95 | | |
| gct | gac | att | cac | tat | atc | cgc | caa | aaa | gaa | cct | aaa | ggt | ctc | gga | cat | 336 |
| Ala | Asp | Ile | His | Tyr | Ile | Arg | Gln | Lys | Glu | Pro | Lys | Gly | Leu | Gly | His | |
| | | | 100 | | | | | 105 | | | | | 110 | | | |
| gct | gtc | tgg | tgc | gca | cgc | aac | ttt | atc | ggc | gat | gag | ccg | ttt | gcg | gta | 384 |
| Ala | Val | Trp | Cys | Ala | Arg | Asn | Phe | Ile | Gly | Asp | Glu | Pro | Phe | Ala | Val | |
| | | | 115 | | | | | 120 | | | | | 125 | | | |
| ctg | ctt | ggt | gac | gat | att | gtt | cag | gct | gaa | act | cca | ggg | ttg | cgc | caa | 432 |
| Leu | Leu | Gly | Asp | Asp | Ile | Val | Gln | Ala | Glu | Thr | Pro | Gly | Leu | Arg | Gln | |
| | 130 | | | | | 135 | | | | | 140 | | | | | |
| tta | atg | gat | gaa | tat | gaa | aaa | aca | ctt | tct | tct | att | atc | ggt | gtt | cag | 480 |
| Leu | Met | Asp | Glu | Tyr | Glu | Lys | Thr | Leu | Ser | Ser | Ile | Ile | Gly | Val | Gln | |
| 145 | | | | | 150 | | | | | 155 | | | | | 160 | |
| cag | gtg | ccc | gaa | gaa | gaa | aca | cac | cgc | tac | ggc | att | att | gac | ccg | ctg | 528 |
| Gln | Val | Pro | Glu | Glu | Glu | Thr | His | Arg | Tyr | Gly | Ile | Ile | Asp | Pro | Leu | |
| | | | | 165 | | | | | 170 | | | | | 175 | | |
| aca | agt | gaa | ggc | cgc | cgt | tat | cag | gtg | aaa | aac | ttc | gtt | gaa | aaa | ccg | 576 |
| Thr | Ser | Glu | Gly | Arg | Arg | Tyr | Gln | Val | Lys | Asn | Phe | Val | Glu | Lys | Pro | |
| | | | 180 | | | | | 185 | | | | | 190 | | | |
| cct | aaa | ggc | aca | gca | cct | tct | aat | ctt | gcc | atc | tta | ggc | cgt | tac | gta | 624 |
| Pro | Lys | Gly | Thr | Ala | Pro | Ser | Asn | Leu | Ala | Ile | Leu | Gly | Arg | Tyr | Val | |
| | | | | 195 | | | | | 200 | | | | | 205 | | |
| ttc | acg | cct | gag | atc | ttc | atg | tat | tta | gaa | gag | cag | cag | gtt | ggc | gcc | 672 |
| Phe | Thr | Pro | Glu | Ile | Phe | Met | Tyr | Leu | Glu | Glu | Gln | Gln | Val | Gly | Ala | |
| | | 210 | | | | | 215 | | | | | 220 | | | | |
| ggc | gga | gaa | att | cag | ctc | aca | gac | gcc | att | caa | aag | ctg | aat | gaa | att | 720 |
| Gly | Gly | Glu | Ile | Gln | Leu | Thr | Asp | Ala | Ile | Gln | Lys | Leu | Asn | Glu | Ile | |
| 225 | | | | | 230 | | | | | 235 | | | | | 240 | |
| caa | aga | gtg | ttt | gct | tac | gat | ttt | gaa | ggc | aag | cgt | tat | gat | gtt | ggt | 768 |
| Gln | Arg | Val | Phe | Ala | Tyr | Asp | Phe | Glu | Gly | Lys | Arg | Tyr | Asp | Val | Gly | |
| | | | | 245 | | | | | 250 | | | | | 255 | | |
| gaa | aag | ctc | ggc | ttt | atc | aca | aca | act | ctt | gaa | ttt | gcg | atg | cag | gat | 816 |
| Glu | Lys | Leu | Gly | Phe | Ile | Thr | Thr | Thr | Leu | Glu | Phe | Ala | Met | Gln | Asp | |
| | | | 260 | | | | | 265 | | | | | 270 | | | |
| aaa | gag | ctt | cgc | gat | cag | ctc | gtt | cca | ttt | atg | gaa | ggt | tta | cta | aac | 864 |
| Lys | Glu | Leu | Arg | Asp | Gln | Leu | Val | Pro | Phe | Met | Glu | Gly | Leu | Leu | Asn | |
| | | 275 | | | | | 280 | | | | | 285 | | | | |

```
aaa gaa gaa atc                                                          876
Lys Glu Glu Ile
    290

<210> SEQ ID NO 22
<211> LENGTH: 292
<212> TYPE: PRT
<213> ORGANISM: Bacillus subtilis

<400> SEQUENCE: 22

Met Lys Lys Val Arg Lys Ala Ile Ile Pro Ala Ala Gly Leu Gly Thr
1               5                   10                  15

Arg Phe Leu Pro Ala Thr Lys Ala Met Pro Lys Glu Met Leu Pro Ile
            20                  25                  30

Val Asp Lys Pro Thr Ile Gln Tyr Ile Ile Glu Glu Ala Val Glu Ala
        35                  40                  45

Gly Ile Glu Asp Ile Ile Val Thr Gly Lys Ser Lys Arg Ala Ile
    50                  55                  60

Glu Asp His Phe Asp Tyr Ser Pro Glu Leu Glu Arg Asn Leu Glu Glu
65              70                  75                  80

Lys Gly Lys Thr Glu Leu Leu Glu Lys Val Lys Ala Ser Asn Leu
                85                  90                  95

Ala Asp Ile His Tyr Ile Arg Gln Lys Glu Pro Lys Gly Leu Gly His
            100                 105                 110

Ala Val Trp Cys Ala Arg Asn Phe Ile Gly Asp Glu Pro Phe Ala Val
            115                 120                 125

Leu Leu Gly Asp Asp Ile Val Gln Ala Glu Thr Pro Gly Leu Arg Gln
    130                 135                 140

Leu Met Asp Glu Tyr Glu Lys Thr Leu Ser Ser Ile Ile Gly Val Gln
145                 150                 155                 160

Gln Val Pro Glu Glu Glu Thr His Arg Tyr Gly Ile Ile Asp Pro Leu
                165                 170                 175

Thr Ser Glu Gly Arg Arg Tyr Gln Val Lys Asn Phe Val Glu Lys Pro
            180                 185                 190

Pro Lys Gly Thr Ala Pro Ser Asn Leu Ala Ile Leu Gly Arg Tyr Val
        195                 200                 205

Phe Thr Pro Glu Ile Phe Met Tyr Leu Glu Glu Gln Gln Val Gly Ala
    210                 215                 220

Gly Gly Glu Ile Gln Leu Thr Asp Ala Ile Gln Lys Leu Asn Glu Ile
225                 230                 235                 240

Gln Arg Val Phe Ala Tyr Asp Phe Glu Gly Lys Arg Tyr Asp Val Gly
                245                 250                 255

Glu Lys Leu Gly Phe Ile Thr Thr Leu Glu Phe Ala Met Gln Asp
            260                 265                 270

Lys Glu Leu Arg Asp Gln Leu Val Pro Phe Met Glu Gly Leu Leu Asn
        275                 280                 285

Lys Glu Glu Ile
    290

<210> SEQ ID NO 23
<211> LENGTH: 27
<212> TYPE: DNA
<213> ORGANISM: Bacillus subtilis

<400> SEQUENCE: 23
tctagatttt tcgatcataa ggaaggt                                             27
```

-continued

```
<210> SEQ ID NO 24
<211> LENGTH: 49
<212> TYPE: DNA
<213> ORGANISM: Bacillus subtilis

<400> SEQUENCE: 24
gttaacgaat tccagctatg taggatccaa tgtccaatag ccttttttgt           49

<210> SEQ ID NO 25
<211> LENGTH: 20
<212> TYPE: DNA
<213> ORGANISM: Bacillus subtilis

<400> SEQUENCE: 25
aaaaaggctt ctaacctggc                                            20

<210> SEQ ID NO 26
<211> LENGTH: 20
<212> TYPE: DNA
<213> ORGANISM: Bacillus subtilis

<400> SEQUENCE: 26
aaaccgccta aaggcacagc                                            20

<210> SEQ ID NO 27
<211> LENGTH: 20
<212> TYPE: DNA
<213> ORGANISM: Bacillus subtilis

<400> SEQUENCE: 27
gccaggttag aagccttttt                                            20

<210> SEQ ID NO 28
<211> LENGTH: 20
<212> TYPE: DNA
<213> ORGANISM: Bacillus subtilis

<400> SEQUENCE: 28
gctgtgcctt taggcggttt                                            20

<210> SEQ ID NO 29
<211> LENGTH: 1368
<212> TYPE: DNA
<213> ORGANISM: Bacillus subtilis
<220> FEATURE:
<221> NAME/KEY: CDS
<222> LOCATION: (1)..(1368)
<223> OTHER INFORMATION:

<400> SEQUENCE: 29
```

| | | | | | | | | | | | | | | | | |
|---|---|---|---|---|---|---|---|---|---|---|---|---|---|---|---|---|
| atg | gat | aag | cgg | ttt | gca | gtt | gtt | tta | gcg | gct | gga | caa | gga | acg | aga | 48 |
| Met | Asp | Lys | Arg | Phe | Ala | Val | Val | Leu | Ala | Ala | Gly | Gln | Gly | Thr | Arg | |
| 1 | | | | 5 | | | | | 10 | | | | | 15 | | |
| atg | aaa | tcg | aag | ctt | tat | aaa | gtc | ctt | cat | cca | gtt | tgc | ggt | aag | cct | 96 |
| Met | Lys | Ser | Lys | Leu | Tyr | Lys | Val | Leu | His | Pro | Val | Cys | Gly | Lys | Pro | |
| | | 20 | | | | | 25 | | | | | 30 | | | | |
| atg | gta | gag | cac | gtc | gtg | gac | gaa | gcc | tta | aaa | tta | tct | tta | tca | aag | 144 |
| Met | Val | Glu | His | Val | Val | Asp | Glu | Ala | Leu | Lys | Leu | Ser | Leu | Ser | Lys | |
| | | 35 | | | | | 40 | | | | | 45 | | | | |
| ctt | gtc | acg | att | gtc | gga | cat | ggt | gcg | gaa | gaa | gtg | aaa | aag | cag | ctt | 192 |
| Leu | Val | Thr | Ile | Val | Gly | His | Gly | Ala | Glu | Glu | Val | Lys | Lys | Gln | Leu | |
| | 50 | | | | | 55 | | | | | 60 | | | | | |
| ggt | gat | aaa | agc | gag | tac | gcg | ctt | caa | gca | aaa | cag | ctt | ggc | act | gct | 240 |
| Gly | Asp | Lys | Ser | Glu | Tyr | Ala | Leu | Gln | Ala | Lys | Gln | Leu | Gly | Thr | Ala | |

|  |  |  |  |  |  |  |  |  |  |  |  |  |  |  |  |
|---|---|---|---|---|---|---|---|---|---|---|---|---|---|---|---|
| Gly | Asp | Lys | Ser | Glu | Tyr | Ala | Leu | Gln | Ala | Lys | Gln | Leu | Gly | Thr | Ala |
| 65 |  |  |  |  | 70 |  |  |  |  | 75 |  |  |  |  | 80 |

```
cat gct gta aaa cag gca cag cca ttt ctt gct gac gaa aaa ggc gtc      288
His Ala Val Lys Gln Ala Gln Pro Phe Leu Ala Asp Glu Lys Gly Val
                 85                  90                  95 aca att gtc att tgc gga gat acg ccg ctt ttg aca gca gag acg atg      336
Thr Ile Val Ile Cys Gly Asp Thr Pro Leu Leu Thr Ala Glu Thr Met
            100                 105                 110 gaa cag atg ctg aaa gaa cat aca caa aga gaa gcg aaa gct acg att      384
Glu Gln Met Leu Lys Glu His Thr Gln Arg Glu Ala Lys Ala Thr Ile
        115                 120                 125 tta act gcg gtt gca gaa gat cca act gga tac ggc cgc att att cgc      432
Leu Thr Ala Val Ala Glu Asp Pro Thr Gly Tyr Gly Arg Ile Ile Arg
    130                 135                 140 agc gaa aac gga gcg gtt caa aaa ata gtt gag cat aag gac gcc tct      480
Ser Glu Asn Gly Ala Val Gln Lys Ile Val Glu His Lys Asp Ala Ser
145                 150                 155                 160 gaa gaa gaa cgt ctt gta act gag atc aac acc ggt acg tat tgt ttt      528
Glu Glu Glu Arg Leu Val Thr Glu Ile Asn Thr Gly Thr Tyr Cys Phe
                165                 170                 175 gac aat gaa gcg cta ttt cgg gct att gat cag gtg tct aat gat aat      576
Asp Asn Glu Ala Leu Phe Arg Ala Ile Asp Gln Val Ser Asn Asp Asn
            180                 185                 190 gca caa ggc gag tat tat ttg ccg gat gtc ata gag att ctt aaa aat      624
Ala Gln Gly Glu Tyr Tyr Leu Pro Asp Val Ile Glu Ile Leu Lys Asn
        195                 200                 205 gaa ggc gaa act gtt gcc gct tac cag act ggt aat ttc caa gaa acg      672
Glu Gly Glu Thr Val Ala Ala Tyr Gln Thr Gly Asn Phe Gln Glu Thr
    210                 215                 220 ctc gga gtt aat gat aga gtt gct ctt tct cag gca gaa caa ttt atg      720
Leu Gly Val Asn Asp Arg Val Ala Leu Ser Gln Ala Glu Gln Phe Met
225                 230                 235                 240 aaa gag cgc att aat aaa cgg cat atg caa aat ggc gtg acg ttg att      768
Lys Glu Arg Ile Asn Lys Arg His Met Gln Asn Gly Val Thr Leu Ile
                245                 250                 255 gac ccg atg aat acg tat att tct cct gac gct gtt atc gga agc gat      816
Asp Pro Met Asn Thr Tyr Ile Ser Pro Asp Ala Val Ile Gly Ser Asp
            260                 265                 270 act gtg att tac cct gga act gtg att aaa ggt gag gtg caa atc gga      864
Thr Val Ile Tyr Pro Gly Thr Val Ile Lys Gly Glu Val Gln Ile Gly
        275                 280                 285 gaa gat acg att att ggc cct cat acg gag att atg aat agt gcc att      912
Glu Asp Thr Ile Ile Gly Pro His Thr Glu Ile Met Asn Ser Ala Ile
    290                 295                 300 ggc agc cgt acg gtt att aaa caa tcg gta gtc aat cac agt aaa gtg      960
Gly Ser Arg Thr Val Ile Lys Gln Ser Val Val Asn His Ser Lys Val
305                 310                 315                 320 ggg aat gat gta aac ata gga cct ttt gct cac atc aga cct gat tct     1008
Gly Asn Asp Val Asn Ile Gly Pro Phe Ala His Ile Arg Pro Asp Ser
                325                 330                 335 gtc atc ggg aat gaa gtg aag atc ggg aat ttt gta gaa att aaa aag     1056
Val Ile Gly Asn Glu Val Lys Ile Gly Asn Phe Val Glu Ile Lys Lys
            340                 345                 350 act caa ttc gga gac cga agc aag gca tct cat cta agc tat gtc ggc     1104
Thr Gln Phe Gly Asp Arg Ser Lys Ala Ser His Leu Ser Tyr Val Gly
        355                 360                 365 gat gct gag gta ggc act gat gta aac ctg ggc tgc ggt tca att act     1152
Asp Ala Glu Val Gly Thr Asp Val Asn Leu Gly Cys Gly Ser Ile Thr
    370                 375                 380
```

```
gtc aat tat gat gga aag aat aag tat ttg aca aaa att gaa gat ggc    1200
Val Asn Tyr Asp Gly Lys Asn Lys Tyr Leu Thr Lys Ile Glu Asp Gly
385                 390                 395                 400 gcg ttt atc ggc tgc aat tcc aac ttg gtt gcc cct gtc aca gtc gga    1248
Ala Phe Ile Gly Cys Asn Ser Asn Leu Val Ala Pro Val Thr Val Gly
                405                 410                 415 gaa ggc gct tat gtg gcg gca ggt tca act gtt acg gaa gat gta cct    1296
Glu Gly Ala Tyr Val Ala Ala Gly Ser Thr Val Thr Glu Asp Val Pro
            420                 425                 430 gga aaa gca ctt gct att gcc aga gcg aga caa gta aat aaa gac gat    1344
Gly Lys Ala Leu Ala Ile Ala Arg Ala Arg Gln Val Asn Lys Asp Asp
        435                 440                 445 tat gtg aaa aat att cat aaa aaa                                    1368
Tyr Val Lys Asn Ile His Lys Lys
    450                 455
```

<210> SEQ ID NO 30
<211> LENGTH: 456
<212> TYPE: PRT
<213> ORGANISM: Bacillus subtilis

<400> SEQUENCE: 30

```
Met Asp Lys Arg Phe Ala Val Val Leu Ala Gly Gln Gly Thr Arg
1               5                   10                  15

Met Lys Ser Lys Leu Tyr Lys Val Leu His Pro Val Cys Gly Lys Pro
                20                  25                  30

Met Val Glu His Val Val Asp Glu Ala Leu Lys Leu Ser Leu Ser Lys
                35                  40                  45

Leu Val Thr Ile Val Gly His Gly Ala Glu Glu Val Lys Lys Gln Leu
        50                  55                  60

Gly Asp Lys Ser Glu Tyr Ala Leu Gln Ala Lys Gln Leu Gly Thr Ala
65                  70                  75                  80

His Ala Val Lys Gln Ala Gln Pro Phe Leu Ala Asp Glu Lys Gly Val
                85                  90                  95

Thr Ile Val Ile Cys Gly Asp Thr Pro Leu Leu Thr Ala Glu Thr Met
                100                 105                 110

Glu Gln Met Leu Lys Glu His Thr Gln Arg Glu Ala Lys Ala Thr Ile
            115                 120                 125

Leu Thr Ala Val Ala Glu Asp Pro Thr Gly Tyr Gly Arg Ile Ile Arg
        130                 135                 140

Ser Glu Asn Gly Ala Val Gln Lys Ile Val Glu His Lys Asp Ala Ser
145                 150                 155                 160

Glu Glu Glu Arg Leu Val Thr Glu Ile Asn Thr Gly Thr Tyr Cys Phe
                165                 170                 175

Asp Asn Glu Ala Leu Phe Arg Ala Ile Asp Gln Val Ser Asn Asp Asn
                180                 185                 190

Ala Gln Gly Glu Tyr Tyr Leu Pro Asp Val Ile Glu Ile Leu Lys Asn
            195                 200                 205

Glu Gly Glu Thr Val Ala Ala Tyr Gln Thr Gly Asn Phe Gln Glu Thr
        210                 215                 220

Leu Gly Val Asn Asp Arg Val Ala Leu Ser Gln Ala Glu Gln Phe Met
225                 230                 235                 240

Lys Glu Arg Ile Asn Lys Arg His Met Gln Asn Gly Val Thr Leu Ile
                245                 250                 255

Asp Pro Met Asn Thr Tyr Ile Ser Pro Asp Ala Val Ile Gly Ser Asp
                260                 265                 270
```

-continued

```
Thr Val Ile Tyr Pro Gly Thr Val Lys Gly Glu Val Gln Ile Gly
        275                 280                 285

Glu Asp Thr Ile Ile Gly Pro His Thr Glu Ile Met Asn Ser Ala Ile
    290                 295                 300

Gly Ser Arg Thr Val Ile Lys Gln Ser Val Val Asn His Ser Lys Val
305                 310                 315                 320

Gly Asn Asp Val Asn Ile Gly Pro Phe Ala His Ile Arg Pro Asp Ser
                325                 330                 335

Val Ile Gly Asn Glu Val Lys Ile Gly Asn Phe Val Glu Ile Lys Lys
            340                 345                 350

Thr Gln Phe Gly Asp Arg Ser Lys Ala Ser His Leu Ser Tyr Val Gly
        355                 360                 365

Asp Ala Glu Val Gly Thr Asp Val Asn Leu Gly Cys Gly Ser Ile Thr
    370                 375                 380

Val Asn Tyr Asp Gly Lys Asn Lys Tyr Leu Thr Lys Ile Glu Asp Gly
385                 390                 395                 400

Ala Phe Ile Gly Cys Asn Ser Asn Leu Val Ala Pro Val Thr Val Gly
                405                 410                 415

Glu Gly Ala Tyr Val Ala Ala Gly Ser Thr Val Thr Glu Asp Val Pro
            420                 425                 430

Gly Lys Ala Leu Ala Ile Ala Arg Ala Arg Gln Val Asn Lys Asp Asp
        435                 440                 445

Tyr Val Lys Asn Ile His Lys Lys
    450                 455

<210> SEQ ID NO 31
<211> LENGTH: 26
<212> TYPE: DNA
<213> ORGANISM: Bacillus subtilis

<400> SEQUENCE: 31
ggatcctttc tatggataaa agggat                                        26

<210> SEQ ID NO 32
<211> LENGTH: 31
<212> TYPE: DNA
<213> ORGANISM: Bacillus subtilis

<400> SEQUENCE: 32
gttaacagga ttatttttta tgaatatttt t                                  31

<210> SEQ ID NO 33
<211> LENGTH: 20
<212> TYPE: DNA
<213> ORGANISM: Bacillus subtilis

<400> SEQUENCE: 33
cagagacgat ggaacagatg                                               20

<210> SEQ ID NO 34
<211> LENGTH: 20
<212> TYPE: DNA
<213> ORGANISM: Bacillus subtilis

<400> SEQUENCE: 34
ggagttaatg atagagttgc                                               20

<210> SEQ ID NO 35
<211> LENGTH: 20
```

<210> SEQ ID NO 35
<211> LENGTH: 20
<212> TYPE: DNA
<213> ORGANISM: Bacillus subtilis

<400> SEQUENCE: 35
gaagatcggg aattttgtag                                              20

<210> SEQ ID NO 36
<211> LENGTH: 20
<212> TYPE: DNA
<213> ORGANISM: Bacillus subtilis

<400> SEQUENCE: 36
catctgttcc atcgtctctg                                              20

<210> SEQ ID NO 37
<211> LENGTH: 20
<212> TYPE: DNA
<213> ORGANISM: Bacillus subtilis

<400> SEQUENCE: 37
gcaactctat cattaactcc                                              20

<210> SEQ ID NO 38
<211> LENGTH: 20
<212> TYPE: DNA
<213> ORGANISM: Bacillus subtilis

<400> SEQUENCE: 38
ctacaaaatt cccgatcttc                                              20

<210> SEQ ID NO 39
<211> LENGTH: 54
<212> TYPE: DNA
<213> ORGANISM: Streptococcus equisimilis

<400> SEQUENCE: 39
gtgtcggaac attcattaca tgcttaagca cccgctgtcc ttcttgttat ctcc        54

<210> SEQ ID NO 40
<211> LENGTH: 1203
<212> TYPE: DNA
<213> ORGANISM: Streptococcus equisimilis
<220> FEATURE:
<221> NAME/KEY: CDS
<222> LOCATION: (1)..(1203)
<223> OTHER INFORMATION:

<400> SEQUENCE: 40

| gtg | aaa | att | tct | gta | gca | ggc | tca | gga | tat | gtc | ggc | cta | tcc | ttg | agt | 48 |
|---|---|---|---|---|---|---|---|---|---|---|---|---|---|---|---|---|
| Val | Lys | Ile | Ser | Val | Ala | Gly | Ser | Gly | Tyr | Val | Gly | Leu | Ser | Leu | Ser | |
| 1 | | | | 5 | | | | | 10 | | | | | 15 | | |

| att | tta | ctg | gca | caa | cat | aat | gac | gtc | act | gtt | gtt | gat | att | att | gat | 96 |
|---|---|---|---|---|---|---|---|---|---|---|---|---|---|---|---|---|
| Ile | Leu | Leu | Ala | Gln | His | Asn | Asp | Val | Thr | Val | Val | Asp | Ile | Ile | Asp | |
| | | | 20 | | | | | 25 | | | | | 30 | | | |

| gaa | aag | gtg | aga | ttg | atc | aat | caa | ggc | ata | tct | cca | atc | aag | gat | gct | 144 |
|---|---|---|---|---|---|---|---|---|---|---|---|---|---|---|---|---|
| Glu | Lys | Val | Arg | Leu | Ile | Asn | Gln | Gly | Ile | Ser | Pro | Ile | Lys | Asp | Ala | |
| | | 35 | | | | | 40 | | | | | 45 | | | | |

| gat | att | gag | gag | tat | tta | aaa | aat | gcg | ccg | cta | aat | ctc | aca | gcg | acc | 192 |
|---|---|---|---|---|---|---|---|---|---|---|---|---|---|---|---|---|
| Asp | Ile | Glu | Glu | Tyr | Leu | Lys | Asn | Ala | Pro | Leu | Asn | Leu | Thr | Ala | Thr | |
| | 50 | | | | | 55 | | | | | 60 | | | | | |

| ctt | gat | ggc | gca | agc | gct | tat | agc | aat | gca | gac | ctt | att | atc | att | gct | 240 |
|---|---|---|---|---|---|---|---|---|---|---|---|---|---|---|---|---|
| Leu | Asp | Gly | Ala | Ser | Ala | Tyr | Ser | Asn | Ala | Asp | Leu | Ile | Ile | Ile | Ala | |
| 65 | | | | 70 | | | | | 75 | | | | | 80 | | |

| | | |
|---|---|---|
| act ccg aca aat tat gac agc gaa cgc aac tac ttt gac aca agg cat<br>Thr Pro Thr Asn Tyr Asp Ser Glu Arg Asn Tyr Phe Asp Thr Arg His<br>                        85                     90                    95 | 288 |
| gtt gaa gag gtc att gag cag gtc cta gac cta aat gcg tca gca acc<br>Val Glu Glu Val Ile Glu Gln Val Leu Asp Leu Asn Ala Ser Ala Thr<br>                 100                    105                  110 | 336 |
| att att atc aaa tca acc ata cca cta ggc ttt atc aag cat gtt agg<br>Ile Ile Ile Lys Ser Thr Ile Pro Leu Gly Phe Ile Lys His Val Arg<br>        115                    120                  125 | 384 |
| gaa aaa tac cag aca gat cgt att att ttt agc cca gaa ttt tta aga<br>Glu Lys Tyr Gln Thr Asp Arg Ile Ile Phe Ser Pro Glu Phe Leu Arg<br>130                    135                  140 | 432 |
| gaa tca aaa gcc tta tac gat aac ctt tac cca agt cgg atc att gtt<br>Glu Ser Lys Ala Leu Tyr Asp Asn Leu Tyr Pro Ser Arg Ile Ile Val<br>145                   150                  155                  160 | 480 |
| tct tat gaa aag gac gac tca cca agg gtt att cag gct gct aaa gcc<br>Ser Tyr Glu Lys Asp Asp Ser Pro Arg Val Ile Gln Ala Ala Lys Ala<br>                   165                  170                 175 | 528 |
| ttt gct ggt ctt tta aag gaa gga gcc aaa agc aag gat act ccg gtc<br>Phe Ala Gly Leu Leu Lys Glu Gly Ala Lys Ser Lys Asp Thr Pro Val<br>               180                    185                  190 | 576 |
| tta ttt atg ggc tca cag gag gct gag gcg gtc aag cta ttt gcg aat<br>Leu Phe Met Gly Ser Gln Glu Ala Glu Ala Val Lys Leu Phe Ala Asn<br>               195                    200                  205 | 624 |
| acc ttt ttg gct atg cgg gtg tct tac ttt aat gaa tta gac acc tat<br>Thr Phe Leu Ala Met Arg Val Ser Tyr Phe Asn Glu Leu Asp Thr Tyr<br>        210                    215                  220 | 672 |
| tcc gaa agc aag ggt cta gat gct cag cgc gtg att gaa gga gtc tgt<br>Ser Glu Ser Lys Gly Leu Asp Ala Gln Arg Val Ile Glu Gly Val Cys<br>225                   230                  235                  240 | 720 |
| cat gat cag cgc att ggt aac cat tac aat aac cct tcc ttt gga tat<br>His Asp Gln Arg Ile Gly Asn His Tyr Asn Asn Pro Ser Phe Gly Tyr<br>                   245                  250               255 | 768 |
| ggc ggc tat tgc ctg cca aag gac agc aaa cag ctg ttg gca aat tat<br>Gly Gly Tyr Cys Leu Pro Lys Asp Ser Lys Gln Leu Leu Ala Asn Tyr<br>               260                    265                  270 | 816 |
| aga ggc att ccc cag tcc ttg atg tca gcg att gtt gag tcc aac aag<br>Arg Gly Ile Pro Gln Ser Leu Met Ser Ala Ile Val Glu Ser Asn Lys<br>             275                    280                  285 | 864 |
| ata cga aaa tcc tat tta gct gaa caa ata tta gac aga gcc tct agt<br>Ile Arg Lys Ser Tyr Leu Ala Glu Gln Ile Leu Asp Arg Ala Ser Ser<br>290                    295                    300 | 912 |
| caa aag cag gct ggt gta cca tta acg att ggc ttt tac cgc ttg att<br>Gln Lys Gln Ala Gly Val Pro Leu Thr Ile Gly Phe Tyr Arg Leu Ile<br>305                   310                  315                  320 | 960 |
| atg aaa agc aac tct gat aat ttc cga gaa agc gcc att aaa gat att<br>Met Lys Ser Asn Ser Asp Asn Phe Arg Glu Ser Ala Ile Lys Asp Ile<br>                   325                  330                 335 | 1008 |
| att gat atc atc aac gac tat ggg gtt aat att gtc att tac gaa ccc<br>Ile Asp Ile Ile Asn Asp Tyr Gly Val Asn Ile Val Ile Tyr Glu Pro<br>               340                    345                  350 | 1056 |
| atg ctt ggc gag gat att ggc tac agg gtt gtc aag gac tta gag cag<br>Met Leu Gly Glu Asp Ile Gly Tyr Arg Val Val Lys Asp Leu Glu Gln<br>             355                    360                  365 | 1104 |
| ttc aaa aac gag tct aca atc att gtg tca aat cgc ttt gag gac gac<br>Phe Lys Asn Glu Ser Thr Ile Ile Val Ser Asn Arg Phe Glu Asp Asp<br>370                    375                  380 | 1152 |
| cta gga gat gtc att gat aag gtt tat acg aga gat gtc ttt gga aga<br>Leu Gly Asp Val Ile Asp Lys Val Tyr Thr Arg Asp Val Phe Gly Arg<br>385                   390                  395                  400 | 1200 |

```
gac                                                        1203
Asp

<210> SEQ ID NO 41
<211> LENGTH: 401
<212> TYPE: PRT
<213> ORGANISM: Streptococcus equisimilis

<400> SEQUENCE: 41
```

Val Lys Ile Ser Val Ala Gly Ser Gly Tyr Val Gly Leu Ser Leu Ser
1               5                   10                  15

Ile Leu Leu Ala Gln His Asn Asp Val Thr Val Asp Ile Ile Asp
            20                  25                  30

Glu Lys Val Arg Leu Ile Asn Gln Gly Ile Ser Pro Ile Lys Asp Ala
        35                  40                  45

Asp Ile Glu Glu Tyr Leu Lys Asn Ala Pro Leu Asn Leu Thr Ala Thr
    50                  55                  60

Leu Asp Gly Ala Ser Ala Tyr Ser Asn Ala Asp Leu Ile Ile Ile Ala
65                  70                  75                  80

Thr Pro Thr Asn Tyr Asp Ser Glu Arg Asn Tyr Phe Asp Thr Arg His
                85                  90                  95

Val Glu Glu Val Ile Glu Gln Val Leu Asp Leu Asn Ala Ser Ala Thr
            100                 105                 110

Ile Ile Ile Lys Ser Thr Ile Pro Leu Gly Phe Ile Lys His Val Arg
        115                 120                 125

Glu Lys Tyr Gln Thr Asp Arg Ile Ile Phe Ser Pro Glu Phe Leu Arg
    130                 135                 140

Glu Ser Lys Ala Leu Tyr Asp Asn Leu Tyr Pro Ser Arg Ile Ile Val
145                 150                 155                 160

Ser Tyr Glu Lys Asp Asp Ser Pro Arg Val Ile Gln Ala Ala Lys Ala
                165                 170                 175

Phe Ala Gly Leu Leu Lys Glu Gly Ala Lys Ser Lys Asp Thr Pro Val
            180                 185                 190

Leu Phe Met Gly Ser Gln Glu Ala Glu Val Lys Leu Phe Ala Asn
        195                 200                 205

Thr Phe Leu Ala Met Arg Val Ser Tyr Phe Asn Glu Leu Asp Thr Tyr
    210                 215                 220

Ser Glu Ser Lys Gly Leu Asp Ala Gln Arg Val Ile Glu Gly Val Cys
225                 230                 235                 240

His Asp Gln Arg Ile Gly Asn His Tyr Asn Asn Pro Ser Phe Gly Tyr
                245                 250                 255

Gly Gly Tyr Cys Leu Pro Lys Asp Ser Lys Gln Leu Leu Ala Asn Tyr
            260                 265                 270

Arg Gly Ile Pro Gln Ser Leu Met Ser Ala Ile Val Glu Ser Asn Lys
        275                 280                 285

Ile Arg Lys Ser Tyr Leu Ala Glu Gln Ile Leu Asp Arg Ala Ser Ser
    290                 295                 300

Gln Lys Gln Ala Gly Val Pro Leu Thr Ile Gly Phe Tyr Arg Leu Ile
305                 310                 315                 320

Met Lys Ser Asn Ser Asp Asn Phe Arg Glu Ser Ala Ile Lys Asp Ile
                325                 330                 335

Ile Asp Ile Ile Asn Asp Tyr Gly Val Asn Ile Val Ile Tyr Glu Pro
            340                 345                 350

Met Leu Gly Glu Asp Ile Gly Tyr Arg Val Val Lys Asp Leu Glu Gln

```
                        355                 360                 365
            Phe Lys Asn Glu Ser Thr Ile Ile Val Ser Asn Arg Phe Glu Asp Asp
                370                 375                 380
            Leu Gly Asp Val Ile Asp Lys Val Tyr Thr Arg Asp Val Phe Gly Arg
            385                 390                 395                 400
            Asp

<210> SEQ ID NO 42
<211> LENGTH: 900
<212> TYPE: DNA
<213> ORGANISM: Streptococcus equisimilis
<220> FEATURE:
<221> NAME/KEY: CDS
<222> LOCATION: (1)..(900)
<223> OTHER INFORMATION:

<400> SEQUENCE: 42 atg aca aag gtc aga aaa gcc att atc cca gcc gcc ggc cta ggc act        48
Met Thr Lys Val Arg Lys Ala Ile Ile Pro Ala Ala Gly Leu Gly Thr
 1               5                  10                  15 cgc ttc cta ccc gcc acc aag gca ctg gcc aag gaa atg ctc cca atc        96
Arg Phe Leu Pro Ala Thr Lys Ala Leu Ala Lys Glu Met Leu Pro Ile
                20                  25                  30 gtc gat aag cca acc att caa ttc atc gtc gag gaa gct cta aag gcc       144
Val Asp Lys Pro Thr Ile Gln Phe Ile Val Glu Glu Ala Leu Lys Ala
            35                  40                  45 ggt atc gag gag att ctt gtc gtc acc ggc aag gcc aaa cgc tct att       192
Gly Ile Glu Glu Ile Leu Val Val Thr Gly Lys Ala Lys Arg Ser Ile
        50                  55                  60 gaa gac cac ttt gac tcc aac ttc gag ctc gaa tac aat ctc caa gcc       240
Glu Asp His Phe Asp Ser Asn Phe Glu Leu Glu Tyr Asn Leu Gln Ala
65                  70                  75                  80 aag ggc aaa acc gag ctg ctc aag ctc gtt gat gag acc act gcc atc       288
Lys Gly Lys Thr Glu Leu Leu Lys Leu Val Asp Glu Thr Thr Ala Ile
                85                  90                  95 aac ctg cac ttc att cgt cag agc cac cct aga gga cta ggg gac gct       336
Asn Leu His Phe Ile Arg Gln Ser His Pro Arg Gly Leu Gly Asp Ala
               100                 105                 110 gtc ctc cag gcc aag gcc ttt gtg ggc aat gag ccc ttt gtg gtc atg       384
Val Leu Gln Ala Lys Ala Phe Val Gly Asn Glu Pro Phe Val Val Met
           115                 120                 125 ctg ggg gat gac ctc atg gat att acc aat cct agt gcc aag ccc ttg       432
Leu Gly Asp Asp Leu Met Asp Ile Thr Asn Pro Ser Ala Lys Pro Leu
       130                 135                 140 gcc aag cag ctc att gag gat tat gat tgc aca cac gcc tca acg att       480
Ala Lys Gln Leu Ile Glu Asp Tyr Asp Cys Thr His Ala Ser Thr Ile
145                 150                 155                 160 gca gtg atg agg gtg ccg cat gag gag gtt tcc aat tat ggc gtg att       528
Ala Val Met Arg Val Pro His Glu Glu Val Ser Asn Tyr Gly Val Ile
                165                 170                 175 gca ccg caa ggg aag gct gtt aag ggc ttg tat agt gtg gag acc ttt       576
Ala Pro Gln Gly Lys Ala Val Lys Gly Leu Tyr Ser Val Glu Thr Phe
            180                 185                 190 gtt gag aag cca agt cca gat gag gca ccg agt gac tta gcg att att       624
Val Glu Lys Pro Ser Pro Asp Glu Ala Pro Ser Asp Leu Ala Ile Ile
        195                 200                 205 ggt cga tat ttg ttg acg cct gag att ttt gcc ata ttg gag aat cag       672
Gly Arg Tyr Leu Leu Thr Pro Glu Ile Phe Ala Ile Leu Glu Asn Gln
   210                 215                 220 gcg cct ggg gct ggc aat gag gta cag cta gcc gat gcg att gac aag       720
```

```
Ala Pro Gly Ala Gly Asn Glu Val Gln Leu Ala Asp Ala Ile Asp Lys
225                 230                 235                 240 ctc aac aag act cag cgg gtt ttt gcg agg gag ttt aag gga gag cgg      768
Leu Asn Lys Thr Gln Arg Val Phe Ala Arg Glu Phe Lys Gly Glu Arg
                245                 250                 255 tat gat gtt ggg gac aag ttt ggc ttt atg aag acc tca ctt gac tat      816
Tyr Asp Val Gly Asp Lys Phe Gly Phe Met Lys Thr Ser Leu Asp Tyr
            260                 265                 270 gct ctc aag cac cct cag gtc aag gac gac ctc act gac tac att ata      864
Ala Leu Lys His Pro Gln Val Lys Asp Asp Leu Thr Asp Tyr Ile Ile
        275                 280                 285 aag ctc agt aag caa ctg aac aag gac gtt aaa aaa                      900
Lys Leu Ser Lys Gln Leu Asn Lys Asp Val Lys Lys
    290                 295                 300

<210> SEQ ID NO 43
<211> LENGTH: 300
<212> TYPE: PRT
<213> ORGANISM: Streptococcus equisimilis

<400> SEQUENCE: 43

Met Thr Lys Val Arg Lys Ala Ile Ile Pro Ala Ala Gly Leu Gly Thr
1               5                   10                  15

Arg Phe Leu Pro Ala Thr Lys Ala Leu Ala Lys Glu Met Leu Pro Ile
            20                  25                  30

Val Asp Lys Pro Thr Ile Gln Phe Ile Val Glu Glu Ala Leu Lys Ala
        35                  40                  45

Gly Ile Glu Glu Ile Leu Val Val Thr Gly Lys Ala Lys Arg Ser Ile
    50                  55                  60

Glu Asp His Phe Asp Ser Asn Phe Glu Leu Glu Tyr Asn Leu Gln Ala
65                  70                  75                  80

Lys Gly Lys Thr Glu Leu Leu Lys Leu Val Asp Glu Thr Thr Ala Ile
                85                  90                  95

Asn Leu His Phe Ile Arg Gln Ser His Pro Arg Gly Leu Gly Asp Ala
            100                 105                 110

Val Leu Gln Ala Lys Ala Phe Val Gly Asn Glu Pro Phe Val Val Met
        115                 120                 125

Leu Gly Asp Asp Leu Met Asp Ile Thr Asn Pro Ser Ala Lys Pro Leu
    130                 135                 140

Ala Lys Gln Leu Ile Glu Asp Tyr Asp Cys Thr His Ala Ser Thr Ile
145                 150                 155                 160

Ala Val Met Arg Val Pro His Glu Glu Val Ser Asn Tyr Gly Val Ile
                165                 170                 175

Ala Pro Gln Gly Lys Ala Val Lys Gly Leu Tyr Ser Val Glu Thr Phe
            180                 185                 190

Val Glu Lys Pro Ser Pro Asp Glu Ala Pro Ser Asp Leu Ala Ile Ile
        195                 200                 205

Gly Arg Tyr Leu Leu Thr Pro Glu Ile Phe Ala Ile Leu Glu Asn Gln
    210                 215                 220

Ala Pro Gly Ala Gly Asn Glu Val Gln Leu Ala Asp Ala Ile Asp Lys
225                 230                 235                 240

Leu Asn Lys Thr Gln Arg Val Phe Ala Arg Glu Phe Lys Gly Glu Arg
                245                 250                 255

Tyr Asp Val Gly Asp Lys Phe Gly Phe Met Lys Thr Ser Leu Asp Tyr
            260                 265                 270

Ala Leu Lys His Pro Gln Val Lys Asp Asp Leu Thr Asp Tyr Ile Ile
```

```
                275                 280                 285
Lys Leu Ser Lys Gln Leu Asn Lys Asp Val Lys Lys
    290                 295                 300

<210> SEQ ID NO 44
<211> LENGTH: 1380
<212> TYPE: DNA
<213> ORGANISM: Streptococcus equisimilis
<220> FEATURE:
<221> NAME/KEY: CDS
<222> LOCATION: (1)..(1380)
<223> OTHER INFORMATION:

<400> SEQUENCE: 44 atg aaa aac tac gcc att atc cta gca gct gga aag gga acc cgc atg        48
Met Lys Asn Tyr Ala Ile Ile Leu Ala Ala Gly Lys Gly Thr Arg Met
1               5                   10                  15 aat tca ggg ctt tcc aag gtg ctg cac aag gta tca ggc cta agc atg        96
Asn Ser Gly Leu Ser Lys Val Leu His Lys Val Ser Gly Leu Ser Met
            20                  25                  30 ctg gag cat gtc ctc aag agc gtc tca gcc cta gct cct caa aag caa       144
Leu Glu His Val Leu Lys Ser Val Ser Ala Leu Ala Pro Gln Lys Gln
        35                  40                  45 ctc aca gtg atc ggt cat cag gca gag caa gta cgt gcc gtc cta ggt       192
Leu Thr Val Ile Gly His Gln Ala Glu Gln Val Arg Ala Val Leu Gly
    50                  55                  60 gat caa tta ctg aca gtg gtg caa gag gag cag cta gga aca ggc cat       240
Asp Gln Leu Leu Thr Val Val Gln Glu Glu Gln Leu Gly Thr Gly His
65                  70                  75                  80 gca gtc atg atg gca gaa gag gag cta tct ggc tta gaa ggg cag acc       288
Ala Val Met Met Ala Glu Glu Glu Leu Ser Gly Leu Glu Gly Gln Thr
                85                  90                  95 cta gtg att gca ggt gac acc ccc ttg atc aga gga gaa agc ctc aag       336
Leu Val Ile Ala Gly Asp Thr Pro Leu Ile Arg Gly Glu Ser Leu Lys
            100                 105                 110 gct ctg cta gac tat cat atc aga gaa aag aat gtg gca acc att ctc       384
Ala Leu Leu Asp Tyr His Ile Arg Glu Lys Asn Val Ala Thr Ile Leu
        115                 120                 125 aca gcc aat gcc aag gat ccc ttt ggc tac ggc cga atc att cgc aat       432
Thr Ala Asn Ala Lys Asp Pro Phe Gly Tyr Gly Arg Ile Ile Arg Asn
    130                 135                 140 gca gca gga gag gtg gtc aac atc gtt gaa caa aag gac gct aat gag       480
Ala Ala Gly Glu Val Val Asn Ile Val Glu Gln Lys Asp Ala Asn Glu
145                 150                 155                 160 gca gag caa gag gtc aag gag atc aac aca ggg acc tat atc ttt gac       528
Ala Glu Gln Glu Val Lys Glu Ile Asn Thr Gly Thr Tyr Ile Phe Asp
                165                 170                 175 aat aag cgc ctc ttt gag gct cta aag cat ctc acg act gat aat gcc       576
Asn Lys Arg Leu Phe Glu Ala Leu Lys His Leu Thr Thr Asp Asn Ala
            180                 185                 190 caa ggg gaa tat tac cta acc gat gtg atc agt att ttc aag gcc agc       624
Gln Gly Glu Tyr Tyr Leu Thr Asp Val Ile Ser Ile Phe Lys Ala Ser
        195                 200                 205 caa gaa aag gtt gga gct tac ctg ctg aag gat ttt gat gaa agc cta       672
Gln Glu Lys Val Gly Ala Tyr Leu Leu Lys Asp Phe Asp Glu Ser Leu
    210                 215                 220 ggg gtt aat gat cgc cta gct cta gcc cag gct gag gtg atc atg cag       720
Gly Val Asn Asp Arg Leu Ala Leu Ala Gln Ala Glu Val Ile Met Gln
225                 230                 235                 240 gag cgg atc aac aag cag cac atg ctt aat ggg gtg acc ctg caa aac       768
Glu Arg Ile Asn Lys Gln His Met Leu Asn Gly Val Thr Leu Gln Asn
```

```
               245                 250                 255
cct gca gct acc tat atc gaa agc agt gta gag att gcg ccg gac gtc      816
Pro Ala Ala Thr Tyr Ile Glu Ser Ser Val Glu Ile Ala Pro Asp Val
        260                 265                 270 ttg att gaa gct aat gtg acc cta aag gga cag act aga att ggc agc      864
Leu Ile Glu Ala Asn Val Thr Leu Lys Gly Gln Thr Arg Ile Gly Ser
            275                 280                 285 aga agt gtt ata acc aat ggg agc tat atc ctt gat tca agg ctt ggt      912
Arg Ser Val Ile Thr Asn Gly Ser Tyr Ile Leu Asp Ser Arg Leu Gly
        290                 295                 300 gag ggc gta gtg tgt agc cag tca gtg att gag ggc tca gtc cta gca      960
Glu Gly Val Val Val Ser Gln Ser Val Ile Glu Gly Ser Val Leu Ala
305                 310                 315                 320 gat ggt gtg aca gta ggg ccc tat gca cac att cgc ccg gac tct cag     1008
Asp Gly Val Thr Val Gly Pro Tyr Ala His Ile Arg Pro Asp Ser Gln
                325                 330                 335 ctc gat gag tgt gtt cat att ggg aac ttt gta gag gtt aag ggg tct     1056
Leu Asp Glu Cys Val His Ile Gly Asn Phe Val Glu Val Lys Gly Ser
            340                 345                 350 cat cta ggg gcc aat acc aag gca ggg cat ttg act tat ctg ggg aat     1104
His Leu Gly Ala Asn Thr Lys Ala Gly His Leu Thr Tyr Leu Gly Asn
        355                 360                 365 gcc gag att ggc tca gag gtt aat att ggt gca gga agc att acg gtt     1152
Ala Glu Ile Gly Ser Glu Val Asn Ile Gly Ala Gly Ser Ile Thr Val
    370                 375                 380 aat tat gat ggt caa cgg aaa tac cag aca gtg att ggc gat cac gct     1200
Asn Tyr Asp Gly Gln Arg Lys Tyr Gln Thr Val Ile Gly Asp His Ala
385                 390                 395                 400 ttt att ggg agt cat tcg act ttg ata gct ccg gta gag gtt ggg gag     1248
Phe Ile Gly Ser His Ser Thr Leu Ile Ala Pro Val Glu Val Gly Glu
                405                 410                 415 aat gct tta aca gca gca ggg tct acg ata gcc cag tcg gtg cca gca     1296
Asn Ala Leu Thr Ala Ala Gly Ser Thr Ile Ala Gln Ser Val Pro Ala
            420                 425                 430 gac agt gtg gct ata ggg cgt agc cgt cag gtg gtg aag gaa ggc tat     1344
Asp Ser Val Ala Ile Gly Arg Ser Arg Gln Val Val Lys Glu Gly Tyr
        435                 440                 445 gcc aag agg cta cca cat cac ccg gat cag ccc cag                     1380
Ala Lys Arg Leu Pro His His Pro Asp Gln Pro Gln
    450                 455                 460

<210> SEQ ID NO 45
<211> LENGTH: 460
<212> TYPE: PRT
<213> ORGANISM: Streptococcus equisimilis

<400> SEQUENCE: 45

Met Lys Asn Tyr Ala Ile Ile Leu Ala Ala Gly Lys Gly Thr Arg Met
1               5                   10                  15

Asn Ser Gly Leu Ser Lys Val Leu His Lys Val Ser Gly Leu Ser Met
            20                  25                  30

Leu Glu His Val Leu Lys Ser Val Ser Ala Leu Ala Pro Gln Lys Gln
        35                  40                  45

Leu Thr Val Ile Gly His Gln Ala Glu Gln Val Arg Ala Val Leu Gly
    50                  55                  60

Asp Gln Leu Leu Thr Val Val Gln Glu Glu Leu Gly Thr Gly His
65                  70                  75                  80

Ala Val Met Met Ala Glu Glu Glu Leu Ser Gly Leu Glu Gly Gln Thr
                85                  90                  95
```

```
Leu Val Ile Ala Gly Asp Thr Pro Leu Ile Arg Gly Glu Ser Leu Lys
                100                 105                 110

Ala Leu Leu Asp Tyr His Ile Arg Glu Lys Asn Val Ala Thr Ile Leu
            115                 120                 125

Thr Ala Asn Ala Lys Asp Pro Phe Gly Tyr Gly Arg Ile Ile Arg Asn
130                 135                 140

Ala Ala Gly Glu Val Val Asn Ile Val Glu Gln Lys Asp Ala Asn Glu
145                 150                 155                 160

Ala Glu Gln Glu Val Lys Glu Ile Asn Thr Gly Thr Tyr Ile Phe Asp
                165                 170                 175

Asn Lys Arg Leu Phe Glu Ala Leu Lys His Leu Thr Thr Asp Asn Ala
            180                 185                 190

Gln Gly Glu Tyr Tyr Leu Thr Asp Val Ile Ser Ile Phe Lys Ala Ser
                195                 200                 205

Gln Glu Lys Val Gly Ala Tyr Leu Leu Lys Asp Phe Asp Glu Ser Leu
        210                 215                 220

Gly Val Asn Asp Arg Leu Ala Leu Ala Gln Ala Glu Val Ile Met Gln
225                 230                 235                 240

Glu Arg Ile Asn Lys Gln His Met Leu Asn Gly Val Thr Leu Gln Asn
                245                 250                 255

Pro Ala Ala Thr Tyr Ile Glu Ser Ser Val Glu Ile Ala Pro Asp Val
            260                 265                 270

Leu Ile Glu Ala Asn Val Thr Leu Lys Gly Gln Thr Arg Ile Gly Ser
        275                 280                 285

Arg Ser Val Ile Thr Asn Gly Ser Tyr Ile Leu Asp Ser Arg Leu Gly
290                 295                 300

Glu Gly Val Val Val Ser Gln Ser Val Ile Glu Gly Ser Val Leu Ala
305                 310                 315                 320

Asp Gly Val Thr Val Gly Pro Tyr Ala His Ile Arg Pro Asp Ser Gln
                325                 330                 335

Leu Asp Glu Cys Val His Ile Gly Asn Phe Val Glu Val Lys Gly Ser
            340                 345                 350

His Leu Gly Ala Asn Thr Lys Ala Gly His Leu Thr Tyr Leu Gly Asn
        355                 360                 365

Ala Glu Ile Gly Ser Glu Val Asn Ile Gly Ala Gly Ser Ile Thr Val
                370                 375                 380

Asn Tyr Asp Gly Gln Arg Lys Tyr Gln Thr Val Ile Gly Asp His Ala
385                 390                 395                 400

Phe Ile Gly Ser His Ser Thr Leu Ile Ala Pro Val Glu Val Gly Glu
                405                 410                 415

Asn Ala Leu Thr Ala Ala Gly Ser Thr Ile Ala Gln Ser Val Pro Ala
            420                 425                 430

Asp Ser Val Ala Ile Gly Arg Ser Arg Gln Val Val Lys Glu Gly Tyr
        435                 440                 445

Ala Lys Arg Leu Pro His His Pro Asp Gln Pro Gln
450                 455                 460
```

<210> SEQ ID NO 46
<211> LENGTH: 29
<212> TYPE: DNA
<213> ORGANISM: Bacillus subtilis

<400> SEQUENCE: 46
gcggccgcgg tacctgtgtt acacctgtt                              29

```
<210> SEQ ID NO 47
<211> LENGTH: 38
<212> TYPE: DNA
<213> ORGANISM: Bacillus subtilis

<400> SEQUENCE: 47
gtcaagctta attctcatgt ttgacagctt atcatcgg                             38

<210> SEQ ID NO 48
<211> LENGTH: 18
<212> TYPE: DNA
<213> ORGANISM: Bacillus subtilis

<400> SEQUENCE: 48
catgggagag acctttgg                                                   18

<210> SEQ ID NO 49
<211> LENGTH: 17
<212> TYPE: DNA
<213> ORGANISM: Bacillus subtilis

<400> SEQUENCE: 49
gtcggtcttc catttgc                                                    17

<210> SEQ ID NO 50
<211> LENGTH: 17
<212> TYPE: DNA
<213> ORGANISM: Bacillus subtilis

<400> SEQUENCE: 50
cgaccactgt atcttgg                                                    17

<210> SEQ ID NO 51
<211> LENGTH: 17
<212> TYPE: DNA
<213> ORGANISM: Bacillus subtilis

<400> SEQUENCE: 51
gagatgccaa acagtgc                                                    17

<210> SEQ ID NO 52
<211> LENGTH: 16
<212> TYPE: DNA
<213> ORGANISM: Bacillus subtilis

<400> SEQUENCE: 52
catgtccatc gtgacg                                                     16

<210> SEQ ID NO 53
<211> LENGTH: 17
<212> TYPE: DNA
<213> ORGANISM: Bacillus subtilis

<400> SEQUENCE: 53
caggagcatt tgatacg                                                    17

<210> SEQ ID NO 54
<211> LENGTH: 16
<212> TYPE: DNA
<213> ORGANISM: Bacillus subtilis

<400> SEQUENCE: 54
```

```
ccttcagatg tgatcc                                                  16

<210> SEQ ID NO 55
<211> LENGTH: 17
<212> TYPE: DNA
<213> ORGANISM: Bacillus subtilis

<400> SEQUENCE: 55
gtgttgacgt caactgc                                                 17

<210> SEQ ID NO 56
<211> LENGTH: 18
<212> TYPE: DNA
<213> ORGANISM: Bacillus subtilis

<400> SEQUENCE: 56
gttcagcctt tcctctcg                                                18

<210> SEQ ID NO 57
<211> LENGTH: 18
<212> TYPE: DNA
<213> ORGANISM: Bacillus subtilis

<400> SEQUENCE: 57
gctaccttct ttcttagg                                                18

<210> SEQ ID NO 58
<211> LENGTH: 18
<212> TYPE: DNA
<213> ORGANISM: Bacillus subtilis

<400> SEQUENCE: 58
cgtcaatatg atctgtgc                                                18

<210> SEQ ID NO 59
<211> LENGTH: 17
<212> TYPE: DNA
<213> ORGANISM: Bacillus subtilis

<400> SEQUENCE: 59
ggaaagaagg tctgtgc                                                 17

<210> SEQ ID NO 60
<211> LENGTH: 17
<212> TYPE: DNA
<213> ORGANISM: Bacillus subtilis

<400> SEQUENCE: 60
cagctatcag ctgacag                                                 17

<210> SEQ ID NO 61
<211> LENGTH: 20
<212> TYPE: DNA
<213> ORGANISM: Bacillus subtilis

<400> SEQUENCE: 61
gctcagctat gacatattcc                                              20

<210> SEQ ID NO 62
<211> LENGTH: 17
<212> TYPE: DNA
<213> ORGANISM: Bacillus subtilis

<400> SEQUENCE: 62
```

```
gatcgtcttg attaccg                                                  17

<210> SEQ ID NO 63
<211> LENGTH: 16
<212> TYPE: DNA
<213> ORGANISM: Bacillus subtilis

<400> SEQUENCE: 63
agctttatcg gtgacg                                                   16

<210> SEQ ID NO 64
<211> LENGTH: 16
<212> TYPE: DNA
<213> ORGANISM: Bacillus subtilis

<400> SEQUENCE: 64
tgagcacgat tgcagg                                                   16

<210> SEQ ID NO 65
<211> LENGTH: 17
<212> TYPE: DNA
<213> ORGANISM: Bacillus subtilis

<400> SEQUENCE: 65
cattgcggag acattgc                                                  17

<210> SEQ ID NO 66
<211> LENGTH: 26
<212> TYPE: DNA
<213> ORGANISM: Bacillus subtilis

<400> SEQUENCE: 66
tagacaattg gaagagaaaa gagata                                        26

<210> SEQ ID NO 67
<211> LENGTH: 20
<212> TYPE: DNA
<213> ORGANISM: Bacillus subtilis

<400> SEQUENCE: 67
ccgtcgctat tgtaaccagt                                               20

<210> SEQ ID NO 68
<211> LENGTH: 29
<212> TYPE: DNA
<213> ORGANISM: Bacillus subtilis

<400> SEQUENCE: 68
ggaattccaa agctgcagcg gccggcgcg                                     29

<210> SEQ ID NO 69
<211> LENGTH: 32
<212> TYPE: DNA
<213> ORGANISM: Bacillus subtilis

<400> SEQUENCE: 69
gaagatctcg tatacttggc ttctgcagct gc                                 32

<210> SEQ ID NO 70
<211> LENGTH: 31
<212> TYPE: DNA
<213> ORGANISM: Bacillus subtilis
```

-continued

```
<400> SEQUENCE: 70
gaagatctgg tcaacaagct ggaaagcact c                            31

<210> SEQ ID NO 71
<211> LENGTH: 33
<212> TYPE: DNA
<213> ORGANISM: Bacillus subtilis

<400> SEQUENCE: 71
cccaagcttc gtgacgtaca gcaccgttcc ggc                          33

<210> SEQ ID NO 72
<211> LENGTH: 50
<212> TYPE: DNA
<213> ORGANISM: Bacillus subtilis

<400> SEQUENCE: 72
ccttaagggc cgaatattta tacggagctc cctgaaacaa caaaaacggc        50

<210> SEQ ID NO 73
<211> LENGTH: 34
<212> TYPE: DNA
<213> ORGANISM: Bacillus subtilis

<400> SEQUENCE: 73
ggtgttctct agagcggccg cggttgcggt cagc                         34

<210> SEQ ID NO 74
<211> LENGTH: 27
<212> TYPE: DNA
<213> ORGANISM: Bacillus subtilis

<400> SEQUENCE: 74
gtccttcttg gtacctggaa gcagagc                                 27

<210> SEQ ID NO 75
<211> LENGTH: 39
<212> TYPE: DNA
<213> ORGANISM: Bacillus subtilis

<400> SEQUENCE: 75
gtataaatat tcggccctta aggccagtac cattttccc                    39

<210> SEQ ID NO 76
<211> LENGTH: 13
<212> TYPE: DNA
<213> ORGANISM: Bacillus subtilis

<400> SEQUENCE: 76
gggccggatc cgc                                                13

<210> SEQ ID NO 77
<211> LENGTH: 20
<212> TYPE: DNA
<213> ORGANISM: Bacillus subtilis

<400> SEQUENCE: 77
attcccggcc taggcgccgg                                         20

<210> SEQ ID NO 78
<211> LENGTH: 19
<212> TYPE: DNA
<213> ORGANISM: Bacillus subtilis
```

```
<400> SEQUENCE: 78
ggaaattatc gtgatcaac                                                  19

<210> SEQ ID NO 79
<211> LENGTH: 21
<212> TYPE: DNA
<213> ORGANISM: Bacillus subtilis

<400> SEQUENCE: 79
gcacgagcac tgataaatat g                                               21

<210> SEQ ID NO 80
<211> LENGTH: 21
<212> TYPE: DNA
<213> ORGANISM: Bacillus subtilis

<400> SEQUENCE: 80
catatttatc agtgctcgtg c                                               21

<210> SEQ ID NO 81
<211> LENGTH: 17
<212> TYPE: DNA
<213> ORGANISM: Bacillus subtilis

<400> SEQUENCE: 81
tcgtagacct catatgc                                                    17

<210> SEQ ID NO 82
<211> LENGTH: 17
<212> TYPE: DNA
<213> ORGANISM: Bacillus subtilis

<400> SEQUENCE: 82
gtcgttaaac cgtgtgc                                                    17

<210> SEQ ID NO 83
<211> LENGTH: 39
<212> TYPE: DNA
<213> ORGANISM: Bacillus subtilis

<400> SEQUENCE: 83
ctagaggatc cccgggtacc gtgctctgcc ttttagtcc                            39

<210> SEQ ID NO 84
<211> LENGTH: 37
<212> TYPE: DNA
<213> ORGANISM: Bacillus subtilis

<400> SEQUENCE: 84
gtacatcgaa ttcgtgctca ttattaatct gttcagc                              37

<210> SEQ ID NO 85
<211> LENGTH: 20
<212> TYPE: DNA
<213> ORGANISM: Bacillus subtilis

<400> SEQUENCE: 85
aactattgcc gatgataagc                                                 20

<210> SEQ ID NO 86
<211> LENGTH: 1260
<212> TYPE: DNA
```

```
<213> ORGANISM: Bacillus subtilis
<220> FEATURE:
<221> NAME/KEY: CDS
<222> LOCATION: (1)..(1260)
<223> OTHER INFORMATION:

<400> SEQUENCE: 86 atg aaa aaa gtg atg tta gct acg gct ttg ttt tta gga ttg act cca      48
Met Lys Lys Val Met Leu Ala Thr Ala Leu Phe Leu Gly Leu Thr Pro
1               5                   10                  15 gct ggc gcg aac gca gct gat tta ggc cac cag acg ttg gga tcc aat      96
Ala Gly Ala Asn Ala Ala Asp Leu Gly His Gln Thr Leu Gly Ser Asn
            20                  25                  30 gat ggc tgg ggc gcg tac tcg acc ggc acg aca ggc gga tca aaa gca     144
Asp Gly Trp Gly Ala Tyr Ser Thr Gly Thr Thr Gly Gly Ser Lys Ala
        35                  40                  45 tcc tcc tca aat gtg tat acc gtc agc aac aga aac cag ctt gtc tcg     192
Ser Ser Ser Asn Val Tyr Thr Val Ser Asn Arg Asn Gln Leu Val Ser
    50                  55                  60 gca tta ggg aag gaa acg aac aca acg cca aaa atc att tat atc aag     240
Ala Leu Gly Lys Glu Thr Asn Thr Thr Pro Lys Ile Ile Tyr Ile Lys
65                  70                  75                  80 gga acg att gac atg aac gtg gat gac aat ctg aag ccg ctt ggc cta     288
Gly Thr Ile Asp Met Asn Val Asp Asp Asn Leu Lys Pro Leu Gly Leu
                85                  90                  95 aat gac tat aaa gat ccg gag tat gat ttg gac aaa tat ttg aaa gcc     336
Asn Asp Tyr Lys Asp Pro Glu Tyr Asp Leu Asp Lys Tyr Leu Lys Ala
            100                 105                 110 tat gat cct agc aca tgg ggc aaa aaa gag ccg tcg gga aca caa gaa     384
Tyr Asp Pro Ser Thr Trp Gly Lys Lys Glu Pro Ser Gly Thr Gln Glu
        115                 120                 125 gaa gcg aga gca cgc tct cag aaa aac caa aaa gca cgg gtc atg gtg     432
Glu Ala Arg Ala Arg Ser Gln Lys Asn Gln Lys Ala Arg Val Met Val
    130                 135                 140 gat atc cct gca aac acg acg atc gtc ggt tca ggg act aac gct aaa     480
Asp Ile Pro Ala Asn Thr Thr Ile Val Gly Ser Gly Thr Asn Ala Lys
145                 150                 155                 160 gtc gtg gga gga aac ttc caa atc aag agt gat aac gtc att att cgc     528
Val Val Gly Gly Asn Phe Gln Ile Lys Ser Asp Asn Val Ile Ile Arg
                165                 170                 175 aac att gaa ttc cag gat gcc tat gac tat ttt ccg caa tgg gat ccg     576
Asn Ile Glu Phe Gln Asp Ala Tyr Asp Tyr Phe Pro Gln Trp Asp Pro
            180                 185                 190 act gac gga agc tca ggg aac tgg aac tca caa tac gac aac atc acg     624
Thr Asp Gly Ser Ser Gly Asn Trp Asn Ser Gln Tyr Asp Asn Ile Thr
        195                 200                 205 ata aac ggc ggc aca cac atc tgg att gat cac tgt aca ttt aat gac     672
Ile Asn Gly Gly Thr His Ile Trp Ile Asp His Cys Thr Phe Asn Asp
    210                 215                 220 ggt tcg cgt ccg gac agc aca tca ccg aaa tat tat gga aga aaa tat     720
Gly Ser Arg Pro Asp Ser Thr Ser Pro Lys Tyr Tyr Gly Arg Lys Tyr
225                 230                 235                 240 cag cac cat gac ggc caa acg gat gct tcc aac ggt gct aac tat atc     768
Gln His His Asp Gly Gln Thr Asp Ala Ser Asn Gly Ala Asn Tyr Ile
                245                 250                 255 acg atg tcc tac aac tat tat cac gat cat gat aaa agc tcc att ttc     816
Thr Met Ser Tyr Asn Tyr Tyr His Asp His Asp Lys Ser Ser Ile Phe
            260                 265                 270 gga tca agt gac agc aaa acc tcc gat gac ggc aaa tta aaa att acg     864
Gly Ser Ser Asp Ser Lys Thr Ser Asp Asp Gly Lys Leu Lys Ile Thr
        275                 280                 285
```

```
ctg cat cat aac cgc tat aaa aat att gtc cag cgc gcg ccg aga gtc    912
Leu His His Asn Arg Tyr Lys Asn Ile Val Gln Arg Ala Pro Arg Val
    290             295                 300 cgc ttc ggg caa gtg cac gta tac aac aac tat tat gaa gga agc aca    960
Arg Phe Gly Gln Val His Val Tyr Asn Asn Tyr Tyr Glu Gly Ser Thr
305             310                 315                 320 agc tct tca agt tat cct ttt agc tat gca tgg gga atc gga aag tca   1008
Ser Ser Ser Ser Tyr Pro Phe Ser Tyr Ala Trp Gly Ile Gly Lys Ser
                325                 330                 335 tct aaa atc tat gcc caa aac aat gtc att gac gta ccg gga ctg tca   1056
Ser Lys Ile Tyr Ala Gln Asn Asn Val Ile Asp Val Pro Gly Leu Ser
            340                 345                 350 gct gct aaa acg atc agc gta ttc agc ggg gga acg gct tta tat gac   1104
Ala Ala Lys Thr Ile Ser Val Phe Ser Gly Gly Thr Ala Leu Tyr Asp
        355                 360                 365 tcc ggc acg ttg ctg aac ggc aca cag atc aac gca tcg gct gca aac   1152
Ser Gly Thr Leu Leu Asn Gly Thr Gln Ile Asn Ala Ser Ala Ala Asn
370                 375                 380 ggg ctg agc tct tct gtc ggc tgg acg ccg tct ctg cat gga tcg att   1200
Gly Leu Ser Ser Ser Val Gly Trp Thr Pro Ser Leu His Gly Ser Ile
385                 390                 395                 400 gat gct tct gct aat gtg aaa tca aat gtt ata aat caa gcg ggt gcg   1248
Asp Ala Ser Ala Asn Val Lys Ser Asn Val Ile Asn Gln Ala Gly Ala
                405                 410                 415 ggt aaa tta aat                                                    1260
Gly Lys Leu Asn
            420

<210> SEQ ID NO 87
<211> LENGTH: 420
<212> TYPE: PRT
<213> ORGANISM: Bacillus subtilis

<400> SEQUENCE: 87

Met Lys Lys Val Met Leu Ala Thr Ala Leu Phe Leu Gly Leu Thr Pro
1               5                   10                  15

Ala Gly Ala Asn Ala Ala Asp Leu Gly His Gln Thr Leu Gly Ser Asn
            20                  25                  30

Asp Gly Trp Gly Ala Tyr Ser Thr Gly Thr Thr Gly Gly Ser Lys Ala
        35                  40                  45

Ser Ser Ser Asn Val Tyr Thr Val Ser Asn Arg Asn Gln Leu Val Ser
    50                  55                  60

Ala Leu Gly Lys Glu Thr Asn Thr Thr Pro Lys Ile Ile Tyr Ile Lys
65                  70                  75                  80

Gly Thr Ile Asp Met Asn Val Asp Asp Asn Leu Lys Pro Leu Gly Leu
                85                  90                  95

Asn Asp Tyr Lys Asp Pro Glu Tyr Asp Leu Asp Lys Tyr Leu Lys Ala
            100                 105                 110

Tyr Asp Pro Ser Thr Trp Gly Lys Lys Glu Pro Ser Gly Thr Gln Glu
        115                 120                 125

Glu Ala Arg Ala Arg Ser Gln Lys Asn Gln Lys Ala Arg Val Met Val
    130                 135                 140

Asp Ile Pro Ala Asn Thr Thr Ile Val Gly Ser Gly Thr Asn Ala Lys
145                 150                 155                 160

Val Val Gly Gly Asn Phe Gln Ile Lys Ser Asp Asn Val Ile Ile Arg
                165                 170                 175

Asn Ile Glu Phe Gln Asp Ala Tyr Asp Tyr Phe Pro Gln Trp Asp Pro
```

```
                180             185             190
Thr Asp Gly Ser Ser Gly Asn Trp Asn Ser Gln Tyr Asp Asn Ile Thr
            195                 200                 205
Ile Asn Gly Gly Thr His Ile Trp Ile Asp His Cys Thr Phe Asn Asp
        210                 215                 220
Gly Ser Arg Pro Asp Ser Thr Ser Pro Lys Tyr Tyr Gly Arg Lys Tyr
225                 230                 235                 240
Gln His His Asp Gly Gln Thr Asp Ala Ser Asn Gly Ala Asn Tyr Ile
                245                 250                 255
Thr Met Ser Tyr Asn Tyr Tyr His Asp His Lys Ser Ser Ile Phe
            260                 265                 270
Gly Ser Ser Asp Ser Lys Thr Ser Asp Asp Gly Lys Leu Lys Ile Thr
        275                 280                 285
Leu His His Asn Arg Tyr Lys Asn Ile Val Gln Arg Ala Pro Arg Val
        290                 295                 300
Arg Phe Gly Gln Val His Val Tyr Asn Asn Tyr Tyr Glu Gly Ser Thr
305                 310                 315                 320
Ser Ser Ser Ser Tyr Pro Phe Ser Tyr Ala Trp Gly Ile Gly Lys Ser
                325                 330                 335
Ser Lys Ile Tyr Ala Gln Asn Asn Val Ile Asp Val Pro Gly Leu Ser
            340                 345                 350
Ala Ala Lys Thr Ile Ser Val Phe Ser Gly Gly Thr Ala Leu Tyr Asp
        355                 360                 365
Ser Gly Thr Leu Leu Asn Gly Thr Gln Ile Asn Ala Ser Ala Ala Asn
370                 375                 380
Gly Leu Ser Ser Val Gly Trp Thr Pro Ser Leu His Gly Ser Ile
385                 390                 395                 400
Asp Ala Ser Ala Asn Val Lys Ser Asn Val Ile Asn Gln Ala Gly Ala
                405                 410                 415
Gly Lys Leu Asn
        420

<210> SEQ ID NO 88
<211> LENGTH: 26
<212> TYPE: DNA
<213> ORGANISM: Bacillus subtilis

<400> SEQUENCE: 88
actagtaatg atggctgggg cgcgta                                        26

<210> SEQ ID NO 89
<211> LENGTH: 26
<212> TYPE: DNA
<213> ORGANISM: Bacillus subtilis

<400> SEQUENCE: 89
gtcgacatgt tgtcgtattg tgagtt                                        26

<210> SEQ ID NO 90
<211> LENGTH: 52
<212> TYPE: DNA
<213> ORGANISM: Bacillus subtilis

<400> SEQUENCE: 90
gagctctaca acgcttatgg atccgcggcc gcggcggcac acacatctgg at            52

<210> SEQ ID NO 91
```

```
<211> LENGTH: 26
<212> TYPE: DNA
<213> ORGANISM: Bacillus subtilis

<400> SEQUENCE: 91
gacgtcagcc cgtttgcagc cgatgc                                            26

<210> SEQ ID NO 92
<211> LENGTH: 1257
<212> TYPE: DNA
<213> ORGANISM: Streptococcus pyogenes
<220> FEATURE:
<221> NAME/KEY: CDS
<222> LOCATION: (1)..(1257)
<223> OTHER INFORMATION:

<400> SEQUENCE: 92 gtg cct att ttt aaa aaa act tta att gtt tta tcc ttt att ttt ttg        48
Val Pro Ile Phe Lys Lys Thr Leu Ile Val Leu Ser Phe Ile Phe Leu
1               5                   10                  15 ata tct atc ttg att tat cta aat atg tat cta ttt gga aca tca act        96
Ile Ser Ile Leu Ile Tyr Leu Asn Met Tyr Leu Phe Gly Thr Ser Thr
            20                  25                  30 gta gga att tat gga gta ata tta ata acc tat cta gtt att aaa ctt       144
Val Gly Ile Tyr Gly Val Ile Leu Ile Thr Tyr Leu Val Ile Lys Leu
        35                  40                  45 gga tta tct ttc ctt tat gag cca ttt aaa gga aag cca cat gac tat       192
Gly Leu Ser Phe Leu Tyr Glu Pro Phe Lys Gly Lys Pro His Asp Tyr
    50                  55                  60 aaa gtt gct gct gta att cct tct tat aat gaa gat gcc gag tca tta       240
Lys Val Ala Ala Val Ile Pro Ser Tyr Asn Glu Asp Ala Glu Ser Leu
65                  70                  75                  80 tta gaa act ctt aaa agt gtg tta gca cag acc tat ccg tta tca gaa       288
Leu Glu Thr Leu Lys Ser Val Leu Ala Gln Thr Tyr Pro Leu Ser Glu
                85                  90                  95 att tat att gtt gat gat ggg agt tca aac aca gat gca ata caa tta       336
Ile Tyr Ile Val Asp Asp Gly Ser Ser Asn Thr Asp Ala Ile Gln Leu
            100                 105                 110 att gaa gag tat gta aat aga gaa gtg gat att tgt cga aac gtt atc       384
Ile Glu Glu Tyr Val Asn Arg Glu Val Asp Ile Cys Arg Asn Val Ile
        115                 120                 125 gtt cac cgt tcc ctt gtc aat aaa gga aaa cgc cat gct caa gcg tgg       432
Val His Arg Ser Leu Val Asn Lys Gly Lys Arg His Ala Gln Ala Trp
    130                 135                 140 gca ttt gaa aga tct gac gct gac gtt ttt tta acc gta gat tca gat       480
Ala Phe Glu Arg Ser Asp Ala Asp Val Phe Leu Thr Val Asp Ser Asp
145                 150                 155                 160 act tat atc tat cca aat gcc tta gaa gaa ctc cta aaa agc ttc aat       528
Thr Tyr Ile Tyr Pro Asn Ala Leu Glu Glu Leu Leu Lys Ser Phe Asn
                165                 170                 175 gat gag aca gtt tat gct gca aca gga cat ttg aat gct aga aac aga       576
Asp Glu Thr Val Tyr Ala Ala Thr Gly His Leu Asn Ala Arg Asn Arg
            180                 185                 190 caa act aat cta tta acg cga ctt aca gat atc cgt tac gat aat gcc       624
Gln Thr Asn Leu Leu Thr Arg Leu Thr Asp Ile Arg Tyr Asp Asn Ala
        195                 200                 205 ttt ggg gtg gag cgt gct gct caa tca tta aca ggt aat att tta gtt       672
Phe Gly Val Glu Arg Ala Ala Gln Ser Leu Thr Gly Asn Ile Leu Val
    210                 215                 220 tgc tca gga cca ttg agt att tat cga cgt gaa gtg att att cct aac       720
Cys Ser Gly Pro Leu Ser Ile Tyr Arg Arg Glu Val Ile Ile Pro Asn
225                 230                 235                 240
```

```
tta gag cgc tat aaa aat caa aca ttc cta ggt tta cct gtt agc att      768
Leu Glu Arg Tyr Lys Asn Gln Thr Phe Leu Gly Leu Pro Val Ser Ile
            245                 250                 255 ggg gat gat cga tgt tta aca aat tat gct att gat tta gga cgc act      816
Gly Asp Asp Arg Cys Leu Thr Asn Tyr Ala Ile Asp Leu Gly Arg Thr
        260                 265                 270 gtc tac caa tca aca gct aga tgt gat act gat gta cct ttc caa tta      864
Val Tyr Gln Ser Thr Ala Arg Cys Asp Thr Asp Val Pro Phe Gln Leu
    275                 280                 285 aaa agt tat tta aag caa caa aat cga tgg aat aaa tct ttt ttt aaa      912
Lys Ser Tyr Leu Lys Gln Gln Asn Arg Trp Asn Lys Ser Phe Phe Lys
290                 295                 300 gaa tct att att tct gtt aaa aaa att ctt tct aat ccc atc gtt gcc      960
Glu Ser Ile Ile Ser Val Lys Lys Ile Leu Ser Asn Pro Ile Val Ala
305                 310                 315                 320 tta tgg act att ttc gaa gtc gtt atg ttt atg atg ttg att gtc gca     1008
Leu Trp Thr Ile Phe Glu Val Val Met Phe Met Met Leu Ile Val Ala
                325                 330                 335 att ggg aat ctt ttg ttt aat caa gct att caa tta gac ctt att aaa     1056
Ile Gly Asn Leu Leu Phe Asn Gln Ala Ile Gln Leu Asp Leu Ile Lys
            340                 345                 350 ctt ttt gcc ttt tta tcc atc atc ttt atc gtt gct tta tgt cgt aat     1104
Leu Phe Ala Phe Leu Ser Ile Ile Phe Ile Val Ala Leu Cys Arg Asn
        355                 360                 365 gtt cat tat atg atc aaa cat cct gct agt ttt ttg tta tct cct ctg     1152
Val His Tyr Met Ile Lys His Pro Ala Ser Phe Leu Leu Ser Pro Leu
    370                 375                 380 tat gga ata tta cac ttg ttt gtc tta cag ccc cta aaa ctt tat tct     1200
Tyr Gly Ile Leu His Leu Phe Val Leu Gln Pro Leu Lys Leu Tyr Ser
385                 390                 395                 400 tta tgc acc att aaa aat acg gaa tgg gga aca cgt aaa aag gtc act     1248
Leu Cys Thr Ile Lys Asn Thr Glu Trp Gly Thr Arg Lys Lys Val Thr
                405                 410                 415 att ttt aaa                                                         1257
Ile Phe Lys <210> SEQ ID NO 93
<211> LENGTH: 419
<212> TYPE: PRT
<213> ORGANISM: Streptococcus pyogenes

<400> SEQUENCE: 93

Val Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Lys Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125
```

```
Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Lys
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Ile Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 94
<211> LENGTH: 2916
<212> TYPE: DNA
<213> ORGANISM: Pasteurella multocida
<220> FEATURE:
<221> NAME/KEY: CDS
<222> LOCATION: (1)..(2916)
<223> OTHER INFORMATION:

<400> SEQUENCE: 94 atg aat aca tta tca caa gca ata aaa gca tat aac agc aat gac tat       48
Met Asn Thr Leu Ser Gln Ala Ile Lys Ala Tyr Asn Ser Asn Asp Tyr
1               5                   10                  15 caa tta gca ctc aaa tta ttt gaa aag tcg gcg gaa atc tat gga cgg       96
Gln Leu Ala Leu Lys Leu Phe Glu Lys Ser Ala Glu Ile Tyr Gly Arg
            20                  25                  30 aaa att gtt gaa ttt caa att acc aaa tgc caa gaa aaa ctc tca gca      144
Lys Ile Val Glu Phe Gln Ile Thr Lys Cys Gln Glu Lys Leu Ser Ala
```

```
                    35                  40                  45
cat cct tct gtt aat tca gca cat ctt tct gta aat aaa gaa gaa aaa       192
His Pro Ser Val Asn Ser Ala His Leu Ser Val Asn Lys Glu Glu Lys
    50                  55                  60 gtc aat gtt tgc gat agt ccg tta gat att gca aca caa ctg tta ctt       240
Val Asn Val Cys Asp Ser Pro Leu Asp Ile Ala Thr Gln Leu Leu Leu
65                  70                  75                  80 tcc aac gta aaa aaa tta gta ctt tct gac tcg gaa aaa aac acg tta       288
Ser Asn Val Lys Lys Leu Val Leu Ser Asp Ser Glu Lys Asn Thr Leu
                85                  90                  95 aaa aat aaa tgg aaa ttg ctc act gag aag aaa tct gaa aat gcg gag       336
Lys Asn Lys Trp Lys Leu Leu Thr Glu Lys Lys Ser Glu Asn Ala Glu
            100                 105                 110 gta aga gcg gtc gcc ctt gta cca aaa gat ttt ccc aaa gat ctg gtt       384
Val Arg Ala Val Ala Leu Val Pro Lys Asp Phe Pro Lys Asp Leu Val
        115                 120                 125 tta gcg cct tta cct gat cat gtt aat gat ttt aca tgg tac aaa aag       432
Leu Ala Pro Leu Pro Asp His Val Asn Asp Phe Thr Trp Tyr Lys Lys
    130                 135                 140 cga aag aaa aga ctt ggc ata aaa cct gaa cat caa cat gtt ggt ctt       480
Arg Lys Lys Arg Leu Gly Ile Lys Pro Glu His Gln His Val Gly Leu
145                 150                 155                 160 tct att atc gtt aca aca ttc aat cga cca gca att tta tcg att aca       528
Ser Ile Ile Val Thr Thr Phe Asn Arg Pro Ala Ile Leu Ser Ile Thr
                165                 170                 175 tta gcc tgt tta gta aac caa aaa aca cat tac ccg ttt gaa gtt atc       576
Leu Ala Cys Leu Val Asn Gln Lys Thr His Tyr Pro Phe Glu Val Ile
            180                 185                 190 gtg aca gat gat ggt agt cag gaa gat cta tca ccg atc att cgc caa       624
Val Thr Asp Asp Gly Ser Gln Glu Asp Leu Ser Pro Ile Ile Arg Gln
        195                 200                 205 tat gaa aat aaa ttg gat att cgc tac gtc aga caa aaa gat aac ggt       672
Tyr Glu Asn Lys Leu Asp Ile Arg Tyr Val Arg Gln Lys Asp Asn Gly
    210                 215                 220 ttt caa gcc agt gcc gct cgg aat atg gga tta cgc tta gca aaa tat       720
Phe Gln Ala Ser Ala Ala Arg Asn Met Gly Leu Arg Leu Ala Lys Tyr
225                 230                 235                 240 gac ttt att ggc tta ctc gac tgt gat atg gcg cca aat cca tta tgg       768
Asp Phe Ile Gly Leu Leu Asp Cys Asp Met Ala Pro Asn Pro Leu Trp
                245                 250                 255 gtt cat tct tat gtt gca gag cta tta gaa gat gat gat tta aca atc       816
Val His Ser Tyr Val Ala Glu Leu Leu Glu Asp Asp Asp Leu Thr Ile
            260                 265                 270 att ggt cca aga aaa tac atc gat aca caa cat att gac cca aaa gac       864
Ile Gly Pro Arg Lys Tyr Ile Asp Thr Gln His Ile Asp Pro Lys Asp
        275                 280                 285 ttc tta aat aac gcg agt ttg ctt gaa tca tta cca gaa gtg aaa acc       912
Phe Leu Asn Asn Ala Ser Leu Leu Glu Ser Leu Pro Glu Val Lys Thr
    290                 295                 300 aat aat agt gtt gcc gca aaa ggg gaa gga aca gtt tct ctg gat tgg       960
Asn Asn Ser Val Ala Ala Lys Gly Glu Gly Thr Val Ser Leu Asp Trp
305                 310                 315                 320 cgc tta gaa caa ttc gaa aaa aca gaa aat ctc cgc tta tcc gat tcg      1008
Arg Leu Glu Gln Phe Glu Lys Thr Glu Asn Leu Arg Leu Ser Asp Ser
                325                 330                 335 cct ttc cgt ttt ttt gcg gcg ggt aat gtt gct ttc gct aaa aaa tgg      1056
Pro Phe Arg Phe Phe Ala Ala Gly Asn Val Ala Phe Ala Lys Lys Trp
            340                 345                 350 cta aat aaa tcc ggt ttc ttt gat gag gaa ttt aat cac tgg ggt gga      1104
```

```
Leu Asn Lys Ser Gly Phe Phe Asp Glu Glu Phe Asn His Trp Gly Gly
        355                 360                 365 gaa gat gtg gaa ttt gga tat cgc tta ttc cgt tac ggt agt ttc ttt         1152
Glu Asp Val Glu Phe Gly Tyr Arg Leu Phe Arg Tyr Gly Ser Phe Phe
370                 375                 380 aaa act att gat ggc att atg gcc tac cat caa gag cca cca ggt aaa         1200
Lys Thr Ile Asp Gly Ile Met Ala Tyr His Gln Glu Pro Pro Gly Lys
385                 390                 395                 400 gaa aat gaa acc gat cgt gaa gcg gga aaa aat att acg ctc gat att         1248
Glu Asn Glu Thr Asp Arg Glu Ala Gly Lys Asn Ile Thr Leu Asp Ile
                405                 410                 415 atg aga gaa aag gtc cct tat atc tat aga aaa ctt tta cca ata gaa         1296
Met Arg Glu Lys Val Pro Tyr Ile Tyr Arg Lys Leu Leu Pro Ile Glu
            420                 425                 430 gat tcg cat atc aat aga gta cct tta gtt tca att tat atc cca gct         1344
Asp Ser His Ile Asn Arg Val Pro Leu Val Ser Ile Tyr Ile Pro Ala
        435                 440                 445 tat aac tgt gca aac tat att caa cgt tgc gta gat agt gca ctg aat         1392
Tyr Asn Cys Ala Asn Tyr Ile Gln Arg Cys Val Asp Ser Ala Leu Asn
    450                 455                 460 cag act gtt gtt gat ctc gag gtt tgt att tgt aac gat ggt tca aca         1440
Gln Thr Val Val Asp Leu Glu Val Cys Ile Cys Asn Asp Gly Ser Thr
465                 470                 475                 480 gat aat acc tta gaa gtg atc aat aag ctt tat ggt aat aat cct agg         1488
Asp Asn Thr Leu Glu Val Ile Asn Lys Leu Tyr Gly Asn Asn Pro Arg
                485                 490                 495 gta cgc atc atg tct aaa cca aat ggc gga ata gcc tca gca tca aat         1536
Val Arg Ile Met Ser Lys Pro Asn Gly Gly Ile Ala Ser Ala Ser Asn
            500                 505                 510 gca gcc gtt tct ttt gct aaa ggt tat tac att ggg cag tta gat tca         1584
Ala Ala Val Ser Phe Ala Lys Gly Tyr Tyr Ile Gly Gln Leu Asp Ser
        515                 520                 525 gat gat tat ctt gag cct gat gca gtt gaa ctg tgt tta aaa gaa ttt         1632
Asp Asp Tyr Leu Glu Pro Asp Ala Val Glu Leu Cys Leu Lys Glu Phe
    530                 535                 540 tta aaa gat aaa acg cta gct tgt gtt tat acc act aat aga aac gtc         1680
Leu Lys Asp Lys Thr Leu Ala Cys Val Tyr Thr Thr Asn Arg Asn Val
545                 550                 555                 560 aat ccg gat ggt agc tta atc gct aat ggt tac aat tgg cca gaa ttt         1728
Asn Pro Asp Gly Ser Leu Ile Ala Asn Gly Tyr Asn Trp Pro Glu Phe
                565                 570                 575 tca cga gaa aaa ctc aca acg gct atg att gct cac cac ttt aga atg         1776
Ser Arg Glu Lys Leu Thr Thr Ala Met Ile Ala His His Phe Arg Met
            580                 585                 590 ttc acg att aga gct tgg cat tta act gat gga ttc aat gaa aaa att         1824
Phe Thr Ile Arg Ala Trp His Leu Thr Asp Gly Phe Asn Glu Lys Ile
        595                 600                 605 gaa aat gcc gta gac tat gac atg ttc ctc aaa ctc agt gaa gtt gga         1872
Glu Asn Ala Val Asp Tyr Asp Met Phe Leu Lys Leu Ser Glu Val Gly
    610                 615                 620 aaa ttt aaa cat ctt aat aaa atc tgc tat aac cgt gta tta cat ggt         1920
Lys Phe Lys His Leu Asn Lys Ile Cys Tyr Asn Arg Val Leu His Gly
625                 630                 635                 640 gat aac aca tca att aag aaa ctt ggc att caa aag aaa aac cat ttt         1968
Asp Asn Thr Ser Ile Lys Lys Leu Gly Ile Gln Lys Lys Asn His Phe
                645                 650                 655 gtt gta gtc aat cag tca tta aat aga caa ggc ata act tat tat aat         2016
Val Val Val Asn Gln Ser Leu Asn Arg Gln Gly Ile Thr Tyr Tyr Asn
            660                 665                 670
```

```
tat gac gaa ttt gat gat tta gat gaa agt aga aag tat att ttc aat    2064
Tyr Asp Glu Phe Asp Asp Leu Asp Glu Ser Arg Lys Tyr Ile Phe Asn
            675                 680                 685 aaa acc gct gaa tat caa gaa gag att gat atc tta aaa gat att aaa    2112
Lys Thr Ala Glu Tyr Gln Glu Glu Ile Asp Ile Leu Lys Asp Ile Lys
        690                 695                 700 atc atc cag aat aaa gat gcc aaa atc gca gtc agt att ttt tat ccc    2160
Ile Ile Gln Asn Lys Asp Ala Lys Ile Ala Val Ser Ile Phe Tyr Pro
705                 710                 715                 720 aat aca tta aac ggc tta gtg aaa aaa cta aac aat att att gaa tat    2208
Asn Thr Leu Asn Gly Leu Val Lys Lys Leu Asn Asn Ile Ile Glu Tyr
                725                 730                 735 aat aaa aat ata ttc gtt att gtt cta cat gtt gat aag aat cat ctt    2256
Asn Lys Asn Ile Phe Val Ile Val Leu His Val Asp Lys Asn His Leu
            740                 745                 750 aca cca gat atc aaa aaa gaa ata cta gcc ttc tat cat aaa cat caa    2304
Thr Pro Asp Ile Lys Lys Glu Ile Leu Ala Phe Tyr His Lys His Gln
        755                 760                 765 gtg aat att tta cta aat aat gat atc tca tat tac acg agt aat aga    2352
Val Asn Ile Leu Leu Asn Asn Asp Ile Ser Tyr Tyr Thr Ser Asn Arg
    770                 775                 780 tta ata aaa act gag gcg cat tta agt aat att aat aaa tta agt cag    2400
Leu Ile Lys Thr Glu Ala His Leu Ser Asn Ile Asn Lys Leu Ser Gln
785                 790                 795                 800 tta aat cta aat tgt gaa tac atc att ttt gat aat cat gac agc cta    2448
Leu Asn Leu Asn Cys Glu Tyr Ile Ile Phe Asp Asn His Asp Ser Leu
                805                 810                 815 ttc gtt aaa aat gac agc tat gct tat atg aaa aaa tat gat gtc ggc    2496
Phe Val Lys Asn Asp Ser Tyr Ala Tyr Met Lys Lys Tyr Asp Val Gly
            820                 825                 830 atg aat ttc tca gca tta aca cat gat tgg atc gag aaa atc aat gcg    2544
Met Asn Phe Ser Ala Leu Thr His Asp Trp Ile Glu Lys Ile Asn Ala
        835                 840                 845 cat cca cca ttt aaa aag ctc att aaa act tat ttt aat gac aat gac    2592
His Pro Pro Phe Lys Lys Leu Ile Lys Thr Tyr Phe Asn Asp Asn Asp
    850                 855                 860 tta aaa agt atg aat gtg aaa ggg gca tca caa ggt atg ttt atg acg    2640
Leu Lys Ser Met Asn Val Lys Gly Ala Ser Gln Gly Met Phe Met Thr
865                 870                 875                 880 tat gcg cta gcg cat gag ctt ctg acg att att aaa gaa gtc atc aca    2688
Tyr Ala Leu Ala His Glu Leu Leu Thr Ile Ile Lys Glu Val Ile Thr
                885                 890                 895 tct tgc cag tca att gat agt gtg cca gaa tat aac act gag gat att    2736
Ser Cys Gln Ser Ile Asp Ser Val Pro Glu Tyr Asn Thr Glu Asp Ile
            900                 905                 910 tgg ttc caa ttt gca ctt tta atc tta gaa aag aaa acc ggc cat gta    2784
Trp Phe Gln Phe Ala Leu Leu Ile Leu Glu Lys Lys Thr Gly His Val
        915                 920                 925 ttt aat aaa aca tcg acc ctg act tat atg cct tgg gaa cga aaa tta    2832
Phe Asn Lys Thr Ser Thr Leu Thr Tyr Met Pro Trp Glu Arg Lys Leu
    930                 935                 940 caa tgg aca aat gaa caa att gaa agt gca aaa aga gga gaa aat ata    2880
Gln Trp Thr Asn Glu Gln Ile Glu Ser Ala Lys Arg Gly Glu Asn Ile
945                 950                 955                 960 cct gtt aac aag ttc att att aat agt ata act cta                    2916
Pro Val Asn Lys Phe Ile Ile Asn Ser Ile Thr Leu
                965                 970

<210> SEQ ID NO 95
<211> LENGTH: 972
```

-continued

```
<212> TYPE: PRT
<213> ORGANISM: Pasteurella multocida

<400> SEQUENCE: 95

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Gln Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400
```

-continued

```
Glu Asn Glu Thr Asp Arg Glu Ala Gly Lys Asn Ile Thr Leu Asp Ile
            405                 410                 415
Met Arg Glu Lys Val Pro Tyr Ile Tyr Arg Lys Leu Leu Pro Ile Glu
            420                 425                 430
Asp Ser His Ile Asn Arg Val Pro Leu Val Ser Ile Tyr Ile Pro Ala
            435                 440                 445
Tyr Asn Cys Ala Asn Tyr Ile Gln Arg Cys Val Asp Ser Ala Leu Asn
        450                 455                 460
Gln Thr Val Val Asp Leu Glu Val Cys Ile Cys Asn Asp Gly Ser Thr
465                 470                 475                 480
Asp Asn Thr Leu Glu Val Ile Asn Lys Leu Tyr Gly Asn Asn Pro Arg
            485                 490                 495
Val Arg Ile Met Ser Lys Pro Asn Gly Ile Ala Ser Ala Ser Asn
            500                 505                 510
Ala Ala Val Ser Phe Ala Lys Gly Tyr Tyr Ile Gly Gln Leu Asp Ser
            515                 520                 525
Asp Asp Tyr Leu Glu Pro Asp Ala Val Glu Leu Cys Leu Lys Glu Phe
        530                 535                 540
Leu Lys Asp Lys Thr Leu Ala Cys Val Tyr Thr Thr Asn Arg Asn Val
545                 550                 555                 560
Asn Pro Asp Gly Ser Leu Ile Ala Asn Gly Tyr Asn Trp Pro Glu Phe
            565                 570                 575
Ser Arg Glu Lys Leu Thr Thr Ala Met Ile Ala His His Phe Arg Met
            580                 585                 590
Phe Thr Ile Arg Ala Trp His Leu Thr Asp Gly Phe Asn Glu Lys Ile
            595                 600                 605
Glu Asn Ala Val Asp Tyr Asp Met Phe Leu Lys Leu Ser Glu Val Gly
            610                 615                 620
Lys Phe Lys His Leu Asn Lys Ile Cys Tyr Asn Arg Val Leu His Gly
625                 630                 635                 640
Asp Asn Thr Ser Ile Lys Lys Leu Gly Ile Gln Lys Lys Asn His Phe
            645                 650                 655
Val Val Val Asn Gln Ser Leu Asn Arg Gln Gly Ile Thr Tyr Tyr Asn
            660                 665                 670
Tyr Asp Glu Phe Asp Asp Leu Asp Glu Ser Arg Lys Tyr Ile Phe Asn
        675                 680                 685
Lys Thr Ala Glu Tyr Gln Glu Glu Ile Asp Ile Leu Lys Asp Ile Lys
            690                 695                 700
Ile Ile Gln Asn Lys Asp Ala Lys Ile Ala Val Ser Ile Phe Tyr Pro
705                 710                 715                 720
Asn Thr Leu Asn Gly Leu Val Lys Lys Leu Asn Asn Ile Ile Glu Tyr
            725                 730                 735
Asn Lys Asn Ile Phe Val Ile Val Leu His Val Asp Lys Asn His Leu
            740                 745                 750
Thr Pro Asp Ile Lys Lys Glu Ile Leu Ala Phe Tyr His Lys His Gln
            755                 760                 765
Val Asn Ile Leu Leu Asn Asn Asp Ile Ser Tyr Tyr Thr Ser Asn Arg
            770                 775                 780
Leu Ile Lys Thr Glu Ala His Leu Ser Asn Ile Asn Lys Leu Ser Gln
785                 790                 795                 800
Leu Asn Leu Asn Cys Glu Tyr Ile Ile Phe Asp Asn His Asp Ser Leu
            805                 810                 815
```

```
Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
            835                 840                 845

His Pro Pro Phe Lys Lys Leu Ile Lys Thr Tyr Phe Asn Asp Asn Asp
            850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
            915                 920                 925

Phe Asn Lys Thr Ser Thr Leu Thr Tyr Met Pro Trp Glu Arg Lys Leu
            930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970

<210> SEQ ID NO 96
<211> LENGTH: 1206
<212> TYPE: DNA
<213> ORGANISM: Streptococcus pyogenes
<220> FEATURE:
<221> NAME/KEY: CDS
<222> LOCATION: (1)..(1206)
<223> OTHER INFORMATION:

<400> SEQUENCE: 96 atg aaa ata gca gtt gct gga tca gga tat gtt gga tta tca cta gga    48
Met Lys Ile Ala Val Ala Gly Ser Gly Tyr Val Gly Leu Ser Leu Gly
1               5                   10                  15 gtt ctt tta tca ctt caa aac gaa gtc act att gtt gat att ctt ccc    96
Val Leu Leu Ser Leu Gln Asn Glu Val Thr Ile Val Asp Ile Leu Pro
            20                  25                  30 tct aaa gtt gat aag att aat aat ggc tta tca cca att caa gat gaa   144
Ser Lys Val Asp Lys Ile Asn Asn Gly Leu Ser Pro Ile Gln Asp Glu
        35                  40                  45 tat att gaa tat tac tta aaa agt aag caa tta tct att aaa gca act   192
Tyr Ile Glu Tyr Tyr Leu Lys Ser Lys Gln Leu Ser Ile Lys Ala Thr
    50                  55                  60 tta gat agc aaa gca gct tat aaa gaa gcg gaa ctg gtc att att gcc   240
Leu Asp Ser Lys Ala Ala Tyr Lys Glu Ala Glu Leu Val Ile Ile Ala
65                  70                  75                  80 aca cct aca aat tac aac agt aga att aat tat ttt gat aca cag cat   288
Thr Pro Thr Asn Tyr Asn Ser Arg Ile Asn Tyr Phe Asp Thr Gln His
                85                  90                  95 gtt gaa aca gtt atc aaa gag gta cta agc gtt aat agc cat gca act   336
Val Glu Thr Val Ile Lys Glu Val Leu Ser Val Asn Ser His Ala Thr
            100                 105                 110 ctt atc atc aaa tca aca att cca ata ggt ttc att act gaa atg aga   384
Leu Ile Ile Lys Ser Thr Ile Pro Ile Gly Phe Ile Thr Glu Met Arg
        115                 120                 125 cag aaa ttc caa act gat cgt att atc ttc agc cct gaa ttt tta aga   432
Gln Lys Phe Gln Thr Asp Arg Ile Ile Phe Ser Pro Glu Phe Leu Arg
    130                 135                 140 gaa tct aaa gct tta tat gac aac tta tat cca agc cga att att gtt   480
Glu Ser Lys Ala Leu Tyr Asp Asn Leu Tyr Pro Ser Arg Ile Ile Val
```

| | | |
|---|---|---|
| Glu Ser Lys Ala Leu Tyr Asp Asn Leu Tyr Pro Ser Arg Ile Ile Val<br>145                    150                    155                    160 | | |
| tct tgt gaa gaa aac gat tct cca aaa gta aag gca gac gca gaa aaa<br>Ser Cys Glu Glu Asn Asp Ser Pro Lys Val Lys Ala Asp Ala Glu Lys<br>                    165                    170                    175 | 528 | |
| ttt gca ctt tta tta aag tct gca gct aaa aaa aat aat gta cca gta<br>Phe Ala Leu Leu Leu Lys Ser Ala Ala Lys Lys Asn Asn Val Pro Val<br>              180                    185                    190 | 576 | |
| ctt att atg gga gct tca gaa gct gaa gca gta aaa cta ttt gcc aat<br>Leu Ile Met Gly Ala Ser Glu Ala Glu Ala Val Lys Leu Phe Ala Asn<br>            195                    200                    205 | 624 | |
| act tat tta gcg tta agg gta gct tat ttt aat gag tta gac act tac<br>Thr Tyr Leu Ala Leu Arg Val Ala Tyr Phe Asn Glu Leu Asp Thr Tyr<br>210                    215                    220 | 672 | |
| gca gaa tcg aga aaa tta aat agt cac atg att att caa gga att tct<br>Ala Glu Ser Arg Lys Leu Asn Ser His Met Ile Ile Gln Gly Ile Ser<br>225                    230                    235                    240 | 720 | |
| tat gat gat cga ata gga atg cat tat aat aac cca tca ttt ggt tat<br>Tyr Asp Asp Arg Ile Gly Met His Tyr Asn Asn Pro Ser Phe Gly Tyr<br>                    245                    250                    255 | 768 | |
| gga ggt tat tgt cta cct aaa gat acg aag caa tta ttg gca aat tac<br>Gly Gly Tyr Cys Leu Pro Lys Asp Thr Lys Gln Leu Leu Ala Asn Tyr<br>            260                    265                    270 | 816 | |
| aat aat att cct caa acg cta att gaa gct atc gtt tca tca aat aat<br>Asn Asn Ile Pro Gln Thr Leu Ile Glu Ala Ile Val Ser Ser Asn Asn<br>            275                    280                    285 | 864 | |
| gtg cgc aag tcc tat att gct aag caa att atc aac gtc tta gaa gag<br>Val Arg Lys Ser Tyr Ile Ala Lys Gln Ile Ile Asn Val Leu Glu Glu<br>290                    295                    300 | 912 | |
| cgg gag tcc cca gta aaa gta gtc ggg gtt tac cgt tta att atg aaa<br>Arg Glu Ser Pro Val Lys Val Val Gly Val Tyr Arg Leu Ile Met Lys<br>305                    310                    315                    320 | 960 | |
| agt aac tca gat aat ttt aga gaa agt gct atc aaa gat gtt att gac<br>Ser Asn Ser Asp Asn Phe Arg Glu Ser Ala Ile Lys Asp Val Ile Asp<br>                    325                    330                    335 | 1008 | |
| att ctt aaa agt aaa gac att aag ata att att tat gag cca atg tta<br>Ile Leu Lys Ser Lys Asp Ile Lys Ile Ile Ile Tyr Glu Pro Met Leu<br>              340                    345                    350 | 1056 | |
| aac aaa ctt gaa tct gaa gat caa tct gta ctt gta aat gat tta gag<br>Asn Lys Leu Glu Ser Glu Asp Gln Ser Val Leu Val Asn Asp Leu Glu<br>            355                    360                    365 | 1104 | |
| aat ttc aag aaa caa gca aat att atc gta act aat cgc tat gat aat<br>Asn Phe Lys Lys Gln Ala Asn Ile Ile Val Thr Asn Arg Tyr Asp Asn<br>370                    375                    380 | 1152 | |
| gaa tta caa gat gtt aaa aat aaa gtt tac agt aga gat att ttt aat<br>Glu Leu Gln Asp Val Lys Asn Lys Val Tyr Ser Arg Asp Ile Phe Asn<br>385                    390                    395                    400 | 1200 | |
| aga gac<br>Arg Asp | 1206 | |

<210> SEQ ID NO 97
<211> LENGTH: 402
<212> TYPE: PRT
<213> ORGANISM: Streptococcus pyogenes

<400> SEQUENCE: 97

Met Lys Ile Ala Val Ala Gly Ser Gly Tyr Val Gly Leu Ser Leu Gly
1                 5                      10                    15

Val Leu Leu Ser Leu Gln Asn Glu Val Thr Ile Val Asp Ile Leu Pro
                 20                      25                    30

Ser Lys Val Asp Lys Ile Asn Asn Gly Leu Ser Pro Ile Gln Asp Glu
         35                  40                  45

Tyr Ile Glu Tyr Tyr Leu Lys Ser Lys Gln Leu Ser Ile Lys Ala Thr
     50                  55                  60

Leu Asp Ser Lys Ala Ala Tyr Lys Glu Ala Glu Leu Val Ile Ile Ala
 65                  70                  75                  80

Thr Pro Thr Asn Tyr Asn Ser Arg Ile Asn Tyr Phe Asp Thr Gln His
                 85                  90                  95

Val Glu Thr Val Ile Lys Glu Val Leu Ser Val Asn Ser His Ala Thr
            100                 105                 110

Leu Ile Ile Lys Ser Thr Ile Pro Ile Gly Phe Ile Thr Glu Met Arg
        115                 120                 125

Gln Lys Phe Gln Thr Asp Arg Ile Ile Phe Ser Pro Glu Phe Leu Arg
    130                 135                 140

Glu Ser Lys Ala Leu Tyr Asp Asn Leu Tyr Pro Ser Arg Ile Ile Val
145                 150                 155                 160

Ser Cys Glu Glu Asn Asp Ser Pro Lys Val Lys Ala Asp Ala Glu Lys
                165                 170                 175

Phe Ala Leu Leu Leu Lys Ser Ala Ala Lys Lys Asn Asn Val Pro Val
            180                 185                 190

Leu Ile Met Gly Ala Ser Glu Ala Glu Ala Val Lys Leu Phe Ala Asn
        195                 200                 205

Thr Tyr Leu Ala Leu Arg Val Ala Tyr Phe Asn Glu Leu Asp Thr Tyr
    210                 215                 220

Ala Glu Ser Arg Lys Leu Asn Ser His Met Ile Ile Gln Gly Ile Ser
225                 230                 235                 240

Tyr Asp Asp Arg Ile Gly Met His Tyr Asn Asn Pro Ser Phe Gly Tyr
                245                 250                 255

Gly Gly Tyr Cys Leu Pro Lys Asp Thr Lys Gln Leu Leu Ala Asn Tyr
            260                 265                 270

Asn Asn Ile Pro Gln Thr Leu Ile Glu Ala Ile Val Ser Ser Asn Asn
    275                 280                 285

Val Arg Lys Ser Tyr Ile Ala Lys Gln Ile Ile Asn Val Leu Glu Glu
290                 295                 300

Arg Glu Ser Pro Val Lys Val Gly Val Tyr Arg Leu Ile Met Lys
305                 310                 315                 320

Ser Asn Ser Asp Asn Phe Arg Glu Ser Ala Ile Lys Asp Val Ile Asp
                325                 330                 335

Ile Leu Lys Ser Lys Asp Ile Lys Ile Ile Tyr Glu Pro Met Leu
            340                 345                 350

Asn Lys Leu Glu Ser Glu Asp Gln Ser Val Leu Val Asn Asp Leu Glu
    355                 360                 365

Asn Phe Lys Lys Gln Ala Asn Ile Ile Val Thr Asn Arg Tyr Asp Asn
    370                 375                 380

Glu Leu Gln Asp Val Lys Asn Lys Val Tyr Ser Arg Asp Ile Phe Asn
385                 390                 395                 400

Arg Asp

<210> SEQ ID NO 98
<211> LENGTH: 912
<212> TYPE: DNA
<213> ORGANISM: Streptococcus pyogenes
<220> FEATURE:
<221> NAME/KEY: CDS

<220> LOCATION: (1)..(912)
<223> OTHER INFORMATION:

<400> SEQUENCE: 98

```
atg acc aaa gtc aga aaa gcc att att cct gct gca ggt cta gga aca      48
Met Thr Lys Val Arg Lys Ala Ile Ile Pro Ala Ala Gly Leu Gly Thr
1               5                   10                  15 cgt ttt tta cct gct acc aaa gct ctt gcc aaa gag atg ttg ccc atc      96
Arg Phe Leu Pro Ala Thr Lys Ala Leu Ala Lys Glu Met Leu Pro Ile
                20                  25                  30 gtt gat aaa cca acc atc cag ttt atc gtc gaa gaa gcg cta aaa tct     144
Val Asp Lys Pro Thr Ile Gln Phe Ile Val Glu Glu Ala Leu Lys Ser
            35                  40                  45 ggc atc gag gaa atc ctt gtg gtg acc gga aaa gct aaa cgc tct atc     192
Gly Ile Glu Glu Ile Leu Val Val Thr Gly Lys Ala Lys Arg Ser Ile
        50                  55                  60 gag gac cat ttt gat tca aac ttt gaa tta gaa tac aac ctc caa gct     240
Glu Asp His Phe Asp Ser Asn Phe Glu Leu Glu Tyr Asn Leu Gln Ala
65                  70                  75                  80 aag ggg aaa aat gaa ctg ttg aaa tta gtg gat gaa acc act gcc att     288
Lys Gly Lys Asn Glu Leu Leu Lys Leu Val Asp Glu Thr Thr Ala Ile
                85                  90                  95 aac ctt cat ttt atc cgt caa agc cac cca aga ggg ctg gga gat gct     336
Asn Leu His Phe Ile Arg Gln Ser His Pro Arg Gly Leu Gly Asp Ala
                100                 105                 110 gtc tta caa gcc aaa gcc ttt gtg ggc aat gaa ccc ttt gtg gtc atg     384
Val Leu Gln Ala Lys Ala Phe Val Gly Asn Glu Pro Phe Val Val Met
            115                 120                 125 ctt gga gat gac tta atg gac att aca aat gca tcc gct aaa cct ctc     432
Leu Gly Asp Asp Leu Met Asp Ile Thr Asn Ala Ser Ala Lys Pro Leu
        130                 135                 140 acc aaa caa ctc atg gag gac tat gac aag acg cat gca tcc act atc     480
Thr Lys Gln Leu Met Glu Asp Tyr Asp Lys Thr His Ala Ser Thr Ile
145                 150                 155                 160 gct gtg atg aaa gtt cct cat gaa gat gtg tct agc tat ggg gtt atc     528
Ala Val Met Lys Val Pro His Glu Asp Val Ser Ser Tyr Gly Val Ile
                165                 170                 175 gct cct caa ggc aag gct gtc aag ggc ctt tac agt gta gac acc ttt     576
Ala Pro Gln Gly Lys Ala Val Lys Gly Leu Tyr Ser Val Asp Thr Phe
                180                 185                 190 gtt gaa aaa cca caa cca gaa gat gcg cct agt gat ttg gct att att     624
Val Glu Lys Pro Gln Pro Glu Asp Ala Pro Ser Asp Leu Ala Ile Ile
            195                 200                 205 ggt cgt tac ctc cta acc cct gaa att ttt ggt att ttg gaa aga cag     672
Gly Arg Tyr Leu Leu Thr Pro Glu Ile Phe Gly Ile Leu Glu Arg Gln
        210                 215                 220 acc cct gga gca ggt aac gaa gtg caa ctc aca gat gct atc gat acc     720
Thr Pro Gly Ala Gly Asn Glu Val Gln Leu Thr Asp Ala Ile Asp Thr
225                 230                 235                 240 ctc aat aaa act cag cgt gtc ttt gca cga gaa ttt aaa ggc aat cgt     768
Leu Asn Lys Thr Gln Arg Val Phe Ala Arg Glu Phe Lys Gly Asn Arg
                245                 250                 255 tac gat gtt ggg gat aaa ttt gga ttc atg aaa aca tct atc gac tat     816
Tyr Asp Val Gly Asp Lys Phe Gly Phe Met Lys Thr Ser Ile Asp Tyr
                260                 265                 270 gcc tta gaa cac cca cag gtc aaa gag gac ttg aaa aat tac att atc     864
Ala Leu Glu His Pro Gln Val Lys Glu Asp Leu Lys Asn Tyr Ile Ile
            275                 280                 285 aaa cta gga aaa gct ttg gaa aaa agt aaa gta cca aca cat tca aag     912
Lys Leu Gly Lys Ala Leu Glu Lys Ser Lys Val Pro Thr His Ser Lys
        290                 295                 300
```

<210> SEQ ID NO 99
<211> LENGTH: 304
<212> TYPE: PRT
<213> ORGANISM: Streptococcus pyogenes

<400> SEQUENCE: 99

```
Met Thr Lys Val Arg Lys Ala Ile Ile Pro Ala Ala Gly Leu Gly Thr
 1               5                  10                  15
Arg Phe Leu Pro Ala Thr Lys Ala Leu Ala Lys Glu Met Leu Pro Ile
                20                  25                  30
Val Asp Lys Pro Thr Ile Gln Phe Ile Val Glu Glu Ala Leu Lys Ser
            35                  40                  45
Gly Ile Glu Glu Ile Leu Val Val Thr Gly Lys Ala Lys Arg Ser Ile
        50                  55                  60
Glu Asp His Phe Asp Ser Asn Phe Glu Leu Glu Tyr Asn Leu Gln Ala
65                  70                  75                  80
Lys Gly Lys Asn Glu Leu Leu Lys Leu Val Asp Glu Thr Thr Ala Ile
                85                  90                  95
Asn Leu His Phe Ile Arg Gln Ser His Pro Arg Gly Leu Gly Asp Ala
            100                 105                 110
Val Leu Gln Ala Lys Ala Phe Val Gly Asn Glu Pro Phe Val Val Met
        115                 120                 125
Leu Gly Asp Asp Leu Met Asp Ile Thr Asn Ala Ser Ala Lys Pro Leu
    130                 135                 140
Thr Lys Gln Leu Met Glu Asp Tyr Asp Lys Thr His Ala Ser Thr Ile
145                 150                 155                 160
Ala Val Met Lys Val Pro His Glu Asp Val Ser Ser Tyr Gly Val Ile
                165                 170                 175
Ala Pro Gln Gly Lys Ala Val Lys Gly Leu Tyr Ser Val Asp Thr Phe
            180                 185                 190
Val Glu Lys Pro Gln Pro Glu Asp Ala Pro Ser Asp Leu Ala Ile Ile
        195                 200                 205
Gly Arg Tyr Leu Leu Thr Pro Glu Ile Phe Gly Ile Leu Glu Arg Gln
    210                 215                 220
Thr Pro Gly Ala Gly Asn Glu Val Gln Leu Thr Asp Ala Ile Asp Thr
225                 230                 235                 240
Leu Asn Lys Thr Gln Arg Val Phe Ala Arg Glu Phe Lys Gly Asn Arg
                245                 250                 255
Tyr Asp Val Gly Asp Lys Phe Gly Phe Met Lys Thr Ser Ile Asp Tyr
            260                 265                 270
Ala Leu Glu His Pro Gln Val Lys Glu Asp Leu Lys Asn Tyr Ile Ile
        275                 280                 285
Lys Leu Gly Lys Ala Leu Glu Lys Ser Lys Val Pro Thr His Ser Lys
    290                 295                 300
```

<210> SEQ ID NO 100
<211> LENGTH: 1347
<212> TYPE: DNA
<213> ORGANISM: Streptococcus equi zooepidemicus
<220> FEATURE:
<221> NAME/KEY: CDS
<222> LOCATION: (1)..(1347)
<223> OTHER INFORMATION:

<400> SEQUENCE: 100

```
atg tca cat att aca ttt gat tat tca aag gtt ctt gag caa ttt gcc    48
Met Ser His Ile Thr Phe Asp Tyr Ser Lys Val Leu Glu Gln Phe Ala
1               5                  10                 15 gga cag cat gaa att gac ttt tta caa ggt cag gta aca gag gct gat    96
Gly Gln His Glu Ile Asp Phe Leu Gln Gly Gln Val Thr Glu Ala Asp
            20                  25                 30 cag gca cta cgt cag ggc act gga cct gga tca gat ttc ttg ggc tgg   144
Gln Ala Leu Arg Gln Gly Thr Gly Pro Gly Ser Asp Phe Leu Gly Trp
        35                  40                 45 ctt gag tta cct gaa aac tat gac aaa gaa gaa ttt gct cgt atc ctt   192
Leu Glu Leu Pro Glu Asn Tyr Asp Lys Glu Glu Phe Ala Arg Ile Leu
    50                  55                 60 aaa gca gct gag aag att aag gct gac agt gac gtt ctt gtt gtg att   240
Lys Ala Ala Glu Lys Ile Lys Ala Asp Ser Asp Val Leu Val Val Ile
65              70                  75                 80 ggt att ggt ggc tct tac ctt ggt gct aag gct gca att gac ttt ttg   288
Gly Ile Gly Gly Ser Tyr Leu Gly Ala Lys Ala Ala Ile Asp Phe Leu
                85                  90                 95 aac agc cat ttt gcc aac cta caa aca gca aaa gag cgc aaa gca cca   336
Asn Ser His Phe Ala Asn Leu Gln Thr Ala Lys Glu Arg Lys Ala Pro
            100                 105                110 caa att ctt tat gct ggt aac tcc atc tca tca agc tat ctt gct gat   384
Gln Ile Leu Tyr Ala Gly Asn Ser Ile Ser Ser Ser Tyr Leu Ala Asp
        115                 120                125 ctt gtg gac tat gtt caa gat aaa gat ttc tct gtt aac gtg att tct   432
Leu Val Asp Tyr Val Gln Asp Lys Asp Phe Ser Val Asn Val Ile Ser
    130                 135                140 aag tct ggt aca aca aca gag cct gca atc gcc ttt cgt gtc ttt aaa   480
Lys Ser Gly Thr Thr Thr Glu Pro Ala Ile Ala Phe Arg Val Phe Lys
145             150                 155                160 gaa tta ctt gtt aaa aag tac ggt caa gaa gag gcc aac aag cgt atc   528
Glu Leu Leu Val Lys Lys Tyr Gly Gln Glu Glu Ala Asn Lys Arg Ile
                165                 170                175 tat gca acg act gat aag gtc aag ggt gct gtt aag gtt gag gct gat   576
Tyr Ala Thr Thr Asp Lys Val Lys Gly Ala Val Lys Val Glu Ala Asp
            180                 185                190 gca aat cat tgg gaa acc ttt gtt gtg cca gat aat gtt ggt ggc cgt   624
Ala Asn His Trp Glu Thr Phe Val Val Pro Asp Asn Val Gly Gly Arg
        195                 200                205 ttc tca gtg ctg aca gct gtg ggc ttg cta cca att gca gca tca ggg   672
Phe Ser Val Leu Thr Ala Val Gly Leu Leu Pro Ile Ala Ala Ser Gly
    210                 215                220 gct gat att acc gcg ctg atg gaa gga gca aat gca gct cgt aag gac   720
Ala Asp Ile Thr Ala Leu Met Glu Gly Ala Asn Ala Ala Arg Lys Asp
225             230                 235                240 ctg tca tca gat aaa atc tca gaa aac atc gct tac caa tat gct gtg   768
Leu Ser Ser Asp Lys Ile Ser Glu Asn Ile Ala Tyr Gln Tyr Ala Val
                245                 250                255 gtc cgc aat atc ctc tat cgc aaa ggc tat gta act gaa att ttg gca   816
Val Arg Asn Ile Leu Tyr Arg Lys Gly Tyr Val Thr Glu Ile Leu Ala
            260                 265                270 aac tat gag cca tca ttg cag tat ttt agc gaa tgg tgg aag caa ctg   864
Asn Tyr Glu Pro Ser Leu Gln Tyr Phe Ser Glu Trp Trp Lys Gln Leu
        275                 280                285 gct ggt gag tct gaa gga aag gac caa aag ggt att tac cca act tca   912
Ala Gly Glu Ser Glu Gly Lys Asp Gln Lys Gly Ile Tyr Pro Thr Ser
    290                 295                300 gct aat ttc tcg aca gac ctg cat tct ctt ggt caa ttt atc caa gaa   960
Ala Asn Phe Ser Thr Asp Leu His Ser Leu Gly Gln Phe Ile Gln Glu
305             310                 315                320
```

```
ggc tac cgt aac ctc ttt gag aca gtg att cgt gtg gac aag cca cgt    1008
Gly Tyr Arg Asn Leu Phe Glu Thr Val Ile Arg Val Asp Lys Pro Arg
            325                 330                 335 caa aat gtg att atc cca gaa atg gct gag gac ctt gat ggc ctt ggc    1056
Gln Asn Val Ile Ile Pro Glu Met Ala Glu Asp Leu Asp Gly Leu Gly
        340                 345                 350 tac cta caa gga aaa gac gtt gac ttt gtc aac aaa aaa gca aca gat    1104
Tyr Leu Gln Gly Lys Asp Val Asp Phe Val Asn Lys Lys Ala Thr Asp
    355                 360                 365 ggt gtc ctt ctt gcc cat aca gat ggt ggt gtg cca aat atg ttt atc    1152
Gly Val Leu Leu Ala His Thr Asp Gly Gly Val Pro Asn Met Phe Ile
370                 375                 380 acg ctt cca gag caa gac gaa ttt aca cta ggc tat acg atc tac ttc    1200
Thr Leu Pro Glu Gln Asp Glu Phe Thr Leu Gly Tyr Thr Ile Tyr Phe
385                 390                 395                 400 ttt gag ctt gct att gcc ctt tca ggc tac ctc aac ggg gtc aat cca    1248
Phe Glu Leu Ala Ile Ala Leu Ser Gly Tyr Leu Asn Gly Val Asn Pro
                405                 410                 415 ttt gat cag cca ggc gtt gag gct tac aag aaa aac atg ttt gcc ctt    1296
Phe Asp Gln Pro Gly Val Glu Ala Tyr Lys Lys Asn Met Phe Ala Leu
            420                 425                 430 ctt ggt aag cca ggc ttt gaa gag cta gga gca gcg ctc aac gca cgc    1344
Leu Gly Lys Pro Gly Phe Glu Glu Leu Gly Ala Ala Leu Asn Ala Arg
        435                 440                 445 ttg                                                                 1347
Leu

<210> SEQ ID NO 101
<211> LENGTH: 449
<212> TYPE: PRT
<213> ORGANISM: Streptococcus equi zooepidemicus

<400> SEQUENCE: 101

Met Ser His Ile Thr Phe Asp Tyr Ser Lys Val Leu Glu Gln Phe Ala
1               5                   10                  15

Gly Gln His Glu Ile Asp Phe Leu Gln Gly Gln Val Thr Glu Ala Asp
            20                  25                  30

Gln Ala Leu Arg Gln Gly Thr Gly Pro Gly Ser Asp Phe Leu Gly Trp
        35                  40                  45

Leu Glu Leu Pro Glu Asn Tyr Asp Lys Glu Phe Ala Arg Ile Leu
    50                  55                  60

Lys Ala Ala Glu Lys Ile Lys Ala Asp Ser Asp Val Leu Val Val Ile
65                  70                  75                  80

Gly Ile Gly Gly Ser Tyr Leu Gly Ala Lys Ala Ala Ile Asp Phe Leu
                85                  90                  95

Asn Ser His Phe Ala Asn Leu Gln Thr Ala Lys Glu Arg Lys Ala Pro
            100                 105                 110

Gln Ile Leu Tyr Ala Gly Asn Ser Ile Ser Ser Tyr Leu Ala Asp
        115                 120                 125

Leu Val Asp Tyr Val Gln Asp Lys Asp Phe Ser Val Asn Val Ile Ser
    130                 135                 140

Lys Ser Gly Thr Thr Thr Glu Pro Ala Ile Ala Phe Arg Val Phe Lys
145                 150                 155                 160

Glu Leu Leu Val Lys Lys Tyr Gly Gln Glu Glu Ala Asn Lys Arg Ile
                165                 170                 175

Tyr Ala Thr Thr Asp Lys Val Lys Gly Ala Val Lys Val Glu Ala Asp
            180                 185                 190
```

```
Ala Asn His Trp Glu Thr Phe Val Val Pro Asp Asn Val Gly Gly Arg
        195                 200                 205

Phe Ser Val Leu Thr Ala Val Gly Leu Leu Pro Ile Ala Ala Ser Gly
        210                 215                 220

Ala Asp Ile Thr Ala Leu Met Glu Gly Ala Asn Ala Ala Arg Lys Asp
225                 230                 235                 240

Leu Ser Ser Asp Lys Ile Ser Glu Asn Ile Ala Tyr Gln Tyr Ala Val
        245                 250                 255

Val Arg Asn Ile Leu Tyr Arg Lys Gly Tyr Val Thr Glu Ile Leu Ala
        260                 265                 270

Asn Tyr Glu Pro Ser Leu Gln Tyr Phe Ser Glu Trp Trp Lys Gln Leu
        275                 280                 285

Ala Gly Glu Ser Glu Gly Lys Asp Gln Lys Gly Ile Tyr Pro Thr Ser
        290                 295                 300

Ala Asn Phe Ser Thr Asp Leu His Ser Leu Gly Gln Phe Ile Gln Glu
305                 310                 315                 320

Gly Tyr Arg Asn Leu Phe Glu Thr Val Ile Arg Val Asp Lys Pro Arg
        325                 330                 335

Gln Asn Val Ile Ile Pro Glu Met Ala Glu Asp Leu Asp Gly Leu Gly
        340                 345                 350

Tyr Leu Gln Gly Lys Asp Val Asp Phe Val Asn Lys Lys Ala Thr Asp
        355                 360                 365

Gly Val Leu Leu Ala His Thr Asp Gly Gly Val Pro Asn Met Phe Ile
370                 375                 380

Thr Leu Pro Glu Gln Asp Glu Phe Thr Leu Gly Tyr Thr Ile Tyr Phe
385                 390                 395                 400

Phe Glu Leu Ala Ile Ala Leu Ser Gly Tyr Leu Asn Gly Val Asn Pro
        405                 410                 415

Phe Asp Gln Pro Gly Val Glu Ala Tyr Lys Lys Asn Met Phe Ala Leu
        420                 425                 430

Leu Gly Lys Pro Gly Phe Glu Glu Leu Gly Ala Ala Leu Asn Ala Arg
        435                 440                 445

Leu

<210> SEQ ID NO 102
<211> LENGTH: 1251
<212> TYPE: DNA
<213> ORGANISM: Streptococcus uberis
<220> FEATURE:
<221> NAME/KEY: CDS
<222> LOCATION: (1)..(1251)
<223> OTHER INFORMATION:

<400> SEQUENCE: 102 atg gaa aaa cta aaa aat ctc att aca ttt atg act ttt att ttc ctg     48
Met Glu Lys Leu Lys Asn Leu Ile Thr Phe Met Thr Phe Ile Phe Leu
1               5                   10                  15 tgg ctc ata att att ggg ctt aat gtt ttt gta ttt gga act aaa gga     96
Trp Leu Ile Ile Ile Gly Leu Asn Val Phe Val Phe Gly Thr Lys Gly
            20                  25                  30 agt cta aca gtg tat ggg att att cta tta acc tat ttg tcg ata aaa    144
Ser Leu Thr Val Tyr Gly Ile Ile Leu Leu Thr Tyr Leu Ser Ile Lys
        35                  40                  45 atg gga tta tct ttt ttt tat cgt ccc tat aaa gga agt gta ggt caa    192
Met Gly Leu Ser Phe Phe Tyr Arg Pro Tyr Lys Gly Ser Val Gly Gln
    50                  55                  60
```

```
tat aag gta gca gct att atc cca tct tat aat gag gat ggt gtc ggt     240
Tyr Lys Val Ala Ala Ile Ile Pro Ser Tyr Asn Glu Asp Gly Val Gly
 65              70                  75                  80 tta cta gaa act cta aag agt gtt caa aaa caa aca tat cca att gca     288
Leu Leu Glu Thr Leu Lys Ser Val Gln Lys Gln Thr Tyr Pro Ile Ala
                 85                  90                  95 gaa att ttc gta att gac gat ggg tca gta gat aaa aca ggt ata aaa     336
Glu Ile Phe Val Ile Asp Asp Gly Ser Val Asp Lys Thr Gly Ile Lys
            100                 105                 110 ttg gtc gaa gac tat gtg aag tta aat ggc ttt gga gac caa gtt atc     384
Leu Val Glu Asp Tyr Val Lys Leu Asn Gly Phe Gly Asp Gln Val Ile
        115                 120                 125 gtt cat cag atg cct gaa aat gtt ggt aaa aga cat gct cag gct tgg     432
Val His Gln Met Pro Glu Asn Val Gly Lys Arg His Ala Gln Ala Trp
    130                 135                 140 gca ttt gaa agg tct gat gct gat gtt ttc tta aca gtg gat tca gat     480
Ala Phe Glu Arg Ser Asp Ala Asp Val Phe Leu Thr Val Asp Ser Asp
145                 150                 155                 160 acc tac atc tat cct gat gct ctt gaa gaa tta tta aag aca ttt aat     528
Thr Tyr Ile Tyr Pro Asp Ala Leu Glu Glu Leu Leu Lys Thr Phe Asn
                165                 170                 175 gat cca gag gtc tac gct gca act ggt cat tta aat gca aga aat aga     576
Asp Pro Glu Val Tyr Ala Ala Thr Gly His Leu Asn Ala Arg Asn Arg
            180                 185                 190 caa act aat ctc tta act aga ctg act gat att cgt tac gat aat gca     624
Gln Thr Asn Leu Leu Thr Arg Leu Thr Asp Ile Arg Tyr Asp Asn Ala
        195                 200                 205 ttt ggt gta gaa cgt gct gct cag tct gtt acg gga aat att ttg gtt     672
Phe Gly Val Glu Arg Ala Ala Gln Ser Val Thr Gly Asn Ile Leu Val
    210                 215                 220 tgt tcc gga cct tta agt att tat aga cgt tcc gtc ggt att cca aat     720
Cys Ser Gly Pro Leu Ser Ile Tyr Arg Arg Ser Val Gly Ile Pro Asn
225                 230                 235                 240 ctt gaa cgc tat acc tca caa aca ttt ctt ggt gtc cct gta agc ata     768
Leu Glu Arg Tyr Thr Ser Gln Thr Phe Leu Gly Val Pro Val Ser Ile
                245                 250                 255 ggg gat gac cgt tgt ttg aca aat tat gca act gat ttg gga aaa acg     816
Gly Asp Asp Arg Cys Leu Thr Asn Tyr Ala Thr Asp Leu Gly Lys Thr
            260                 265                 270 gtt tat cag tca act gca aga tgt gat act gac gtt cca gat aag ttt     864
Val Tyr Gln Ser Thr Ala Arg Cys Asp Thr Asp Val Pro Asp Lys Phe
        275                 280                 285 aag gtt ttc atc aaa caa caa aat cgt tgg aat aag tca ttt ttt agg     912
Lys Val Phe Ile Lys Gln Gln Asn Arg Trp Asn Lys Ser Phe Phe Arg
    290                 295                 300 gag tct att atc tct gtt aag aag tta tta gcc aca cca agt gtt gct     960
Glu Ser Ile Ile Ser Val Lys Lys Leu Leu Ala Thr Pro Ser Val Ala
305                 310                 315                 320 gtt tgg act att aca gaa gtt tcc atg ttc atc atg cta gtt tat tct    1008
Val Trp Thr Ile Thr Glu Val Ser Met Phe Ile Met Leu Val Tyr Ser
                325                 330                 335 atc ttt agc tta ttg ata gga gag gct caa gaa ttt aat ctc ata aaa    1056
Ile Phe Ser Leu Leu Ile Gly Glu Ala Gln Glu Phe Asn Leu Ile Lys
            340                 345                 350 ctg gtt gct ttt tta gtt att att ttc ata gta gct ctt tgt aga aat    1104
Leu Val Ala Phe Leu Val Ile Ile Phe Ile Val Ala Leu Cys Arg Asn
        355                 360                 365 gtt cat tac atg gtt aag cat cca ttt gct ttt tta ttg tca ccg ttt    1152
Val His Tyr Met Val Lys His Pro Phe Ala Phe Leu Leu Ser Pro Phe
    370                 375                 380
```

```
tat gga ttg ata cat cta ttc gtt ttg caa cct ctt aag ata tat tcg    1200
Tyr Gly Leu Ile His Leu Phe Val Leu Gln Pro Leu Lys Ile Tyr Ser
385                 390                 395                 400 tta ttt act ata aga aat gct aca tgg gga act cgt aaa aag aca agt    1248
Leu Phe Thr Ile Arg Asn Ala Thr Trp Gly Thr Arg Lys Lys Thr Ser
                405                 410                 415 aaa                                                                 1251
Lys
```

<210> SEQ ID NO 103
<211> LENGTH: 417
<212> TYPE: PRT
<213> ORGANISM: Streptococcus uberis

<400> SEQUENCE: 103

```
Met Glu Lys Leu Lys Asn Leu Ile Thr Phe Met Thr Phe Ile Phe Leu
1               5                   10                  15

Trp Leu Ile Ile Ile Gly Leu Asn Val Phe Val Phe Gly Thr Lys Gly
                20                  25                  30

Ser Leu Thr Val Tyr Gly Ile Ile Leu Leu Thr Tyr Leu Ser Ile Lys
            35                  40                  45

Met Gly Leu Ser Phe Phe Tyr Arg Pro Tyr Lys Gly Ser Val Gly Gln
        50                  55                  60

Tyr Lys Val Ala Ala Ile Ile Pro Ser Tyr Asn Glu Asp Gly Val Gly
65                  70                  75                  80

Leu Leu Glu Thr Leu Lys Ser Val Gln Lys Gln Thr Tyr Pro Ile Ala
                85                  90                  95

Glu Ile Phe Val Ile Asp Asp Gly Ser Val Asp Lys Thr Gly Ile Lys
            100                 105                 110

Leu Val Glu Asp Tyr Val Lys Leu Asn Gly Phe Gly Asp Gln Val Ile
        115                 120                 125

Val His Gln Met Pro Glu Asn Val Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asp Ala Leu Glu Glu Leu Leu Lys Thr Phe Asn
                165                 170                 175

Asp Pro Glu Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Val Thr Gly Asn Ile Leu Val
210                 215                 220

Cys Ser Gly Pro Leu Ser Ile Tyr Arg Arg Ser Val Gly Ile Pro Asn
225                 230                 235                 240

Leu Glu Arg Tyr Thr Ser Gln Thr Phe Leu Gly Val Pro Val Ser Ile
                245                 250                 255

Gly Asp Asp Arg Cys Leu Thr Asn Tyr Ala Thr Asp Leu Gly Lys Thr
            260                 265                 270

Val Tyr Gln Ser Thr Ala Arg Cys Asp Thr Asp Val Pro Asp Lys Phe
        275                 280                 285

Lys Val Phe Ile Lys Gln Gln Asn Arg Trp Asn Lys Ser Phe Phe Arg
290                 295                 300

Glu Ser Ile Ile Ser Val Lys Lys Leu Leu Ala Thr Pro Ser Val Ala
305                 310                 315                 320
```

| | | | | | | | | | | | | |
|---|---|---|---|---|---|---|---|---|---|---|---|---|
|Val|Trp|Thr|Ile|Thr|Glu|Val|Ser|Met|Phe|Ile|Met|Leu|Val|Tyr|Ser|
| | | | |325| | | |330| | | |335| | | |

Ile Phe Ser Leu Leu Ile Gly Glu Ala Gln Glu Phe Asn Leu Ile Lys
              340                 345                 350

Leu Val Ala Phe Leu Val Ile Phe Ile Val Ala Leu Cys Arg Asn
              355                 360                 365

Val His Tyr Met Val Lys His Pro Phe Ala Phe Leu Leu Ser Pro Phe
        370                 375                 380

Tyr Gly Leu Ile His Leu Phe Val Leu Gln Pro Leu Lys Ile Tyr Ser
385                 390                 395                 400

Leu Phe Thr Ile Arg Asn Ala Thr Trp Gly Thr Arg Lys Lys Thr Ser
                405                 410                 415

Lys

<210> SEQ ID NO 104
<211> LENGTH: 1203
<212> TYPE: DNA
<213> ORGANISM: Streptococcus uberis
<220> FEATURE:
<221> NAME/KEY: CDS
<222> LOCATION: (1)..(1203)
<223> OTHER INFORMATION:

<400> SEQUENCE: 104

```
gtg aaa att gca gtt gca ggt tct ggc tat gtt ggc cta tca tta agt        48
Val Lys Ile Ala Val Ala Gly Ser Gly Tyr Val Gly Leu Ser Leu Ser
 1               5                  10                  15 gta tta tta gca cag aaa aat cct gtt aca gtt gta gat att att gag       96
Val Leu Leu Ala Gln Lys Asn Pro Val Thr Val Val Asp Ile Ile Glu
             20                  25                  30 aag aaa gta aat ctc ata aat caa aaa caa tca cca atc cag gat gtt      144
Lys Lys Val Asn Leu Ile Asn Gln Lys Gln Ser Pro Ile Gln Asp Val
         35                  40                  45 gat att gaa aac tat tta aaa gaa aaa aag tta caa tta aga gct act      192
Asp Ile Glu Asn Tyr Leu Lys Glu Lys Lys Leu Gln Leu Arg Ala Thr
     50                  55                  60 cta gac gcc gat caa gca ttt agg gat gca gat ata cta att att gct      240
Leu Asp Ala Asp Gln Ala Phe Arg Asp Ala Asp Ile Leu Ile Ile Ala
 65                  70                  75                  80 aca cca acc aat tat gat gtg gag aag aat ttt ttt gat act agt cat      288
Thr Pro Thr Asn Tyr Asp Val Glu Lys Asn Phe Phe Asp Thr Ser His
                 85                  90                  95 gtt gag act gta att gag aaa gct tta gct tta aat agt cag gct ttg      336
Val Glu Thr Val Ile Glu Lys Ala Leu Ala Leu Asn Ser Gln Ala Leu
            100                 105                 110 tta gtt att aaa tca acg ata cca ctt ggt ttt att aaa aag atg cgt      384
Leu Val Ile Lys Ser Thr Ile Pro Leu Gly Phe Ile Lys Lys Met Arg
        115                 120                 125 caa aaa tat cag aca gac cgt att att ttt agt ccc gaa ttt ctt aga      432
Gln Lys Tyr Gln Thr Asp Arg Ile Ile Phe Ser Pro Glu Phe Leu Arg
    130                 135                 140 gag tct aaa gct tta aaa gat aat ctt tat cct agt cga ata att gtt      480
Glu Ser Lys Ala Leu Lys Asp Asn Leu Tyr Pro Ser Arg Ile Ile Val
145                 150                 155                 160 tcc ttt gaa gat gat gat tct atg gaa gta ata gaa gca gca aag act      528
Ser Phe Glu Asp Asp Asp Ser Met Glu Val Ile Glu Ala Ala Lys Thr
                165                 170                 175 ttt gct caa ttg tta aaa gat ggt tct ttg gat aaa gat gtt cct gta      576
Phe Ala Gln Leu Leu Lys Asp Gly Ser Leu Asp Lys Asp Val Pro Val
```

```
             180                 185                 190
ctt ttt atg ggt tca gca gag gct gaa gca gta aaa tta ttt gcc aat        624
Leu Phe Met Gly Ser Ala Glu Ala Glu Ala Val Lys Leu Phe Ala Asn
        195                 200                 205 acc tat tta gct atg cgt gtc tcc tat ttt aat gag tta gat aca tat        672
Thr Tyr Leu Ala Met Arg Val Ser Tyr Phe Asn Glu Leu Asp Thr Tyr
    210                 215                 220 gct gaa aag aat ggt tta cgt gtg gat aat att att gag ggc gtt tgc        720
Ala Glu Lys Asn Gly Leu Arg Val Asp Asn Ile Ile Glu Gly Val Cys
225                 230                 235                 240 cat gat cga cgc ata gga att cat tat aat aac cct tct ttt ggc tat        768
His Asp Arg Arg Ile Gly Ile His Tyr Asn Asn Pro Ser Phe Gly Tyr
                245                 250                 255 gga gga tac tgc tta cct aaa gat acc aaa cag ttg cta gca ggc tat        816
Gly Gly Tyr Cys Leu Pro Lys Asp Thr Lys Gln Leu Leu Ala Gly Tyr
            260                 265                 270 gat ggt att cct caa tcg ctt ata aaa gca att gtt gat tct aat aaa        864
Asp Gly Ile Pro Gln Ser Leu Ile Lys Ala Ile Val Asp Ser Asn Lys
        275                 280                 285 att cgt aaa gag tat atc gca tca caa att tta caa caa ttg agt gat        912
Ile Arg Lys Glu Tyr Ile Ala Ser Gln Ile Leu Gln Gln Leu Ser Asp
    290                 295                 300 att aat gta gat cct aaa gat gca acg att ggt att tac cgc ctt atc        960
Ile Asn Val Asp Pro Lys Asp Ala Thr Ile Gly Ile Tyr Arg Leu Ile
305                 310                 315                 320 atg aaa agt aac tct gat aat ttc aga gag agt gca ata aaa gat att       1008
Met Lys Ser Asn Ser Asp Asn Phe Arg Glu Ser Ala Ile Lys Asp Ile
                325                 330                 335 att gat cat att aag agc tat caa att aat ata gtc ttg tat gag cca       1056
Ile Asp His Ile Lys Ser Tyr Gln Ile Asn Ile Val Leu Tyr Glu Pro
            340                 345                 350 atg atg aat gaa gat ttt gat tta cca atc att gat gat tta tct gac       1104
Met Met Asn Glu Asp Phe Asp Leu Pro Ile Ile Asp Asp Leu Ser Asp
        355                 360                 365 ttc aaa gcc atg tca cat att atc gtt tca aat aga tat gat tta gcc       1152
Phe Lys Ala Met Ser His Ile Ile Val Ser Asn Arg Tyr Asp Leu Ala
    370                 375                 380 tta gaa gat gtt aaa gaa aaa gtt tac acc aga gat att tac ggt gtg       1200
Leu Glu Asp Val Lys Glu Lys Val Tyr Thr Arg Asp Ile Tyr Gly Val
385                 390                 395                 400 gat                                                                    1203
Asp

<210> SEQ ID NO 105
<211> LENGTH: 401
<212> TYPE: PRT
<213> ORGANISM: Streptococcus uberis

<400> SEQUENCE: 105

Val Lys Ile Ala Val Ala Gly Ser Gly Tyr Val Gly Leu Ser Leu Ser
1               5                   10                  15

Val Leu Leu Ala Gln Lys Asn Pro Val Thr Val Asp Ile Ile Glu
            20                  25                  30

Lys Lys Val Asn Leu Ile Asn Gln Lys Gln Ser Pro Ile Gln Asp Val
                35                  40                  45

Asp Ile Glu Asn Tyr Leu Lys Glu Lys Lys Leu Gln Leu Arg Ala Thr
            50                  55                  60

Leu Asp Ala Asp Gln Ala Phe Arg Asp Ala Asp Ile Leu Ile Ile Ala
65                  70                  75                  80
```

Thr Pro Thr Asn Tyr Asp Val Glu Lys Asn Phe Phe Asp Thr Ser His
                85                  90                  95

Val Glu Thr Val Ile Glu Lys Ala Leu Ala Leu Asn Ser Gln Ala Leu
            100                 105                 110

Leu Val Ile Lys Ser Thr Ile Pro Leu Gly Phe Ile Lys Lys Met Arg
        115                 120                 125

Gln Lys Tyr Gln Thr Asp Arg Ile Ile Phe Ser Pro Glu Phe Leu Arg
    130                 135                 140

Glu Ser Lys Ala Leu Lys Asp Asn Leu Tyr Pro Ser Arg Ile Ile Val
145                 150                 155                 160

Ser Phe Glu Asp Asp Asp Ser Met Glu Val Ile Glu Ala Ala Lys Thr
                165                 170                 175

Phe Ala Gln Leu Leu Lys Asp Gly Ser Leu Asp Lys Asp Val Pro Val
            180                 185                 190

Leu Phe Met Gly Ser Ala Glu Ala Glu Ala Val Lys Leu Phe Ala Asn
        195                 200                 205

Thr Tyr Leu Ala Met Arg Val Ser Tyr Phe Asn Glu Leu Asp Thr Tyr
    210                 215                 220

Ala Glu Lys Asn Gly Leu Arg Val Asp Asn Ile Ile Glu Gly Val Cys
225                 230                 235                 240

His Asp Arg Arg Ile Gly Ile His Tyr Asn Asn Pro Ser Phe Gly Tyr
                245                 250                 255

Gly Gly Tyr Cys Leu Pro Lys Asp Thr Lys Gln Leu Leu Ala Gly Tyr
            260                 265                 270

Asp Gly Ile Pro Gln Ser Leu Ile Lys Ala Ile Val Asp Ser Asn Lys
        275                 280                 285

Ile Arg Lys Glu Tyr Ile Ala Ser Gln Ile Leu Gln Gln Leu Ser Asp
    290                 295                 300

Ile Asn Val Asp Pro Lys Asp Ala Thr Ile Gly Ile Tyr Arg Leu Ile
305                 310                 315                 320

Met Lys Ser Asn Ser Asp Asn Phe Arg Glu Ser Ala Ile Lys Asp Ile
                325                 330                 335

Ile Asp His Ile Lys Ser Tyr Gln Ile Asn Ile Val Leu Tyr Glu Pro
            340                 345                 350

Met Met Asn Glu Asp Phe Asp Leu Pro Ile Ile Asp Asp Leu Ser Asp
        355                 360                 365

Phe Lys Ala Met Ser His Ile Ile Val Ser Asn Arg Tyr Asp Leu Ala
    370                 375                 380

Leu Glu Asp Val Lys Glu Lys Val Tyr Thr Arg Asp Ile Tyr Gly Val
385                 390                 395                 400

Asp

<210> SEQ ID NO 106
<211> LENGTH: 912
<212> TYPE: DNA
<213> ORGANISM: Streptococcus uberis
<220> FEATURE:
<221> NAME/KEY: CDS
<222> LOCATION: (1)..(912)
<223> OTHER INFORMATION:

<400> SEQUENCE: 106 atg act aaa gta aga aaa gcc att att cca gct gcc gga ctt ggc aca      48
Met Thr Lys Val Arg Lys Ala Ile Ile Pro Ala Ala Gly Leu Gly Thr
1               5                   10                  15

```
cgt ttt tta cca gca aca aaa gct ctc gct aag gaa atg ttg ccc atc      96
Arg Phe Leu Pro Ala Thr Lys Ala Leu Ala Lys Glu Met Leu Pro Ile
         20                  25                  30 gtt gac aaa cca acc att caa ttc atc gtg gaa gaa gct ttg cgt tct     144
Val Asp Lys Pro Thr Ile Gln Phe Ile Val Glu Glu Ala Leu Arg Ser
         35                  40                  45 ggc att gaa gaa atc ttg gtc gta aca gga aaa tca aaa cgc tcc att     192
Gly Ile Glu Glu Ile Leu Val Val Thr Gly Lys Ser Lys Arg Ser Ile
 50                  55                  60 gaa gac cat ttt gat tcc aac ttt gaa ctc gaa tat aat ttg caa gaa     240
Glu Asp His Phe Asp Ser Asn Phe Glu Leu Glu Tyr Asn Leu Gln Glu
 65                  70                  75                  80 aaa ggg aaa act gaa ctc tta aaa tta gtt gat gaa acc act tct ata     288
Lys Gly Lys Thr Glu Leu Leu Lys Leu Val Asp Glu Thr Thr Ser Ile
                 85                  90                  95 aac ttg cat ttc att cgt caa agt cat ccc aaa ggc tta ggg gat gct     336
Asn Leu His Phe Ile Arg Gln Ser His Pro Lys Gly Leu Gly Asp Ala
            100                 105                 110 gtt tta caa gca aaa gct ttt gta gga aat gaa ccc ttc att gtt atg     384
Val Leu Gln Ala Lys Ala Phe Val Gly Asn Glu Pro Phe Ile Val Met
        115                 120                 125 ctt ggt gac gat ttg atg gac att aca aat acc aaa gct gtc cca tta     432
Leu Gly Asp Asp Leu Met Asp Ile Thr Asn Thr Lys Ala Val Pro Leu
    130                 135                 140 acc aaa caa tta atg gac gat tat gaa aca aca cat gct tct aca ata     480
Thr Lys Gln Leu Met Asp Asp Tyr Glu Thr Thr His Ala Ser Thr Ile
145                 150                 155                 160 gcc gta atg aaa gtt cct cac gat gac gta tcc tct tat ggt gtc att     528
Ala Val Met Lys Val Pro His Asp Asp Val Ser Ser Tyr Gly Val Ile
                165                 170                 175 gct cca aac ggc aaa gcc ttg aat ggc tta tat agc gtg gat acc ttt     576
Ala Pro Asn Gly Lys Ala Leu Asn Gly Leu Tyr Ser Val Asp Thr Phe
            180                 185                 190 gtt gaa aaa cca aaa cct gag gac gca cca agt gac ctt gct atc att     624
Val Glu Lys Pro Lys Pro Glu Asp Ala Pro Ser Asp Leu Ala Ile Ile
        195                 200                 205 gga cgt tat ctc tta aca cct gaa att ttt gac att ctt gaa aat caa     672
Gly Arg Tyr Leu Leu Thr Pro Glu Ile Phe Asp Ile Leu Glu Asn Gln
    210                 215                 220 gca cca ggt gcc gga aac gaa gtc caa tta act gat gct atc gat acc     720
Ala Pro Gly Ala Gly Asn Glu Val Gln Leu Thr Asp Ala Ile Asp Thr
225                 230                 235                 240 ctc aac aaa aca caa cgt gtt ttt gct cgt gag ttt act ggc aaa cgc     768
Leu Asn Lys Thr Gln Arg Val Phe Ala Arg Glu Phe Thr Gly Lys Arg
                245                 250                 255 tac gat gtt gga gac aag ttt ggc ttc atg aaa aca tct atc gat tat     816
Tyr Asp Val Gly Asp Lys Phe Gly Phe Met Lys Thr Ser Ile Asp Tyr
            260                 265                 270 gcc cta aaa cac cat caa gtc aaa gat gac cta aaa gct tat att atc     864
Ala Leu Lys His His Gln Val Lys Asp Asp Leu Lys Ala Tyr Ile Ile
        275                 280                 285 aag tta ggt aaa gaa tta gaa aaa gca caa gat tcc aaa gaa agc aaa     912
Lys Leu Gly Lys Glu Leu Glu Lys Ala Gln Asp Ser Lys Glu Ser Lys
    290                 295                 300
```

<210> SEQ ID NO 107
<211> LENGTH: 304
<212> TYPE: PRT
<213> ORGANISM: Streptococcus uberis

<400> SEQUENCE: 107

```
Met Thr Lys Val Arg Lys Ala Ile Ile Pro Ala Ala Gly Leu Gly Thr
1               5                   10                  15

Arg Phe Leu Pro Ala Thr Lys Ala Leu Ala Lys Glu Met Leu Pro Ile
                20                  25                  30

Val Asp Lys Pro Thr Ile Gln Phe Ile Val Glu Glu Ala Leu Arg Ser
            35                  40                  45

Gly Ile Glu Glu Ile Leu Val Val Thr Gly Lys Ser Lys Arg Ser Ile
    50                  55                  60

Glu Asp His Phe Asp Ser Asn Phe Glu Leu Glu Tyr Asn Leu Gln Glu
65                  70                  75                  80

Lys Gly Lys Thr Glu Leu Leu Lys Leu Val Asp Glu Thr Thr Ser Ile
                85                  90                  95

Asn Leu His Phe Ile Arg Gln Ser His Pro Lys Gly Leu Gly Asp Ala
            100                 105                 110

Val Leu Gln Ala Lys Ala Phe Val Gly Asn Glu Pro Phe Ile Val Met
        115                 120                 125

Leu Gly Asp Asp Leu Met Asp Ile Thr Asn Thr Lys Ala Val Pro Leu
130                 135                 140

Thr Lys Gln Leu Met Asp Asp Tyr Glu Thr Thr His Ala Ser Thr Ile
145                 150                 155                 160

Ala Val Met Lys Val Pro His Asp Asp Val Ser Ser Tyr Gly Val Ile
                165                 170                 175

Ala Pro Asn Gly Lys Ala Leu Asn Gly Leu Tyr Ser Val Asp Thr Phe
            180                 185                 190

Val Glu Lys Pro Lys Pro Glu Asp Ala Pro Ser Asp Leu Ala Ile Ile
        195                 200                 205

Gly Arg Tyr Leu Leu Thr Pro Glu Ile Phe Asp Ile Leu Glu Asn Gln
    210                 215                 220

Ala Pro Gly Ala Gly Asn Glu Val Gln Leu Thr Asp Ala Ile Asp Thr
225                 230                 235                 240

Leu Asn Lys Thr Gln Arg Val Phe Ala Arg Glu Phe Thr Gly Lys Arg
                245                 250                 255

Tyr Asp Val Gly Asp Lys Phe Gly Phe Met Lys Thr Ser Ile Asp Tyr
            260                 265                 270

Ala Leu Lys His His Gln Val Lys Asp Asp Leu Lys Ala Tyr Ile Ile
        275                 280                 285

Lys Leu Gly Lys Glu Leu Glu Lys Ala Gln Asp Ser Lys Glu Ser Lys
    290                 295                 300

<210> SEQ ID NO 108
<211> LENGTH: 5158
<212> TYPE: DNA
<213> ORGANISM: Streptococcus equisimilis

<400> SEQUENCE: 108
tcaatttatg gcttttttgct gatagcttac ctattagtca aaatgtcctt atcctttttt      60
tacaagccat ttaagggaag ggctgggcaa tataaggttg cagccattat tccctcttat     120
aacgaagatg ctgagtcatt gctagagacc ttaaaaagtg ttcagcagca aacctatccc     180
ctagcagaaa tttatgttgt tgacgatgga agtgctgatg agacaggtat taagcgcatt     240
gaagactatg tgcgtgacac tggtgaccta tcaagcaatg tcattgttca tcggtcagag     300
aaaaatcaag gaaagcgtca tgcacaggcc tgggcctttg aaagatcaga cgctgatgtc     360
tttttgaccg ttgactcaga tacttatatc taccctgatc ctttagagga gttgttaaaa     420
```

-continued

```
acctttaatg acccaactgt ttttgctgcg acgggtcacc ttaatgtcag aaatagacaa    480
accaatctct taacacgctt gacagatatt cgctatgata atgcttttgg cgttgaacga    540
gctgcccaat ccgttacagg taatatcctt gtttgctcag gtccgcttag cgtttacaga    600
cgcgaggtgg ttgttcctaa catagataga tacatcaacc agaccttcct gggtattcct    660
gtaagtattg gtgatgacag gtgcttgacc aactatgcaa ctgatttagg aaagactgtt    720
tatcaatcca ctgctaaatg tattacagat gttcctgaca agatgtctac ttacttgaag    780
cagcaaaacc gctggaacaa gtccttcttt agagagtcca ttatttctgt taagaaaatc    840
atgaacaatc cttttgtagc cctatggacc atacttgagg tgtctatgtt tatgatgctt    900
gtttattctg tggtggattt cttttgtaggc aatgtcagag aatttgattg gctcagggtt   960
ttagcctttc tggtgattat cttcattgtt gccctgtgtc ggaacattca ttacatgctt    1020
aagcacccgc tgtccttctt gttatctccg ttttatgggg tgctgcattt gtttgtccta   1080
cagcccttga aattatattc tcttttttact attagaaatg ctgactgggg aacacgtaaa   1140
aaattattat aaaccaacta gacctaggtt ctgacaaggg agctaagcta gggataaaaca   1200 aagagttttg atccgactcg agcagctcat aaacgaaagc tatcccactt gtaattgaag   1260
ctaagagctt ttagcttgca gctctataaa gacgaaccag aggctgagtg tcagctttgg   1320
tgtgagggct aggtcattat gatccttcag gtgtggcacc tgagctccgg cagtagctaa   1380
ctgtactaag gtatcaaagg aaaaaatgaa gtgaaaattt ctgtagcagg ctcaggatat   1440
gtcggcctat ccttgagtat tttactggca aacataatg acgtcactgt tgttgacatt    1500
attgatgaaa aggtgagatt gatcaatcaa ggcatatcgc caatcaagga tgctgatatt   1560
gaggagtatt taaaaaatgc gccgctaaat ctcacagcga cgcttgatgg cgcaagcgct   1620
tatagcaatg cagaccttat tatcattgct actccgacaa attatgacag cgaacgcaac   1680
tactttgaca caaggcatgt tgaagaggtc atcgagcagg tcctagacct aaatgcgtca   1740
gcaaccatta ttatcaaatc aaccatacca ctaggcttta tcaagcatgt tagggaaaaa   1800
taccagacag atcgtattat ttttagccca gaattttaa gagaatcaaa agccttatac    1860
gataaccttt acccaagtcg gatcattgtt tcttatgaaa aggacgactc accaagggtt   1920
attcaggctg ctaaagcctt tgctggtctt ttaaaggaag gagccaaaag caaggatact   1980
ccggtcttat ttatgggctc acaggaggct gaggcggtca agctatttgc gaatacccttt  2040 ttggctatgc gggtgtctta ctttaatgaa ttagacacct attccgaaag caagggtcta   2100
gatgctcagc gcgtgattga aggagtctgt catgatcagc gcattggtaa ccattacaat   2160
aacccttcct ttggatatgg cggctattgc ctgccaaagg acagcaagca gctgttggca   2220
aattatagag gcattcccca gtccttgatg tcagcgattg ttgaatccaa caagatacga   2280
aaatcttatt tggctgaaca aatattagac agagcctcta gtcaaaagca ggctggtgta   2340
ccattaacga ttggctttta ccgcttgatt atgaaaagca actctgataa tttccgagaa   2400
agcgccatta aagatattat tgatatcatc aacgactatg gggttaatat tgtcatttac   2460
gaacccatgc ttggcgagga tattggctac agggttgtca aggacttaga gcagttcaaa   2520
aacgagtcta caatcattgt gtcaaatcgc tttgaggacg acctaggaga tgtcattgat   2580
aaggtttata cgagagatgt ctttggaaga gactagtcag aaaacgaatg gcactcataa   2640
ggaaccacaa atcaaggagg aactcatgac aaaggtcaga aaagccatta tcccagccgc   2700
cggcctaggc actcgcttcc tgcccgccac caaggcactg gccaaggaaa tgctcccaat   2760
```

```
cgtcgataag ccaaccattc aattcatcgt cgaggaagcc ctaaaggcag gtatcgagga      2820
gattcttgtc gtcaccggca aggccaaacg ctctatcgag gaccactttg actccaactt      2880
cgagctcgaa tacaatctcc aagccaaggg caaaaccgag ctactcaagc tcgttgatga      2940
gaccactgcc atcaacctgc acttcattcg tcagagccac cctagaggac taggggacgc      3000
tgtcctccaa gccaaggcct tgttggcaa tgagcccttt gtggtcatgc tggggatga       3060 cctcatggat attaccaatc ctagtgccaa gcccttgacc aagcagctta ttgaggatta      3120
tgattgcaca cacgcctcaa cgattgcagt gatgagggtg ccgcatgagg aggtttccaa      3180
ttatggtgtg attgcaccgc aagggaaggc tgttaagggc ttgtatagtg tggagaccct      3240
tgttgagaag ccaagtccag atgaggcacc gagtgactta gcgattattg gtcgatattt      3300
gttgacgcct gagattttg ccatattgga gaagcaggcg cctggagctg caatgaggt        3360 acagctgacc gatgcgattg acaagctcaa taagacacag cgggtttttg cgagggagtt      3420
taagggagag cggtatgatg ttggggacaa gtttggcttt atgaagacct cacttgacta      3480
tgctctcaag caccctcagg tcaaggacga cctcactgac tacattataa agctcagtaa      3540
gcaactgaac aaggacgtca agaaataggc gtttattgat cagctattgc agagctattt      3600
aaaagcattt agagctttaa ggtgggatac tagaggattg gtatctcact ttttaggctg      3660
acttgtatta ataccaaaag ccaaaactag gcagataagc ataaggaatt agattaaaaa      3720
taaggaacca aaacatgaaa aactacgcca ttatcctagc agctggaaag gaacgcgca       3780 tgaagtcagc gcttcccaag gtgctgcaca aggtatcagg cctaagcatg ctggagcatg      3840
tcctcaagag tgtctcagcc ctagcccctc aaaagcagct cacagtgatc ggtcatcagg      3900
cagagcaggt gcgtgctgtc ctaggagagc aatcgctaac agtggtgcaa gaggagcagc      3960
tagggacagg ccatgcagtc atgatggcag aagaggagct atctggctta gagggcaaa       4020 ccctagtgat tgcaggtgac accccctga tcagaggaga aagcctcaag gctctgctag       4080
actatcatat cagagaaaag aatgtggcaa ccattctcac agccaatgcc aaggatccct      4140
ttggctatgg acgaatcatt cgcaatgcag caggagaggt ggtcaacatc gttgagcaaa      4200
aggatgctaa tgaggcagag caagaggtca aggagatcaa cacagggact tatatctttg      4260
acaataagcg ccttttgag gctctaaagc atctcacgac tgataatgcc caaggggagt       4320
actacctaac cgatgtgatc agtattttca aggctggcca agaaagggtt ggcgcttacc      4380
tgctgaagga ctttgatgag agcctagggg ttaatgatcg cttagctcta gcccaggccg      4440
aggtgattat gcaagagcgg atcaacaggc agcacatgct taatgggtg accctgcaaa       4500 acccggcagc tacctatatt gaaagcagtg tagagattgc accagacgtc ttgattgaag      4560
ccaatgtgac cttaaaggga cagactagaa ttggcagcag aagtgtcata agcaatggga      4620
gctatatcct tgattcgagg cttggtgagg gtgtagtggt tagccagtcg gtgattgagg      4680
cttcagtctt agcagatgga gtgacagtag gccatatgc acacattcgc ccggactccc       4740
agctcgatga gtgtgttcat attgggaact tgtagaggt taaggggtct catctagggg       4800
ccaataccaa ggcagggcat ttgacttacc tggggaatgc cgagattggc tcagaggtta      4860
acattggtgc aggaagcatt acggttaatt atgatggtca acggaaatac cagacagtga      4920
ttggcgatca cgcttttatt gggagtcatt cgactttgat agctccggta gaggttgggg      4980
```

```
agaatgcttt aacagcagca gggtctacga tagcccagtc agtgccggca gacagtgtgg    5040
ctatagggcg cagccgtcag gtggtgaagg aaggctatgc caagaggctg ccgcaccacc    5100
caaatcaagc ctaatcgctc aaccaaaaga ggcaggtgag aaaacctagg ccattaaa     5158
```

METHODS FOR PRODUCING HYALURONAN IN A RECOMBINANT HOST CELL

CROSS-REFERENCES TO RELATED APPLICATION

This application claims priority from U.S. provisional patent application Ser. No. 60/342,644 filed Dec. 21, 2001, which application is fully incorporated herein by reference.

BACKGROUND OF THE INVENTION

1. Field of the Invention

The present invention relates to methods for producing a hyaluronan in a recombinant host cell.

2. Description of the Related Art

The most abundant heteropolysaccharides of the body are the glycosaminoglycans. Glycosaminoglycans are unbranched carbohydrate polymers, consisting of repeating disaccharide units (only keratan sulphate is branched in the core region of the carbohydrate). The disaccharide units generally comprise, as a first saccharide unit, one of two modified sugars —N-acetylgalactosamine (GalNAc) or N-acetylglucosamine (GlcNAc). The second unit is usually an uronic acid, such as glucuronic acid (GlcUA) or iduronate.

Glycosaminoglycans are negatively charged molecules, and have an extended conformation that imparts high viscosity when in solution. Glycosaminoglycans are located primarily on the surface of cells or in the extracellular matrix. Glycosaminoglycans also have low compressibility in solution and, as a result, are ideal as a physiological lubricating fluid, e.g., joints. The rigidity of glycosaminoglycans provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Hyaluronan forms large aggregates with certain proteoglycans, but is an exception as free carbohydrate chains form non-covalent complexes with proteoglycans.

Numerous roles of hyaluronan in the body have been identified (see, Laurent T. C. and Fraser J. R. E., 1992, *FASEB J.* 6: 2397-2404; and Toole B. P., 1991, "Proteoglycans and hyaluronan in morphogenesis and differentiation." In: Cell Biology of the Extracellular Matrix, pp. 305-341, Hay E. D., ed., Plenum, N.Y.). Hyaluronan is present in hyaline cartilage, synovial joint fluid, and skin tissue, both dermis and epidermis. Hyaluronan is also suspected of having a role in numerous physiological functions, such as adhesion, development, cell motility, cancer, angiogenesis, and wound healing. Due to the unique physical and biological properties of hyaluronan, it is employed in eye and joint surgery and is being evaluated in other medical procedures. Products of hyaluronan have also been developed for use in orthopaedics, rheumatology, and dermatology.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter.

The microorganisms used for production of hyaluronic acid by fermentation are strains of pathogenic bacteria, foremost among them being several *Streptococcus* spp. The group A and group C streptococci surround themselves with a nonantigenic capsule composed of hyaluronan, which is identical in composition to that found in connective tissue and joints. *Pasteurella multocida*, another pathogenic encapsulating bacteria, also surrounds its cells with hyaluronan.

Hyaluronan synthases have been described from vertebrates, bacterial pathogens, and algal viruses (DeAngelis, P. L., 1999, *Cell. Mol. Life Sci.* 56: 670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al. disclose the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (*Proc. Natl. Acad. Sci. USA.* 98, 4658-4663, 2001). WO 99/51265 describes a nucleic acid segment having a coding region for a *Streptococcus equisimilis* hyaluronan synthase.

Bacilli are well established as host cell systems for the production of native and recombinant proteins. It is an object of the present invention to provide methods for producing a hyaluronan in a recombinant *Bacillus* host cell.

BRIEF SUMMARY OF THE INVENTION

The present invention relates to methods for producing a hyaluronic acid, comprising: (a) cultivating a *Bacillus* host cell under conditions suitable for production of the hyaluronic acid, wherein the *Bacillus* host cell comprises a nucleic acid construct comprising a hyaluronan synthase encoding sequence operably linked to a promoter sequence foreign to the hyaluronan synthase encoding sequence; and (b) recovering the hyaluronic acid from the cultivation medium.

In preferred embodiments, the nucleic acid construct further comprises one or more genes encoding enzymes in the biosynthesis of a precursor sugar of the hyaluronic acid or the *Bacillus* host cell further comprises one or more second nucleic acid constructs comprising one or more genes encoding enzymes in the biosynthesis of the precursor sugar.

In another preferred embodiment, the one or more genes encoding a precursor sugar are under the control of the same or a different promoter(s) as the hyaluronan synthase encoding sequence.

The present invention also relates to *Bacillus* host cells comprising a nucleic acid construct comprising a hyaluronan synthase encoding sequence operably linked to a promoter sequence foreign to the hyaluronan synthase encoding sequence, and to such nucleic acid constructs.

The present invention also relates to an isolated nucleic acid sequence encoding a hyaluronan synthase operon comprising a hyaluronan synthase gene or a portion thereof and a UDP-glucose 6-dehydrogenase gene, and optionally one or more genes selected from the group consisting of a UDP-glucose pyrophosphorylase gene, UDP-N-acetylglucosamine pyrophosphorylase gene, and glucose-6-phosphate isomerase gene.

The present invention also relates to isolated nucleic acid sequences encoding a UDP-glucose 6-dehydrogenase selected from the group consisting of: (a) a nucleic acid sequence encoding a polypeptide having an amino acid sequence which has at least about 75%, about 80%, about 85%, about 90%, or about 95% identity to SEQ ID NO: 41; (b) a nucleic acid sequence having at least about 75%, about 80%, about 85%, about 90%, or about 95% homology to SEQ ID NO: 40; (c) a nucleic acid sequence which hybridizes under medium or high stringency conditions with (i) the nucleic acid sequence of SEQ ID NO: 40, (ii) the cDNA sequence contained in SEQ ID NO: 40, or (iii) a complementary strand of (i) or (ii); and (d) a subsequence of (a), (b), or (c), wherein the subsequence encodes a polypeptide fragment which has UDP-glucose 6-dehydrogenase activity.

The present invention also relates to isolated nucleic acid sequences encoding a UDP-glucose pyrophosphorylase selected from the group consisting of: (a) a nucleic acid sequence encoding a polypeptide having an amino acid sequence which has at least about 90%, about 95%, or about 97% identity to SEQ ID NO: 43; (b) a nucleic acid sequence having at least about 90%, about 95%, or about 97% homology to SEQ ID NO: 42; (c) a nucleic acid sequence which hybridizes under low, medium, or high stringency conditions with (i) the nucleic acid sequence of SEQ ID NO: 42, (ii) the cDNA sequence contained in SEQ ID NO: 42, or (iii) a complementary strand of (i) or (ii); and (d) a subsequence of (a), (b), or (c), wherein the subsequence encodes a polypeptide fragment which has UDP-N-acetylglucosamine pyrophosphorylase activity.

The present invention also relates to isolated nucleic acid sequences encoding a UDP-N-acetylglucosamine pyrophosphorylase selected from the group consisting of: (a) a nucleic acid sequence encoding a polypeptide having an amino acid sequence which has at least about 75%, about 80%, about 85%, about 90%, or about 95% identity to SEQ ID NO: 45; (b) a nucleic acid sequence having at least about 75%, about 80%, about 85%, about 90%, or about 95% homology to SEQ ID NO: 44; (c) a nucleic acid sequence which hybridizes under low, medium, or high stringency conditions with (i) the nucleic acid sequence of SEQ ID NO: 44, (ii) the cDNA sequence contained in SEQ ID NO: 44, or (iii) a complementary strand of (i) or (ii); and (d) a subsequence of (a), (b), or (c), wherein the subsequence encodes a polypeptide fragment which has UDP-N-acetylglucosamine pyrophosphorylase activity.

DETAILED DESCRIPTION OF THE INVENTION

The present invention relates to methods for producing a hyaluronan, comprising: (a) cultivating a *Bacillus* host cell under conditions suitable for production of the hyaluronan, wherein the *Bacillus* host cell comprises a nucleic acid construct comprising a hyaluronan synthase encoding sequence operably linked to a promoter sequence foreign to the hyaluronan synthase encoding sequence; and (b) recovering the hyaluronan from the cultivation medium.

The methods of the present invention represent an improvement over the production of hyaluronan from pathogenic, encapsulating bacteria. In encapsulating bacteria, a large quantity of the hyaluronan is produced in the capsule. In processing and purifying hyaluronan from such sources, it is first necessary to remove the hyaluronan from the capsule, such as by the use of a surfactant, or detergent, such as SDS. This creates a complicating step in commercial production of hyaluronan, as the surfactant must be added in order to liberate a large portion of the hyaluronan, and subsequently the surfactant must be removed prior to final purification.

The present invention allows the production of a large quantity of a hyaluronan, which is produced in a non-encapsulating host cell, as free hyaluronan. When viewed under the microscope, there is no visible capsule associated with the recombinant strains of *Bacillus,* whereas the pathogenic strains traditionally used in hyaluronan production comprise a capsule of hyaluronan that is at least twice the diameter of the cell itself.

Since the hyaluronan of the recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. Alternatively, the hyaluronan may be dried or concentrated from the filtrate solution by using evaporative techniques known to the art, such as spray drying.

The methods of the present invention thus represent an improvement over existing techniques for commercially producing hyaluronan by fermentation, in not requiring the use of a surfactant in the purification of hyaluronan from cells in culture.

Hyaluronic Acid

Figure 1:
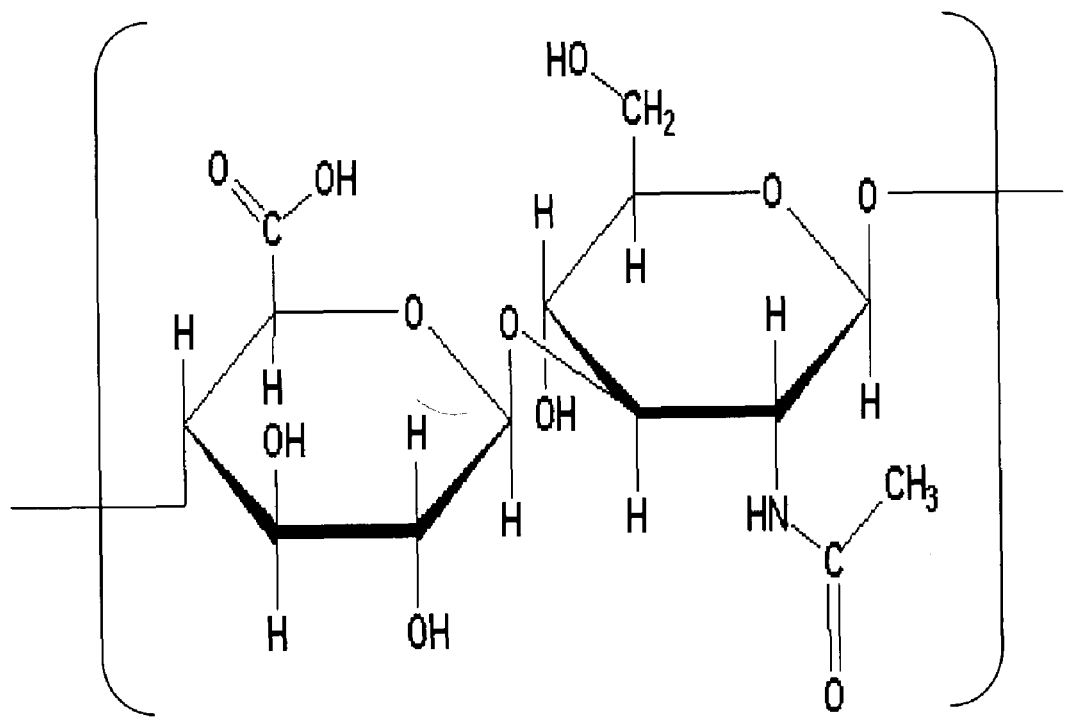
FIG. 1 shows the chemical structure of hyaluronan.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds (FIG. 1). Hyaluronic acid is also known as hyaluronan, hyaluronate, or HA. The terms hyaluronan and hyaluronic acid are used interchangeably herein.

In a preferred embodiment, the hyaluronic acid obtained by the methods of the present invention has a molecular weight of about 10,000 to about 10,000,000 Da. In a more preferred embodiment, the hyaluronic acid obtained by the methods of the present invention has a molecular weight of about 25,000 to about 5,000,000 Da. In a most preferred embodiment, the hyaluronic acid obtained by the methods of the present invention has a molecular weight of about 50,000 to about 3,000,000 Da.

The level of hyaluronic acid produced by a *Bacillus* host cell of the present invention may be determined according to the modified carbazole method (Bitter and Muir, 1962, *Anal Biochem.* 4: 330-334). Moreover, the average molecular weight of the hyaluronic acid may be determined using standard methods in the art, such as those described by Ueno et al., 1988, *Chem. Pharm. Bull.* 36, 4971-4975; Wyatt, 1993, *Anal. Chim. Acta* 272: 1-40; and Wyatt Technologies, 1999, "Light Scattering University DAWN Course Manual" and "DAWN EOS Manual" Wyatt Technology Corporation, Santa Barbara, Calif.

The hyaluronic acid obtained by the methods of the present invention may be subjected to various techniques known in the art to modify the hyaluronic acid, such as crosslinking as described, for example, in U.S. Pat. Nos. 5,616,568, 5,652, 347, and 5,874,417. Moreover, the molecular weight of the hyaluronic acid may be altered using techniques known in the art.

Host Cells

In the methods of the present invention, the *Bacillus* host cell may be any *Bacillus* cell suitable for recombinant production of hyaluronic acid. The *Bacillus* host cell may be a wild-type *Bacillus* cell or a mutant thereof. *Bacillus* cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164 Δ5 (see U.S. Pat. No. 5,891,701) or *Bacillus subtilis* 168 Δ4.

Transformation of the *Bacillus* host cell with a nucleic acid construct of the present invention may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278).

Nucleic Acid Constructs

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence. The term "coding sequence" is defined herein as a sequence which is transcribed into mRNA and translated into an enzyme of interest when placed under the control of the below mentioned control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The techniques used to isolate or clone a nucleic acid sequence encoding a polypeptide are well known in the art and include, for example, isolation from genomic DNA, preparation from cDNA, or a combination thereof. The cloning of the nucleic acid sequences from such genomic DNA can be effected, e.g., by using antibody screening of expression libraries to detect cloned DNA fragments with shared structural features or the well known polymerase chain reaction (PCR). See, for example, Innis et al., 1990, *PCR Protocols: A Guide to Methods and Application*, Academic Press, N.Y. Other nucleic acid amplification procedures such as ligase chain reaction, ligated activated transcription, and nucleic acid sequence-based amplification may be used. The cloning procedures may involve excision and isolation of a desired nucleic acid fragment comprising the nucleic acid sequence encoding the polypeptide, insertion of the fragment into a vector molecule, and incorporation of the recombinant vector into a *Bacillus* cell where clones of the nucleic acid sequence will be replicated. The nucleic acid sequence may be of genomic, cDNA, RNA, semi-synthetic, synthetic origin, or any combinations thereof.

An isolated nucleic acid sequence encoding an enzyme may be manipulated in a variety of ways to provide for expression of the enzyme. Manipulation of the nucleic acid sequence prior to its insertion into a construct or vector may be desirable or necessary depending on the expression vector or *Bacillus* host cell. The techniques for modifying nucleic acid sequences utilizing cloning methods are well known in the art. It will be understood that the nucleic acid sequence may also be manipulated in vivo in the host cell using methods well known in the art.

A number of enzymes are involved in the biosynthesis of hyaluronic acid. These enzymes include hyaluronan synthase, UDP-glucose 6-dehydrogenase, UDP-glucose pyrophosphorylase, UDP-N-acetylglucosamine pyrophosphorylase, glucose-6-phosphate isomerase, hexokinase, phosphoglucomutase, amidotransferase, mutase, and acetyl transferase. Hyaluronan synthase is the key enzyme in the production of hyaluronic acid.

"Hyaluronan synthase" is defined herein as a synthase that catalyzes the elongation of a hyaluronan chain by the addition of GlcUA and GlcNAc sugar precursors. The amino acid sequences of streptococcal hyaluronan synthases, vertebrate hyaluronan synthases, and the viral hyaluronan synthase are distinct from the *Pasteurella* hyaluronan synthase, and have been proposed for classification as Group I and Group II hyaluronan synthases, the Group I hyaluronan synthases including Streptococcal hyaluronan synthases (DeAngelis, 1999). For production of hyaluronan in *Bacillus* host cells, hyaluronan synthases of a eukaryotic origin, such as mammalian hyaluronan synthases, are less preferred.

The hyaluronan synthase encoding sequence may be any nucleic acid sequence capable of being expressed in a *Bacillus* host cell. The nucleic acid sequence may be of any origin. Preferred hyaluronan synthase genes include any of either Group I or Group II, such as the Group I hyaluronan synthase genes from *Streptococcus equisimilis, Streptococcus pyogenes, Streptococcus uberis*, and *Streptococcus equi* subsp. *zooepidemicus*, or the Group II hyaluronan synthase genes of *Pasturella multocida*.

In a preferred embodiment, the hyaluronan synthase encoding sequence is selected from the group consisting of (a) a nucleic acid sequence encoding a polypeptide with an amino acid sequence having at least about 70%, about 75%, about 80%, about 85%, about 90%, or about 95% identity to SEQ ID NO: 2, SEQ ID NO: 93, or SEQ ID NO: 103; (b) a nucleic acid sequence which hybridizes under low, medium, or high stringency conditions with SEQ ID NO: 1, SEQ ID NO: 92, or SEQ ID NO: 102; and (c) a complementary strand of (a) or (b).

In a more preferred embodiment, the hyaluronan synthase encoding sequence encodes a polypeptide having the amino acid sequence of SEQ ID NO: 2, SEQ ID NO: 93, or SEQ ID NO: 103; or a fragment thereof having hyaluronan synthase activity.

In another preferred embodiment, the hyaluronan synthase encoding sequence is selected from the group consisting of (a) a nucleic acid sequence encoding a polypeptide with an amino acid sequence having at least about 70%, about 75%, about 80%, about 85%, about 90%, or about 95% identity to SEQ ID NO: 95; (b) a nucleic acid sequence which hybridizes under low, medium, or high stringency conditions with SEQ ID NO: 94; and (c) a complementary strand of (a) or (b).

In another more preferred embodiment, the hyaluronan synthase encoding sequence encodes a polypeptide having the amino acid sequence of SEQ ID NO: 95, or a fragment thereof having hyaluronan synthase activity.

The methods of the present invention also include constructs whereby precursor sugars of hyaluronan are supplied to the host cell, either to the culture medium, or by being encoded by endogenous genes, by non-endogenous genes, or by a combination of endogenous and non-endogenous genes in the *Bacillus* host cell. The precursor sugar may be D-glucuronic acid or N-acetyl-glucosamine.

Figure 2:
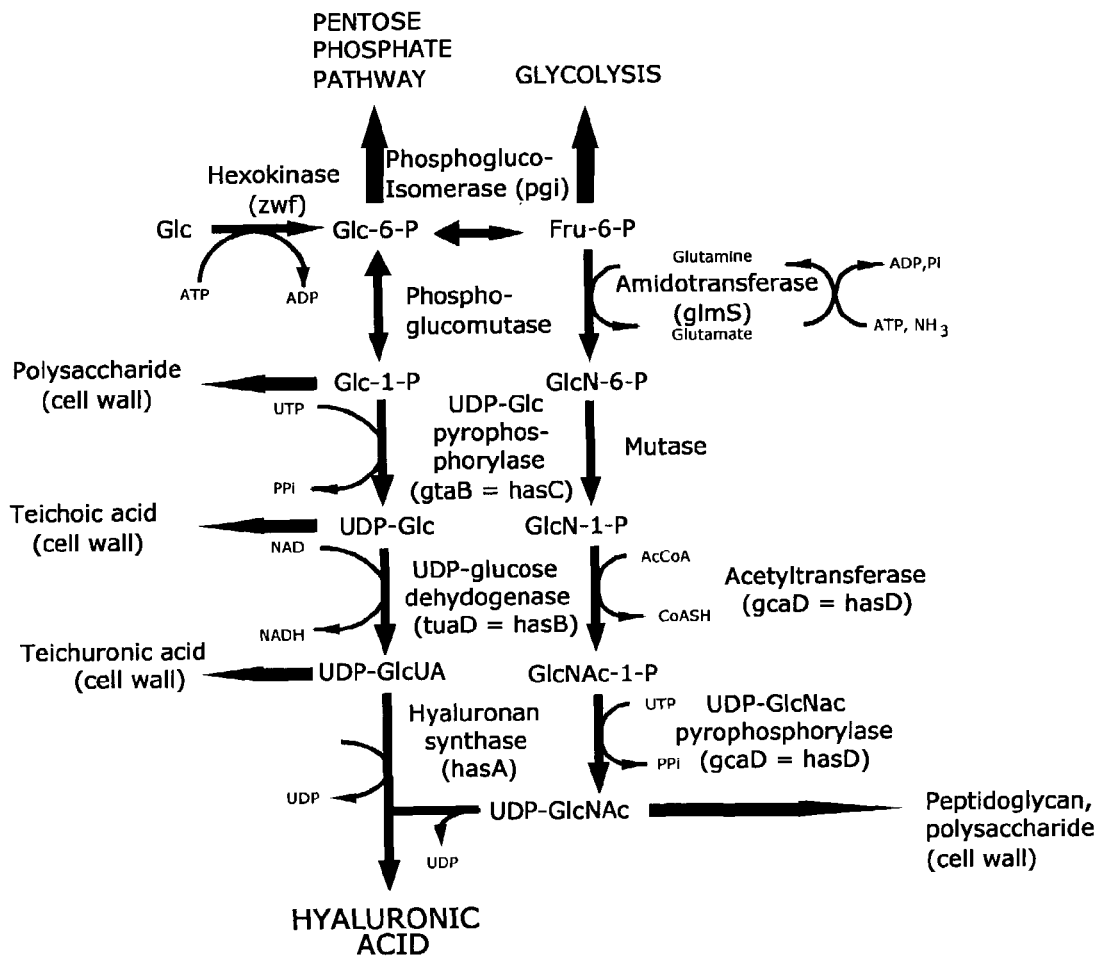
FIG. 2 shows the biosynthetic pathway for hyaluronan synthesis.

In the methods of the present invention, the nucleic acid construct may further comprise one or more genes encoding enzymes in the biosynthesis of a precursor sugar of a hyaluronan. Alternatively, the *Bacillus* host cell may further comprise one or more second nucleic acid constructs comprising one or more genes encoding enzymes in the biosynthesis of the precursor sugar. Hyaluronan production is improved by the use of constructs with a nucleic acid sequence or sequences encoding a gene or genes directing a step in the synthesis pathway of the precursor sugar of hyaluronan. By, "directing a step in the synthesis pathway of a precursor sugar of hyaluronan" is meant that the expressed protein of the gene is active in the formation of N-acetyl-glucosamine or D-glucuronic acid, or a sugar that is a precursor of either of N-acetyl-glucosamine and D-glucuronic acid (FIG. 2).

In a preferred method for supplying precursor sugars, constructs are provided for improving hyaluronan production in a host cell having a hyaluronan synthase, by culturing a host cell having a recombinant construct with a heterologous promoter region operably linked to a nucleic acid sequence encoding a gene directing a step in the synthesis pathway of a precursor sugar of hyaluronan. In a preferred method the host cell also comprises a recombinant construct having a promoter region operably linked to a hyaluronan synthase, which may use the same or a different promoter region than the nucleic acid sequence to a synthase involved in the biosynthesis of N-acetyl-glucosamine. In a further preferred embodiment, the host cell may have a recombinant construct with a promoter region operably linked to different nucleic acid sequences encoding a second gene involved in the synthesis of a precursor sugar of hyaluronan.

Thus, the present invention also relates to constructs for improving hyaluronan production by the use of constructs with a nucleic acid sequence encoding a gene directing a step in the synthesis pathway of a precursor sugar of hyaluronan. The nucleic acid sequence to the precursor sugar may be expressed from the same or a different promoter as the nucleic acid sequence encoding the hyaluronan synthase.

The genes involved in the biosynthesis of precursor sugars for the production of hyaluronic acid include a UDP-glucose 6-dehydrogenase gene, UDP-glucose pyrophosphorylase gene, UDP-N-acetylglucosamine pyrophosphorylase gene, glucose-6-phosphate isomerase gene, hexokinase gene, phosphoglucomutase gene, amidotransferase gene, mutase gene, and acetyl transferase gene.

In a cell containing a hyaluronan synthase, any one or combination of two or more of hasB, hasC and hasD, or the homologs thereof, such as the *Bacillus subtilis* tuaD, gtaB, and gcaD, respectively, as well as hasE, may be expressed to increase the pools of precursor sugars available to the hyaluronan synthase. The *Bacillus* genome is described in Kunst, et al., *Nature* 390, 249-256, "The complete genome sequence of the Gram-positive bacterium *Bacillus subtilis*" (Nov. 20, 1997). In some instances, such as where the host cell does not have a native hyaluronan synthase activity, the construct may include the hasA gene.

The nucleic acid sequence encoding the biosynthetic enzymes may be native to the host cell, while in other cases heterologous sequence may be utilized. If two or more genes are expressed they may be genes that are associated with one another in a native operon, such as the genes of the HAS operon of *Streptococcus equisimilis*, which comprises hasA, hasB, hasC and hasD. In other instances, the use of some combination of the precursor gene sequences may be desired, without each element of the operon included. The use of some genes native to the host cell, and others which are exogenous may also be preferred in other cases. The choice will depend on the available pools of sugars in a given host cell, the ability of the cell to accommodate overproduction without interfering with other functions of the host cell, and whether the cell regulates expression from its native genes differently than exogenous genes.

As one example, depending on the metabolic requirements and growth conditions of the cell, and the available precursor sugar pools, it may be desirable to increase the production of N-acetyl-glucosamine by expression of a nucleic acid sequence encoding UDP-N-acetylglucosamine pyrophosphorylase, such as the hasD gene, the *Bacillus* gcaD gene, and homologs thereof. Alternatively, the precursor sugar may be D-glucuronic acid. In one such embodiment, the nucleic acid sequence encodes UDP-glucose 6-dehydrogenase. Such nucleic acid sequences include the *Bacillus* tuaD gene, the hasB gene of *Streptococcus*, and homologs thereof. The nucleic acid sequence may also encode UDP-glucose pyrophosphorylase, such as in the *Bacillus* gtaB gene, the hasC gene of *Streptococcus*, and homologs thereof.

In the methods of the present invention, the UDP-glucose 6-dehydrogenase gene may be a hasB gene or tuaD gene; or homologs thereof.

In a preferred embodiment, the hasB gene is selected from the group consisting of (a) a nucleic acid sequence encoding a polypeptide with an amino acid sequence having at least about 70%, about 75%, about 80%, about 85%, about 90%, or about 95% identity to SEQ ID NO: 41, SEQ ID NO: 97, or SEQ ID NO: 105; (b) a nucleic acid sequence which hybridizes under low, medium, or high stringency conditions with SEQ ID NO: 40, SEQ ID NO: 96, or SEQ ID NO: 104; and (c) a complementary strand of (a) or (b).

In a more preferred embodiment, the hasB gene encodes a polypeptide having the amino acid sequence of SEQ ID NO: 41, SEQ ID NO: 97, or SEQ ID NO: 105; or a fragment thereof having UDP-glucose 6-dehydrogenase activity.

In another preferred embodiment, the tuaD gene is selected from the group consisting of (a) a nucleic acid sequence encoding a polypeptide with an amino acid sequence having at least about 70%, about 75%, about 80%, about 85%, about 90%, or about 95% identity to SEQ ID NO: 12; (b) a nucleic acid sequence which hybridizes under low, medium, or high stringency conditions with SEQ ID NO: 11; and (c) a complementary strand of (a) or (b).

In another more preferred embodiment, the tuaD gene encodes a polypeptide having the amino acid sequence of SEQ ID NO: 12, or a fragment thereof having UDP-glucose 6-dehydrogenase activity.

In the methods of the present invention, the UDP-glucose pyrophosphorylase gene may be a hasC gene or gtaB gene; or homologs thereof.

In a preferred embodiment, the hasC gene is selected from the group consisting of (a) a nucleic acid sequence encoding a polypeptide with an amino acid sequence having at least about 70%, about 75%, about 80%, about 85%, about 90%, or about 95% identity to SEQ ID NO: 43, SEQ ID NO: 99, or SEQ ID NO: 107; (b) a nucleic acid sequence which hybridizes under low, medium, or high stringency conditions with SEQ ID NO: 42 or SEQ ID NO: 98, or SEQ ID NO: 106; and (c) a complementary strand of (a) or (b).

In another more preferred embodiment, the hasC gene encodes a polypeptide having the amino acid sequence of SEQ ID NO: 43 or SEQ ID NO: 99, or SEQ ID NO: 107; or a fragment thereof having UDP-glucose pyrophosphorylase activity.

In another preferred embodiment, the gtaB gene is selected from the group consisting of (a) a nucleic acid sequence encoding a polypeptide with an amino acid sequence having at least about 70%, about 75%, about 80%, about 85%, about 90%, or about 95% identity to SEQ ID NO: 22; (b) a nucleic acid sequence which hybridizes under low, medium, or high stringency conditions with SEQ ID NO: 21; and (c) a complementary strand of (a) or (b).

In another more preferred embodiment, the gtaB gene encodes a polypeptide having the amino acid sequence of SEQ ID NO: 22, or a fragment thereof having UDP-glucose pyrophosphorylase activity.

In the methods of the present invention, the UDP-N-acetylglucosamine pyrophosphorylase gene may be a hasD or gcaD gene; or homologs thereof.

In a preferred embodiment, the hasD gene is selected from the group consisting of (a) a nucleic acid sequence encoding a polypeptide with an amino acid sequence having at least about 75%, about 80%, about 85%, about 90%, or about 95% identity to SEQ ID NO: 45; (b) a nucleic acid sequence which hybridizes under low, medium, or high stringency conditions with SEQ ID NO: 44; and (c) a complementary strand of (a) or (b).

In another more preferred embodiment, the hasD gene encodes a polypeptide having the amino acid sequence of SEQ ID NO: 45, or a fragment thereof having UDP-N-acetylglucosamine pyrophosphorylase activity.

In another preferred embodiment, the gcaD gene is selected from the group consisting of (a) a nucleic acid sequence encoding a polypeptide with an amino acid sequence having at least about 70%, about 75%, about 80%, about 85%, about 90%, or about 95% identity to SEQ ID NO: 30; (b) a nucleic acid sequence which hybridizes under low, medium, or high stringency conditions with SEQ ID NO: 29; and (c) a complementary strand of (a) or (b).

In another more preferred embodiment, the gcaD gene encodes a polypeptide having the amino acid sequence of SEQ ID NO: 30, or a fragment thereof having UDP-N-acetylglucosamine pyrophosphorylase activity.

In the methods of the present invention, the glucose-6-phosphate isomerase gene may be a hasE or homolog thereof.

In a preferred embodiment, the hasE gene is selected from the group consisting of (a) a nucleic acid sequence encoding a polypeptide with an amino acid sequence having at least about 70%, about 75%, about 80%, about 85%, about 90%, or about 95% identity to SEQ ID NO: 101; (b) a nucleic acid sequence which hybridizes under low, medium, or high stringency conditions with SEQ ID NO: 100; and (c) a complementary strand of (a) or (b).

In another more preferred embodiment, the hasE gene encodes a polypeptide having the amino acid sequence of SEQ ID NO: 101, or a fragment thereof having glucose-6-phosphate isomerase activity.

In the methods of the present invention, the hyaluronan synthase gene and the one or more genes encoding a precursor sugar are under the control of the same promoter. Alternatively, the one or more genes encoding a precursor sugar are under the control of the same promoter but a different promoter driving the hyaluronan synthase gene. A further alternative is that the hyaluronan synthase gene and each of the genes encoding a precursor sugar are under the control of different promoters. In a preferred embodiment, the hyaluronan synthase gene and the one or more genes encoding a precursor sugar are under the control of the same promoter.

The present invention also relates to a nucleic acid construct comprising an isolated nucleic acid sequence encoding a hyaluronan synthase operon comprising a hyaluronan synthase gene and a UDP-glucose 6-dehydrogenase gene, and optionally one or more genes selected from the group consisting of a UDP-glucose pyrophosphorylase gene, UDP-N-acetylglucosamine pyrophosphorylase gene, and glucose-6-phosphate isomerase gene. A nucleic acid sequence encoding most of the hyaluronan synthase operon of *Streptococcus equisimilis* is found in SEQ ID NO: 108. This sequence contains the hasB (SEQ ID NO: 40) and hasC (SEQ ID nO: 42) homologs of the *Bacillus subtilis* tuaD gene (SEQ ID NO: 11) and gtaB gene (SEQ ID NO: 21), respectively, as is the case for *Streptococcus pyogenes*, as well as a homolog of the gcaD gene (SEQ ID NO: 29), which has been designated hasD (SEQ ID NO: 44). The *Bacillus subtilis* gcaD encodes UDP-N-acetylglucosamine pyrophosphorylase, which is involved in the synthesis of N-acetyl-glucosamine, one of the two sugars of hyaluronan. The *Streptococcus equisimilis* homolog of gcaD, hasD, is arranged by *Streptococcus equisimilis* on the hyaluronan synthase operon. The nucleic aci sequence also contains a portion of the hasA gene (the last 1156 bp of SEQ ID NO: 1).

In some cases the host cell will have a recombinant construct with a heterologous promoter region operably linked to a nucleic acid sequence encoding a gene directing a step in the synthesis pathway of a precursor sugar of hyaluronan, which may be in concert with the expression of hyaluronan synthase from a recombinant construct. The hyaluronan synthase may be expressed from the same or a different promoter region than the nucleic acid sequence encoding an enzyme involved in the biosynthesis of the precursor. In another preferred embodiment, the host cell may have a recombinant construct with a promoter region operably linked to a different nucleic acid sequence encoding a second gene involved in the synthesis of a precursor sugar of hyaluronan.

The nucleic acid sequence encoding the enzymes involved in the biosynthesis of the precursor sugar(s) may be expressed from the same or a different promoter as the nucleic acid sequence encoding the hyaluronan synthase. In the former sense, "artificial operons" are constructed, which may mimic the operon of *Streptococcus equisimilis* in having each hasA, hasB, hasC and hasD, or homologs thereof, or, alternatively, may utilize less than the full complement present in the *Streptococcus equisimilis* operon. The artificial operons" may also comprise a glucose-6-phosphate isomerase gene (hasE) as well as one or more genes selected from the group consisting of a hexokinase gene, phosphoglucomutase gene, amidotransferase gene, mutase gene, and acetyl transferase gene. In the artificial operon, at least one of the elements is heterologous to one other of the elements, such as the promoter region being heterologous to the encoding sequences.

In a preferred embodiment, the nucleic acid construct comprises hasA, tuaD, and gtaB. In another preferred embodiment, the nucleic acid construct comprises hasA, tuaD, gtaB, and gcaD. In another preferred embodiment, the nucleic acid construct comprises hasA and tuaD. In another preferred embodiment, the nucleic acid construct comprises hasA. In another preferred embodiment, the nucleic acid construct comprises hasA, tuaD, gtaB, gcaD, and hasE. In another preferred embodiment, the nucleic acid construct comprises hasA, hasB, hasC, and hasD. In another preferred embodiment, the nucleic acid construct comprises hasA, hasB, hasC, hasD, and hasE. Based on the above preferred embodiments, the genes noted can be replaced with homologs thereof.

In the methods of the present invention, the nucleic acid constructs comprise a hyaluronan synthase encoding sequence operably linked to a promoter sequence foreign to the hyaluronan synthase encoding sequence. The promoter sequence may be, for example, a single promoter or a tandem promoter.

"Promoter" is defined herein as a nucleic acid sequence involved in the binding of RNA polymerase to initiate transcription of a gene. "Tandem promoter" is defined herein as two or more promoter sequences each of which is operably linked to a coding sequence and mediates the transcription of the coding sequence into mRNA. "Operably linked" is defined herein as a configuration in which a control sequence, e.g., a promoter sequence, is appropriately placed at a position relative to a coding sequence such that the control sequence directs the production of a polypeptide encoded by the coding sequence. As noted earlier, a "coding sequence" is defined herein as a nucleic acid sequence which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

In a preferred embodiment, the promoter sequences may be obtained from a bacterial source. In a more preferred embodiment, the promoter sequences may be obtained from a gram positive bacterium such as a *Bacillus* strain, e.g., *Bacillus agaradherens*, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

Examples of suitable promoters for directing the transcription of a nucleic acid sequence in the methods of the present invention are the promoters obtained from the *E. coli* lac operon, *Streptomyces coelicolor* agarase gene (dagA), *Bacillus lentus* or *Bacillus clausii* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, prokaryotic beta-lactamase gene (Villa-Kamaroff et al., 1978, *Proceedings of the National Academy of Sciences USA* 75:3727-3731). Other examples are the promoter of the spo1 bacterial phage promoter and the tac promoter (DeBoer et al., 1983, *Proceedings of the National Academy of Sciences USA* 80:21-25). Further promoters are described in "Useful proteins from recombinant bacteria" in *Scientific American*, 1980, 242:74-94; and in Sambrook, Fritsch, and Maniatus, 1989, *Molecular Cloning, A Laboratory Manual*, 2d edition, Cold Spring Harbor, N.Y.

The promoter may also be a "consensus" promoter having the sequence TTGACA for the "−35" region and TATAAT for the "−10" region. The consensus promoter may be obtained from any promoter which can function in a *Bacillus* host cell. The construction of a "consensus" promoter may be accomplished by site-directed mutagenesis to create a promoter which conforms more perfectly to the established consensus sequences for the "−10" and "−35" regions of the vegetative "sigma A-type" promoters for *Bacillus subtilis* (Voskuil et al., 1995, *Molecular Microbiology* 17: 271-279).

In a preferred embodiment, the "consensus" promoter is obtained from a promoter obtained from the *E. coli* lac operon, *Streptomyces coelicolor* agarase gene (dagA), *Bacillus clausii* or *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, or prokaryotic beta-lactamase gene spo1 bacterial phage promoter. In a more preferred embodiment, the "consensus" promoter is obtained from *Bacillus amyloliquefaciens* alpha-amylase gene (amyQ).

Widner, et al., U.S. Pat. Nos. 6,255,076 and 5,955,310 describe tandem promoters and constructs and methods for use in expression in *Bacillus* cells, including the short consensus amyQ promoter (also called scBAN). The use of the cryIIIA stabilizer sequence, and constructs using the sequence, for improved production in *Bacillus* are also described therein.

Each promoter sequence of the tandem promoter may be any nucleic acid sequence which shows transcriptional activity in the *Bacillus* cell of choice including a mutant, truncated, and hybrid promoter, and may be obtained from genes encoding extracellular or intracellular polypeptides either homologous or heterologous to the *Bacillus* cell. Each promoter sequence may be native or foreign to the nucleic acid sequence encoding the polypeptide and native or foreign to the *Bacillus* cell. The promoter sequences may be the same promoter sequence or different promoter sequences.

The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the *Bacillus* cell.

In a preferred embodiment, the tandem promoter contains at least the amyQ promoter of the *Bacillus amyloliquefaciens* alpha-amylase gene. In another preferred embodiment, the tandem promoter contains at least a "consensus" promoter having the sequence TTGACA for the "−35" region and TATAAT for the "−10" region. In another preferred embodiment, the tandem promoter contains at least the amyL promoter of the *Bacillus licheniformis* alpha-amylase gene. In another preferred embodiment, the tandem promoter contains at least the cryIIIA promoter or portions thereof (Agaisse and Lereclus, 1994, *Molecular Microbiology* 13: 97-107).

In a more preferred embodiment, the tandem promoter contains at least the amyL promoter and the cryIIIA promoter. In another more preferred embodiment, the tandem promoter contains at least the amyQ promoter and the cryIIIA promoter. In another more preferred embodiment, the tandem promoter contains at least a "consensus" promoter having the sequence TTGACA for the "−35" region and TATAAT for the "−10" region and the cryIIIA promoter. In another more preferred embodiment, the tandem promoter contains at least two copies of the amyL promoter. In another more preferred embodiment, the tandem promoter contains at least two copies of the amyQ promoter. In another more preferred embodiment, the tandem promoter contains at least two copies of a "consensus" promoter having the sequence TTGACA for the "−35" region and TATAAT for the "−10" region. In another more preferred embodiment, the tandem promoter contains at least two copies of the cryIIIA promoter.

"An mRNA processing/stabilizing sequence" is defined herein as a sequence located downstream of one or more promoter sequences and upstream of a coding sequence to which each of the one or more promoter sequences are operably linked such that all mRNAs synthesized from each promoter sequence may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, *Journal of Bacteriology* 177: 3465-3471). The mRNA processing/stabilizing sequence is complementary to the 3' extremity of a bacterial 16S ribosomal RNA. In a preferred embodiment, the mRNA processing/stabilizing sequence generates essentially single-size transcripts with a stabilizing sequence at the 5' end of the transcripts. The mRNA processing/stabilizing sequence is preferably one, which is complementary to the 3' extremity of a bacterial 16S ribosomal RNA. See, U.S. Pat. Nos. 6,255,076 and 5,955,310.

In a more preferred embodiment, the mRNA processing/stabilizing sequence is the *Bacillus thuringiensis* cryIIIA mRNA processing/stabilizing sequence disclosed in WO 94/25612 and Agaisse and Lereclus, 1994, supra, or portions thereof which retain the mRNA processing/stabilizing function. In another more preferred embodiment, the mRNA processing/stabilizing sequence is the *Bacillus subtilis* SP82 mRNA processing/stabilizing sequence disclosed in Hue et al., 1995, supra, or portions thereof which retain the mRNA processing/stabilizing function.

When the cryIIIA promoter and its mRNA processing/stabilizing sequence are employed in the methods of the present invention, a DNA fragment containing the sequence disclosed in WO 94/25612 and Agaisse and Lereclus, 1994, supra, or portions thereof which retain the promoter and mRNA processing/stabilizing functions, may be used. Furthermore, DNA fragments containing only the cryIIIA promoter or only the cryIIIA mRNA processing/stabilizing sequence may be prepared using methods well known in the art to construct various tandem promoter and mRNA processing/stabilizing sequence combinations. In this embodiment, the cryIIIA promoter and its mRNA processing/stabilizing sequence are preferably placed downstream of the other promoter sequence(s) constituting the tandem promoter and upstream of the coding sequence of the gene of interest.

The isolated nucleic acid sequence encoding the desired enzyme(s) involved in hyaluronic acid production may then be further manipulated to improve expression of the nucleic acid sequence. Expression will be understood to include any step involved in the production of the polypeptide including, but not limited to, transcription, post-transcriptional modification, translation, post-translational modification, and secretion. The techniques for modifying nucleic acid sequences utilizing cloning methods are well known in the art.

A nucleic acid construct comprising a nucleic acid sequence encoding an enzyme may be operably linked to one or more control sequences capable of directing the expression of the coding sequence in a *Bacillus* cell under conditions compatible with the control sequences.

The term "control sequences" is defined herein to include all components which are necessary or advantageous for expression of the coding sequence of a nucleic acid sequence. Each control sequence may be native or foreign to the nucleic acid sequence encoding the enzyme. In addition to promoter sequences described above, such control sequences include, but are not limited to, a leader, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding an enzyme.

The control sequence may also be a suitable transcription terminator sequence, a sequence recognized by a *Bacillus* cell to terminate transcription. The terminator sequence is operably linked to the 3' terminus of the nucleic acid sequence encoding the enzyme or the last enzyme of an operon. Any terminator which is functional in the *Bacillus* cell of choice may be used in the present invention.

The control sequence may also be a suitable leader sequence, a nontranslated region of a mRNA which is important for translation by the *Bacillus* cell. The leader sequence is operably linked to the 5' terminus of the nucleic acid sequence encoding the enzyme. Any leader sequence which is functional in the *Bacillus* cell of choice may be used in the present invention.

The control sequence may also be a signal peptide coding region, which codes for an amino acid sequence linked to the amino terminus of a polypeptide which can direct the expressed polypeptide into the cell's secretory pathway. The signal peptide coding region may be native to the polypeptide or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a *Bacillus* cell of choice may be used in the present invention.

An effective signal peptide coding region for *Bacillus* cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109-137.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE) and *Bacillus subtilis* neutral protease (nprT).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Expression Vectors

In the methods of the present invention, a recombinant expression vector comprising a nucleic acid sequence, a promoter, and transcriptional and translational stop signals may be used for the recombinant production of an enzyme involved in hyaluronic acid production. The various nucleic acid and control sequences described above may be joined together to produce a recombinant expression vector which may include one or more convenient restriction sites to allow for insertion or substitution of the nucleic acid sequence encoding the polypeptide or enzyme at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the *Bacillus* cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the *Bacillus* cell, is integrated into the genome and replicated together with the chromosome(s) into which it has been integrated. The vector system may be a single vector or plasmid or two or more vectors or plasmids which together contain the total DNA to be introduced into the genome of the *Bacillus* cell, or a transposon may be used.

The vectors of the present invention preferably contain an element(s) that permits integration of the vector into the *Bacillus* host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the *Bacillus* cell. The additional nucleic acid sequences enable the vector to be integrated into the *Bacillus* cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the *Bacillus* cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the *Bacillus* cell in question. Examples of bacterial origins of replication are the origins of replication of plasmids pUB110, pE194, pTA1060, and pAMβ1 permitting replication in *Bacillus*. The origin of replication may be one having a mutation to make its function temperature-sensitive in the *Bacillus* cell (see, e.g., Ehrlich, 1978, *Proceedings of the National Academy of Sciences USA* 75:1433).

The vectors preferably contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Furthermore, selection may be accomplished by co-transformation, e.g., as described in WO 91/09129, where the selectable marker is on a separate vector.

More than one copy of a nucleic acid sequence may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. A convenient method for achieving amplification of genomic DNA sequences is described in WO 94/14968.

The procedures used to ligate the elements described above to construct the recombinant expression vectors are well known to one skilled in the art (see, e.g., Sambrook et al., 1989, supra).

Production

In the methods of the present invention, the *Bacillus* host cells are cultivated in a nutrient medium suitable for production of the hyaluronic acid using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the enzymes involved in hyaluronic acid synthesis to be expressed and the hyaluronic acid to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted hyaluronic acid can be recovered directly from the medium.

The resulting hyaluronic acid may be isolated by methods known in the art. For example, the hyaluronic acid may be isolated from the nutrient medium by conventional procedures including, but not limited to, centrifugation, filtration, extraction, spray-drying, evaporation, or precipitation. The isolated hyaluronic acid may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, N.Y., 1989).

In the methods of the present invention, the *Bacillus* host cells produce greater than about 4 g, preferably greater than about 6 g, more preferably greater than about 8 g, even more preferably greater than about 10 g, and most preferably greater than about 12 g of hyaluronic acid per liter.

Deletions/Disruptions

Gene deletion or replacement techniques may be used for the complete removal of a selectable marker gene or other undesirable gene. In such methods, the deletion of the selectable marker gene may be accomplished by homologous recombination using a plasmid that has been constructed to contiguously contain the 5' and 3' regions flanking the selectable marker gene. The contiguous 5' and 3' regions may be introduced into a Bacillus cell on a temperature-sensitive plasmid, e.g., pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, for example, Perego, 1993, *In* A. L. Sonneshein, J. A. Hoch, and R. Losick, editors, *Bacillus subtilis and Other Gram-Positive Bacteria*, Chapter 42, American Society of Microbiology, Washington, D.C., 1993).

A selectable marker gene may also be removed by homologous recombination by introducing into the mutant cell a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

U.S. Pat. No. 5,891,701 discloses techniques for deleting several genes including spoIIAC, aprE, nprE, and amyE.

Other undesirable biological compounds may also be removed by the above described methods such as the red pigment synthesized by cypX (accession no. BG12580) and/or yvmC (accession no. BG14121).

In a preferred embodiment, the *Bacillus* host cell is unmarked with any heterologous or exogenous selectable markers. In another preferred embodiment, the *Bacillus* host cell does not produce any red pigment synthesized by cypX and yvmC.

Isolated Nucleic Acid Sequences Encoding Polypeptides Having UDP-Glucose 6-Dehydrogenase Activity, UDP-Glucose Pyrophosphorylase Activity, or UDP-N-Acetylglucosamine Pyrophosphorylase Activity The term "UDP-glucose 6-dehydrogenase activity" is defined herein as a UDP glucose:NAD$^+$6-oxidoreductase activity which catalyzes the conversion of UDP-glucose in the presence of 2NAD$^+$ and water to UDP-glucuronate and 2NADH. For purposes of the present invention UDP-glucose 6-dehydrogenase activity is determined according to the procedure described by Jaenicke and Rudolph, 1986, *Biochemistry* 25: 7283-7287. One unit of UDP-glucose 6-dehydrogenase activity is defined as 1.0 μmole of UDP-glucuronate produced per minute at 25° C., pH 7.

The term "UDP-glucose pyrophosphorylase activity" is defined herein as a UTP:☐-D-glucose-1-phosphate uridylyltransferase activity which catalyzes the conversion of glucose-1-phosphate in the presence of UTP to diphosphate and UDP-glucose. For purposes of the present invention UDP-glucose pyrophosphorylase activity is determined according to the procedure described by Kamogawa et al., 1965, *J. Biochem.* (Tokyo) 57: 758-765 or Hansen et al., 1966, *Method Enzymol.* 8: 248-253. One unit of UDP-glucose pyrophosphorylase activity is defined as 1.0 μmole of UDP-glucose produced per minute at 25° C., pH 7.

The term "UDP-N-acetylglucosamine pyrophosphorylase activity" is defined herein as a UTP:N-acetyl-alpha-D-glucoamine-1-phosphate uridyltransferase activity which catalyzes the conversion of N-acetyl-alpha-D-glucosamine-1-phosphate in the presence of UTP to diphosphate and UDP-N-acetyl-alpha-D-glucoamine. For purposes of the present invention, UDP-N-acetylglucosamine pyrophosphorylase activity is determined according to the procedure described by Mangin-Lecreuix et al., 1994, *J. Bacteriology* 176: 5788-5795. One unit of UDP-N-acetylglucosamine pyrophosphorylase activity is defined as 1.0 μmole of UDP-N-acetyl-alpha-D-glucoamine produced per minute at 25° C., pH 7.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to SEQ ID NO: 41 of at least about 75%, preferably at least about 80%, more preferably at least about 85%, even more preferably at least about 90%, most preferably at least about 95%, and even most preferably at least about 97%, which have UDP-glucose 6-dehydrogenase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from SEQ ID NO: 41.

In another first embodiment, the present invention relates to isolated nucleic acid sequences encoding polypeptides having an amino acid sequence which has a degree of identity to SEQ ID NO: 43 of at least about 90%, preferably at least about 95%, and more preferably at least about 97%, which have UDP-glucose pyrophosphorylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from SEQ ID NO: 43.

In another first embodiment, the present invention relates to isolated nucleic acid sequences encoding polypeptides having an amino acid sequence which has a degree of identity to SEQ ID NO: 45 of at least about 75%, preferably at least about 80%, more preferably at least about 85%, even more preferably at least about 90%, most preferably at least about 95%, and even most preferably at least about 97%, which have UDP-N-acetylglucosamine pyrophosphorylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from SEQ ID NO: 45.

For purposes of the present invention, the degree of identity between two amino acid sequences is determined by the Clustal method (Higgins, 1989, *CABIOS* 5: 151-153) using the Vector NTI AlignX software package (Informax Inc., Bethesda, Md.) with the following defaults: pairwise alignment, gap opening penalty of 10, gap extension penalty of 0.1, and score matrix: blosum62mt2.

Preferably, the nucleic acid sequences of the present invention encode polypeptides that comprise the amino acid sequence of SEQ ID NO: 41, SEQ ID NO: 43, or SEQ ID NO: 45; or an allelic variant thereof; or a fragment thereof that has UDP-glucose 6-dehydrogenase, UDP-glucose pyrophosphorylase, or UDP-N-acetylglucosamine pyrophosphorylase activity, respectively. In a more preferred embodiment, the nucleic acid sequence of the present invention encodes a polypeptide that comprises the amino acid sequence of SEQ ID NO: 41, SEQ ID NO: 43, or SEQ ID NO: 45. In another preferred embodiment, the nucleic acid sequence of the present invention encodes a polypeptide that consists of the amino acid sequence of SEQ ID NO: 41, SEQ ID NO: 43, or SEQ ID NO: 45; or an allelic variant thereof; or a fragment thereof, wherein the polypeptide fragment has UDP-glucose 6-dehydrogenase, UDP-glucose pyrophosphorylase, or UDP-N-acetylglucosamine pyrophosphorylase activity, respectively. In another preferred embodiment, the nucleic acid sequence of the present invention encodes a polypeptide that consists of the amino acid sequence of SEQ ID NO: 41, SEQ ID NO: 43, or SEQ ID NO: 45.

The present invention also encompasses nucleic acid sequences which encode a polypeptide having the amino acid sequence of SEQ ID NO: 41, SEQ ID NO: 43, or SEQ ID NO: 45, which differ from SEQ ID NO: 40, SEQ ID NO: 42, or SEQ ID NO: 44 by virtue of the degeneracy of the genetic code. The present invention also relates to subsequences of SEQ ID NO: 40, SEQ ID NO: 42, or SEQ ID NO: 44 which encode fragments of SEQ ID NO: 41, SEQ ID NO: 43, or SEQ ID NO: 45, respectively, which have UDP-glucose 6-dehydrogenase, UDP-glucose pyrophosphorylase, or UDP-N-acetylglucosamine pyrophosphorylase activity, respectively.

A subsequence of SEQ ID NO: 40 is a nucleic acid sequence encompassed by SEQ ID NO: 40 except that one or more nucleotides from the 5' and/or 3' end have been deleted. Preferably, a subsequence contains at least 1020 nucleotides, more preferably at least 1080 nucleotides, and most preferably at least 1140 nucleotides. A fragment of SEQ ID NO: 41 is a polypeptide having one or more amino acids deleted from the amino and/or carboxy terminus of this amino acid sequence. Preferably, a fragment contains at least 340 amino acid residues, more preferably at least 360 amino acid residues, and most preferably at least 380 amino acid residues.

A subsequence of SEQ ID NO: 42 is a nucleic acid sequence encompassed by SEQ ID NO: 42 except that one or more nucleotides from the 5' and/or 3' end have been deleted. Preferably, a subsequence contains at least 765 nucleotides, more preferably at least 810 nucleotides, and most preferably at least 855 nucleotides. A fragment of SEQ ID NO: 43 is a polypeptide having one or more amino acids deleted from the amino and/or carboxy terminus of this amino acid sequence. Preferably, a fragment contains at least 255 amino acid residues, more preferably at least 270 amino acid residues, and most preferably at least 285 amino acid residues.

A subsequence of SEQ ID NO: 44 is a nucleic acid sequence encompassed by SEQ ID NO: 44 except that one or more nucleotides from the 5' and/or 3' end have been deleted. Preferably, a subsequence contains at least 1110 nucleotides, more preferably at least 1200 nucleotides, and most preferably at least 1290 nucleotides. A fragment of SEQ ID NO: 45 is a polypeptide having one or more amino acids deleted from the amino and/or carboxy terminus of this amino acid sequence. Preferably, a fragment contains at least 370 amino acid residues, more preferably at least 400 amino acid residues, and most preferably at least 430 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

In a second embodiment, the present invention relates to isolated nucleic acid sequences which have a degree of homology to SEQ ID NO: 40 of at least about 75%, preferably at least about 80%, more preferably at least about 85%, even more preferably at least about 90%, most preferably at least about 95%, and even most preferably at least about 97%.

In another second embodiment, the present invention relates to isolated nucleic acid sequences which have a degree of homology to SEQ ID NO: 42 of at least about 90%, preferably at least about 95%, and more preferably at least about 97%.

In another second embodiment, the present invention relates to isolated nucleic acid sequences which have a degree of homology to SEQ ID NO: 44 of at least about 75%, preferably at least about 80%, more preferably at least about 85%, even more preferably at least about 90%, most preferably at least about 95%, and even most preferably at least about 97%.

For purposes of the present invention, the degree of homology between two nucleic acid sequences is determined by the Vector NTI AlignX software package (Informax Inc., Bethesda, Md.) using the following defaults: pairwise alignment, gap opening penalty of 15, gap extension penalty of 6.6, and score matrix: swgapdnamt.

In a third embodiment, the present invention relates to isolated nucleic acid sequences encoding polypeptides having UDP-glucose 6-dehydrogenase, UDP-glucose pyrophosphorylase, or UDP-N-acetylglucosamine pyrophosphorylase activity, which hybridize under very low stringency conditions, preferably low stringency conditions, more preferably medium stringency conditions, more preferably medium-high stringency conditions, even more preferably high stringency conditions, and most preferably very high stringency conditions with (i) the nucleic acid sequence of SEQ ID NO: 40, SEQ ID NO: 42, or SEQ ID NO: 44, (ii) the cDNA sequence contained in SEQ ID NO: 40, SEQ ID NO: 42, or SEQ ID NO: 44, or (iii) a complementary strand of (i) or (ii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO: 40, SEQ ID NO: 42, or SEQ ID NO: 44 may be at least 100 nucleotides or preferably at least 200 nucleotides. Moreover, the respective subsequence may encode a polypeptide fragment which has UDP-glucose 6-dehydrogenase, UDP-glucose pyrophosphorylase, or UDP-N-acetylglucosamine pyrophosphorylase activity.

The nucleic acid sequence of SEQ ID NO: 40, SEQ ID NO: 42, or SEQ ID NO: 44, or subsequences thereof, as well as the amino acid sequence of SEQ ID NO: 41, SEQ ID NO: 43, or SEQ ID NO: 45, or a fragment thereof, may be used to design nucleic acid probes to identify and clone DNA encoding polypeptides having UDP-glucose 6-dehydrogenase, UDP-glucose pyrophosphorylase, or UDP-N-acetylglucosamine pyrophosphorylase activity, respectively, from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having UDP-glucose 6-dehydrogenase, UDP-glucose pyrophosphorylase, or UDP-N-acetylglucosamine pyrophosphorylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 40, SEQ ID NO: 42, or SEQ ID NO: 44, or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO: 40, SEQ ID NO: 42, or SEQ ID NO: 44, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO: 41, SEQ ID NO: 43, or SEQ ID NO: 45; or a subsequence thereof. In another preferred embodiment, the nucleic acid probe is SEQ ID NO: 40, SEQ ID NO: 42, or SEQ ID NO: 44. In another preferred embodiment, the nucleic acid probe is the nucleic acid sequence contained in plasmid pMRT106 which is contained in *Escherichia coli* NRRL B-30536, wherein the nucleic acid sequence encodes polypeptides having UDP-glucose 6-dehydrogenase, UDP-glucose pyrophosphorylase, and UDP-N-acetylglucosamine pyrophosphorylase activity.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a fourth embodiment, the present invention relates to isolated nucleic acid sequences which encode variants of the polypeptide having an amino acid sequence of SEQ ID NO: 41, SEQ ID NO: 43, or SEQ ID NO: 45 comprising a substitution, deletion, and/or insertion of one or more amino acids.

The amino acid sequences of the variant polypeptides may differ from the amino acid sequence of SEQ ID NO: 41, SEQ ID NO: 43, or SEQ ID NO: 45, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, N.Y. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 40, SEQ ID NO: 42, or SEQ ID NO: 44, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for enzyme activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The polypeptides encoded by the isolated nucleic acid sequences of the present invention have at least 20%, preferably at least 40%, more preferably at least 60%, even more preferably at least 80%, even more preferably at least 90%, and most preferably at least 100% of the UDP-glucose 6-dehydrogenase activity of the polypeptide of SEQ ID NO: 41, the UDP-glucose pyrophosphorylase activity of the polypeptide of SEQ ID NO: 43, or the UDP-N-acetylglucosamine pyrophosphorylase activity of the polypeptide of SEQ ID NO: 45.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide encoded by a nucleic acid sequence of the present invention is secreted extracellularly.

The nucleic acid sequences may be obtained from a bacterial source. For example, these polypeptides may be obtained from a gram positive bacterium such as a *Bacillus* strain, e.g., *Bacillus agaradherens, Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

In a preferred embodiment, the nucleic acid sequences are obtained from a *Streptococcus* or *Pastuerella* strain.

In a more preferred embodiment, the nucleic acid sequences are obtained from a *Streptococcus equisimilis, Streptococcus pyogenes, Streptococcus uberis,* or *Streptococcus equi* subs. *zooepidemicus* strain, or a *Pasteurella multocida* strain.

In a most preferred embodiment, the nucleic acid sequences are obtained from *Streptococcus equisimilis*, e.g., the nucleic acid sequence set forth in SEQ ID NO: 40, SEQ ID NO: 42, or SEQ ID NO: 44. In another most preferred embodiment, the nucleic acid sequence is the sequence contained in plasmid pMRT106 which is contained in *Escherichia coli* NRRL B-30536. In further most preferred embodiment, the nucleic acid sequence is SEQ ID NO: 40, SEQ ID NO: 42, or SEQ ID NO: 44.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The present invention also relates to mutant nucleic acid sequences comprising at least one mutation in the polypeptide coding sequence of SEQ ID NO: 40, SEQ ID NO: 42, and SEQ ID NO: 44, in which the mutant nucleic acid sequence encodes a polypeptide which consists of SEQ ID NO: 42, SEQ ID NO: 43, and SEQ ID NO: 45, respectively.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, N.Y. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Streptococcus*, or another or related organism and thus, for example, may be an allelic or species variant of the polypeptide encoding region of the nucleic acid sequence.

The present invention also relates to nucleic acid constructs comprising a nucleic acid sequence of the present invention operably linked to one or more control sequences which direct the expression of the coding sequence in a suitable host cell under conditions compatible with the control sequences.

The present invention also relates to recombinant expression vectors comprising a nucleic acid sequence of the present invention, a promoter, and transcriptional and translational stop signals.

The present invention also relates to recombinant host cells, comprising a nucleic acid sequence of the invention, which are advantageously used in the recombinant production of the polypeptides.

The present invention also relates to methods for producing a polypeptide having UDP-N-acetylglucosamine pyrophosphorylase activity comprising (a) cultivating a host cell under conditions suitable for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, N.Y., 1989).

The present invention further relates to the isolated polypeptides having UDP-glucose 6-dehydrogenase, UDP-glucose pyrophosphorylase, or UDP-N-acetylglucosamine pyrophosphorylase activity encoded by the nucleic acid sequences described above.

The present invention is further described by the following examples which should not be construed as limiting the scope of the invention.

EXAMPLES

Primers and Oligos

All primers and oligos were purchased (MWG Biotech Inc., High Point, N.C.)

Example 1

PCR Amplification and Cloning of the *Streptococcus equisimilis* hasA Gene and the *Bacillus subtilis* tuaD, gtaB, and gcaD Genes The *Streptococcus equisimilis* hyaluronan synthase gene (hasA, accession number AF023876, SEQ ID NOs: 1 [DNA sequence] and 2 [deduced amino acid sequence]) was PCR amplified from plasmid pKKseD (Weigel, 1997, *Journal of Biological Chemistry* 272: 32539-32546) using primers 1 and 2:

Primer 1:
(SEQ ID NO: 3)
5'-GAGCTCTATAAAAATGAGGAGGGAACCGAATGAGAACATTAAAAAAC
CT-3'

Primer 2:
(SEQ ID NO: 4)
5'-GTTAACGAATTCAGCTATGTAGGTACCTTATAATAATTTTTTACGTG
T-3'

PCR amplifications were conducted in triplicate in 50 μl reactions composed of 1 ng of pKKseD DNA, 0.4 μM each of primers 1 and 2, 200 μM each of dATP, dCTP, dGTP, and dTTP, 1×PCR Buffer II (Applied Biosystems, Inc., Foster City, Calif.) with 2.5 mM $MgCl_2$, and 2.5 units of AmpliTaq Gold™ DNA polymerase (Applied Biosystems, Inc., Foster City, Calif.). The reactions were performed in a RoboCycler 40 thermacycler (Stratagene, Inc., La Jolla, Calif.) programmed for 1 cycle at 95° C. for 9 minutes; 3 cycles each at 95° C. for 1 minute, 52° C. for 1 minute, and 72° C. for 1 minute; 27 cycles each at 95° C. for 1 minute, 55° C. for 1 minute, and 72° C. for 1 minute; and 1 cycle at 72° C. for 5 minutes. The PCR product was visualized using a 0.8% agarose gel with 44 mM Tris Base, 44 mM boric acid, 0.5 mM EDTA buffer (0.5×TBE). The expected fragment was approximately 1200 bp.

Figure 3:
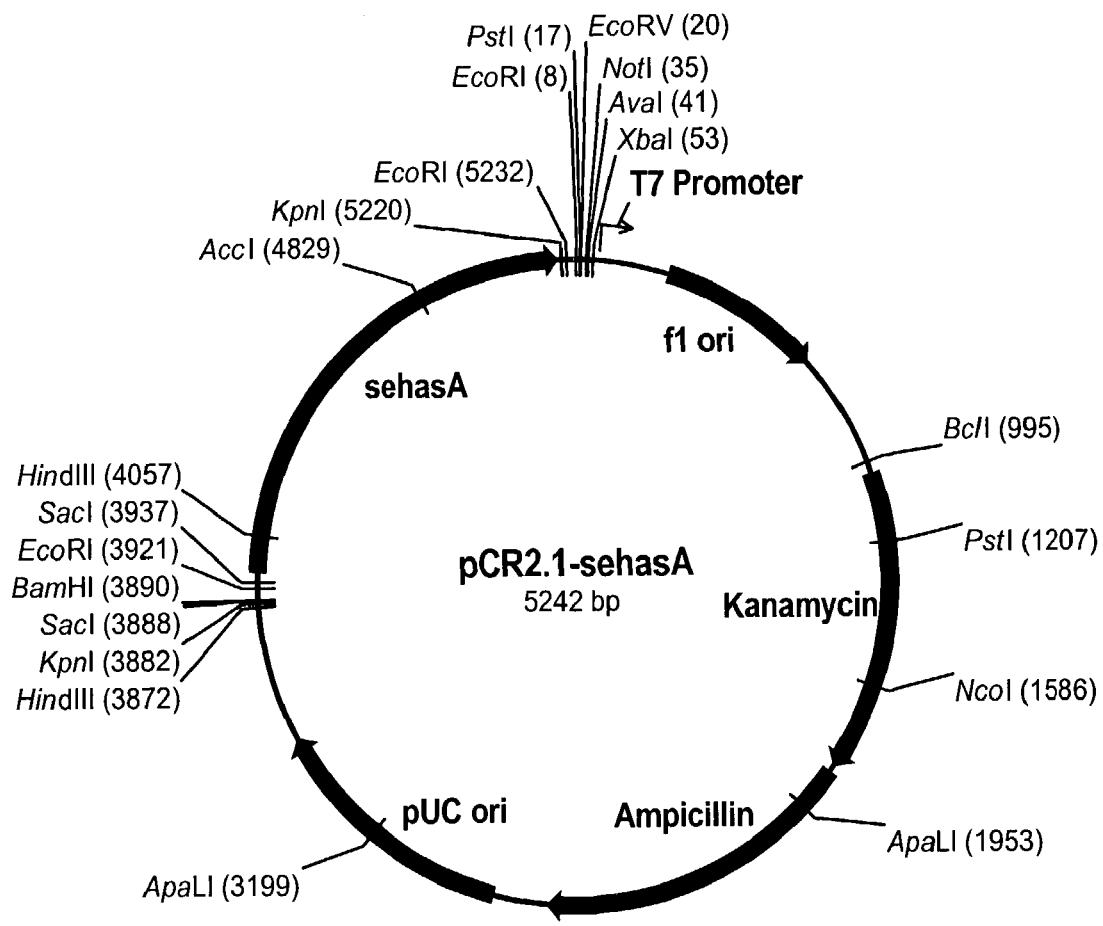
FIG. 3 shows a restriction map of pCR2.1-sehasA.

The 1200 bp PCR fragment was cloned into pCR2.1 using the TA-TOPO Cloning Kit (Stratagene, Inc., La Jolla, Calif.) and transformed into *E. coli* OneShot™ competent cells according to the manufacturers' instructions (Stratagene, Inc., La Jolla, Calif.). Transformants were selected at 37° C. after 16 hours of growth on 2× yeast-tryptone (YT) agar plates supplemented with 100 μg of ampicillin per ml. Plasmid DNA from these transformants was purified using a QIAGEN robot (QIAGEN, Valencia, Calif.) according to the manufacturer's instructions and the DNA sequence of the inserts confirmed by DNA sequencing using M13 (−20) forward and M13 reverse primers (Invitrogen, Inc, Carlsbad, Calif.) and the following internal primers. The plasmid harboring the 1200 bp PCR fragment was designated pCR2.1-sehasA (FIG. 3).

Primer 3:
5'-GTTGACGATGGAAGTGCTGA-3'     (SEQ ID NO: 5)

Primer 4:
5'-ATCCGTTACAGGTAATATCC-3'     (SEQ ID NO: 6)

Primer 5:
5'-TCCTTTTGTAGCCCTATGGA-3'     (SEQ ID NO: 7)

Primer 6:
5'-TCAGCACTTCCATCGTCAAC-3'     (SEQ ID NO: 8)

Primer 7:
5'-GGATATTACCTGTAACGGAT-3'     (SEQ ID NO: 9)

Primer 8:
5'-TCCATAGGGCTACAAAAGGA-3'     (SEQ ID NO: 10)

The *Bacillus subtilis* UDP-glucose-6-dehydrogenase gene (tuaD, accession number BG12691, SEQ ID NOs: 11 [DNA sequence] and 12 [deduced amino acid sequence]) was PCR amplified from *Bacillus subtilis* 168 (BGSC 1A1, Bacillus Genetic Stock Center, Columbus, Ohio) using primers 9 and 10:

Primer 9:
(SEQ ID NO: 13)
5'-GGTACCGACACTGCGACCATTATAAA-3'

Primer 10:
(SEQ ID NO: 14)
5'-GTTAACGAATTCCAGCTATGTATCTAGACAGCTTCAACCAAGTAACA
CT-3'

PCR amplifications were carried out in triplicate in 30 μl reactions composed of 50 ng of *Bacillus subtilis* 168 chromosomal DNA, 0.3 μM each of primers 9 and 10, 200 μM each of dATP, dCTP, dGTP, and dTTP, 1×PCR Buffer II with 2.5 mM $MgCl_2$, and 2.5 units of AmpliTaq Gold™ DNA polymerase. The reactions were performed in a RoboCycler 40 programmed for 1 cycle at 95° C. for 9 minutes; 5 cycles each at 95° C. for 1 minute, 50° C. for 1 minute, and 72° C. for 1.5 minutes; 32 cycles each at 95° C. for 1 minute, 54° C. for 1 minute, and 72° C. for 1.5 minute; and 1 cycle at 72° C. for 7 minutes. The PCR product was visualized in a 0.8% agarose gel using 0.5×TBE buffer. The expected fragment was approximately 1400 bp.

Figure 4:
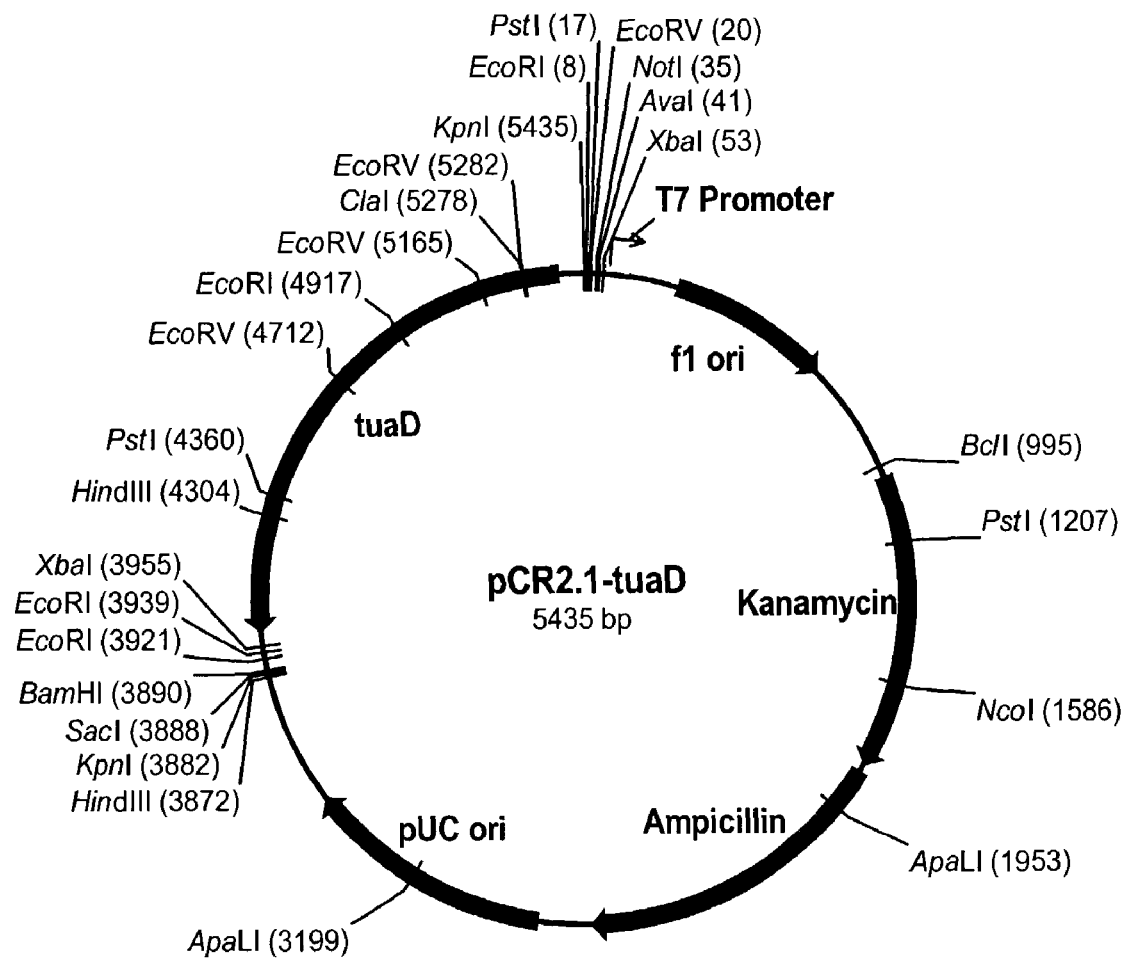
FIG. 4 shows a restriction map of pCR2.1-tuaD.

The 1400 bp PCR fragment was cloned into pCR2.1 using the TA-TOPO Cloning Kit and transformed into *E. coli* OneShot™ competent cells according to the manufacturers' instructions. Plasmid DNA was purified using a QIAGEN robot according to the manufacturer's instructions and the DNA sequence of the inserts confirmed by DNA sequencing using M13 (−20) forward and M13 reverse primers and the following internal primers. The plasmid harboring the 1400 bp PCR fragment was designated pCR2.1-tuaD (FIG. 4).

Primer 11:
5'-AGCATCTTAACGGCTACAAA-3'     (SEQ ID NO: 15)

Primer 12:
5'-TGTGAGCGAGTCGGCGAGA-3'      (SEQ ID NO: 16)

Primer 13:
5'-GGGCGCCCATGTAAAAGCAT-3'     (SEQ ID NO: 17)

Primer 14:
5'-TTTGTAGCCGTTAAGATGCT-3'     (SEQ ID NO: 18)

-continued

```
Primer 15:
5'-TCTGCGCCGACTCGCTCACA-3'      (SEQ ID NO: 19)

Primer 16:
5'-ATGCTTTTACATGGGCGCCC-3'      (SEQ ID NO: 20)
```

The *Bacillus subtilis* UTP-glucose-1-phosphate uridylyltransferase gene (gtaB, accession number BG10402, SEQ ID NOs: 21 [DNA sequence] and 22 [deduced amino acid sequence]) was PCR amplified from *Bacillus subtilis* 168 using primers 17 and 18: Primer 17: 5'-TCTAGATTTTTC-GATCATAAGGAAGGT-3' (SEQ ID NO: 23) Primer 18: 5'-GTTAACGAATTCCAGCTATGTAGGATC-CAATGTCCAATAGCCTTTTTGT-3' (SEQ ID NO: 24)

PCR amplifications were carried out in triplicate in 30 μl reactions composed of 50 ng of *Bacillus subtilis* 168 chromosomal DNA, 0.3 μM each of primers 17 and 18, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 programmed for 1 cycle at 95° C. for 9 minutes; 5 cycles each at 95° C. for 1 minute, 50° C. for 1 minute, and 72° C. for 1.5 minutes; 32 cycles each at 95° C. for 1 minute, 54° C. for 1 minute, and 72° C. for 1.5 minute; and 1 cycle at 72° C. for 7 minutes. The PCR product was visualized in a 0.8% agarose-0.5×TBE gel. The expected fragment was approximately 900 bp.

Figure 5:
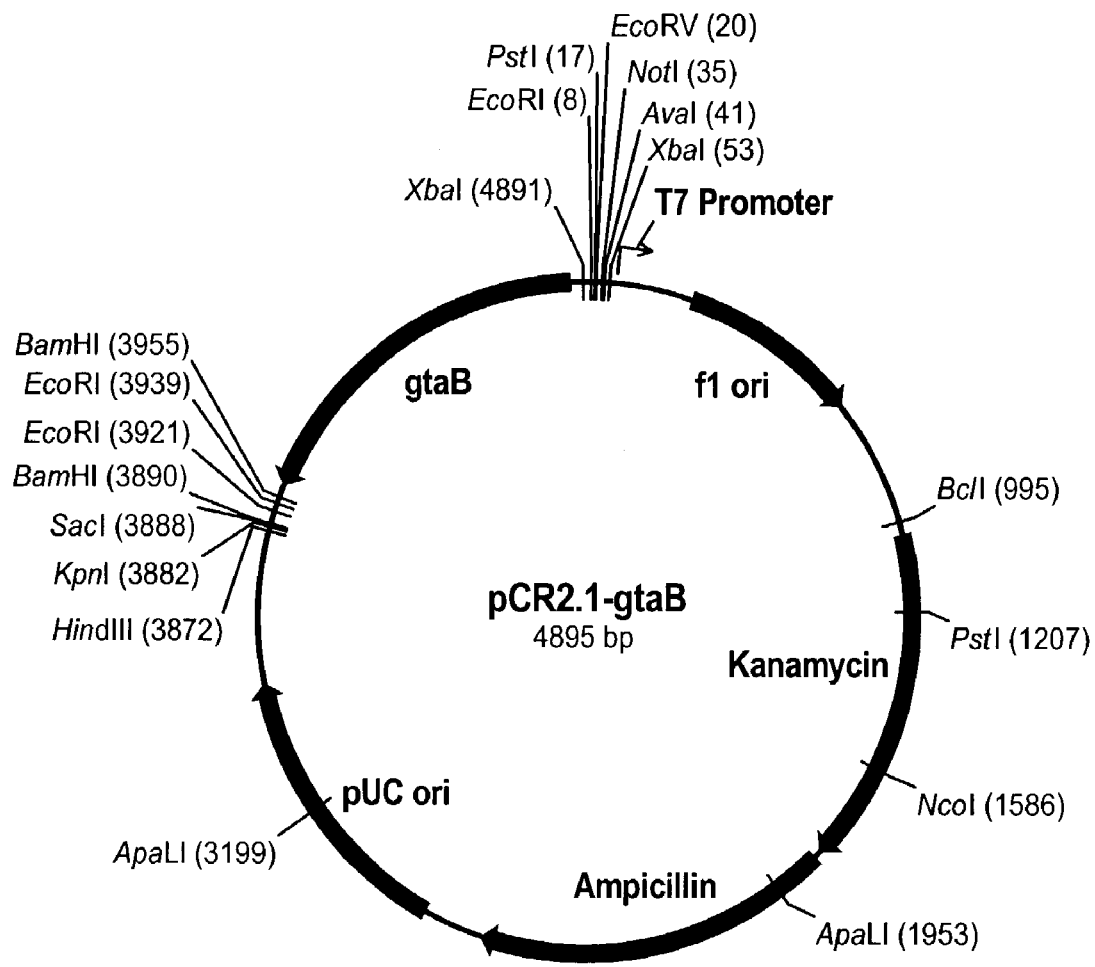
FIG. 5 shows a restriction map of pCR2.1-gtaB.

The 900 bp PCR fragment was cloned into pCR2.1 using the TA-TOPO cloning kit and transformed into *E. coli* One-Shot™ competent cells according to the manufacturer's instructions. Plasmid DNA was purified using a QIAGEN robot according to the manufacturer's instructions and the DNA sequence of the inserts confirmed by DNA sequencing using M13 (−20) forward and M13 reverse primers and the following internal primers. The plasmid harboring the 900 bp PCR fragment was designated pCR2.1-gtaB (FIG. 5).

```
Primer 19:
5'-AAAAAGGCTTCTAACCTGGC-3'     (SEQ ID NO: 25)

Primer 20:
5'-AAACCGCCTAAAGGCACAGC-3'     (SEQ ID NO: 26)

Primer 21:
5'-GCCAGGTTAGAAGCCTTTTT-3'     (SEQ ID NO: 27)

Primer 22:
5'-GCTGTGCCTTTAGGCGGTTT-3'     (SEQ ID NO: 28)
```

The *Bacillus subtilis* UDP-N-acetylglucosamine pyrophosphorylase gene (gcaD, accession number BG10113, SEQ ID NOs: 29 [DNA sequence] and 30 [deduced amino acid sequence]) was PCR amplified from *Bacillus subtilis* 168 using primers 23 and 24: Primer 23: 5'-GGATCCTTTC-TATGGATAAAAGGGAT-3' (SEQ ID NO: 31) Primer 24: 5'-GTTAACAGGATTATTTTTATGAATATTTTT-3' (SEQ ID NO: 32)

PCR amplifications were carried out in triplicate in 30 μl reactions composed of 50 ng of *Bacillus subtilis* 168 chromosomal DNA, 0.3 μM each of primers 23 and 24, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 programmed for 1 cycle at 95° C. for 9 minutes; 5 cycles each at 95° C. for 1 minute, 50° C. for 1 minute, and 72° C. for 1.5 minutes; 32 cycles each at 95° C. for 1 minute, 54° C. for 1 minute, and 72° C. for 1.5 minute; and 1 cycle at 72° C. for 7 minutes. The PCR product was visualized in a 0.8% agarose-0.5×TBE gel. The expected fragment was approximately 1500 bp.

Figure 6:
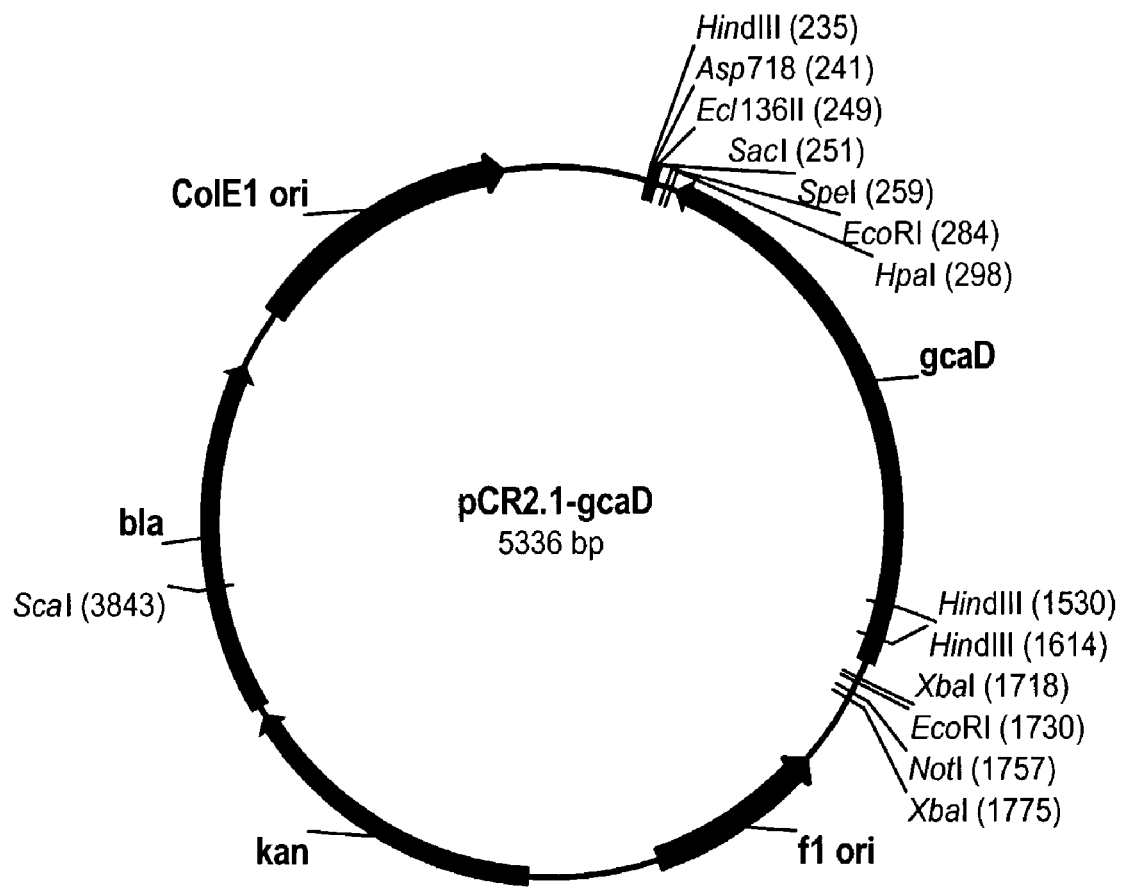
FIG. 6 shows a restriction map of pCR2.1-gcaD.

The 1500 bp PCR fragment was cloned into pCR2.1 using the TA-TOPO cloning kit and transformed into *E. coli* One-Shot™ competent cells according to the manufacturer's instructions. Plasmid DNA was purified using a QIAGEN robot according to the manufacturer's instructions and the DNA sequence of the inserts confirmed by DNA sequencing using M13 (−20) forward and M13 reverse primers and the following internal primers. The plasmid harboring the 900 bp PCR fragment was designated pCR2.1-gcaD (FIG. 6).

```
Primer 25:
5'-CAGAGACGATGGAACAGATG-3'     (SEQ ID NO: 33)

Primer 26:
5'-GGAGTTAATGATAGAGTTGC-3'     (SEQ ID NO: 34)

Primer 27:
5'-GAAGATCGGGAATTTTGTAG-3'     (SEQ ID NO: 35)

Primer 28:
5'-CATCTGTTCCATCGTCTCTG-3'     (SEQ ID NO: 36)

Primer 29:
5'-GCAACTCTATCATTAACTCC-3'     (SEQ ID NO: 37)

Primer 30:
5'-CTACAAAATTCCCGATCTTC-3'     (SEQ ID NO: 38)
```

Example 2

Construction of the hasA/tuaD/gtaB Operon

Plasmids pDG268Δneo-cryIIIAstab/Sav (U.S. Pat. No. 5,955,310) and pCR2.1-tuaD (Example 1, FIG. 4) were digested with KpnI and HpaI. The digestions were resolved on a 0.8% agarose gel using 0.5×TBE buffer and the larger vector fragment (approximately 7700 bp) from pDG268Δneo-cryIIIAstab/Sav and the smaller tuaD fragment (approximately 1500 bp) from pCR2.1-tuaD were gel-purified using the QIAquick DNA Extraction kit according to the manufacturer's instructions (QIAGEN, Valencia, Calif.). The two purified fragments were ligated together with T4 DNA ligase according to the manufacturer's instructions (Roche Applied Science; Indianapolis, Ind.) and the ligation mix was transformed into *E. coli* SURE competent cells (Stratagene, Inc., La Jolla, Calif.). Transformants were selected on 2×YT agar plates supplemented with 100 μg of ampicillin per ml.

Figure 7:
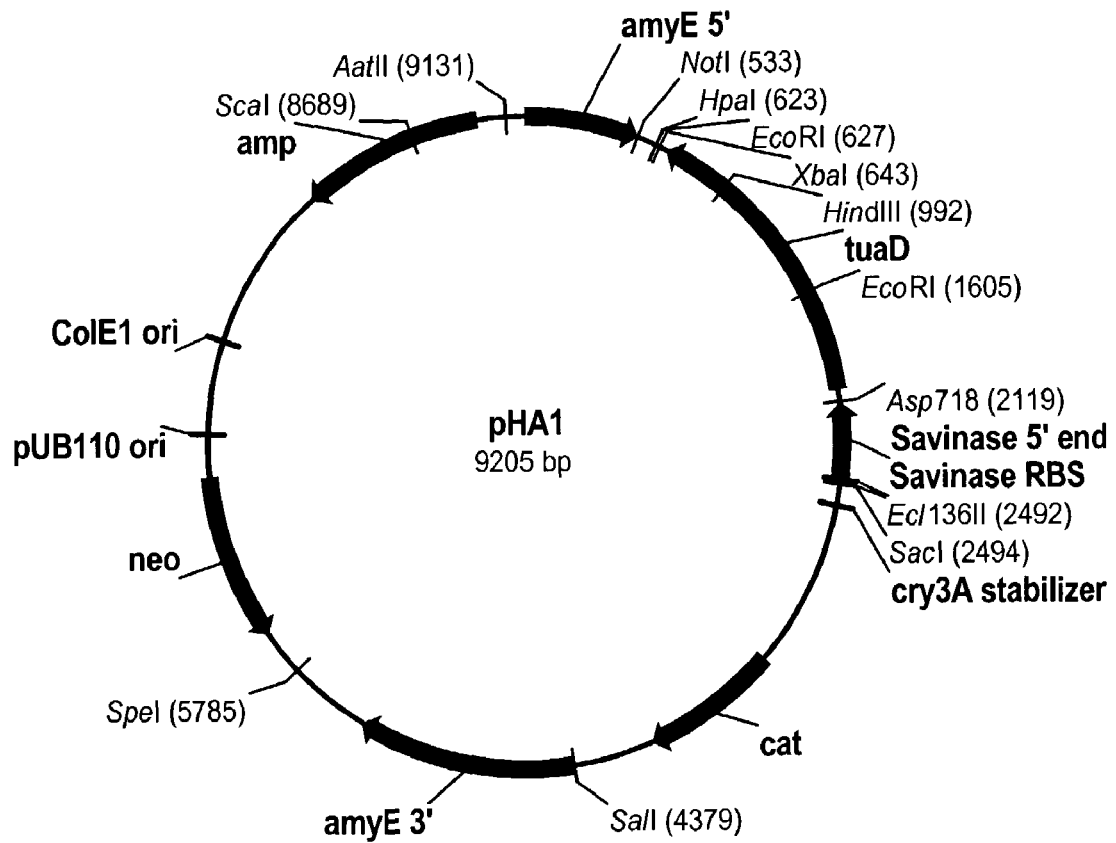
FIG. 7 shows a restriction map of pHA1.

Plasmid DNA was purified from several transformants using a QIAGEN robot according to the manufacturer's instructions and analyzed by KpnI plus HpaI digestion on a 0.8% agarose gel using 0.5×TBE buffer. The correct plasmid was identified by the presence of an approximately 1500 bp KpnI/HpaI tuaD fragment and was designated pHA1(FIG. 7).

Plasmids pHA1 and pCR2.1-gtaB (Example 1, FIG. 5) were digested with XbaI and HpaI. The digestions were resolved on a 0.8% agarose gel using 0.5×TBE buffer and the larger vector fragment from pHA1 (approximately 9200 bp) and the smaller gtaB fragment (approximately 900 bp) from pCR2.1-gtaB were gel-purified from a 0.8% agarose-0.5× TBE buffer gel using the QIAquick DNA Extraction Kit according to the manufacturer's instructions. These two purified fragments were ligated together with T4 DNA ligase and the ligation mix was used to transform *E. coli* SURE competent cells. Transformants were selected on 2×YT agar plates supplemented with 100 μg of ampicillin per ml at 37° C.

Figure 8:
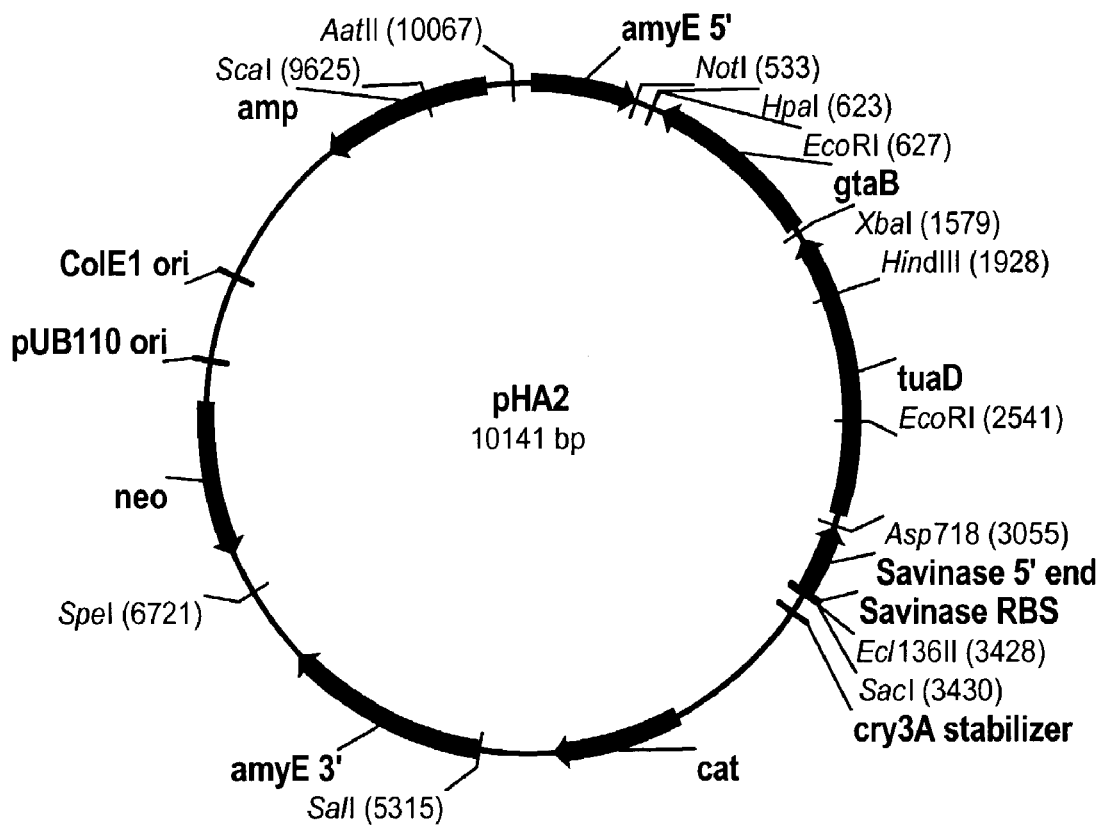
FIG. 8 shows a restriction map of pHA2.

Plasmids were purified from several transformants using a QIAGEN robot according to the manufacturer's instructions and analyzed by XbaI plus HpaI digestion. The digestions were resolved on a 0.8% agarose-0.5×TBE buffer gel. The correct plasmid was identified by the presence of an approximately 900 bp XbaI/HpaI gtaB fragment and was designated pHA2 (FIG. 8).

Figure 9:
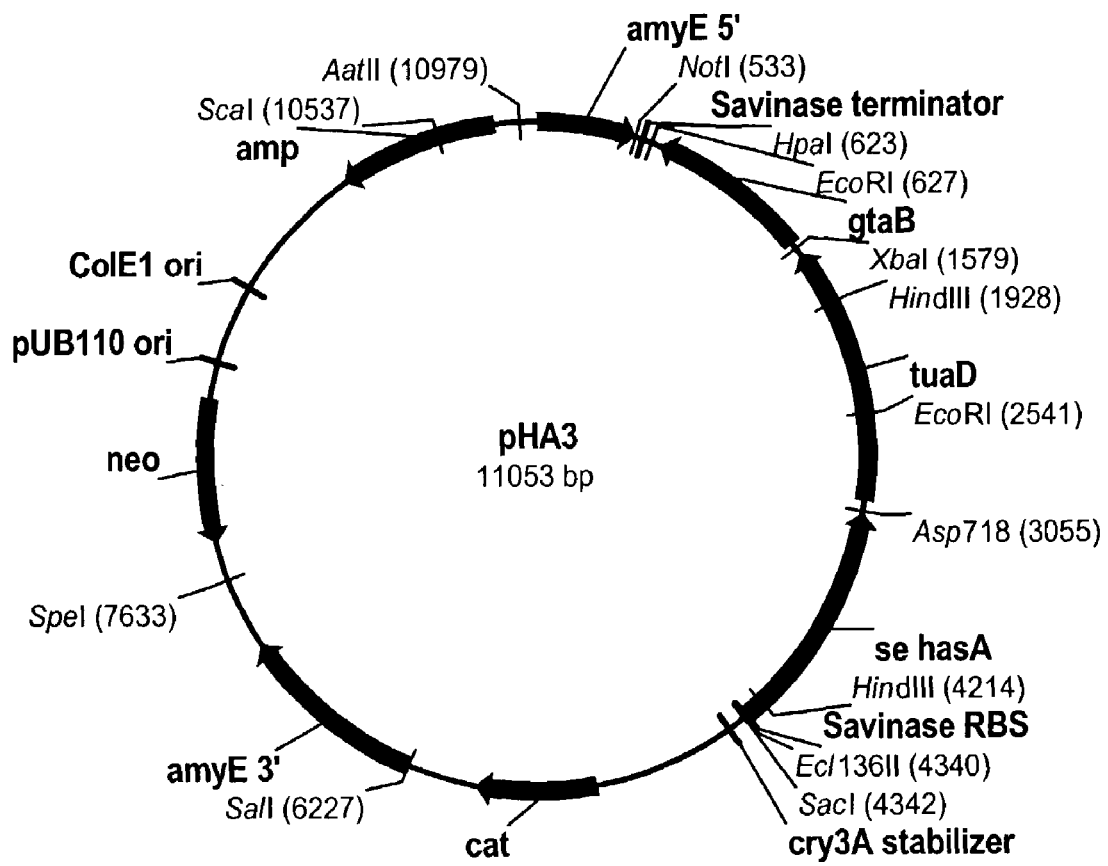
FIG. 9 shows a restriction map of pHA3.

Plasmids pHA2 and pCR2.1-sehasA (Example 1, FIG. 3) were digested with SacI plus KpnI. The digestions were resolved on a 0.8% agarose-0.5×TBE buffer gel. The larger vector fragment (approximately 10000 bp) from pHA2 and the smaller hasA fragment (approximately 1300 bp) from pCR2.1-sehasA were gel-purified from a 0.8% agarose-0.5× TBE buffer gel using the QIAquick DNA Extraction kit according to the manufacturer's instructions. The two purified fragments were ligated together with T4 DNA ligase and the ligation mix was used to transform *E. coli* SURE competent cells. Transformants were selected on 2×YT agar plates supplemented with 100 μg of ampicillin per ml at 37° C. Plasmids were purified from several transformants using a QIAGEN robot according to the manufacturer's instructions and analyzed by SacI plus KpnI digestion. The digestions were resolved on a 0.8% agarose-0.5×TBE buffer gel. The correct plasmid was identified by the presence of an approximately 1300 bp SacI/KpnI hasA fragment and was designated pHA3 (FIG. 9).

Example 3

Construction of the hasA/tuaD/gtaB/gcaD Operon

Plasmids pHA2 (Example 2, FIG. 8) and pCR2.1-gcaD (Example 1, FIG. 6) were digested with BamHI and HpaI. The digestions were resolved on a 0.8% agarose gel using 0.5×TBE buffer and the larger vector fragment (approximately 10,000 bp) from pHA2 and the smaller gcaD fragment (approximately 1,400 bp) from pCR2.1-gcaD were gel-purified from a 0.8% agarose-0.5×TBE buffer gel using the QIAquick DNA Extraction Kit according to the manufacturer's instructions. These two purified fragments were ligated together with T4 DNA ligase and the ligation mix was used to transform *E. coli* SURE competent cells. Transformants were selected on 2×YT agar plates supplemented with 100 μg of ampicillin per ml at 37° C.

Figure 10:
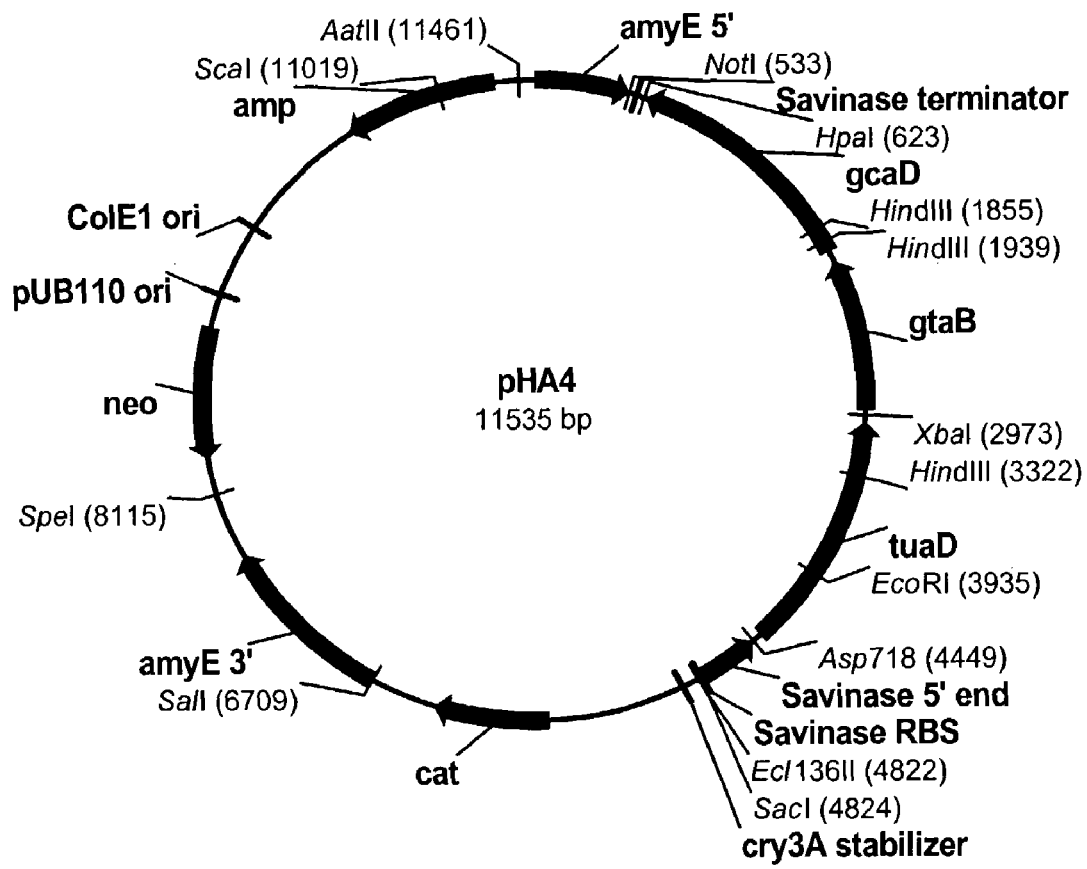
FIG. 10 shows a restriction map of pHA4.

Plasmids were purified from several transformants using a QIAGEN robot according to the manufacturer's instructions and analyzed by XbaI plus HpaI digestion. The digestions were resolved on a 0.8% agarose-0.5×TBE buffer gel. The correct plasmid was identified by the presence of an approximately 1400 bp BamHI/HpaI gcaD fragment and was designated pHA4 (FIG. 10).

Figure 11:
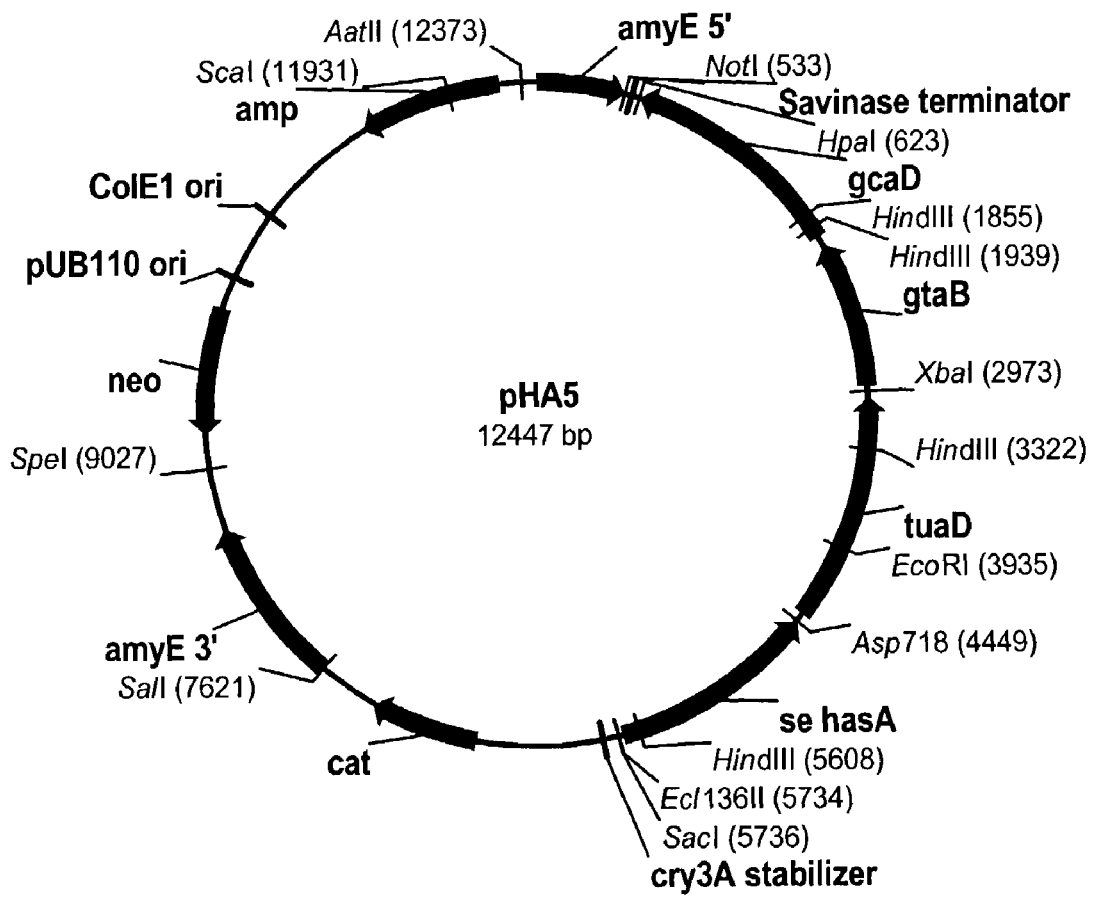
FIG. 11 shows a restriction map of pHA5.

Plasmids pHA4 and pCR2.1-sehasA (Example 1, FIG. 3) were digested with SacI and KpnI. The digestions were resolved on a 0.8% agarose-0.5×TBE buffer gel. The larger vector fragment (approximately 11,000 bp) from pHA4 and the smaller hasA fragment (approximately 1,300 bp) from pCR2.1-sehasA were gel-purified from a 0.8% agarose-0.5× TBE buffer gel using the QIAquick DNA Extraction kit according to the manufacturer's instructions. The two purified fragments were ligated together with T4 DNA ligase and the ligation mix was used to transform *E. coli* SURE competent cells. Transformants were selected on 2×YT agar plates supplemented with 100 μg of ampicillin per ml at 37° C. Plasmids were purified from several transformants using a QIAGEN robot according to the manufacturer's instructions and analyzed by SacI plus KpnI digestion. The digestions were resolved on a 0.8% agarose-0.5×TBE buffer gel. The correct plasmid was identified by the presence of an approximately 1,300 bp SacI/KpnI hasA fragment and was designated pHA5 (FIG. 11).

Example 4

Construction of the hasA/tuaD/gcaD Operon

Plasmids pHA1 (Example 2, FIG. 7) and pCR2.1-gcaD (Example 1, FIG. 6) were digested with BamHI and HpaI. The digestions were resolved on a 0.8% agarose gel using 0.5×TBE buffer and the larger vector fragment from pHA1 (approximately 9,200 bp) and the smaller gcaD fragment (approximately 1400 bp) from pCR2.1-gcaD were gel-purified from a 0.8% agarose-0.5×TBE buffer gel using the QIAquick DNA Extraction Kit according to the manufacturer's instructions. These two purified fragments were ligated together with T4 DNA ligase and the ligation mix was used to transform *E. coli* SURE competent cells. Transformants were selected on 2×YT agar plates supplemented with 100 μg of ampicillin per ml at 37° C.

Figure 12:
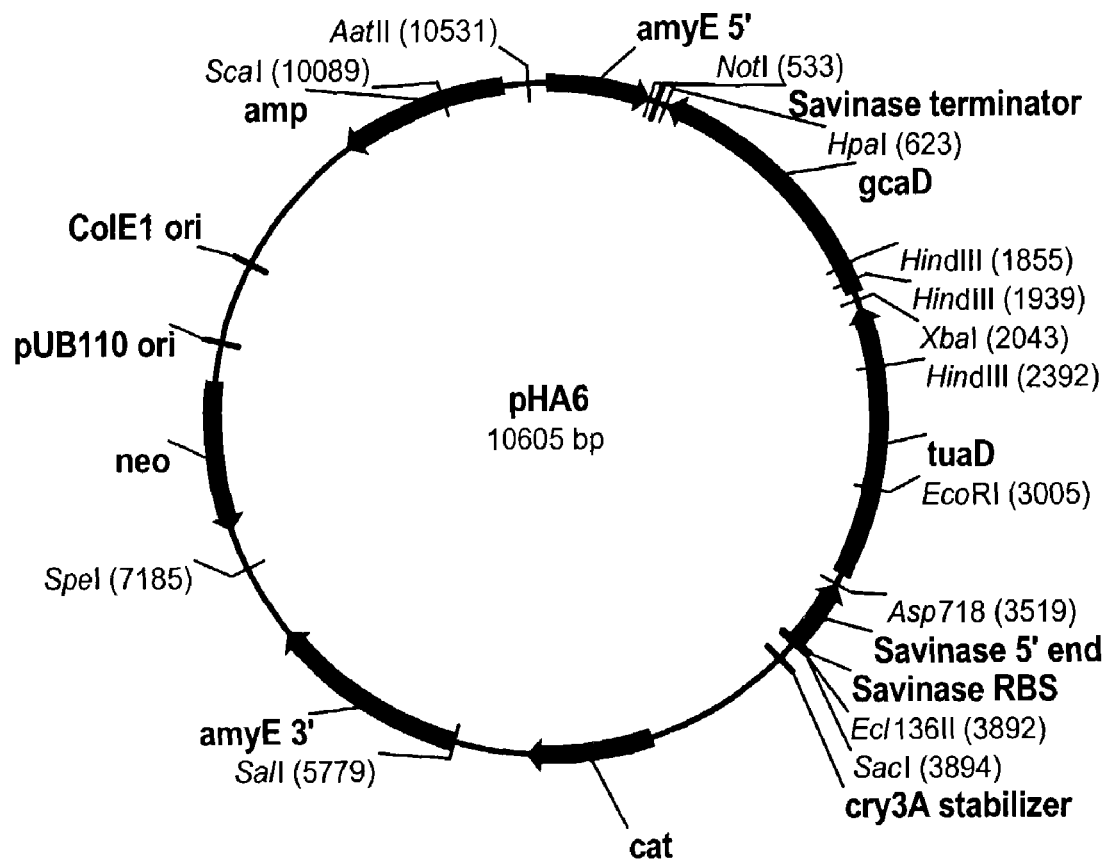
FIG. 12 shows a restriction map of pHA6.

Plasmids were purified from several transformants using a QIAGEN robot according to the manufacturer's instructions and analyzed by BamHI plus HpaI digestion. The digestions were resolved on a 0.8% agarose-0.5×TBE buffer gel. The correct plasmid was identified by the presence of an approximately 1400 bp BamHI/HpaI gtaB fragment and was designated pHA6 (FIG. 12).

Figure 13:
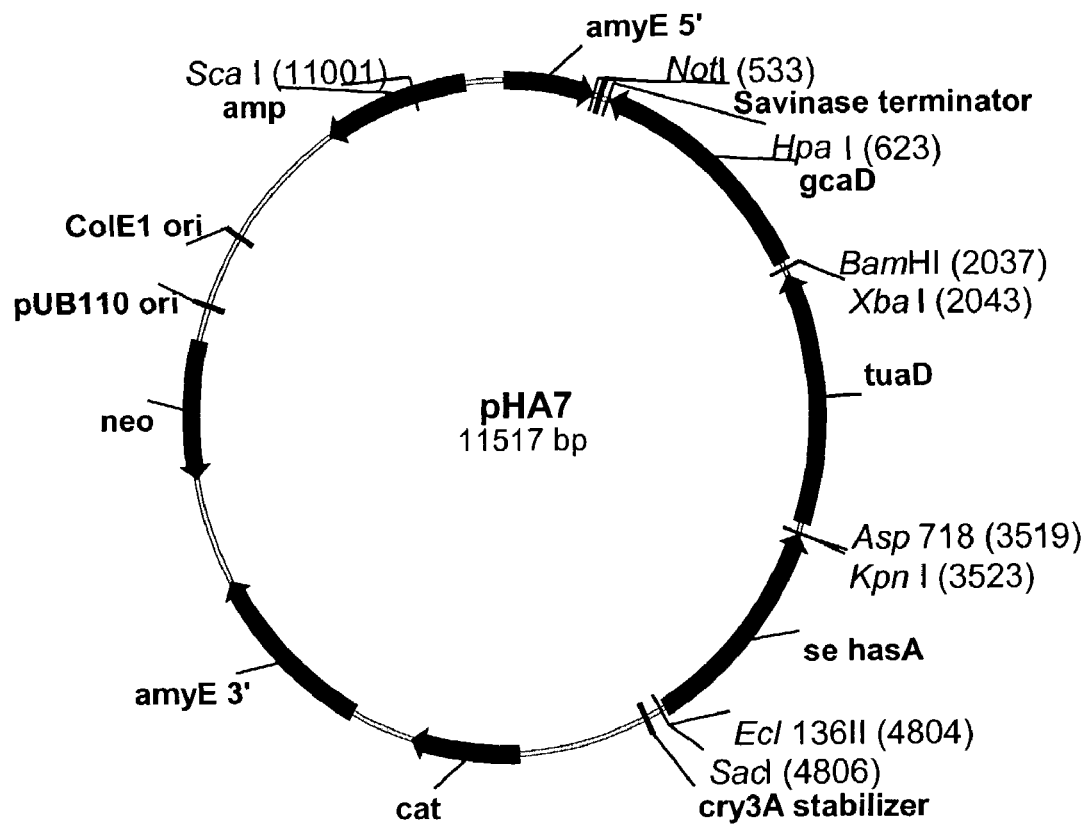
FIG. 13 shows a restriction map of pHA7.

Plasmids pHA6 and pCR2.1-sehasA-(Example 1, FIG. 3) were digested with SacI plus KpnI. The digestions were resolved on a 0.8% agarose-0.5×TBE buffer gel. The larger vector fragment (approximately 10,200 bp) from pHA6 and the smaller hasA fragment (approximately 1,300 bp) from pCR2.1-sehasA were gel-purified from a 0.8% agarose-0.5× TBE buffer gel using the QIAquick DNA Extraction kit according to the manufacturer's instructions. The two purified fragments were ligated together with T4 DNA ligase and the ligation mix was used to transform *E. coli* SURE competent cells. Transformants were selected on 2×YT agar plates supplemented with 100 μg of ampicillin per ml. Plasmids were purified from several transformants using a QIAGEN robot according to the manufacturer's instructions and analyzed by SacI plus KpnI digestion. The digestions were resolved on a 0.8% agarose-0.5×TBE buffer gel. The correct plasmid was identified by the presence of an approximately 1300 bp SacI/KpnI hasA fragment and was designated pHA7 (FIG. 13).

Example 5

Construction of *Bacillus subtilis* RB161

Plasmid pDG268MCSΔneo/scBAN/Sav (U.S. Pat. No. 5,955,310) was digested with SacI. The digested plasmid was then purified using a QIAquick DNA Purification Kit according to the manufacturer's instructions, and finally digested with NotI. The largest plasmid fragment of approximately 6800 bp was gel-purified using a QIAquick DNA Gel Extraction Kit from a 0.8% agarose-0.5×TBE gel according to the manufacturer's instructions (QIAGEN, Valencia, Calif.). The recovered vector DNA was then ligated with the DNA insert described below.

Plasmid pHA3 (Example 2, FIG. 9) was digested with SacI. The digested plasmid was then purified as described above, and finally digested with NotI. The smallest plasmid fragment of approximately 3800 bp was gel-purified as described above. The recovered vector and DNA insert were ligated using the Rapid DNA Cloning Kit (Roche Applied Science; Indianapolis, Ind.) according to the manufacturer's instructions. Prior to transformation in *Bacillus subtilis*, the ligation described above was linearized using ScaI to ensure double cross-over integration in the chromosome rather than single cross-over integration in the chromosome. Competent cells of *Bacillus subtilis* 168Δ4 were transformed with the ligation products digested with ScaI. *Bacillus subtilis* 168Δ4 is derived from the *Bacillus subtilis* type strain 168 (BGSC 1A1, *Bacillus* Genetic Stock Center, Columbus, Ohio) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

*Bacillus subtilis* chloramphenicol-resistant transformants were selected at 34° C. after 16 hours of growth on Tryptose blood agar base (TBAB) plates supplemented with 5 μg of chloramphenicol per ml. To screen for integration of the plasmid by double cross-over at the amyE locus, *Bacillus subtilis* primary transformants were patched on TBAB plates supplemented with 6 μg of neomycin per ml and on TBAB plates supplemented with 5 μg of chloramphenicol per ml. Integration of the plasmid by double cross-over at the amyE locus does not incorporate the neomycin resistance gene and therefore renders the strain neomycin sensitive. Isolates were also patched onto minimal plates to visualize whether or not these were producing hyaluronic acid. Hyaluronic acid producing isolates have a "wet" phenotype on minimal plates. Using this plate screen, chloramphenicol resistant and neomycin sensitive "wet" transformants (due to hyaluronic acid production) were isolated at 37° C.

Genomic DNA was isolated from the "wet", chloramphenicol resistant, and neomycin sensitive *Bacillus subtilis* 168Δ4 transformants using a QIAGEN tip-20 column (QIAGEN, Valencia, Calif.) according to the manufacturer's instructions. PCR amplifications were performed on these transformants using the synthetic oligonucleotides below, which are based on the hasA, tuaD, and gtaB gene sequences, to confirm the presence and integrity of these genes in the operon of the *Bacillus subtilis* transformants.

The amplification reactions (25 μl) were composed of approximately 50 ng of genomic DNA of the *Bacillus subtilis* 168Δ4 transformants, 0.5 μM of each primer, 200 μM each of dATP, dCTP, dGTP, and dTTP, 1×PCR Buffer II, 3 mM MgCl$_2$, and 0.625 units of AmpliTaq Gold™ DNA polymerase. The reactions were incubated in a RoboCycler 40 Temperature Cycler programmed for one cycle at 95° C. for 9 minutes; 30 cycles each at 95° C. for 1 minute, 55° C. for 1 minute, and 72° C. for 2 minutes; and a final cycle at 72° C. for 7 minutes.

Primers 3 and 8 were used to confirm the presence of the hasA gene, primers 3 and 16 to confirm the presence of the tuaD gene, and primers 3 and 22 to confirm the presence of the gtaB gene. The *Bacillus subtilis* 168Δ4 hasA/tuaD/gtaB integrant was designated *Bacillus subtilis* RB158.

Genomic DNA was isolated from *Bacillus subtilis* RB158 using a QIAGEN tip-20 column according to the manufacturer's instructions, and was used to transform competent Bacillus subtilis A164Δ5 (deleted at the spoIIAC, aprE, nprE, amyE, and srfC genes; see U.S. Pat. No. 5,891,701). Transformants were selected on TBAB plates supplemented with 5 μg of chloramphenicol per ml at 37° C. A *Bacillus subtilis* A164Δ5 hasA/tuaD/gtaB integrant was identified by its "wet" phenotype and designated *Bacillus subtilis* RB161.

Example 6

Construction of *Bacillus subtilis* RB163

Plasmid pDG268MCSΔneo/scBAN/Sav (U.S. Pat. No. 5,955,310) was digested with SacI. The digested plasmid was then purified using a QIAquick DNA Purification Kit according to the manufacturer's instructions, and finally digested with NotI. The largest plasmid fragment of approximately 6,800 bp was gel-purified using a QIAquick DNA Gel Extraction Kit from a 0.8% agarose-0.5×TBE gel according to the manufacturer's instructions. The recovered vector DNA was then ligated with the DNA insert described below.

Plasmid pHA7 (Example 4, FIG. 13) was digested with SacI. The digested plasmid was then purified as described above, and finally digested with NotI. The smallest plasmid fragment of approximately 4,300 bp was gel-purified as described above. The recovered vector and DNA insert were ligated using the Rapid DNA Cloning Kit according to the manufacturer's instructions. Prior to transformation in *Bacillus subtilis*, the ligation described above was linearized using ScaI to ensure double cross-over integration in the chromosome rather than single cross-over integration in the chromosome. *Bacillus subtilis* 168Δ4 competent cells were transformed with the ligation digested with the restriction enzyme ScaI.

*Bacillus subtilis* chloramphenicol-resistant transformants were selected on TBAB plates supplemented with 5 μg of chloramphenicol per ml at 37° C. To screen for integration of the plasmid by double cross-over at the amyE locus, *Bacillus subtilis* primary transformants were patched on TBAB plates supplemented with 6 μg of neomycin per ml and on TBAB plates supplemented with 5 μg of chloramphenicol per ml to isolate chloramphenicol resistant and neomycin sensitive "wet" transformants (due to hyaluronic acid production).

Genomic DNA was isolated from the "wet", chloramphenicol resistant, and neomycin sensitive *Bacillus subtilis* 168Δ4 transformants using a QIAGEN tip-20 column according to the manufacturer's instructions. PCR amplifications were performed on these transformants using primers 3, 8, 16, 22 and primer 30 (Example 1) to confirm the presence and integrity of these genes in the operon of the *Bacillus subtilis* transformants. The amplification reactions (25 μl) were composed of approximately 50 ng of genomic DNA of the *Bacillus subtilis* 168Δ4 transformants, 0.5 μM of each primer, 200 μM each of dATP, dCTP, dGTP, and dTTP, 1×PCR buffer, 3 mM MgCl$_2$, and 0.625 units of AmpliTaq Gold™ DNA polymerase. The reactions were incubated in a RoboCycler 40 Temperature Cycler programmed for one cycle at 95° C. for 9 minutes; 30 cycles each at 95° C. for 1 minute, 55° C. for 1 minute, and 72° C. for 2 minutes; and a final cycle at 72° C. for 7 minutes.

Primers 3 and 8 were used to confirm the presence of the hasA gene, primers 3 and 16 to confirm the presence of the tuaD gene, primers 3 and 22 to confirm the presence of the gtaB gene, and primers 3 and 30 to confirm the presence of the gcaD gene. The *Bacillus subtilis* 168Δ4 hasA/tuaD/gcaD integrant was designated *Bacillus subtilis* RB160.

Genomic DNA was isolated from *Bacillus subtilis* RB160 using a QIAGEN tip-20 column according to the manufacturer's instructions, and was used to transform competent *Bacillus subtilis* A164Δ5. Transformants were selected on TBAB plates containing 5 μg of chloramphenicol per ml, and grown at 37° C. for 16 hours. The *Bacillus subtilis* A164Δ5 hasA/tuaD/gcaD integrant was identified by its "wet" phenotype and designated *Bacillus subtilis* RB163.

Example 7

Construction of *Bacillus subtilis* TH-1

The hyaluronan synthase (has) operon was obtained from *Streptococcus equisimilis* using the following procedure. The has operon is composed of the hasA, hasB, hasC, and hasD genes. Approximately 20 μg of *Streptococcus equisimilis* D181 (Kumari and Weigel, 1997, *Journal of Biological Chemistry* 272: 32539-32546) chromosomal DNA was digested with HindIII and resolved on a 0.8% agarose-0.5× TBE gel. DNA in the 3-6 kb range was excised from the gel and purified using the QIAquick DNA Gel Extraction Kit according to the manufacturer's instructions. The recovered DNA insert was then ligated with the vector DNA described below.

Plasmid pUC18 (2 μg) was digested with HindIII and the 5' protruding ends were dephosphorylated with shrimp alkaline phospatase according to the manufacturer's instructions (Roche Applied Science; Indianapolis, Ind.). The dephosphorylated vector and DNA insert were ligated using the Rapid DNA Cloning Kit according to the manufacturer's instructions. The ligation was used to transform *E. coli* XL10 Gold Kan competent cells (Stratagene, Inc., La Jolla, Calif.). Cells were plated onto Luria broth plates (100 μg/ml ampicillin) and incubated overnight at 37° C. Five plates containing approximately 500 colonies/plate were probed with oligo 952-55-1, shown below, which is a 54 bp sequence identical to the coding strand near the 3' end of the *Streptococcus equisimilis* D181 hasA gene (nucleotides 1098-1151 with respect to the A residue of the ATG translation start codon).

Primer 31: 5'-GTGTCGGAACATTCATTACATGCTTAAG-CACCCGCTGTCCTTCTTGTTATCTCC-3' (SEQ ID NO: 39)

The oligonucleotide probe was DIG-labeled using the DIG Oligonucleotide 3'-end Labeling Kit according to the manufacturer's instructions (Roche Applied Science; Indianapolis, Ind.). Colony hybridization and chemiluminescent detection were performed as described in "THE DIG SYSTEM USER'S GUIDE FOR FILTER HYBRIDIZATION", Boehringer Mannheim GmbH.

Figure 14:
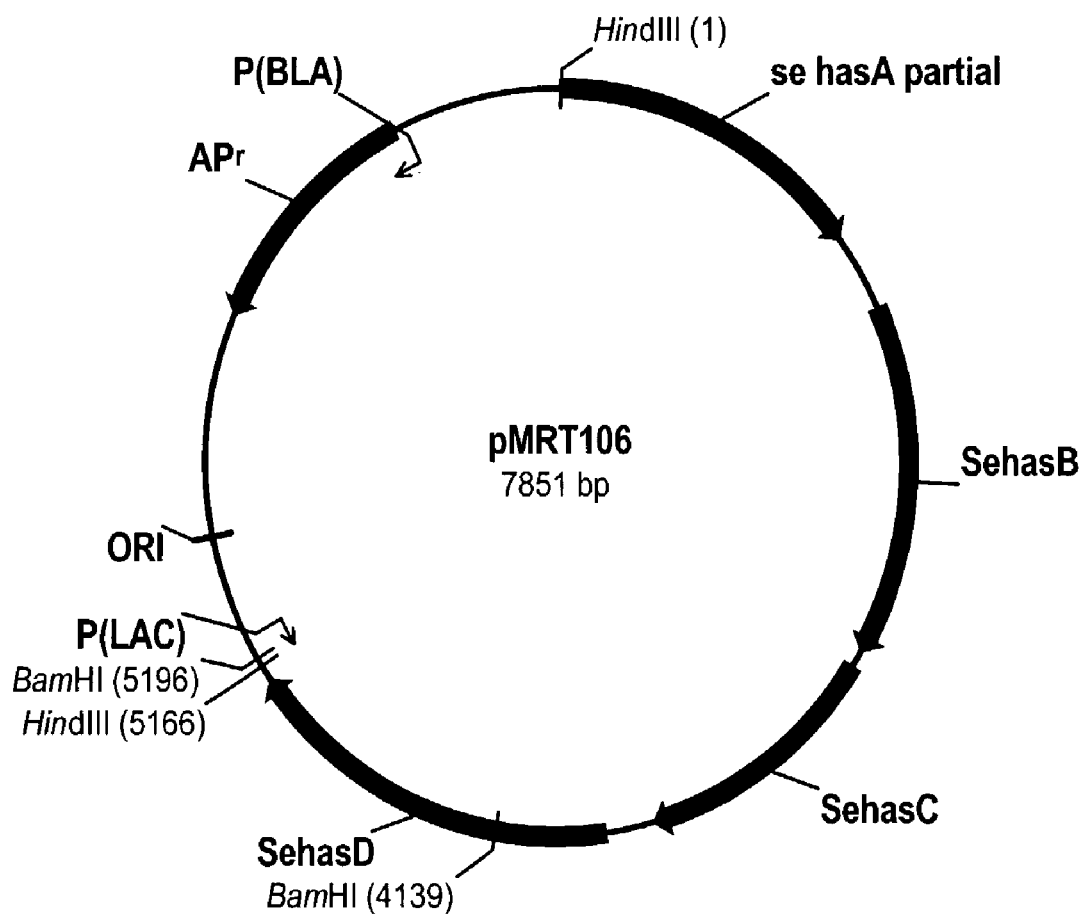
FIG. 14 shows a restriction map of pMRT106.

Seven colonies were identified that hybridized to the probe. Plasmid DNA from one of these transformants was purified using a QIAGEN robot (QIAGEN, Valencia, Calif.) according to the manufacturer's instructions, digested with HindIII, and resolved on a 0.8% agarose gel using 0.5×TBE buffer. The DNA insert was shown to be approximately 5 kb in size. This plasmid was designated pMRT106 (FIG. 14).

The DNA sequence of the cloned fragment was determined using the EZ::TN™ <TET-1> Insertion Kit according to the manufacturer's instructions (Epicenter Technologies, Madison, Wis.). The sequencing revealed that the cloned DNA insert contained the last 1156 bp of the *Streptococcus equisimilis* hasA gene followed by three other genes designated hasB, hasC, and hasD; presumably all four genes are contained within a single operon and are therefore co-transcribed. The *Streptococcus equisimilis* hasB gene is contained in nucleotides 1411-2613 (SEQ ID NOs: 40 [DNA sequence] and 41 [deduced amino acid sequence]) of the fragment, and *Streptococcus equisimilis* hasC gene in nucleotides 2666-3565 (SEQ ID NOs: 42 [DNA sequence] and 43 [deduced amino acid sequence]) of the fragment, and *Streptococcus equisimilis* hasD gene in nucleotides 3735-5114 (SEQ ID NOs: 44 [DNA sequence] and 45 [deduced amino acid sequence]) of the fragment.

The polypeptides encoded by the *Streptococcus equisimilis* hasB and hasC genes show some homology to those encoded by the hasB and hasC genes, respectively, from the *Streptococcus pyogenes* has operon sequence (Ferretti et al., 2001, *Proc. Natl. Acad. Sci. U.S.A.* 98 (8), 4658-4663). The degree of identity was determined by the Clustal method (Higgins, 1989, *CABIOS* 5: 151-153) using using the Vector NTI AlignX software (Informax Inc., Bethesda, Md.) with the following defaults: pairwise alignment, gap opening penalty of 10, gap extension penalty of 0.1, and score matrix: blosum62mt2.

Amino acid sequence comparisons showed that the *Streptococcus equisimilis* HasB protein has 70% identity to the HasB protein from *Streptococcus uberis* (SEQ ID NO: 105); the *Streptococcus equisimilis* HasC protein has 91% identity to the HasC protein from *Streptococcus pyogenes* (SEQ ID NO: 99); and the *Streptococcus equisimilis* HasD protein has 73% identity to the GlmU protein (a putative UDP-N-acetyl-glucosamine pyrophosphorylase) of *Streptococcus pyogenes* (accession # Q8P286). The *Streptococcus equisimilis* hasD gene encodes a polypeptide that shows 50.7% identity to the UDP-N-acetyl-glucosamine pyrophosphorylase enzyme encoded by the gcaD gene of *Bacillus subtilis*.

Plasmid pHA5 (Example 3, FIG. 11) was digested with HpaI and BamHI. The digestion was resolved on a 0.8% agarose gel using 0.5×TBE buffer and the larger vector fragment (approximately 11,000 bp) was gel-purified using the QIAquick DNA Extraction Kit according to the manufacturer's instructions. Plasmid pMRT106 was digested with HindIII, the sticky ends were filled in with Klenow fragment, and the DNA was digested with BamHI. The digestion was resolved on a 0.8% agarose gel using 0.5×TBE buffer and the smaller insert fragment (approximately 1000 bp, the last ⅔ of the *Streptococcus equisimilis* hasD gene) was gel-purified using the QIAquick DNA Extraction kit according to the manufacturer's instructions.

The two purified fragments were ligated together with T4 DNA ligase and the ligation mix was transformed into *E. coli* SURE competent cells. Transformants were selected on 2×YT agar plates supplemented with 100 μg of ampicillin per ml at 37° C.

Figure 15:
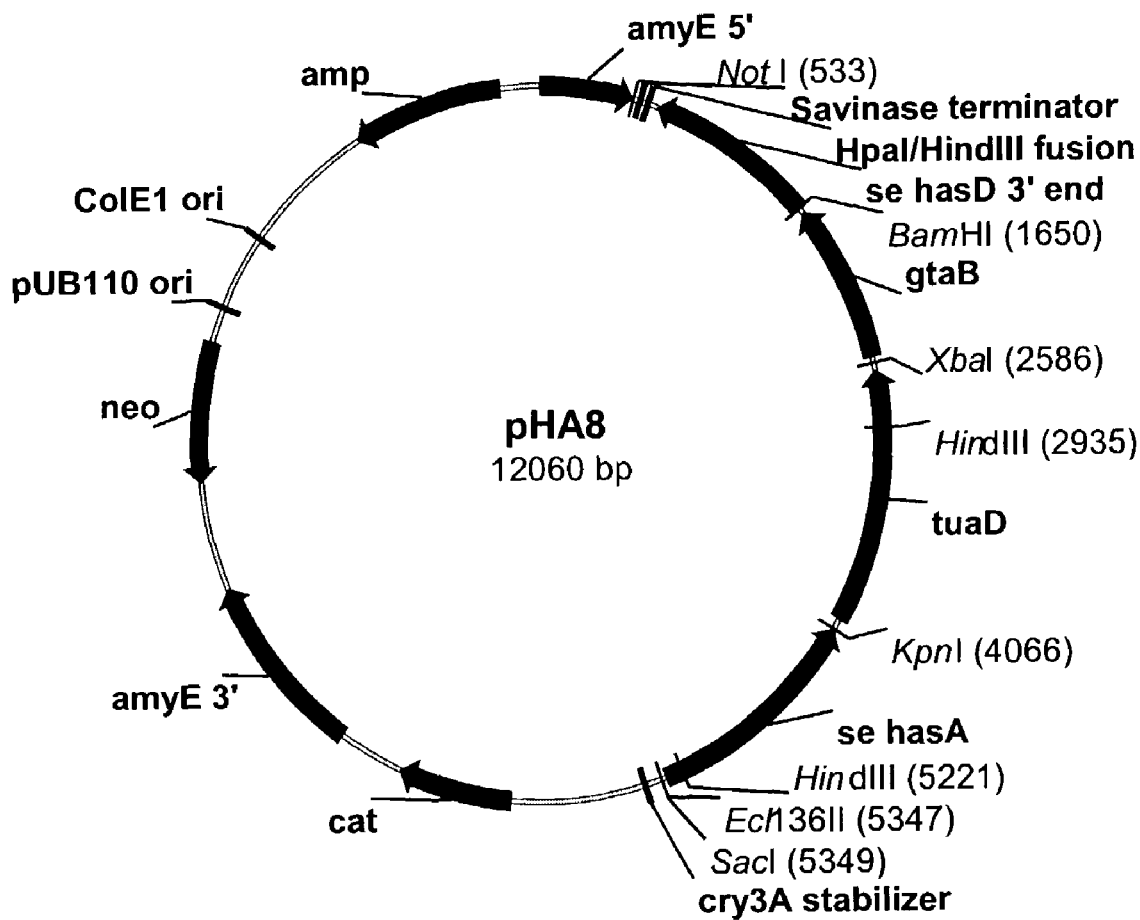
FIG. 15 shows a restriction map of pHA8.
Figure 16:
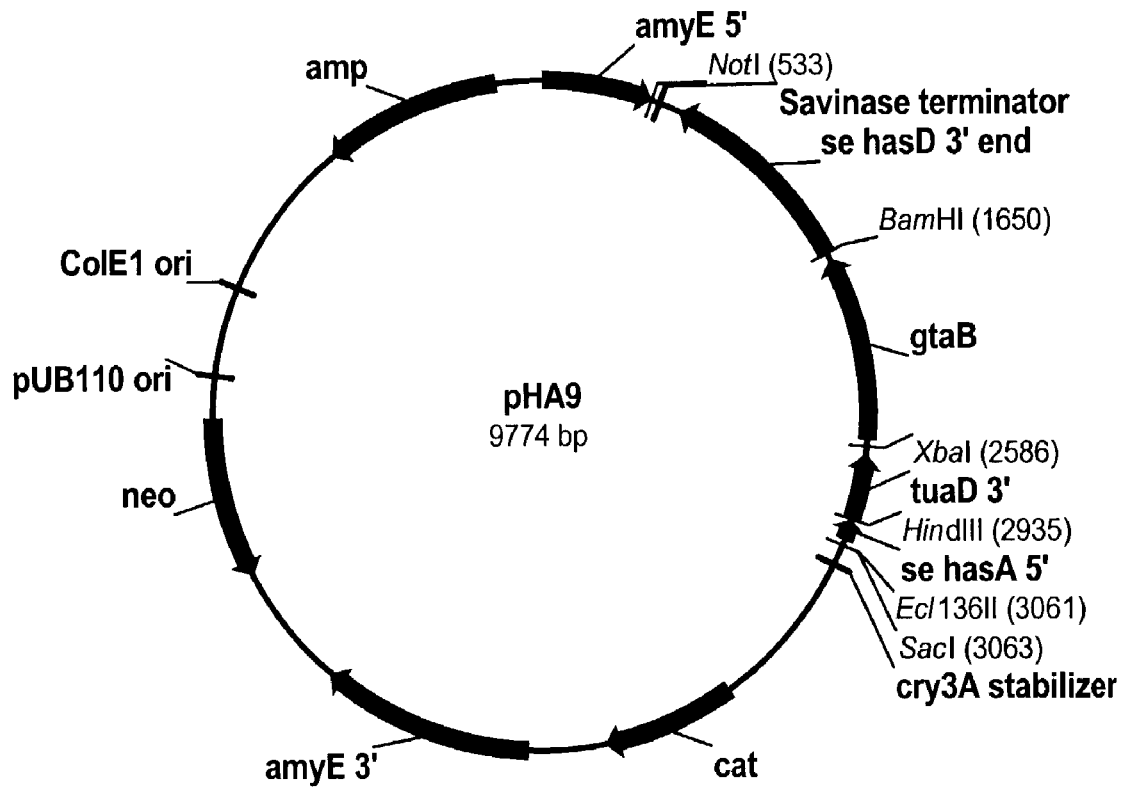
FIG. 16 shows a restriction map of pHA9.

Plasmid DNA was purified from several transformants using a QIAGEN robot according to the manufacturer's instructions and analyzed by BamHI plus NotI digestion on a 0.8% agarose gel using 0.5×TBE buffer. The correct plasmid was identified by the presence of an approximately 1,100 bp BamHI/NotI hasD fragment and was designated pHA8 (FIG. 15). This plasmid was digested with HindIII and ligated together with T4 DNA ligase and the ligation mix was transformed into *E. coli* SURE competent cells. Transformants were selected on 2×YT agar plates supplemented with 100 μg of ampicillin per ml. Plasmid DNA was purified from several transformants using a QIAGEN robot according to the manufacturer's instructions and analyzed by HindIII digestion on a 0.8% agarose gel using 0.5×TBE buffer. The correct plasmid was identified by the presence of a single band of approximately 9,700 bp and was designated pHA9 (FIG. 16).

Plasmid pHA9 was digested with SacI and NotI. The digestion was resolved on a 0.8% agarose gel using 0.5×TBE buffer and the smaller fragment of approximately 2,500 bp was gel-purified using the QIAquick DNA Extraction kit according to the manufacturer's instructions. Plasmid pDG268MCSΔneo/scBAN/Sav (U.S. Pat. No. 5,955,310) was digested with SacI and NotI. The digestion was resolved on a 0.8% agarose gel using 0.5×TBE buffer and the larger vector fragment of approximately 6,800 bp was gel-purified using the QIAquick DNA Extraction kit according to the manufacturer's instructions. The two purified fragments were ligated together with T4 DNA ligase and the ligation mix was transformed into *E. coli* SURE competent cells (Stratagene, Inc., La Jolla, Calif.). Transformants were selected on 2×YT agar plates supplemented with 100 µg of ampicillin per ml.

Figure 17:
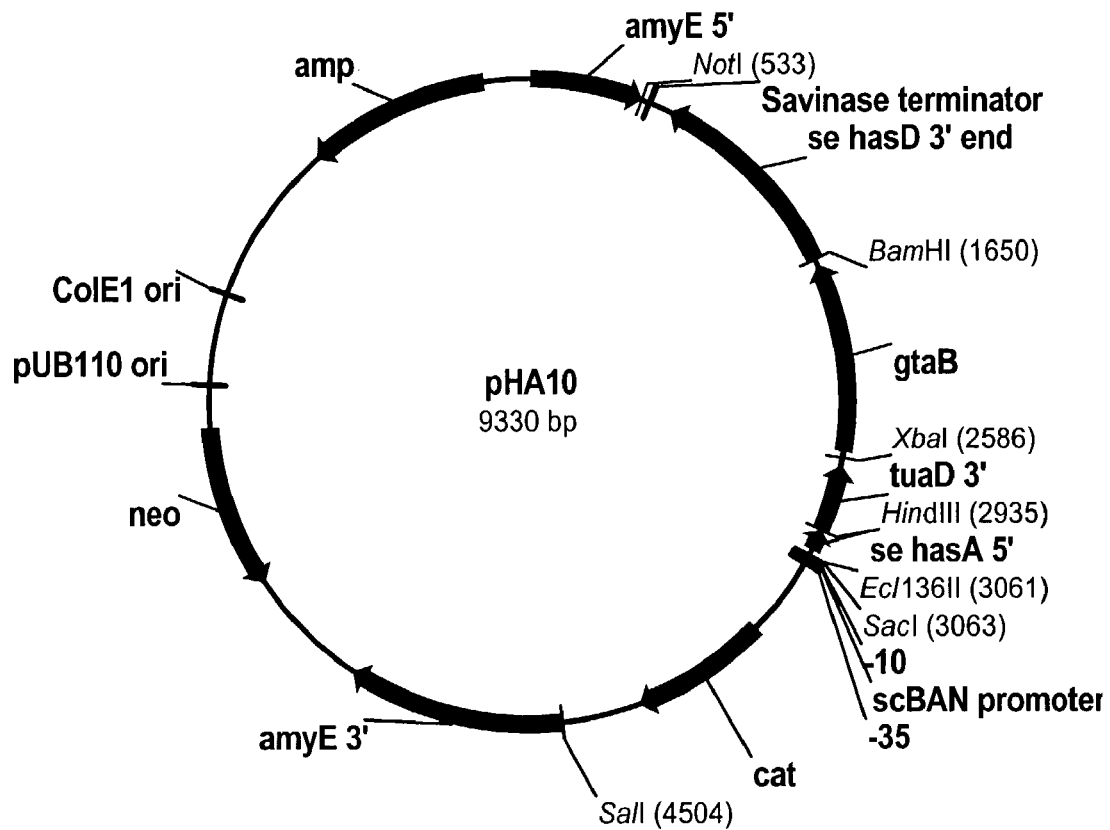
FIG. 17 shows a restriction map of pHA10.

Plasmid DNA was purified from several transformants using a QIAGEN robot according to the manufacturer's instructions and analyzed by SalI plus HindIII digestion on a 0.8% agarose gel using 0.5×TBE buffer. The correct plasmid was identified by the presence of an approximately 1600 bp SalI/HindIII fragment and was designated pHA10 (FIG. 17).

Plasmid pHA10 was digested with HindIII and BamHI. The digestion was resolved on a 0.8% agarose gel using 0.5×TBE buffer and the larger vector fragment (approximately 8100 bp) was gel-purified using the QIAquick DNA Extraction kit according to the manufacturer's instructions. Plasmid pMRT106 was digested with HindIII and BamHI. The digestion was resolved on a 0.8% agarose gel using 0.5×TBE buffer and the larger insert fragment of approximately 4,100 bp was gel-purified using the QIAquick DNA Extraction kit according to the manufacturer's instructions. The two purified fragments were ligated together with T4 DNA ligase and the ligation mix was used to transform *Bacillus subtilis* 168∆4. Transformants were selected on TBAB agar plates supplemented with 5 µg of chloramphenicol per ml at 37° C. Approximately 100 transformants were patched onto TBAB supplemented with chloramphenicol (5 µg/ml) and TBAB supplemented with neomycin (10 µg/ml) to score chloramphenicol resistant, neomycin sensitive colonies; this phenotype is indicative of a double crossover into the amyE locus. A few such colonies were identified, all of which exhibited a "wet" phenotype indicating that hyaluronic acid was being produced. One colony was chosen and designated *Bacillus subtilis* 168∆4::scBAN/se hasA/hasB/hasC/hasD.

Genomic DNA was isolated from *Bacillus subtilis* 168∆4:: scBAN/se hasA/hasB/hasC/hasD using a QIAGEN tip-20 column according to the manufacturer's instructions, and used to transform competent *Bacillus subtilis* A164∆5. Transformants were selected on TBAB plates containing 5 µg of chloramphenicol per ml, and grown at 37° C. for 16 hours. The *Bacillus subtilis* A164∆5 hasA/hasB/hasC/hasD integrant was identified by its "wet" phenotype and designated *Bacillus subtilis* TH-1.

Example 8

Construction of *Bacillus subtilis* RB184

The hasA gene from *Streptococcus equisimilis* (Example 1) and tuaD gene (a *Bacillus subtilis* hasB homologue) (Example 1) were cloned to be under the control of a short "consensus" amyQ (scBAN) promoter (U.S. Pat. No. 5,955,310).

Plasmid pDG268MCS∆neo/scBAN/Sav (U.S. Pat. No. 5,955,310) was digested with SacI. The digested plasmid was then purified using a QIAquick DNA Purification Kit according to the manufacturer's instructions, and finally digested with NotI. The largest plasmid fragment of approximately 6,800 bp was gel-purified from a 0.8% agarose-0.5×TBE gel using a QIAquick DNA Gel Extraction Kit according to the manufacturer's instructions. The recovered vector DNA was then ligated with the DNA insert described below.

Figure 18:
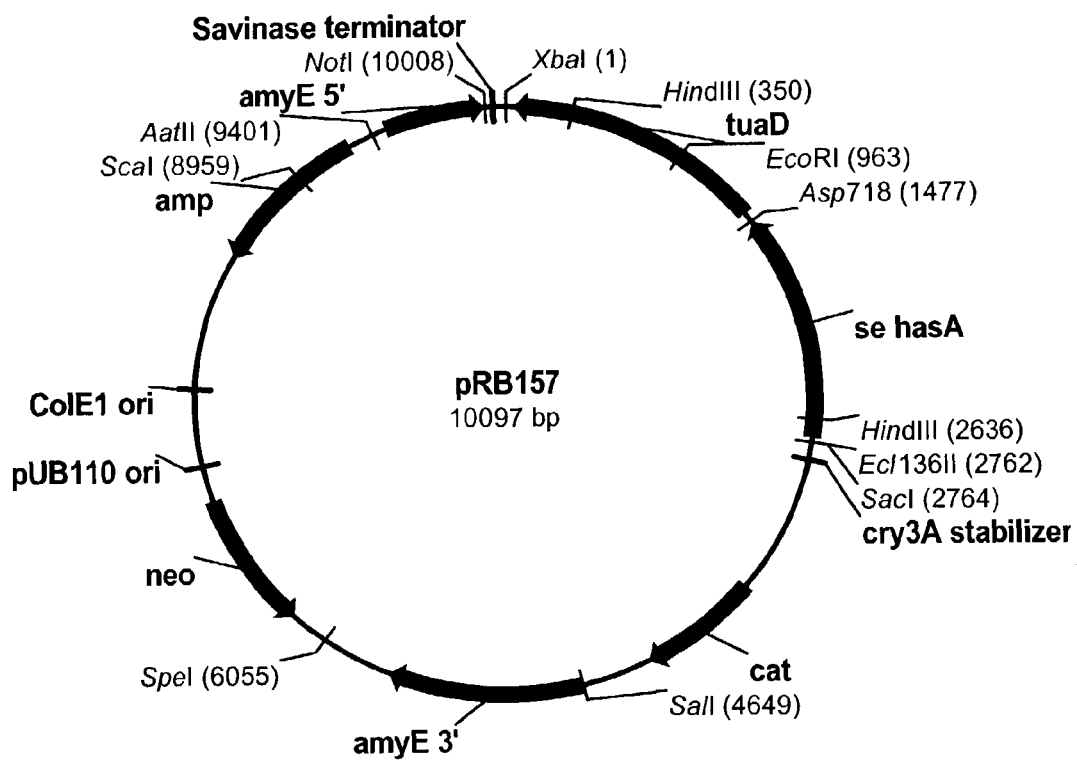
FIG. 18 shows a restriction map of pRB157.

Plasmid pHA5 (Example 3, FIG. 11) was digested with HpaI. The digested plasmid was then purified as described above, and finally digested with XbaI. The double-digested plasmid was then blunted by first inactivating XbaI at 85° C. for 30 minutes. Blunting was performed by adding 0.5 µl of 10 mM each dNTPs, 1 µl of 1 U/µl T4 DNA polymerase (Roche Applied Science; Indianapolis, Ind.) and incubating at 11° C. for 10 minutes. Finally the polymerase was inactivated by incubating the reaction at 75° C. for 10 minutes. The largest plasmid fragment of approximately 11,000 bp was then gel-purified as described above and religated using the Rapid DNA Cloning Kit according to the manufacturer's instructions. The ligation mix was transformed into *E. coli* SURE competent cells. Transformants were selected on 2×YT agar plates supplemented with 100 µg of ampicillin per ml at 37° C. Plasmid DNA was purified from several transformants using a QIAGEN robot according to the manufacturer's instructions and analyzed by ScaI digestion on a 0.8% agarose gel using 0.5×TBE buffer. The correct plasmid was identified by the presence of an approximately 11 kb fragment and was designated pRB157 (FIG. 18).

pRB157 was digested with SacI. The digested plasmid was then purified using a QIAquick DNA Purification Kit according to the manufacturer's instructions, and finally digested with NotI. The smallest plasmid fragment of approximately 2,632 bp was gel-purified using a QIAquick DNA Gel Extraction Kit from a 0.8% agarose-0.5×TBE gel according to the manufacturer's instructions. The recovered DNA insert was then ligated with the vector DNA described above.

Prior to transformation in *Bacillus subtilis*, the ligation described above was linearized using ScaI to ensure double cross-over integration in the chromosome rather than single cross-over integration in the chromosome. *Bacillus subtilis* 168∆4 competent cells were transformed with the ligation digested with the restriction enzyme ScaI.

*Bacillus subtilis* chloramphenicol-resistant transformants were selected on TBAB plates supplemented with 5 µg of chloramphenicol per ml. To screen for integration of the plasmid by double cross-over at the amyE locus, *Bacillus subtilis* primary transformants were patched on TBAB plates supplemented with 6 µg of neomycin per ml and on TBAB plates supplemented with 5 µg of chloramphenicol per ml to isolate chloramphenicol resistant and neomycin sensitive "wet" transformants (due to hyaluronic acid production).

Genomic DNA was isolated from the "wet", chloramphenicol resistant, and neomycin sensitive *Bacillus subtilis* 168∆4 transformants using a QIAGEN tip-20 column according to the manufacturer's instructions. PCR amplifications were performed on these transformants using primers 3, 8, and 16 (Example 1) to confirm the presence and integrity of hasA and tuaD in the operon of the *Bacillus subtilis* transformants. The amplification reactions (25 µl) were composed of approximately 50 ng of genomic DNA of the *Bacillus subtilis* 168∆4 transformants, 0.5 µM of each primer, 200 µM each of dATP, dCTP, dGTP, and dTTP, 1×PCR buffer, 3 mM MgCl$_2$, and 0.625 units of AmpliTaq Gold™ DNA polymerase. The reactions were incubated in a RoboCycler 40 Temperature Cycler programmed for one cycle at 95° C. for 9 minutes; 30 cycles each at 95° C. for 1 minute, 55° C. for 1 minute, and 72° C. for 2 minutes; and a final cycle at 72° C. for 7 minutes.

Primers 3 and 8 were used to confirm the presence of the hasA gene and primers 3 and 16 to confirm the presence of the tuaD gene. A *Bacillus subtilis* 168∆4 hasA/tuaD integrant was designated *Bacillus subtilis* RB183.

*Bacillus subtilis* RB183 genomic DNA was also used to transform competent *Bacillus subtilis* A164∆5. Transformants were selected on TBAB plates containing 5 µg of chloramphenicol per ml, and grown at 37° C. for 16 hours.

The *Bacillus subtilis* A164Δ5 hasA/tuaD integrant was identified by its "wet" phenotype and designated *Bacillus subtilis* RB184.

Example 9

Construction of *Bacillus subtilis* RB187

*Bacillus subtilis* RB161 was made competent and transformed with the cat deletion plasmid pRB115 (Widner et al., 2000, *Journal of Industrial Microbiology & Biotechnology* 25: 204-212). Selection for direct integration into the chromosome was performed at the non-permissive temperature of 45° C. using erythromycin (5 µg/ml) selection. At this temperature, the pE194 origin of replication is inactive. Cells are able to maintain erythromycin resistance only by integration of the plasmid into the cat gene on the bacterial chromosome. These so-called "integrants" were maintained at 45° C. to ensure growth at this temperature with selection. To allow for loss or "looping out" of the plasmid, which will result in the deletion of most of the cat gene from the chromosome, the integrants were grown in Luria-Bertani (LB) medium without selection at the permissive temperature of 34° C. for many generations. At this temperature the pE194 origin of replication is active and promotes excision of the plasmid from the genome (*Molecular Biological Methods for Bacillus*, edited by C. R. Harwood and S. M. Cutting, 1990, John Wiley and Sons Ltd.).

The cells were then plated on non-selective LB agar plates and colonies which contained deletions in the cat gene and loss of the pE194-based replicon were identified by the following criteria: (1) chloramphenicol sensitivity indicated the presence of the cat deletion; (2) erythromycin sensitivity indicated the absence of the erythromycin resistance gene encoded by the vector pRB115; and (3) PCR confirmed the presence of the cat deletion in the strain of interest. PCR was performed to confirm deletion of the cat gene at the amyE locus by using primers 32 and 33:

```
Primer 32:
                                   (SEQ ID NO: 46)
5'-GCGGCCGCGGTACCTGTGTTACACCTGTT-3'

Primer 33:
                                   (SEQ ID NO: 47)
5'-GTCAAGCTTAATTCTCATGTTTGACAGCTTATCATCGG-3'
```

Chromosomal DNA from potential deletants was isolated using the REDextract-N-Amp™ Plant PCR kits (Sigma Chemical Company, St. Louis, Mo.) as follows: Single *Bacillus* colonies were inoculated into 100 µl of Extraction Solution (Sigma Chemical Company, St. Louis, Mo.), incubated at 95° C. for 10 minutes, and then diluted with an equal volume of Dilution Solution (Sigma Chemical Company, St. Louis, Mo.). PCR was performed using 4 µl of extracted DNA in conjunction with the REDextract-N-Amp PCR Reaction Mix and the desired primers according to the manufacturer's instructions, with PCR cycling conditions described in Example 5. PCR reaction products were visualized in a 0.8% agarose-0.5×TBE gel. The verified strain was named *Bacillus subtilis* RB187.

Example 10

Construction of *Bacillus subtilis* RB192

*Bacillus subtilis* RB184 was made unmarked by deleting the chloramphenicol resistance gene (cat gene). This was accomplished using the method described previously in Example 9. The resultant strain was designated *Bacillus subtilis* RB192.

Example 11

Construction of *Bacillus subtilis* RB194

*Bacillus subtilis* RB194 was constructed by deleting the cypX region of the chromosome of *Bacillus subtilis* RB187 (Example 9). The cypX region includes the cypX gene which encodes a cytochrome P450-like enzyme that is involved in the synthesis of a red pigment during fermentation. In order to delete this region of the chromosome plasmid pMRT086 was constructed.

The region of the chromosome which harbors the cypX-yvmC and yvmB-yvmA operons was PCR amplified from *Bacillus subtilis* BRG-1 as a single fragment using primers 34 and 35. *Bacillus subtilis* BRG1 is essentially a chemically mutagenized isolate of an amylase-producing strain of *Bacillus subtilis* which is based on the *Bacillus subtilis* A164Δ5 genetic background that was described in Example 5. The sequence of this region is identical to the published sequence for the *Bacillus subtilis* 168 type strain.

```
Primer 34:
5'-CATGGGAGAGACCTTTGG-3'    (SEQ ID NO: 48)

Primer 35:
5'-GTCGGTCTTCCATTTGC-3'     (SEQ ID NO: 49)
```

The amplification reactions (50 µl) were composed of 200 ng of *Bacillus subtilis* BRG-1 chromosomal DNA, 0.4 µM each of primers 34 and 35, 200 µM each of dATP, dCTP, dGTP, and dTTP, 1× Expand™ High Fidelity buffer (Roche Applied Science; Indianapolis, Ind.) with 1.5 mM MgCl$_2$, and 2.6 units of Expand™ High Fidelity PCR System enzyme mix (Roche Applied Science; Indianapolis, Ind.). *Bacillus subtilis* BRG-1 chromosomal DNA was obtained using a QIAGEN tip-20 column according to the manufacturer's instructions. Amplification reactions were performed in a RoboCycler 40 thermacycler (Stratagene, Inc, La Jolla, Calif.) programmed for 1 cycle at 95° C. for 3 minutes; 10 cycles each at 95° C. for 1 minute, 58° C. for 1 minute, and 68° C. for 4 minutes; 20 cycles each at 95° C. for 1 minute, 58° C. for 1 minute, 68° C. for 4 minutes plus 20 seconds per cycle, followed by 1 cycle at 72° C. for 7 minutes. Reaction products were analyzed by agarose gel electrophoresis using a 0.8% agarose gel using 0.5×TBE buffer.

Figure 19:
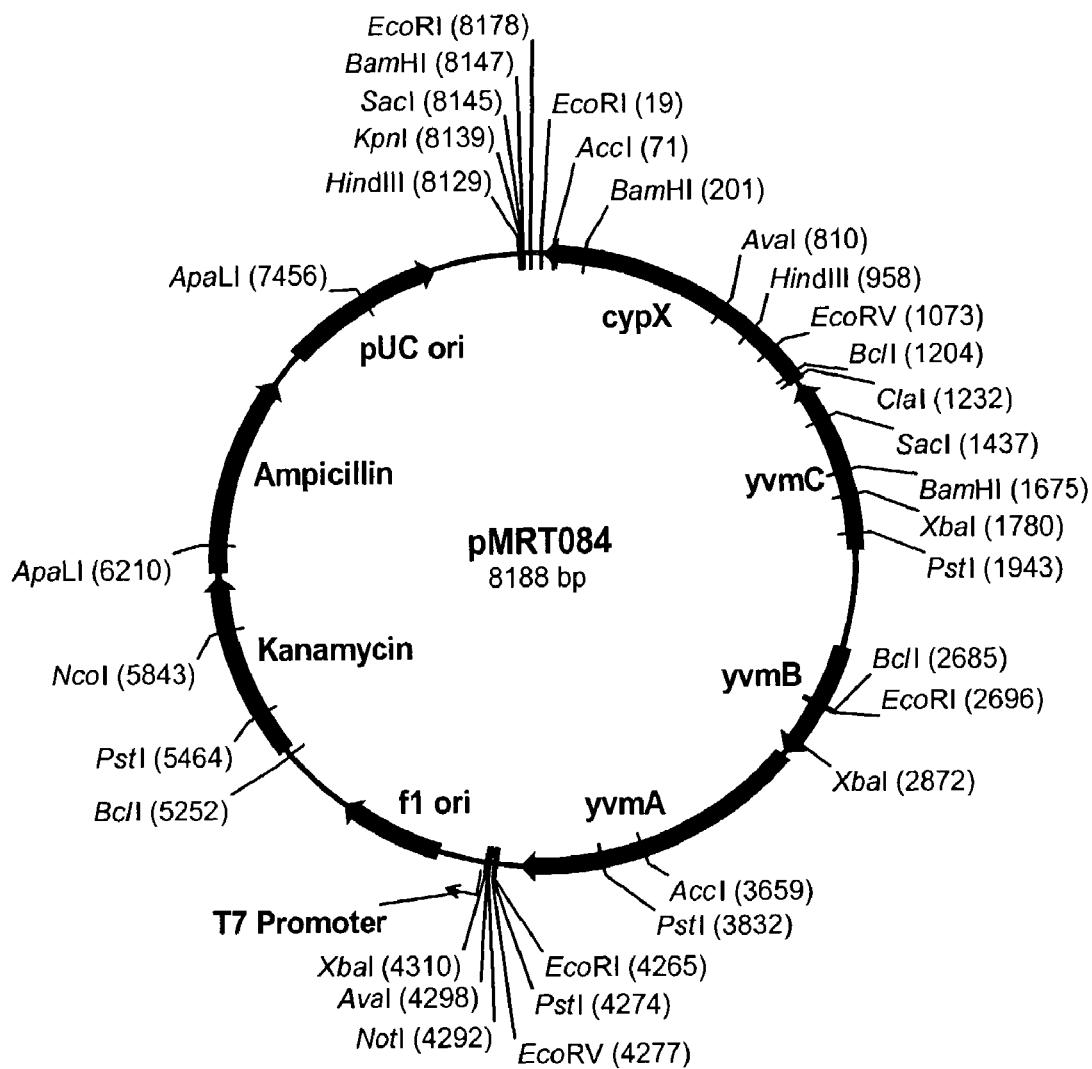
FIG. 19 shows a restriction map of pMRT084.

The resulting fragment comprising the cypX-yvmC and yvmB-yvmA operons was cloned into pCR2.1 using the TA-TOPO Cloning Kit and transformed into *E. coli* OneShot™ cells according to the manufacturer's instructions (Invitrogen, Inc., Carlsbad, Calif.). Transformants were selected on 2×YT agar plates supplemented with 100 µg of ampicillin per ml. Plasmid DNA from several transformants was isolated using QIAGEN tip-20 columns according to the manufacturer's instructions and verified by DNA sequencing with M13 (−20) forward, M13 reverse and primers 36 to 51 shown below. The resulting plasmid was designated pMRT084 (FIG. 19).

```
Primer 36:
5'-CGACCACTGTATCTTGG-3'          (SEQ ID NO: 50)

Primer 37:
5'-GAGATGCCAAACAGTGC-3'          (SEQ ID NO: 51)

Primer 38:
5'-CATGTCCATCGTGACG-3'           (SEQ ID NO: 52)

Primer 39:
5'-CAGGAGCATTTGATACG-3'          (SEQ ID NO: 53)

Primer 40:
5'-CCTTCAGATGTGATCC-3'           (SEQ ID NO: 54)

Primer 41:
5'-GTGTTGACGTCAACTGC-3'          (SEQ ID NO: 55)

Primer 42:
5'-GTTCAGCCTTTCCTCTCG-3'         (SEQ ID NO: 56)

Primer 43:
5'-GCTACCTTCTTTCTTAGG-3'         (SEQ ID NO: 57)

Primer 44:
5'-CGTCAATATGATCTGTGC-3'         (SEQ ID NO: 58)

Primer 45:
5'-GGAAAGAAGGTCTGTGC-3'          (SEQ ID NO: 59)

Primer 46:
5'-CAGCTATCAGCTGACAG-3'          (SEQ ID NO: 60)

Primer 47:
5'-GCTCAGCTATGACATATTCC-3'       (SEQ ID NO: 61)

Primer 48:
5'-GATCGTCTTGATTACCG-3'          (SEQ ID NO: 62)

Primer 49:
5'-AGCTTTATCGGTGACG-3'           (SEQ ID NO: 63)

Primer 50:
5'-TGAGCACGATTGCAGG-3'           (SEQ ID NO: 64)

Primer 51:
5'-CATTGCGGAGACATTGC-3'          (SEQ ID NO: 65)

Primer 52:
5'-TAGACAATTGGAAGAGAAAAGAGATA-3' (SEQ ID NO: 66)

Primer 53:
5'-CCGTCGCTATTGTAACCAGT-3'       (SEQ ID NO: 67)
```

Figure 20:
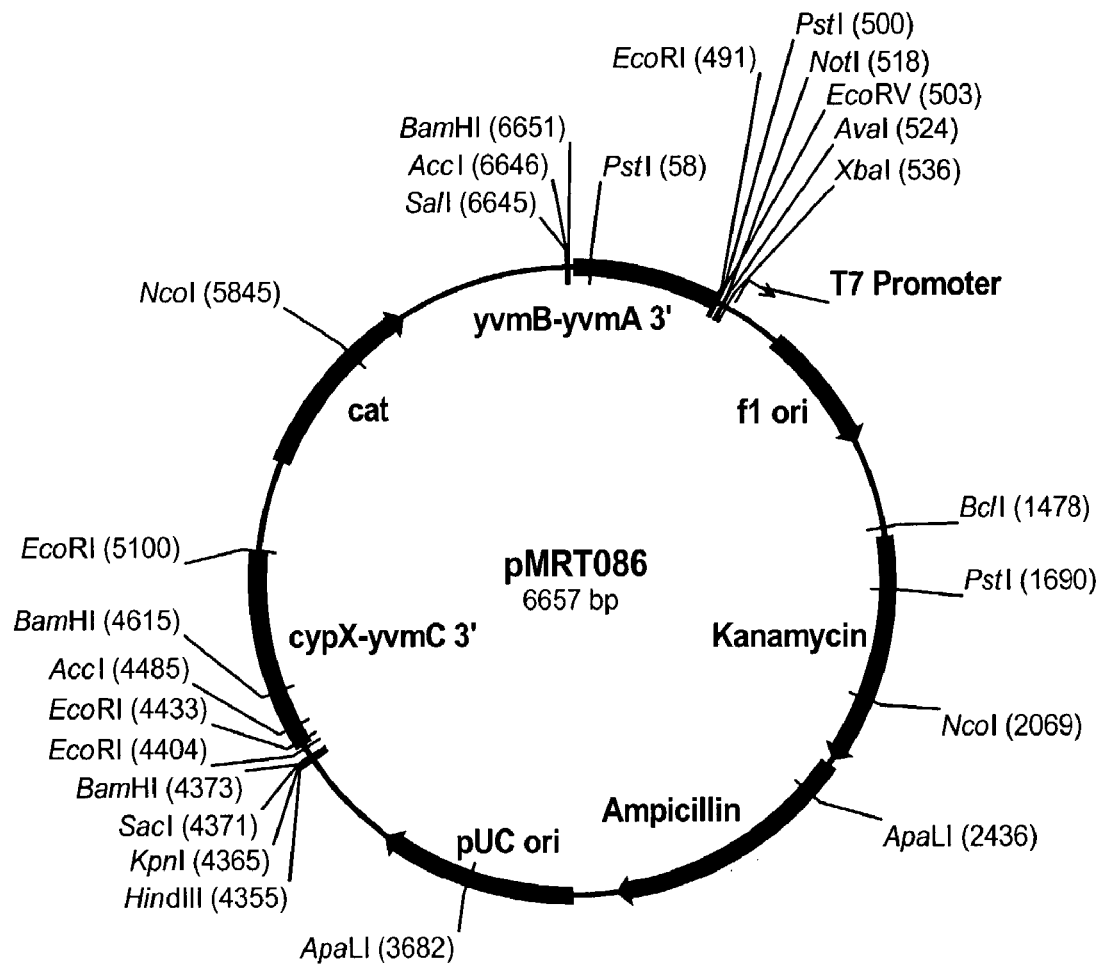
FIG. 20 shows a restriction map of pMRT086.

Plasmid pMRT084 was digested with BsgI to delete most of the cypX-yvmC and yvmB-yvmA operons, leaving about 500 bases at each end. The digested BsgI DNA was treated with T4 DNA polymerase. Plasmid pECC1 (Youngman et al., 1984, *Plasmid* 12: 1-9) was digested with SmaI. A fragment of approximately 5,100 bp from pMRT084 and a fragment of approximately 1,600 bp fragment from pECC1 were isolated from a 0.8% agarose-0.5×TBE gel using the QIAquick DNA Extraction Kit according to the manufacturer's instructions, ligated together, and transformed into *E. coli* XL1 Blue cells according to the manufacturer's instructions (Stratagene, Inc., La Jolla, Calif.). Transformants were selected on 2×YT agar plates supplemented with 100 μg of ampicillin per ml. Transformants carrying the correct plasmid with most of the cypX-yvmC and yvmB-yvmA operons deleted were identified by PCR amplification using primers 52 and 53. PCR amplification was conducted in 50 μl reactions composed of 1 ng of plasmid DNA, 0.4 μM of each primer, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes. The PCR product was visualized using a 0.8% agarose-0.5×TBE gel. This construct was designated pMRT086 (FIG. 20).

Plasmid pMRT086 was linearized with ScaI and transformed into *Bacillus subtilis* RB128 competent cells in the presence of 0.2 μg of chloramphenicol per ml. Transformants were selected on TBAB plates containing 5 μg of chloramphenicol per ml after incubation at 37° C. for 16 hours. Chromosomal DNA was prepared from several transformants using a QIAGEN tip-20 column according to the manufacturer's instructions. Chloramphenicol resistant colonies were screened by PCR for deletion of the cypX-yvmC and yvmB-yvmA operons via PCR using primers 36 and 52, 36 and 53, 37 and 52, and 37 and 53. PCR amplification was conducted in 50 μl reactions composed of 50 ng of chromosomal DNA, 0.4 μM of each primer, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes. The PCR products were visualized using a 0.8% agarose-0.5×TBE gel. The resulting *Bacillus subtilis* RB128 cypX-yvmC and yvmB-yvmA deleted strain was designated *Bacillus subtilis* MaTa17.

Competent cells of *Bacillus subtilis* RB187 (Example 9) were transformed with genomic DNA from *Bacillus subtilis* MaTa17. Genomic DNA was obtained from this strain using a QIAGEN tip-20 column according to the manufacturer's instructions. *Bacillus subtilis* chloramphenicol resistant transformants were selected on TBAB plates supplemented with 5 μg of chloramphenicol per ml at 37° C. Primary transformants were streaked for single colony isolations on TBAB plates containing 5 μg of chloramphenicol per ml at 37° C. The resulting cypX-yvmC and yvmB-yvmA deleted strain was designated *Bacillus subtilis* RB194.

Example 12

Construction of *Bacillus subtilis* RB197

*Bacillus subtilis* RB197 is very similar to *Bacillus subtilis* RB194, the only difference being that RB197 contains a smaller deletion in the cypX region: only a portion of the cypX gene is deleted in this strain to generate a cypX minus phenotype. In order to accomplish this task a plasmid, pMRT122, was constructed as described below.

Plasmid pCJ791 (FIG. 21) was constructed by digestion of plasmid pSJ2739 (WO 96/23073) with EcoRI/HindIII and ligation to a fragment containing a deleted form of the wprA gene (cell wall serine protease) from *Bacillus subtilis*. The 5' region of wprA was amplified using primers 54 and 55 see below, and the 3' region was amplified using primers 56 and 57 shown below from chromosomal DNA obtained from *Bacillus subtilis* DN1885 (Diderichsen et al., 1990, *Journal of Bacteriology* 172: 4315-4321). PCR amplification was conducted in 50 μl reactions composed of 1 ng of *Bacillus subtilis* DN1885 chromosomal DNA, 0.4 μMeach of primers 39 and 40, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes.

Figure 21:
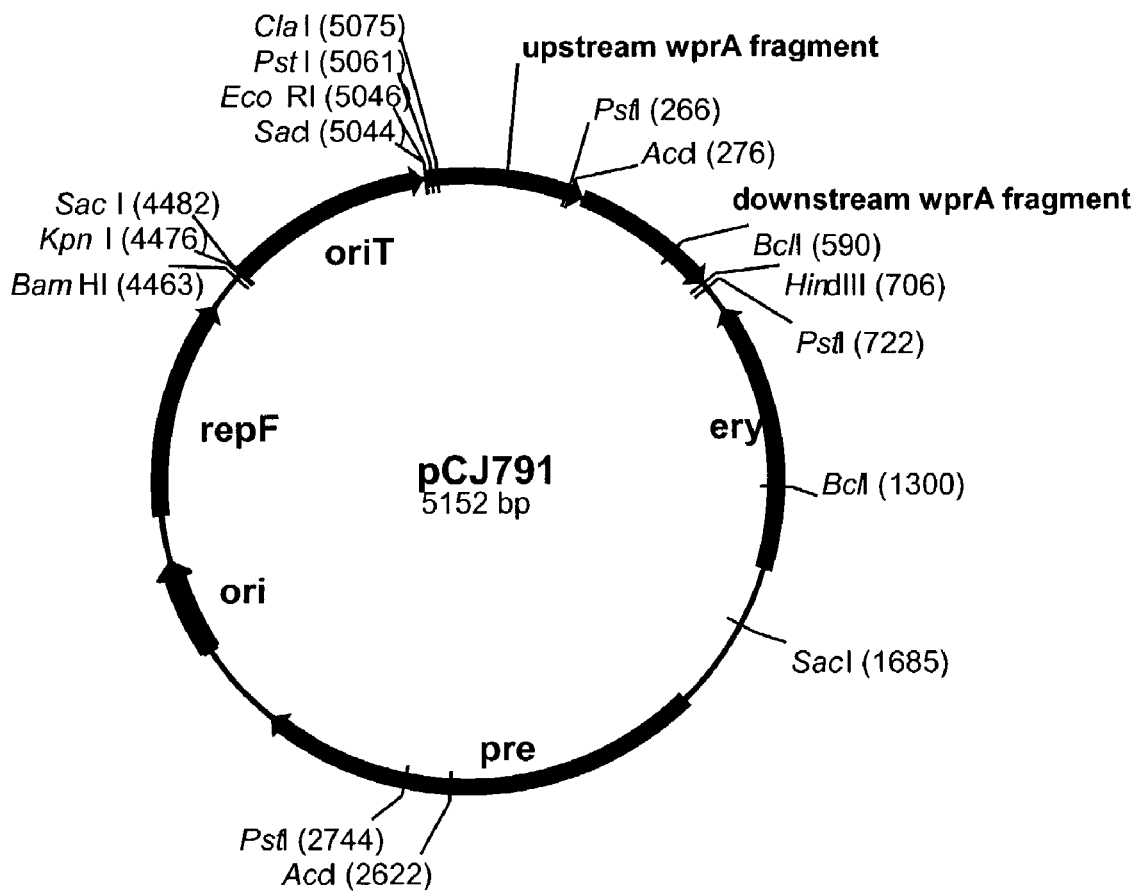
FIG. 21 shows a restriction map of pCJ791.

The 5' and 3' wprA PCR fragments were linked by digestion with BglII followed by ligation, and PCR amplification was performed on the ligation mixture fragments using primers 54 and 57. PCR amplification was conducted in 50 µl reactions composed of 1 ng of the ligated fragment, 0.4 µM of each primer, 200 µM each of dATP, dCTP, dGTP, and dTTP, 1×PCR Buffer II with 2.5 mM MgCl₂, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes. The PCR product was visualized using a 0.8% agarose-0.5×TBE gel. The resulting PCR fragment was cloned into pSJ2739 as an EcoRI/HindIII fragment, resulting in plasmid pCJ791 (FIG. 21). Transformants were selected on TBAB-agar plates supplemented with 1 µg of erythromycin and 25 µg of kanamycin per ml after incubation at 28° C. for 24-48 hours. Plasmid DNA from several transformants was isolated using QIAGEN tip-20 columns according to the manufacturer's instructions and verified by PCR amplification with primers 54 and 57 using the conditions above.

```
Primer 54:
                                              (SEQ ID NO: 68)
5'-GGAATTCCAAAGCTGCAGCGGCCGGCGCG-3'

Primer 55:
                                              (SEQ ID NO: 69)
5'-GAAGATCTCGTATACTTGGCTTCTGCAGCTGC-3'

Primer 56:
                                              (SEQ ID NO: 70)
5'-GAAGATCTGGTCAACAAGCTGGAAAGCACTC-3'

Primer 57:
                                              (SEQ ID NO: 71)
5'-CCCAAGCTTCGTGACGTACAGCACCGTTCCGGC-3'
```

Figure 22:
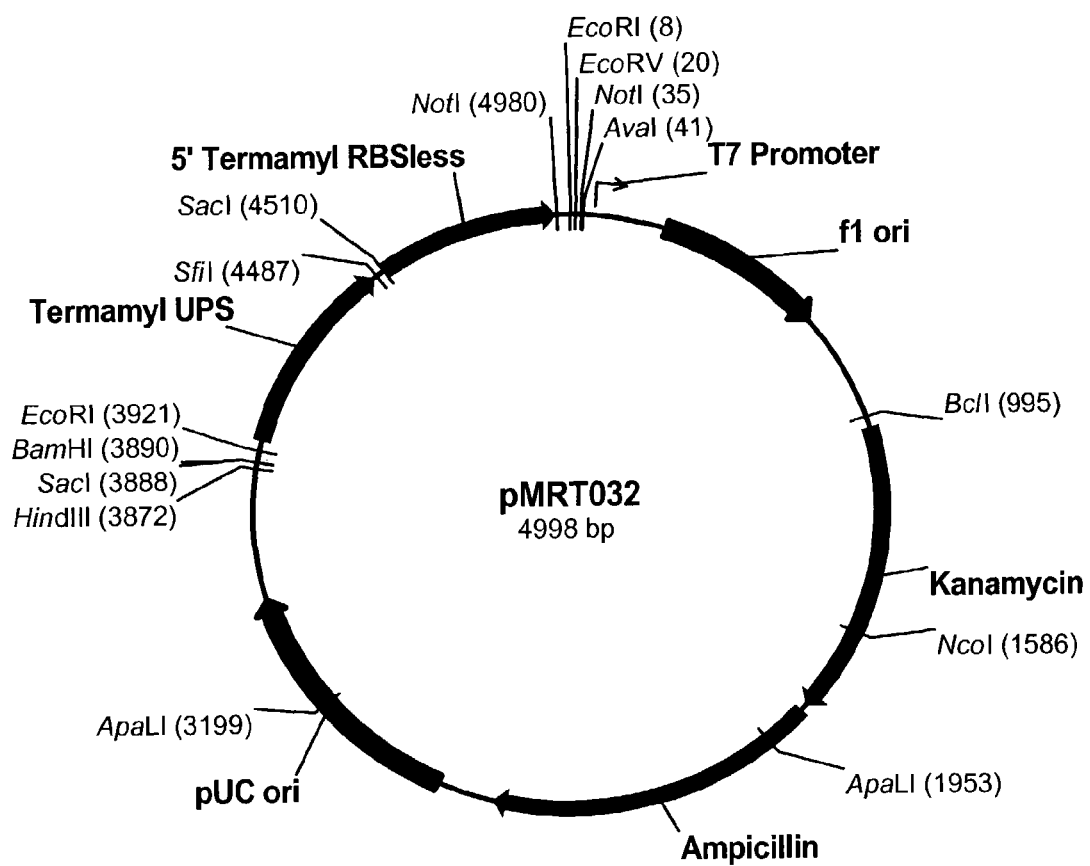
FIG. 22 shows a restriction map of pMRT032.

The amyL upstream sequence and 5' coding region from plasmid pDN1981 (U.S. Pat. No. 5,698,415) were fused together by SOE using the primer pairs 58/59 and 60/61 shown below. The resulting fragment was cloned into vector pCR2.1 to generate plasmid pMRT032 as follows. PCR amplifications were conducted in triplicate in 50 µl reactions composed of 1 ng of pDN1981 DNA, 0.4 µM each of appropriate primers, 200 µM each of dATP, dCTP, dGTP, and dTTP, 1×PCR Buffer II with 2.5 mM MgCl₂, and 2.5 units of AmpliTaq Gold™ DNA polymerase. The reactions were performed in a RoboCycler 40 thermacycler programmed for 1 cycle at 95° C. for 9 minutes; 3 cycles each at 95° C. for 1 minute, 52° C. for 1 minute, and 72° C. for 1 minute; 27 cycles each at 95° C. for 1 minute, 55° C. for 1 minute, and 72° C. for 1 minute; and 1 cycle at 72° C. for 5 minutes. The PCR product was visualized in a 0.8% agarose-0.5×TBE gel. The expected fragments were approximately 530 and 466 bp, respectively. The final SOE fragment was generated using primer pair 59/60 and cloned into pCR2.1 vector using the TA-TOPO Cloning Kit. Transformants were selected on 2×YT agar plates supplemented with 100 µg/ml ampicillin after incubation at 37° C. for 16 hours. Plasmid DNA from several transformants was isolated using QIAGEN tip-20 columns according to the manufacturer's instructions and verified by DNA sequencing with M13 (−20) forward and M13 reverse primers. The plasmid harboring the amyL upstream sequence/5' coding sequence fusion fragment was designated pMRT032 (FIG. 22).

```
Primer 58:  5'-CCTTAAGGGCCGAATATTTATACGGAGCTCCCTGAAACAACAAAAACGGC-3'   (SEQ ID NO: 72)

Primer 59:  5'-GGTGTTCTCTAGAGCGGCCGCGGTTGCGGTCAGC-3'                    (SEQ ID NO: 73)

Primer 60:  5'-GTCCTTCTTGGTACCTGGAAGCAGAGC-3'                           (SEQ ID NO: 74)

Primer 61:  5'-GTATAAATATTCGGCCCTTAAGGCCAGTACCATTTTCCC-3'               (SEQ ID NO: 75)
```

Figure 23:
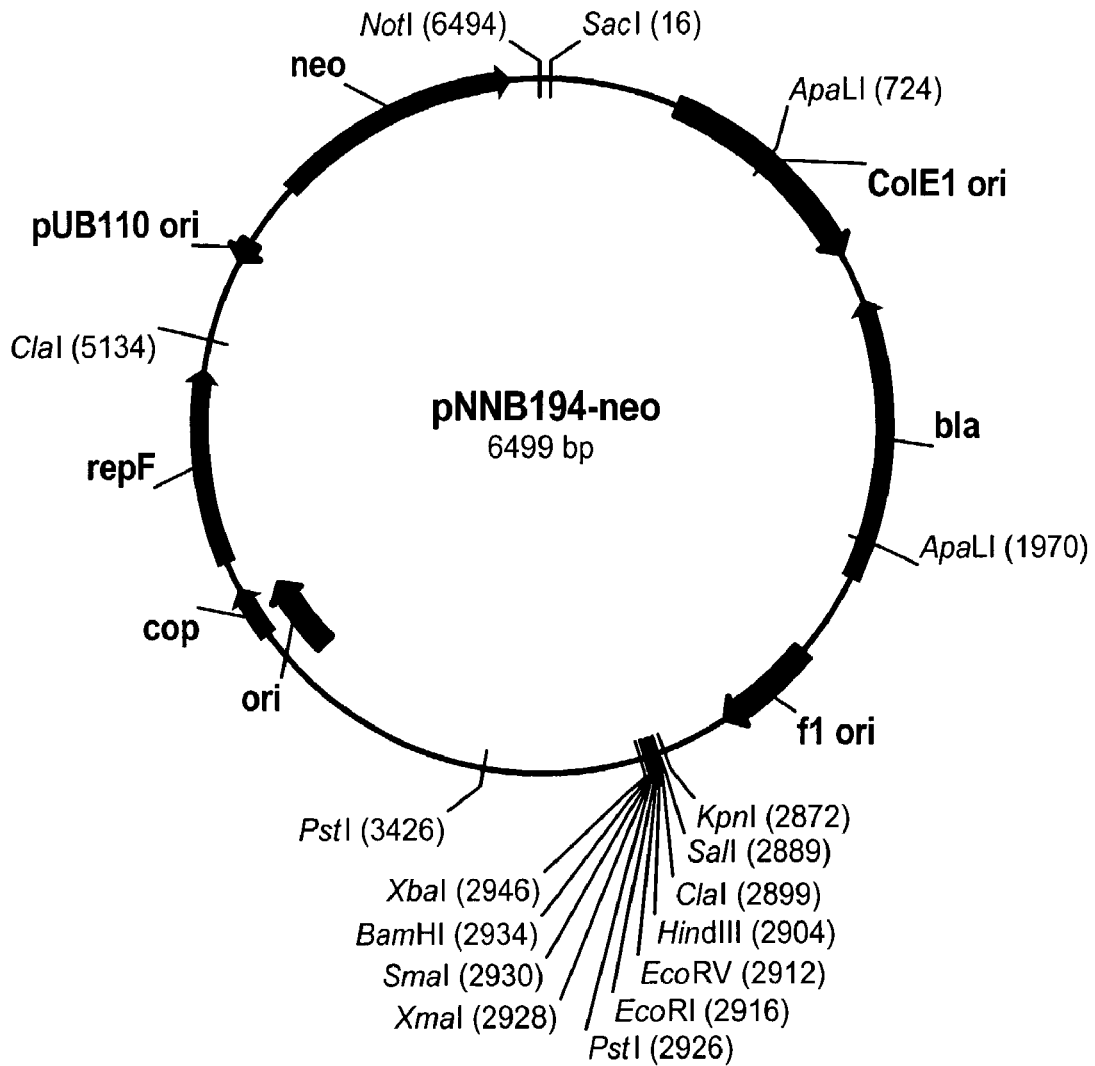
FIG. 23 shows a restriction map of pNNB194neo.

Plasmid pNNB194 (pSK⁺/pE194; U.S. Pat. No. 5,958,728) was digested with NsiI and NotI, and plasmid pBEST501 (Itaya et al. 1989 Nucleic Acids Research 17: 4410) was digested with PstI and NotI. The 5,193 bp vector fragment from pNNB194 and the 1,306 bp fragment bearing the neo gene from pBEST501 were isolated from a 0.8% agarose-0.5×TBE gel using a QIAquick DNA Purification Kit according to the manufacturer's instructions. The isolated fragments were ligated together and used to transform E. coli SURE competent cells according to the manufacturer's instructions. Ampicillin-resistant transformants were selected on 2×YT plates supplemented with 100 µg of ampicillin per ml. Plasmid DNA was isolated from one such transformant using the QIAGEN Plasmid Kit (QIAGEN Inc., Valencia, Calif.), and the plasmid was verified by digestion with NsiI and NotI. This plasmid was designated pNNB194neo (FIG. 23).

Figure 24:
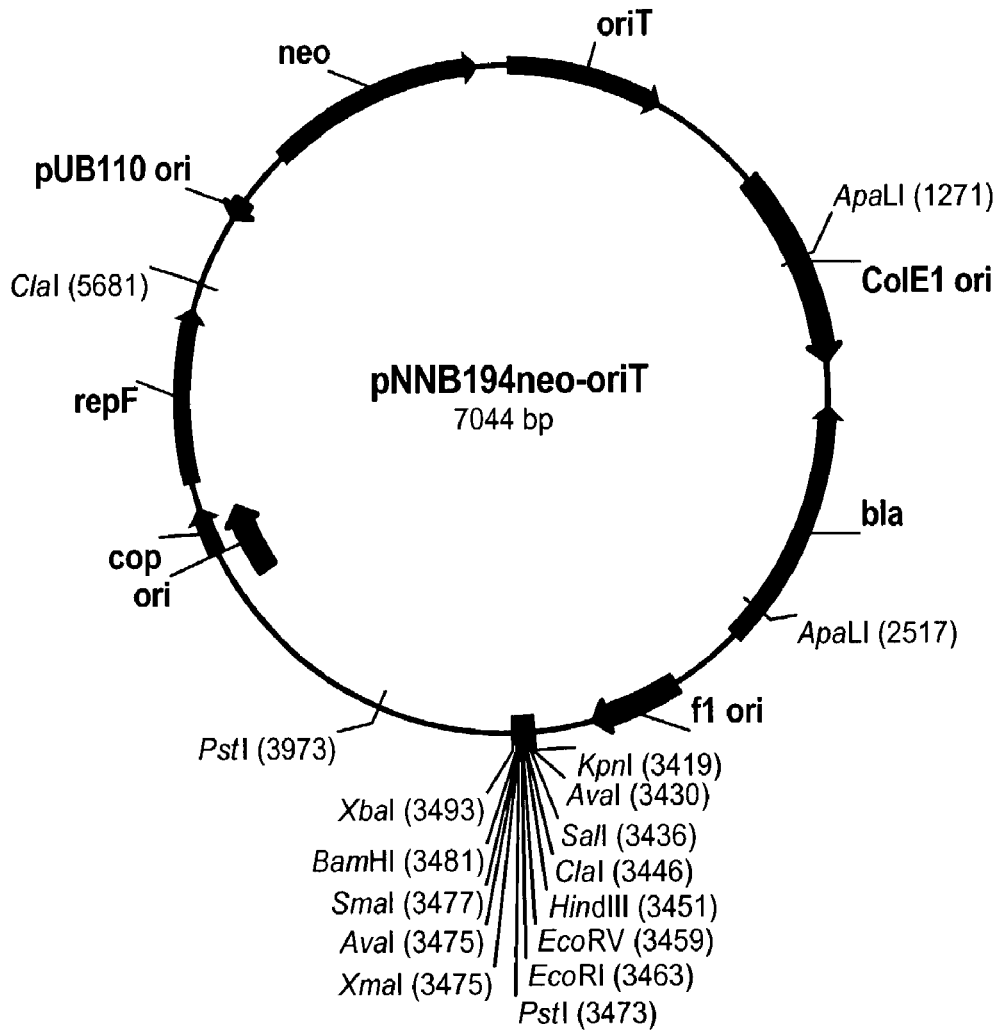
FIG. 24 shows a restriction map of pNNB194neo-oriT.

Plasmid pNNB194neo was digested with SacI/NotI and treated with T4 DNA polymerase and dNTPs to generate blunt ends using standard protocols. Plasmid pPL2419 (U.S. Pat. No. 5,958,728) was digested with Ecl136II. The 6,478 bp vector fragment from pNNB194neo and the 562 bp fragment bearing oriT from pPL2419 were isolated from a 0.8% agarose-0.5×TBE gel using a QIAquick DNA Purification Kit according to the manufacturer's instructions. The gel-purified fragments were ligated together and used to transform E. coli SURE cells according to the manufacturer's instructions. Ampicillin-resistant transformants were selected on 2×YT plates supplemented with 100 µg of ampicillin per ml at 37° C. Plasmid DNA was isolated from one such transformant using the QIAGEN Plasmid Kit, and the plasmid was verified by digestion with NSiI, SacI, and BscI. This plasmid was designated pNNB194neo-oriT (FIG. 24).

Figure 25:
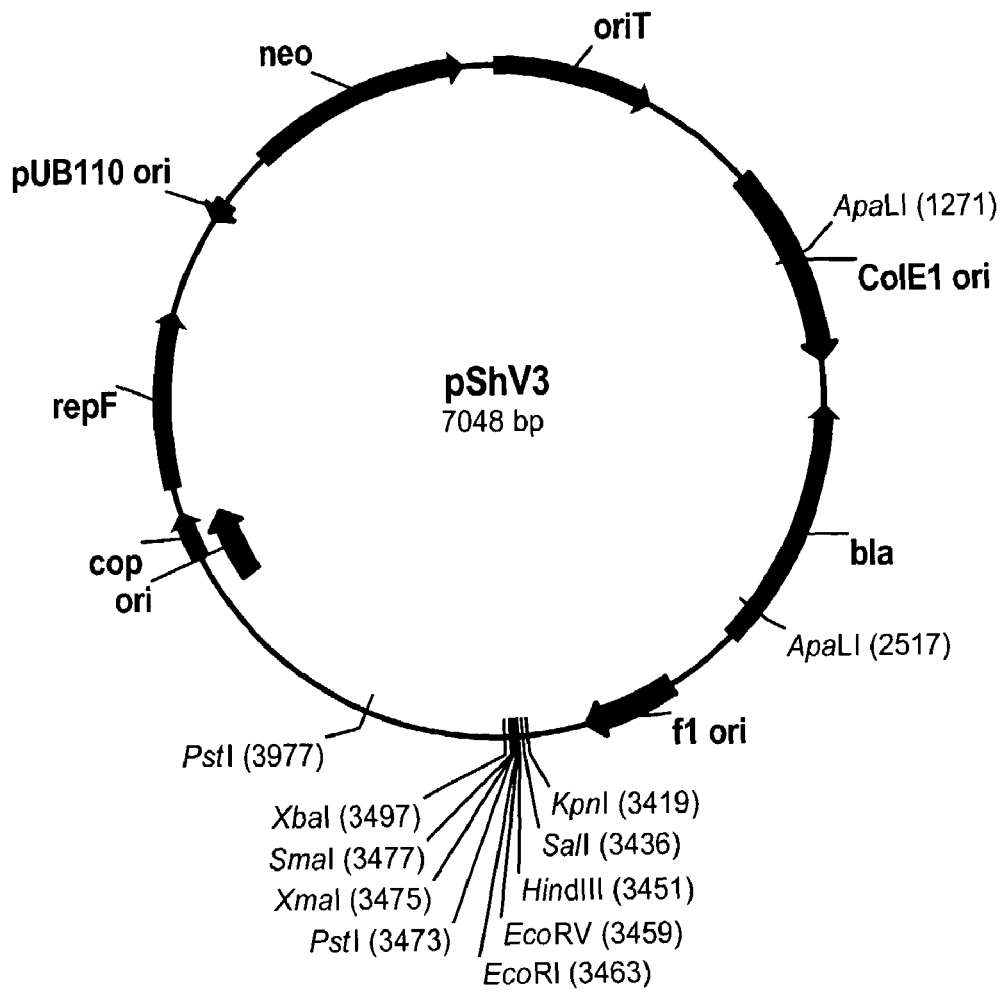
FIG. 25 shows a restriction map of pShV3.

Plasmid pNNB194neo-oriT was digested with BamHI and treated with T4 DNA polymerase and dNTPs to generate blunt ends using standard protocols. The digested plasmid was gel-purified from a 0.8% agarose-0.5×TBE gel using a QIAquick DNA Purification Kit according to the manufacturer's instructions. The purified plasmid was treated with T4 DNA ligase and used to transform E. coli SURE cells according to the manufacturer's instructions. Ampicillin-resistant transformants were selected on 2×YT plates supplemented with 100 µg of ampicillin per ml at 37° C. Plasmid DNA was isolated from one such transformant using the QIAGEN Plasmid Kit, and disruption of the BamHI site was confirmed by digestion with BamHI and ScaI. The resulting plasmid was designated pShV3 (FIG. 25).

Plasmid pShV2.1-amyEΔ (U.S. Pat. No. 5,958,728) was digested with SfiI and NotI, and the 8696 bp vector fragment was gel-purified from a 0.8% agarose-0.5×TBE gel using a QIAquick DNA Purification Kit according to the manufacturer's instructions. In order to insert a BamHI site between the SfiI and NotI sites of pShV2.1-amyEΔ, a synthetic linker was constructed as follows: primers 62 and 63 were annealed by mixing 50 μM of each, boiling the mixture, and allowing the mixture to cool slowly.

```
Primer 62:
5'-GGGCCGGATCCGC-3'           (SEQ ID NO: 76)

Primer 63:
3'-ATTCCCGGCCTAGGCGCCGG-5'    (SEQ ID NO: 77)
```

Figure 26:
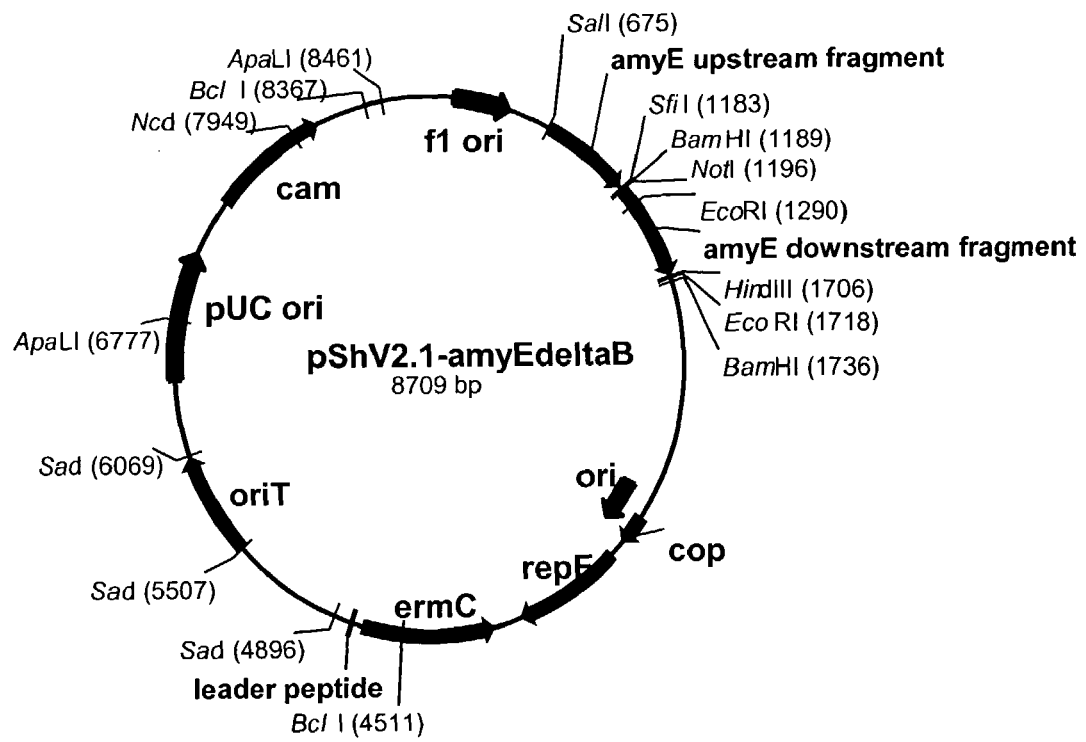
FIG. 26 shows a restriction map of pShV2.1-amyEΔB.

The purified pShV2.1-amyEΔ vector and annealed oligonucleotides were ligated together and used to transform E. coli SURE competent cells according to the manufacturer's instructions. Chloramphenicol-resistant transformants were selected on LB plates supplemented with 30 μg of chloramphenicol per ml at 37° C. Plasmid DNA was isolated from one such transformant using the QIAGEN Plasmid Kit, and insertion of the BamHI site was confirmed by digestion with BamHI. This plasmid was designated pShV2.1-amyEΔB (FIG. 26).

Figure 27:
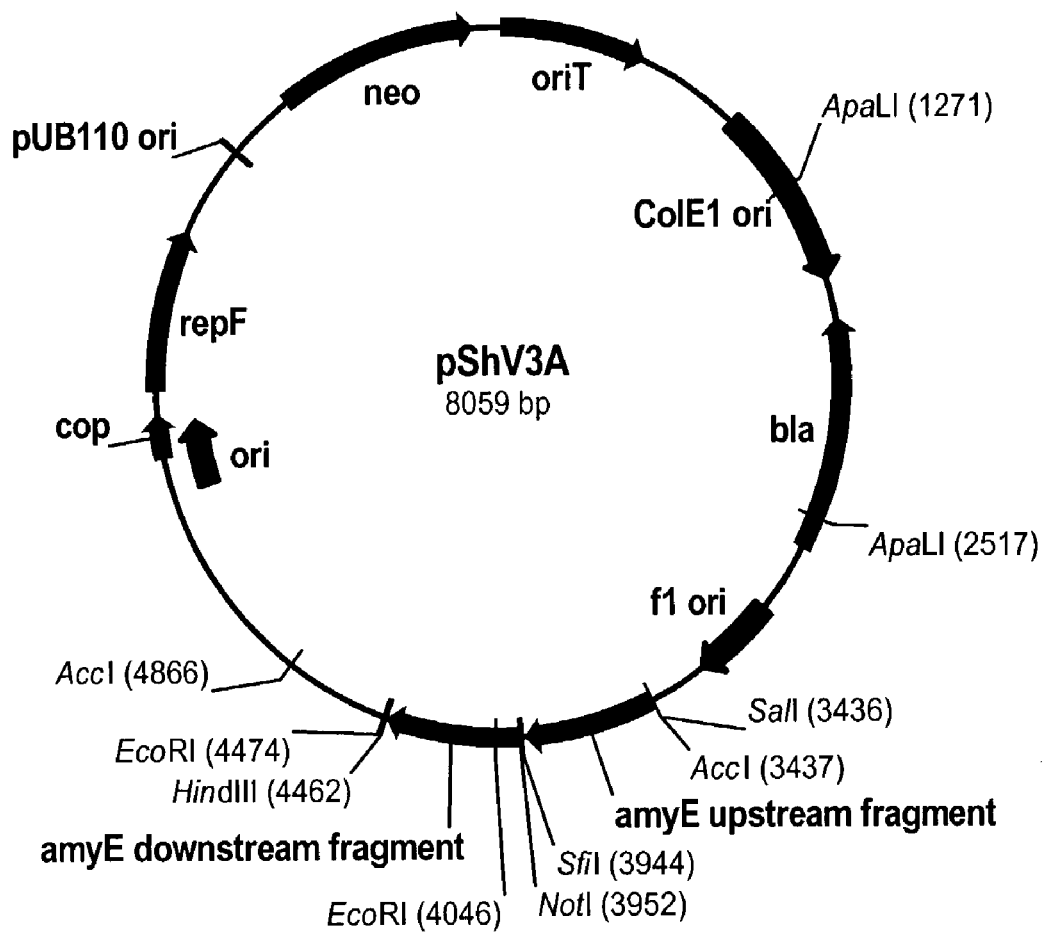
FIG. 27 shows a restriction map of pShV3A.

Plasmids pShV3 and pShV2.1-amyEΔB were digested with SalI/HindIII. A 7033 bp vector fragment from pShV3 and a 1031 bp fragment bearing amyEΔ from pShV2.1-amyEΔ were gel-purified from a 0.8% agarose-0.5×TBE gel using a QIAquick DNA Purification Kit according to the manufacturer's instructions. The gel-purified fragments were ligated together and used to transform E. coli SURE cells according to the manufacturer's instructions. Ampicillin-resistant transformants were selected on 2×YT plates supplemented with 100 μg of ampicillin per ml. Plasmid DNA was isolated from one such transformant using the QIAGEN Plasmid Kit, and the plasmid was verified by digestion with SalI and HindIII. This plasmid was designated pShV3A (FIG. 27).

Figure 28:
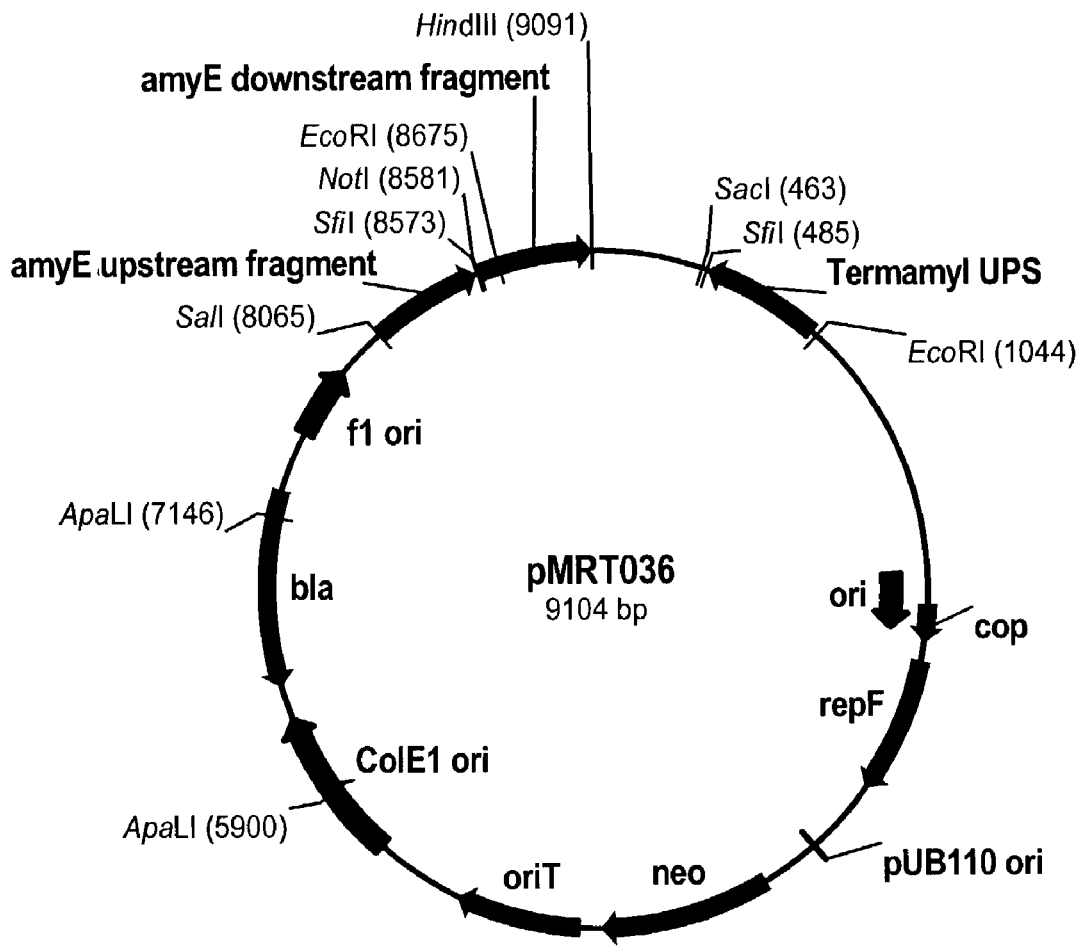
FIG. 28 shows a restriction map of pMRT036.

Plasmid pMRT032 was digested with KpnI/XbaI, filled with Klenow fragment DNA polymerase in the presence of dNTPs, and a fragment of approximately 1000 bp was isolated from a 0.8% agarose-0.5×TBE gel using a QIAquick DNA Purification Kit according to the manufacturer's instructions. This fragment was cloned into plasmid pShV3a digested with EcoRV, and transformed into E. coli XL1 Blue cells according to the manufacturer's instructions. Transformants were selected on 2×YT agar plates supplemented with 100 μg of ampicillin per ml after incubation at 37° C. for 16 hours. Plasmid DNA from several transformants was isolated using QIAGEN tip-20 columns according to the manufacturer's instructions and verified on a 0.8% agarose-0.5×TBE gel by restriction analysis with SacI/SphI. The resulting plasmid was designated pMRT036 (FIG. 28).

Figure 29:
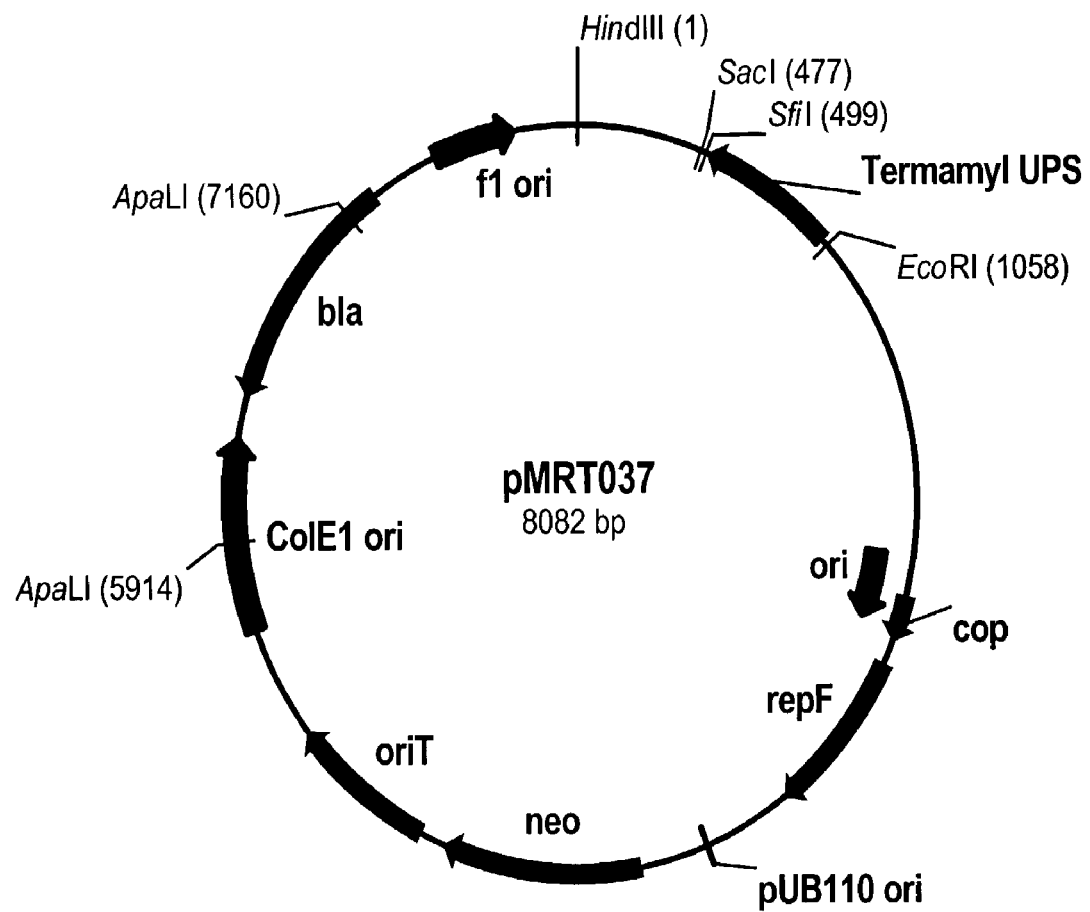
FIG. 29 shows a restriction map of pMRT037.

Plasmid pMRT036 was digested with SalI/HindIII, filled with Klenow fragment DNA polymerase in the presence of dNTPs, ligated and transformed into E. coli XL1 Blue cells according to the manufacturer's instructions. Transformants were selected on 2×YT-agar plates supplemented with 100 μg/ml ampicillin after incubation at 37° C. for 16 hours. Plasmid DNA from several transformants was isolated using QIAGEN tip-20 columns according to the manufacturer's instructions and verified on a 0.8% agarose-0.5×TBE gel by restriction analysis with SacI/XbaI, PstI and NdeI. The resulting plasmid was designated pMRT037 (FIG. 29).

Figure 30:
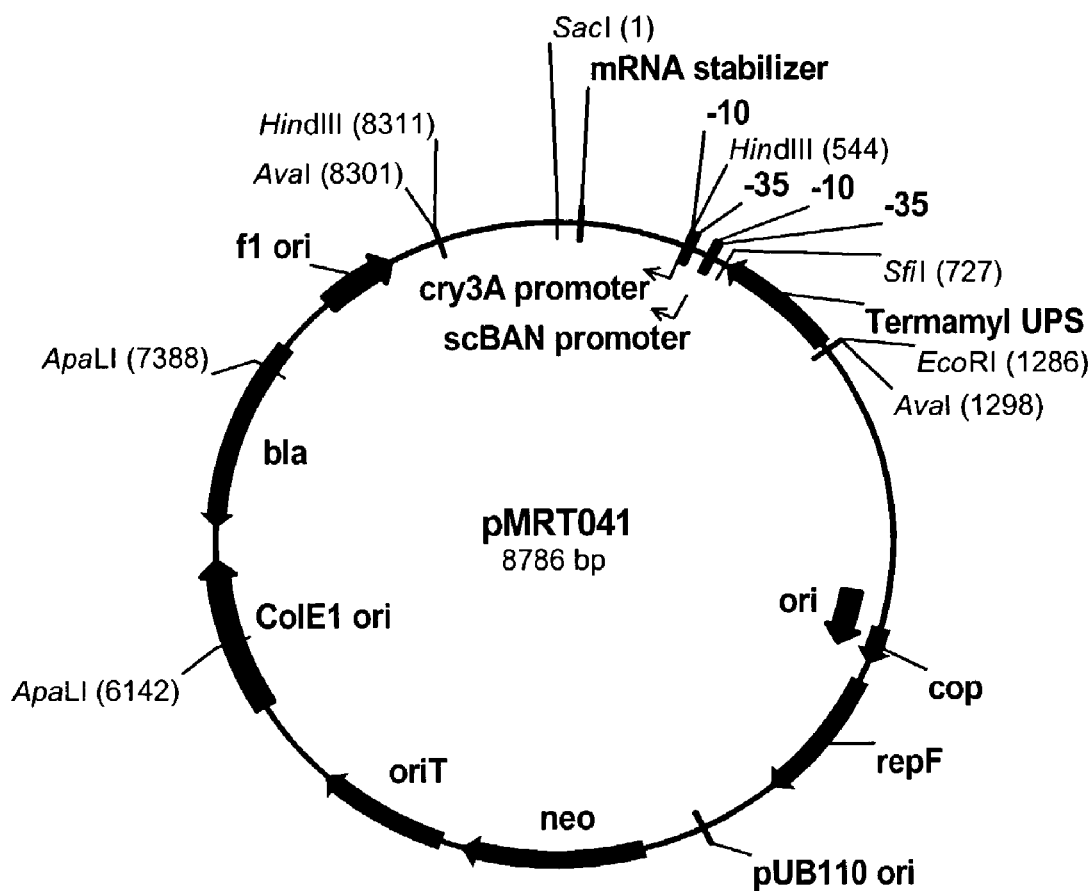
FIG. 30 shows a restriction map of pMRT041.

The scBAN/cryIIIA stabilizer fragment from plasmid pDG268Δneo-cryIIIAstab/Sav (U.S. Pat. No. 5,955,310) was isolated from a 2% agarose-0.5×TBE gel as a SfiI/SacI fragment using a QIAquick DNA Purification Kit according to the manufacturer's instructions, ligated to plasmid pMRT037 digested with SfiI/SacI, and transformed into E. coli XL1 Blue cells. Transformants were selected on 2×YT agar plates supplemented with 100 μg of ampicillin per ml after incubation at 37° C. for 16 hours. Plasmid DNA from several transformants was isolated using QIAGEN tip-20 columns according to the manufacturer's instructions and verified on a 0.8% agarose-0.5×TBE gel by restriction analysis with PstI. The resulting plasmid was designated pMRT041 (FIG. 30).

Figure 31:
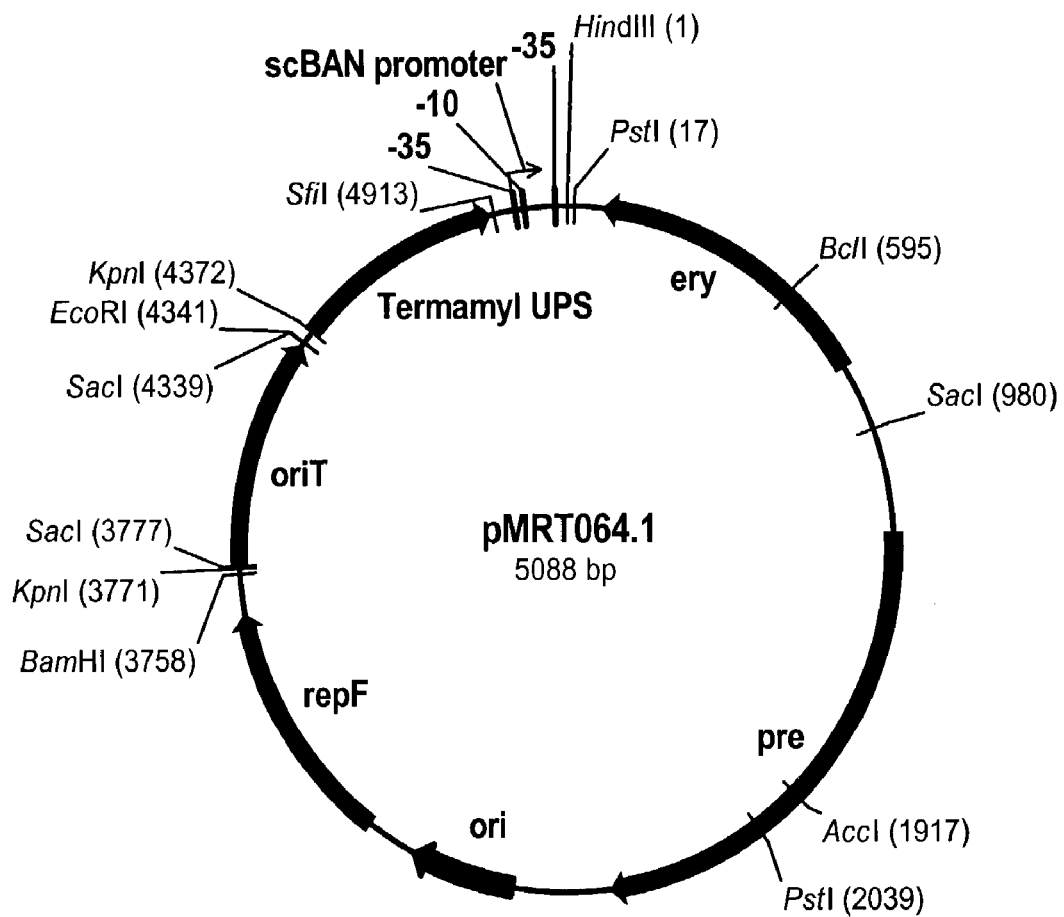
FIG. 31 shows a restriction map of pMRT064.1.

Plasmids pMRT041 and pCJ791 were digested with EcoRI/HindIII. A fragment of approximately 1300 bp from pMRT041 and a fragment of approximately 4500 bp from pCJ791 were isolated from a 0.8% agarose-0.5×TBE gel using a QIAquick DNA Purification Kit according to the manufacturer's instructions, ligated, and transformed into Bacillus subtilis 168Δ4 competent cells. Transformants were selected on TBAB-agar plates supplemented with 1 μg of erythromycin and 25 μg of lincomycin per ml after incubation at 30° C. for 24-48 hours. Plasmid DNA from several transformants was isolated using QIAGEN tip-20 columns according to the manufacturer's instructions and verified on a 0.8% agarose-0.5×TBE gel by restriction analysis with SacI and EcoRI/HindIII. The resulting plasmid was designated pMRT064.1 (FIG. 31).

Figure 32:
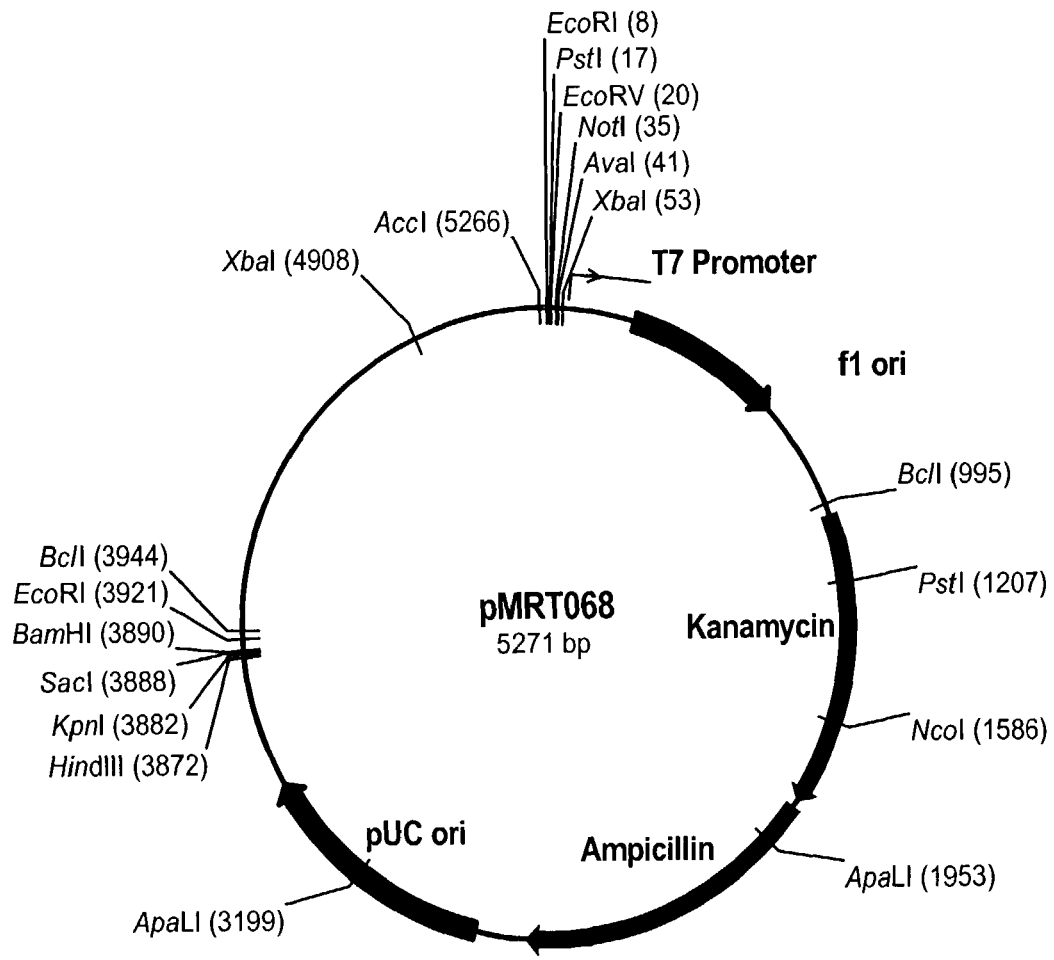
FIG. 32 shows a restriction map of pMRT068.

The SacI site at position 2666 in plasmid pMRT064.1 was deleted by SOE using primer pairs 64 and 65, and primer pairs 66 and 67 shown below. PCR amplification was conducted in 50 μl reactions composed of 1 ng of pMRT064.1 DNA, 0.4 μM of each primer, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 52° C. for 1 minute, and 72° C. for 1 minute; and 1 cycle at 72° C. for 7 minutes. The PCR product was visualized in a 0.8% agarose-0.5×TBE gel. The expected fragments were approximately 400 and 800 bp, respectively. The final fragment for cloning back into pMRT064.1 was amplified using primers 64 and 67. This fragment was cloned into pCR2.1 vector using the TA-TOPO Cloning Kit. Transformants were selected on 2×YT agar plates supplemented with 100 μg/ml ampicillin after incubation at 37° C. for 16 hours. Transformants carrying the correct plasmid were verified by DNA sequencing using M13 forward and reverse primers, and primers 65, 67, and 68. This plasmid was designated pMRT068 (FIG. 32), and was further transformed into E. coli DM1 cells (Stratagene, Inc., La Jolla, Calif.) according to the manufacturer's instructions. Transformants were selected on 2×YT agar plates supplemented with 100 μg of ampicillin per ml.

```
Primer 64:
5'-GGAAATTATCGTGATCAAC-3'       (SEQ ID NO: 78)

Primer 65:
5'-GCACGAGCACTGATAAATATG-3'     (SEQ ID NO: 79)

Primer 66:
5'-CATATTTATCAGTGCTCGTGC-3'     (SEQ ID NO: 80)

Primer 67:
5'-TCGTAGACCTCATATGC-3'         (SEQ ID NO: 81)

Primer 68:
5'-GTCGTTAAACCGTGTGC-3'         (SEQ ID NO: 82)
```

Figure 33:
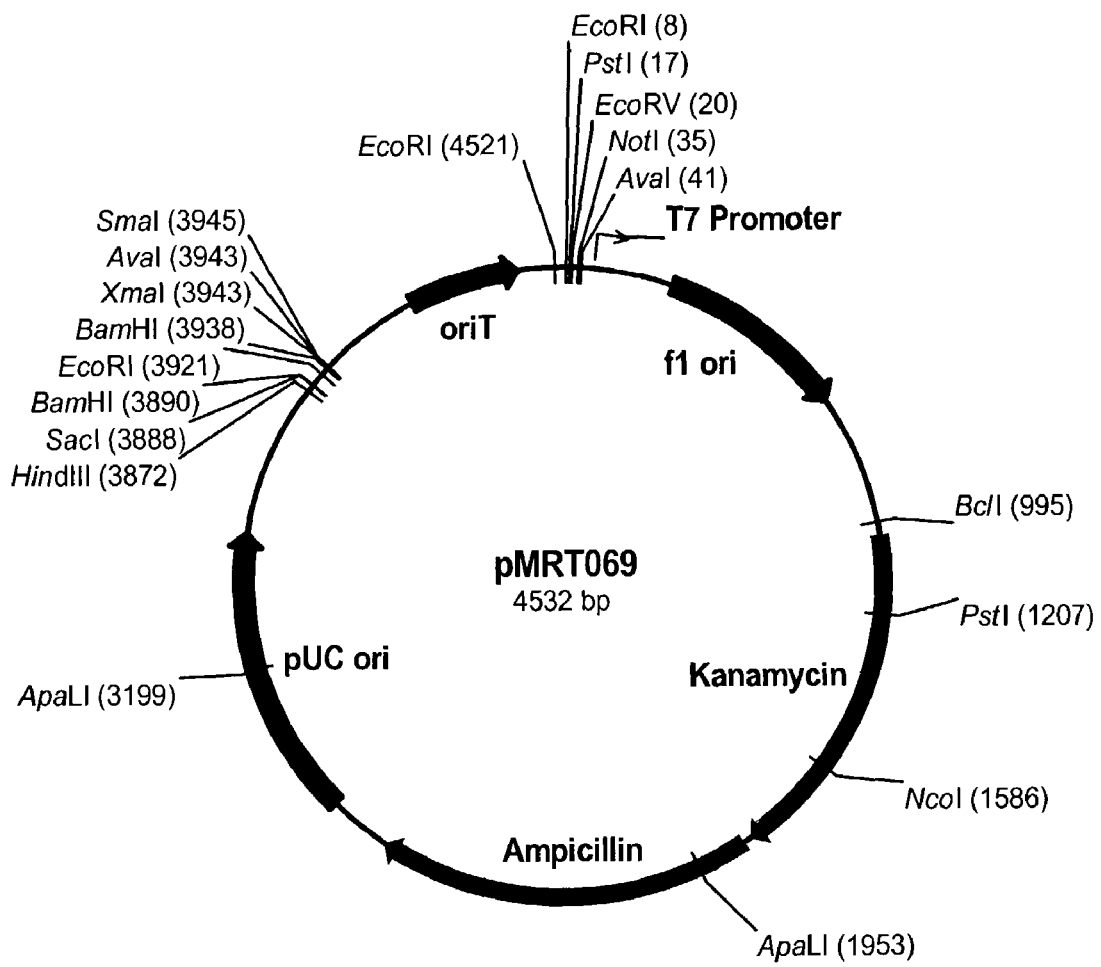
FIG. 33 shows a restriction map of pMRT069.

The SacI sites at positions 5463 and 6025 in plasmid pMRT064.1 were deleted using PCR amplification with primers 69 and 70, and using the PCR conditions described above. The resulting fragment was cloned into pCR2.1 vector using the TA-TOPO Cloning Kit (Invitrogen, Inc., Carlsbad, Calif.). Transformants were selected on 2×YT-agar plates supplemented with 100 µg of ampicillin per ml after incubation at 37° C. for 16 hours. Transformants carrying the correct plasmid were verified by DNA sequencing using M13 forward and reverse primers. This construct was designated pMRT069 (FIG. 33).

```
Primer 69:
                                             (SEQ ID NO: 83)
5'-CTAGAGGATCCCCGGGTACCGTGCTCTGCCTTTTAGTCC-3'

Primer 70:
                                             (SEQ ID NO: 84)
5'-GTACATCGAATTCGTGCTCATTATTAATCTGTTCAGC-3'
```

Figure 34:
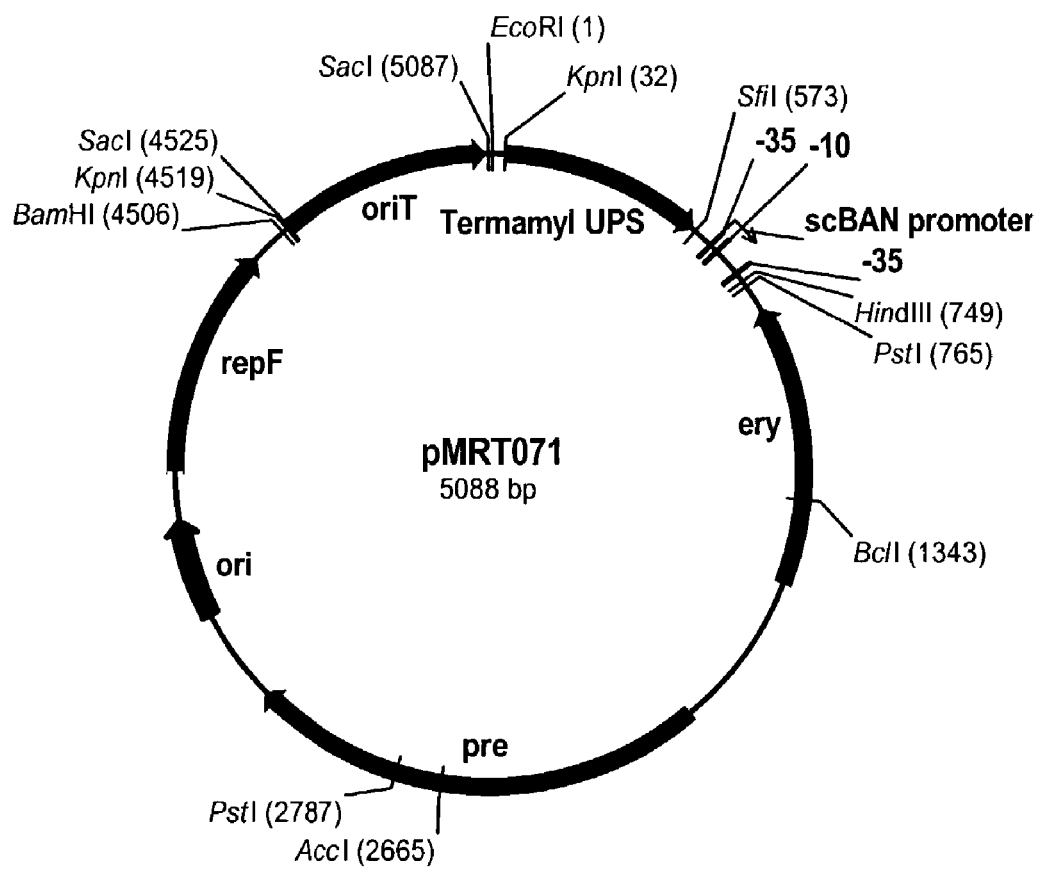
FIG. 34 shows a restriction map of pMRT071.

Plasmids pMRT068 and pMRT064.1 were digested with BclI/AccI. A fragment of approximately 1300 bp from pMRT068 and a fragment of approximately 3800 bp from pMRT064.1 were isolated from a 0.8% agarose-0.5×TBE gel using a QIAquick DNA Purification Kit according to the manufacturer's instructions, ligated, and transformed into *Bacillus subtilis* 168Δ4 competent cells. Transformants were selected on TBAB-agar plates supplemented with 1 µg of erythromycin and 25 µg of lincomycin per ml after incubation at 30° C. for 24-48 hours. Transformants carrying the correct plasmid were identified on a 0.8% agarose-0.5×TBE gel by restriction analysis with SacI and EcoRI/AvaI. The resulting construct was designated pMRT071 (FIG. 34).

Figure 35:
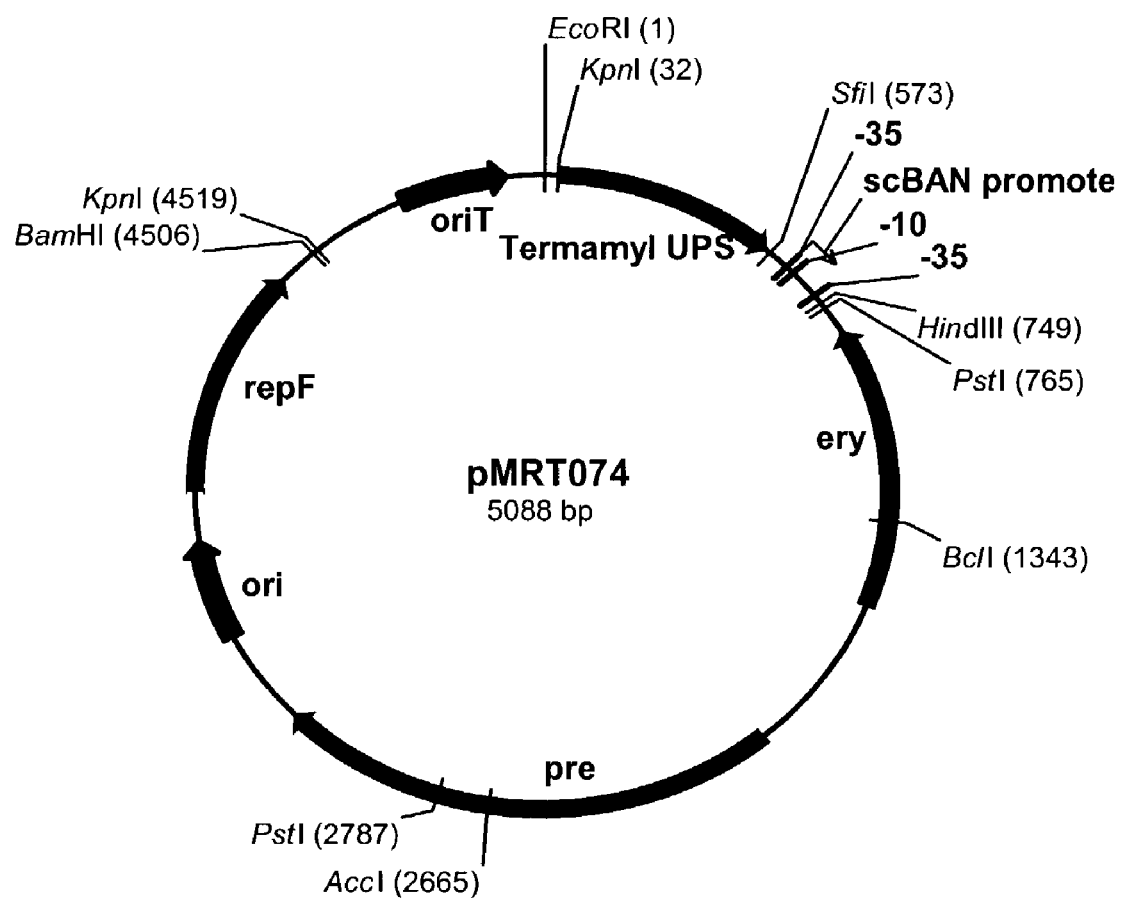
FIG. 35 shows a restriction map of pMRT074.

Plasmids pMRT071 and pMRT069 were digested with AvaI/EcoRI. The 578 bp fragment from pMRT069 and the 4510 bp fragment from pMRT071 were isolated from a 0.8% agarose-0.5×TBE gel using a QIAquick DNA Purification Kit according to the manufacturer's instructions, ligated, and transformed into *Bacillus subtilis* 168Δ4 competent cells. Transformants were selected on TBAB-agar plates supplemented with 1 µg of erythromycin and 25 µg of lincomycin per ml after incubation at 30° C. for 24-48 hours. Transformants carrying the correct plasmid were identified on a 0.8% agarose-0.5×TBE gel by restriction analysis with SacI. The resulting construct was designated pMRT074 (FIG. 35).

Figure 36:
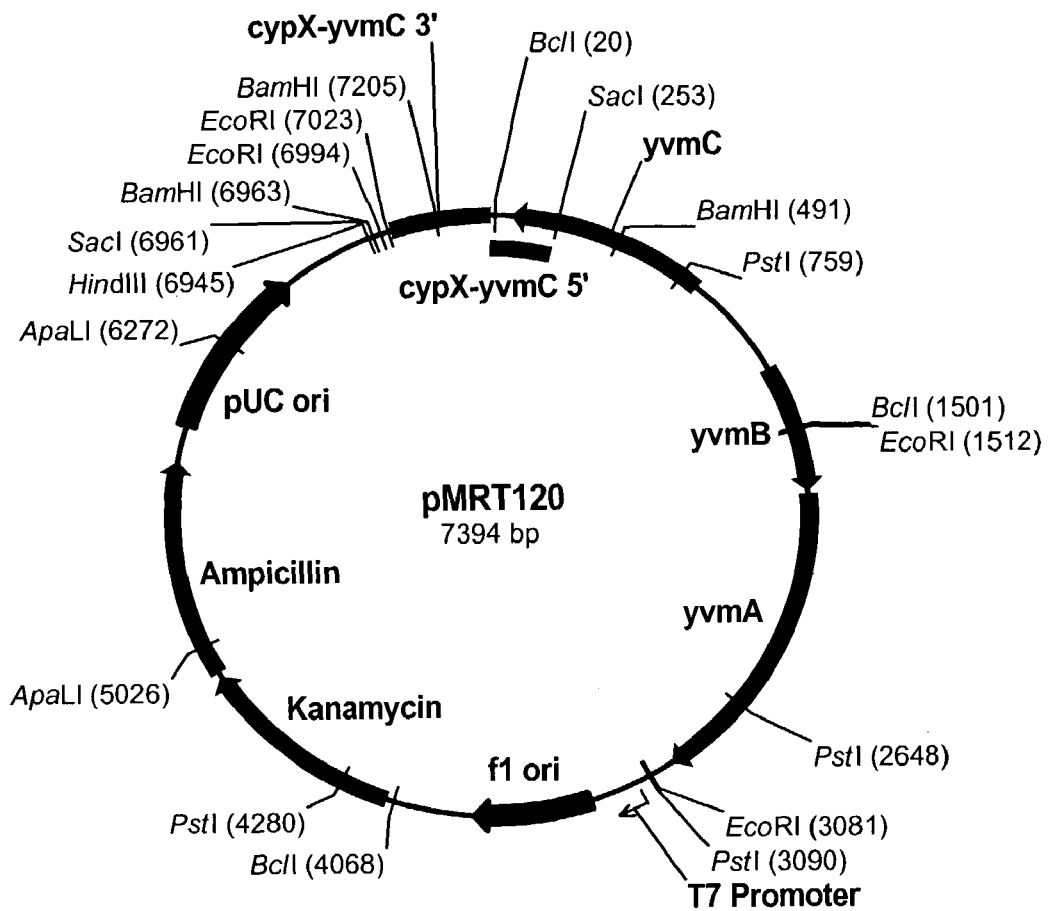
FIG. 36 shows a restriction map of pMRT120.

Plasmid pMRT084 described in Example 11 was digested with SacII/NdeI, treated with T4 DNA polymerase, ligated, and transformed into *E. coli* XL1 Blue cells according to the manufacturer's instructions. Transformants were selected on 2×YT agar plates supplemented with 100 µg of ampicillin per ml after incubation at 37° C. for 16 hours. Transformants carrying the correct plasmid were identified on a 0.8% agarose-0.5×TBE gel by restriction analysis with DraI. The resulting plasmid was named pMRT120 (FIG. 36).

Figure 37:
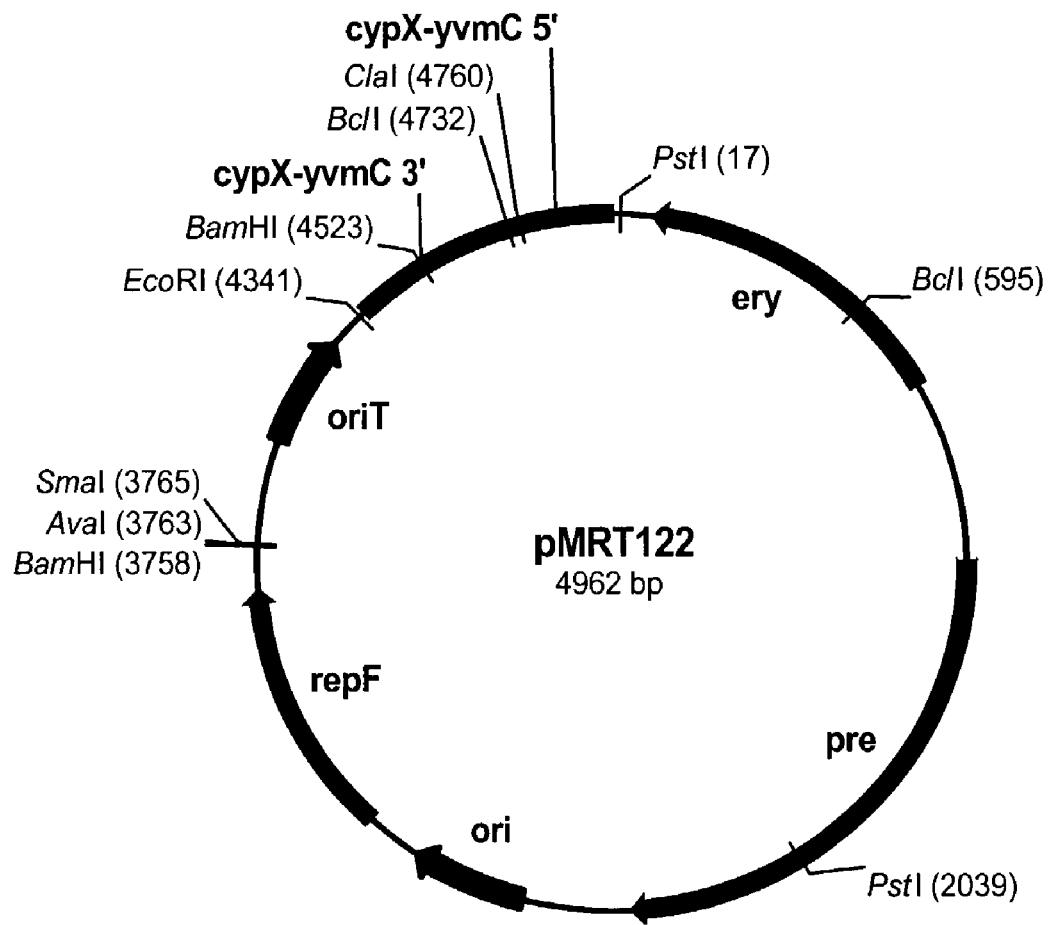
FIG. 37 shows a restriction map of pMRT122.

Plasmid pMRT074 was digested with HindIII, treated with Klenow fragment DNA polymerase, and digested with EcoRI. Plasmid pMRT120 was digested with EcoRI/Ecl136II. A fragment of approximately 600 bp from pMRT120 and a fragment of approximately 4300 bp from pMRT074 were isolated from a 0.8% agarose-0.5×TBE gel using a QIAquick DNA Purification Kit according to the manufacturer's instructions, ligated, and transformed into *Bacillus subtilis* 168Δ4 competent cells. Transformants were selected on TBAB-agar plates supplemented with 1 µg of erythromycin and 25 µg of lincomycin per ml after incubation at 30° C. for 24-48 hours. Transformants carrying the correct plasmid were identified on a 0.8% agarose-0.5×TBE gel by restriction analysis with SspI. The resulting construct was designated pMRT122 (FIG. 37).

Plasmid pMRT122 was transformed into *Bacillus subtilis* A164Δ5 competent cells. Transformants were selected on TBAB-agar plates supplemented with 1 µg of erythromycin and 25 µg of lincomycin per ml after incubation at 30° C. for 24-48 hours. The plasmid was introduced into the chromosome of *Bacillus subtilis* A164Δ5 via homologous recombination into the cypX locus by incubating a freshly streaked plate of *Bacillus subtilis* A164Δ5 (pMRT086) cells at 45° C. for 16 hours and selecting for healthy growing colonies. Genomic DNA was isolated from this strain using a QIAGEN tip-20 column according to the manufacturer's instructions and used to transform *Bacillus subtilis* RB187 (Example 9). Transformants were selected on TBAB plates supplemented with 1 µg of erythromycin and 25 µg of lincomycin per ml after incubation at 45° C. for 16 hours. At this temperature, the pE194 replicon is unable to replicate. Cells are able to maintain erythromycin resistance only by maintaining the plasmid in the bacterial chromosome.

The plasmid was removed from the chromosome via homologous recombination resulting in the deletion of a portion of the cypX gene on the chromosome by growing the transformants in Luria-Bertani (LB) medium without selection at the permissive temperature of 34° C. for many generations. At this temperature the pE194 origin of replication is active and actually promotes the excision of the plasmid from the chromosome (*Molecular Biological Methods for Bacillus*, edited by C. R. Harwood and S. M. Cutting, 1990, John Wiley and Sons Ltd.).

After several generations of outgrowth the cells were plated on non-selective LB agar plates and colonies which had lost the plasmid and were now cypX-deleted and producing hyaluronic acid were identified as follows: (1) cell patches were "wet" when plated on minimal plates indicating production of hyaluronic acid, (2) erythromycin sensitivity indicated loss of the pE194-based plasmid, and (3) PCR confirmed the presence of the 800 bp cypX deletion in the strain of interest by using primers 34 and 45.

Chromosomal DNA from potential cypX deletants was isolated using the REDextract-N-Amp™ Plant PCR kits as follows: Single *Bacillus* colonies were inoculated into 100 µl of Extraction Solution, incubated at 95° C. for 10 minutes, and then diluted with an equal volume of Dilution Solution. PCR was performed using 4 µl of extracted DNA in conjunction with the REDextract-N-Amp™ PCR Reaction Mix and the desired primers according to the manufacturer's instructions, using PCR cycling conditions as described in Example 5. PCR reaction products were visualized using a 0.8% agarose-0.5×TBE gel. The verified strain was designated *Bacillus subtilis* RB197.

Example 13

Construction of *Bacillus subtilis* RB200

The cypX gene of *Bacillus subtilis* RB192 was deleted using the same methods described in Example 9 for *Bacillus subtilis* RB187. The resultant strain was designated *Bacillus subtilis* RB200.

Example 14

Construction of *Bacillus subtilis* RB202

*Bacillus subtilis* A164Δ5ΔcypX was constructed as follows: Plasmid pMRT122 (Example 12) was transformed into Bacillus subtilis A164Δ5 competent cells. Transformants were selected on TBAB-agar plates supplemented with 1 μg of erythromycin and 25 μg of lincomycin per ml after incubation at 30° C. for 24-48 hours. The plasmid was introduced into the chromosome of *Bacillus subtilis* A164Δ5 via homologous recombination into the cypX locus by incubating a freshly streaked plate of *Bacillus subtilis* A164Δ5 (pMRT086) cells at 45° C. for 16 hours and selecting for healthy growing colonies. The plasmid was removed from the chromosome via homologous recombination resulting in the deletion of a portion of the cypX gene on the chromosome by growing the transformants in Luria-Bertani (LB) medium without selection at the permissive temperature of 34° C. for many generations. At this temperature the pE194 origin of replication is active and actually promotes the excision of the plasmid from the chromosome (*Molecular Biological Methods for Bacillus*, edited by C. R. Harwood and S. M. Cutting, 1990, John Wiley and Sons Ltd.). After several generations of outgrowth the cells were plated on non-selective LB agar plates and colonies which had lost the plasmid and were now cypX-deleted were identified as follows: (1) erythromycin sensitivity indicated loss of the pE194-based plasmid, and (2) PCR confirmed the presence of the 800 bp cypX deletion in the strain of interest by using primers 34 and 45 as described above. The verified strain was designated *Bacillus subtilis* A164Δ5ΔcypX.

*Bacillus subtilis* A164Δ5ΔcypX was made competent and transformed with *Bacillus subtilis* TH1 genomic DNA (Example 7) isolated using a QIAGEN tip-20 column according to the manufacturer's instructions. Transformants were selected on TBAB plates containing 5 μg of chloramphenicol per ml at 37° C. The *Bacillus subtilis* A164Δ5ΔcypX hasA/hasB/hasC/hasD integrant was identified by its "wet" phenotype and designated *Bacillus subtilis* RB201. The cat gene was deleted from *Bacillus subtilis* RB201 using the same method described in Example 9. The resultant strain was designated *Bacillus subtilis* RB202.

Example 15

Construction of *Bacillus subtilis* MF002 (tuaD/gtaB)

Plasmid pHA3 (Example 2, FIG. 9) was digested with Asp718. The digested plasmid was then blunted by first inactivating the restriction enzyme at 85° C. for 30 minutes. Blunting was performed by adding 0.5 μl of 10 mM each dNTPs, 1 μl of 1 U/μl T4 polymerase and incubating at 11° C. for 10 minutes. Finally the polymerase was inactivated by incubating the reaction at 75° C. for 10 minutes. The digested plasmid was then purified using a QIAquick DNA Purification Kit according to the manufacturer's instructions and finally digested with NotI. The smallest plasmid fragment of approximately 2522 bp was then gel-purified using a QIAquick DNA Gel Extraction Kit from a 0.8% agarose-0.5× TBE gel according to the manufacturer's instructions. The recovered DNA insert (tuaD/gtaB) was then ligated with the vector DNA described below.

Plasmid pDG268MCSΔneo/scBAN/Sav (U.S. Pat. No. 5,955,310) was digested with Ecl136II. The digested plasmid was then purified using a QIAquick DNA Purification Kit according to the manufacturer's instructions, and finally digested with NotI. The largest plasmid fragment of approximately 6800 bp was gel-purified from a 0.8% agarose-0.5× TBE gel using a QIAquick DNA Gel Extraction Kit according to the manufacturer's instructions.

The recovered vector and DNA insert were ligated using the Rapid DNA Cloning Kit according to the manufacturer's instructions. Prior to transformation in *Bacillus subtilis*, the ligation described above was linearized using ScaI to ensure double cross-over integration in the chromosome rather than single cross-over integration in the chromosome. *Bacillus subtilis* 168Δ4 competent cells were transformed with the ligation digested with the restriction enzyme ScaI.

*Bacillus subtilis* chloramphenicol-resistant transformants were selected on TBAB plates supplemented with 5 μg of chloramphenicol per ml. To screen for integration of the plasmid by double cross-over at the amyE locus, *Bacillus subtilis* primary transformants were patched on TBAB plates supplemented with 6 μg of neomycin per ml and on TBAB plates supplemented with 5 μg of chloramphenicol per ml to isolate chloramphenicol resistant and neomycin sensitive transformants were isolated.

Chromosomal DNA from chloramphenicol resistant and neomycin sensitive Bacillus subtilis 168Δ4 transformants was isolated using the REDextract-N-Amp™ Plant PCR kits (Sigma Chemical Company, St. Louis, Mo.) as follows: Single *Bacillus* colonies were inoculated into 100 μl of Extraction Solution, incubated at 95° C. for 10 minutes, and then diluted with an equal volume of Dilution Solution. PCR was performed using 4 μl of extracted DNA in conjunction with the REDextract-N-Amp PCR Reaction Mix and the desired primers according to the manufacturer's instructions, with PCR cycling conditions described in Example 5.

PCR amplifications were performed on these transformants using the synthetic oligonucleotides described below to confirm the absence/presence and integrity of the genes hasA, gtaB, and tuaD of the operon of the *Bacillus subtilis* transformants. Primers 3 and 8 were used to confirm the absence of the hasA gene, primer 71 and primer 15 to confirm the presence of the tuaD gene, and primers 20 and 71 to confirm the presence of the gtaB gene. PCR reaction products were visualized in a 0.8% agarose-0.5×TBE gel. The verified strain, a *Bacillus subtilis* 168Δ4 hasA/tuaD/gtaB integrant, was designated *Bacillus subtilis* RB176. Primer 71: 5'-AAC-TATTGCCGATGATAAGC-3' (binds upstream of tuaD) (SEQ ID NO: 85)

Genomic DNA was isolated from the chloramphenicol resistant, and neomycin sensitive *Bacillus subtilis* RB176 transformants using a QIAGEN tip-20 column according to the manufacturer's instructions. The *Bacillus subtilis* RB176 genomic DNA was used to transform competent *Bacillus subtilis* A164Δ5. Transformants were selected on TBAB plates containing 5 μg of chloramphenicol per ml, and grown at 37° C. A *Bacillus subtilis* A164Δ5 tuaD/gtaB integrant was designated *Bacillus subtilis* RB177.

The cat gene was deleted in strain *Bacillus subtilis* RB177 using the method described in Example 9. The resultant strain was designated *Bacillus subtilis* MF002.

Example 16

Construction of the pel Integration Plasmid pRB162

Plasmid pDG268MCSΔneo/scBAN/Sav (U.S. Pat. No. 5,955,310) was double-digested with SacI and AatII. The largest plasmid fragment of approximately 6193 bp was gel-purified using a QIAquick DNA Gel Extraction Kit from a 0.8% agarose-0.5×TBE gel according to the manufacturer's instructions. The recovered vector DNA was then ligated with the DNA insert described below.

The 5' and 3' fragments of a *Bacillus subtilis* pectate lyase gene (pel, accession number BG10840, SEQ ID NOs. 86 [DNA sequence] and 87 [deduced amino acid sequence]) was PCR amplified from *Bacillus subtilis* 168 (BGSC 1A1, *Bacil-*

*lus* Genetic Stock Center, Columbus, Ohio) using primers 72 (introduces 5' SpeI restriction site) and 73 (introduces 3' SalI restriction site) for the 5' pel fragment and primers 74 (introduces 5' SacI/BamHI restriction sites) and 75 (introduces 3' NotI/AatII restriction sites) for the 3' pel fragment:

| | | |
|---|---|---|
| Primer 72: | 5'-ACTAGTAATGATGGCTGGGGCGCGTA-3' | (SEQ ID NO: 88) |
| Primer 73: | 5'-GTCGACATGTTGTCGTATTGTGAGTT-3' | (SEQ ID NO: 89) |
| Primer 74: | 5'-GAGCTCTACAACGCTTATGGATCCGCGGCCGCGGCGGCACACACATCTGGAT-3' | (SEQ ID NO: 90) |
| Primer 75: | 5'-GACGTCAGCCCGTTTGCAGCCGATGC-3' | (SEQ ID NO: 91) |

PCR amplifications were carried out in triplicate in 30 μl reactions composed of 50 ng of *Bacillus subtilis* 168 chromosomal DNA, 0.4 μM each of primer pair 72/73 for the 5' pel fragment or primer pair 74/75 for the 3' pel fragment, 200 μM each of dATP, dCTP, dGTP, and dTTP, 1×PCR Buffer II with 2.5 mM $MgCl_2$, and 2.5 units of AmpliTaq Gold™ DNA polymerase. The reactions were performed in a RoboCycler 40 thermacycler programmed for 1 cycle at 95° C. for 9 minutes; 3 cycles each at 95° C. for 1 minute, 52° C. for 1 minute, and 72° C. for 1 minute; 27 cycles each at 95° C. for 1 minute, 55° C. for 1 minute, and 72° C. for 1 minute; and 1 cycle at 72° C. for 5 minutes. The PCR products were visualized using a 0.8% agarose-0.5×TBE gel. The expected fragments were approximately 530 bp for the 5' pel fragment and 530 bp for the 3' pel fragment.

Figure 38:
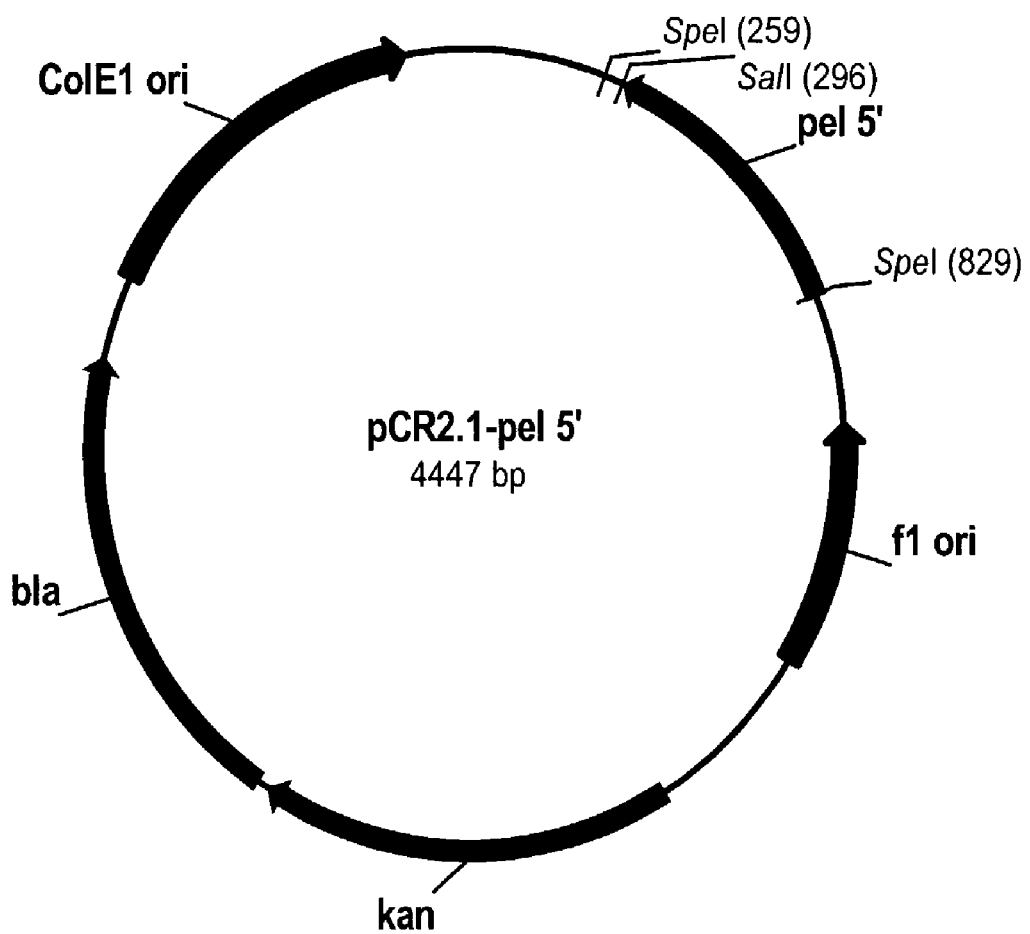
FIG. 38 shows a restriction map of pCR2.1-pel5'.
Figure 39:
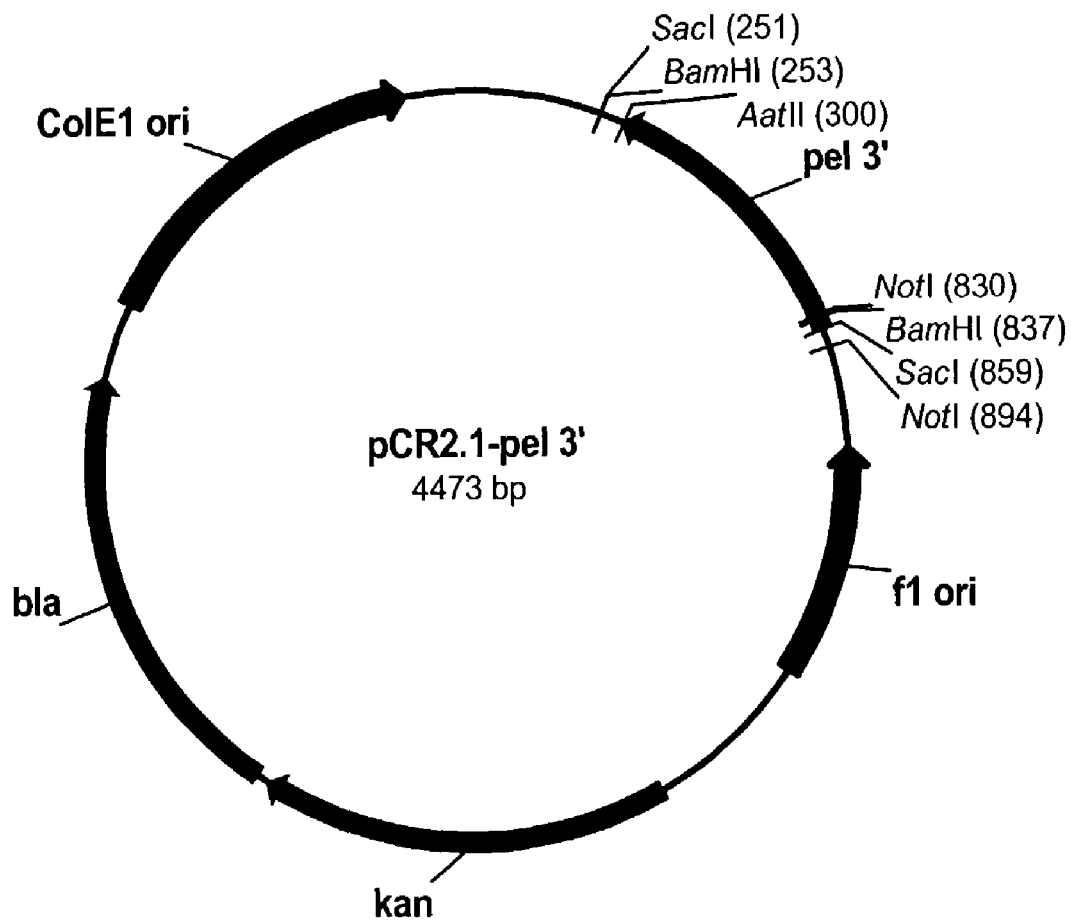
FIG. 39 shows a restriction map of pCR2.1-pel3'.

The 530 bp 5' pel and 530 bp 3' pel PCR fragments were cloned into pCR2.1 using the TA-TOPO Cloning Kit and transformed into *E. coli* OneShot™ competent cells according to the manufacturers' instructions. Transformants were selected on 2×YT agar plates supplemented with 100 μg of ampicillin per ml incubated at 37° C. Plasmid DNA from these transformants was purified using a QIAGEN robot according to the manufacturer's instructions and the DNA sequence of the inserts confirmed by DNA sequencing using the primers described above (primers 72 and 73 for 5' pel and primers 74 and 75 for 3' pel). The plasmids harboring the 530 bp and the 530 bp PCR fragments were designated pCR2.1-pel 5' and pCR2.1-pel3', respectively (FIGS. 38 and 39, respectively).

Plasmid pCR2.1-pel3' was double-digested with SacI and AatII. The smallest plasmid fragment of approximately 530 bp was gel-purified using a QIAquick DNA Gel Extraction Kit from a 0.8% agarose-0.5×TBE gel according to the manufacturer's instructions.

The recovered vector (pDG268MCSΔneo/scBAN) and DNA insert (3' pel) were ligated using the Rapid DNA Cloning Kit according to the manufacturer's instructions. The ligation mix was transformed into *E. coli* SURE competent cells (Stratagene, Inc., La Jolla, Calif.). Transformants were selected on 2×YT agar plates supplemented with 100 μg of ampicillin per ml at 37° C.

Figure 40:
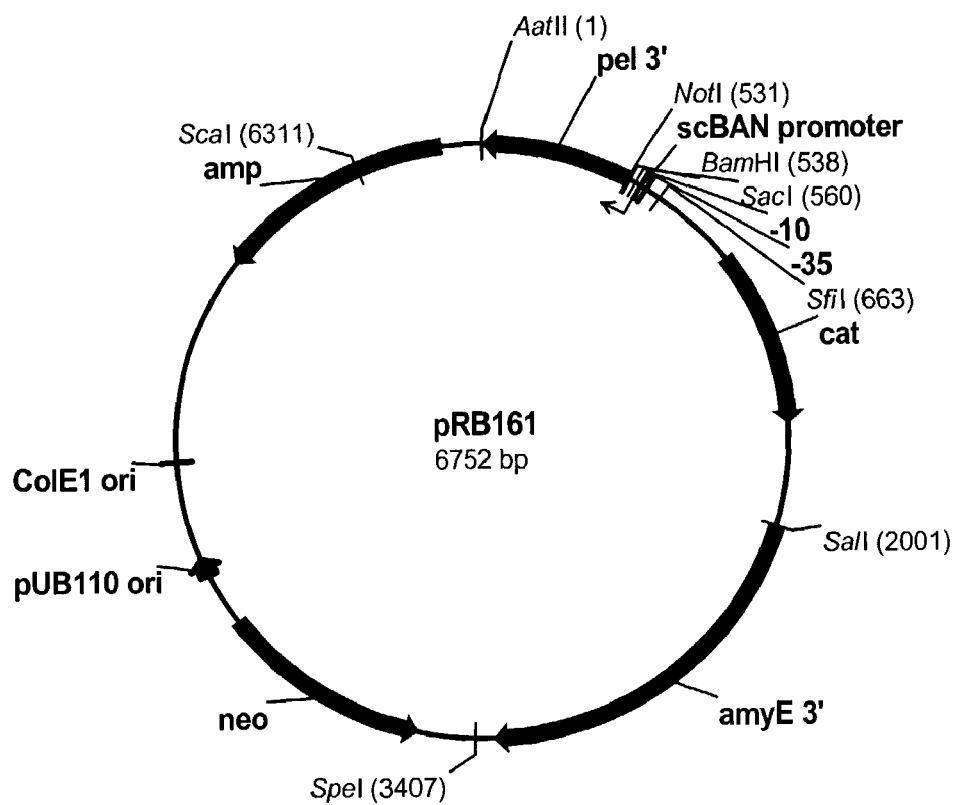
FIG. 40 shows a restriction map of pRB161.

Plasmid DNA was purified from several transformants using a QIAGEN robot according to the manufacturer's instructions and analyzed by SacI and AatII digestion on a 0.8% agarose gel using 0.5×TBE buffer. The correct plasmid was identified by the presence of an approximately 530 bp SacI/AatII 3' pel fragment and was designated pRB161 (FIG. 40).

Plasmid pRB161 was double-digested with SpeI and SalI. The largest plasmid fragment of approximately 5346 bp was gel-purified using a QIAquick DNA Gel Extraction Kit from a 0.8% agarose-0.5×TBE gel according to the manufacturer's instructions. The recovered vector DNA was then ligated with the DNA insert described below.

Plasmid pCR2.1-pel5' was double-digested with SpeI and SalI. The smallest plasmid fragment of approximately 530 bp was gel-purified using a QIAquick DNA Gel Extraction Kit from a 0.8% agarose-0.5×TBE gel according to the manufacturer's instructions.

The recovered vector (pDG268MCSΔneo/scBAN/pel 3') and insert (pel 5') DNA were ligated using the Rapid DNA Cloning Kit according to the manufacturer's instructions. The ligation mix was transformed into *E. coli* SURE competent cells (Stratagene, Inc., La Jolla, Calif.). Transformants were selected on 2×YT agar plates supplemented with 100 μg of ampicillin per ml.

Figure 41:
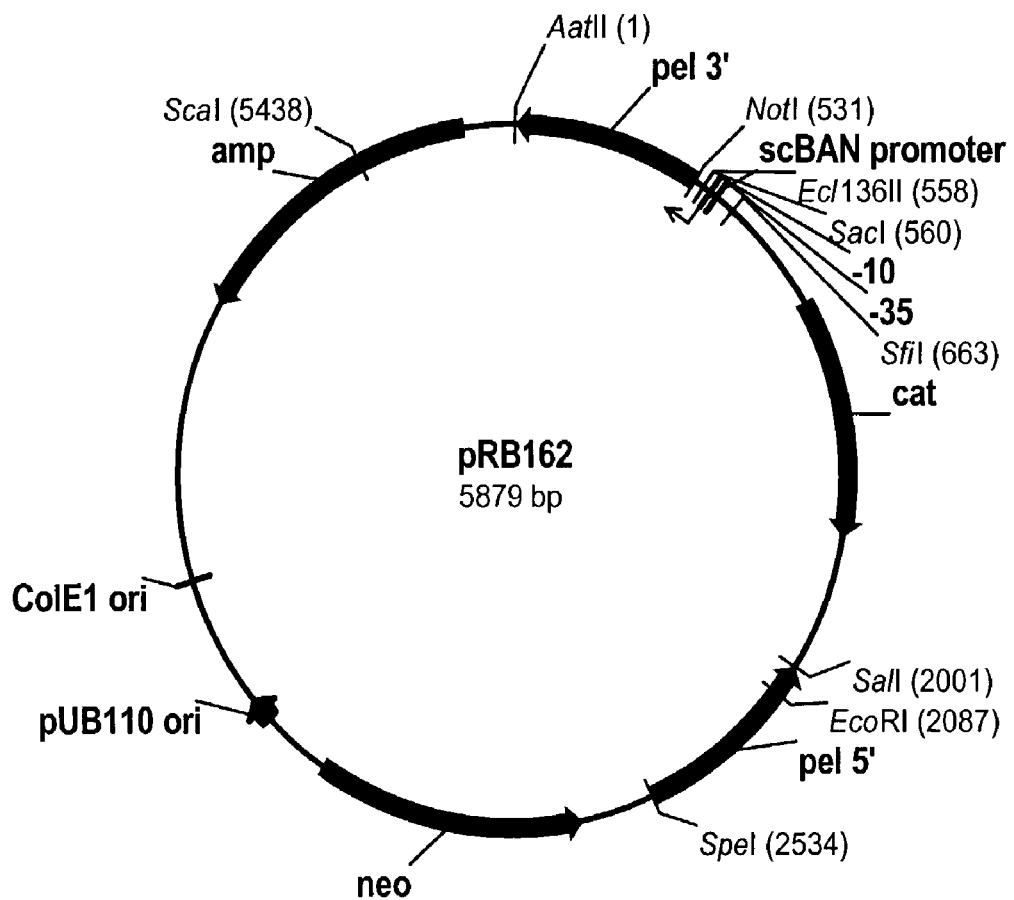
FIG. 41 shows a restriction map of pRB162.

Plasmid DNA was purified from several transformants using a QIAGEN robot according to the manufacturer's instructions and analyzed by SpeI and SalI digestion on a 0.8% agarose gel using 0.5×TBE buffer. The correct plasmid was identified by the presence of an approximately 530 bp SpeI/SalI pel 5' fragment and was designated pRB162 (FIG. 41).

Example 17

Construction of pRB156

Plasmid pHA7 (Example 4, FIG. 13) was digested with HpaI. The digested plasmid was then purified using a QIAquick DNA Purification Kit according to the manufacturer's instructions and finally digested with Asp718. The double-digested plasmid was then blunted by first inactivating the restriction enzyme at 85° C. for 30 minutes. Blunting was performed by adding 0.5 μl of 10 mM each dNTPs and 1 μl of 1 U/μl of T4 polymerase and incubating at 11° C. for 10 minutes. The polymerase was then inactivated by incubating the reaction at 75° C. for 10 minutes. The largest plasmid fragment of approximately 8600 bp was then gel-purified using a QIAquick DNA Gel Extraction Kit from a 0.8% agarose-0.5×TBE gel according to the manufacturer's instructions. The recovered DNA insert (pDG268Δneo-cryII-IAstab/sehasA) was then re-ligated using the Rapid DNA Cloning Kit according to the manufacturer's instructions.

Figure 42:
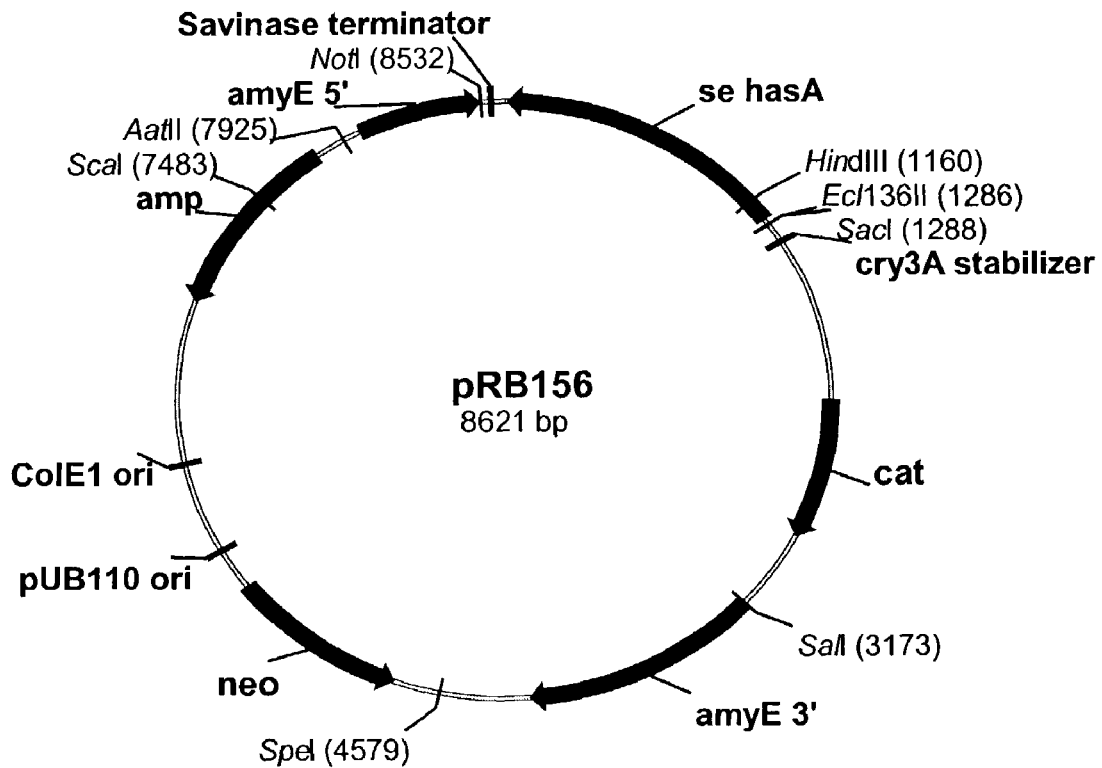
FIG. 42 shows a restriction map of pRB156.

The ligation mix was transformed into *E. coli* SURE competent cells (Stratagene, Inc., La Jolla, Calif.). Transformants were selected on 2×YT agar plates supplemented with 100 μg of ampicillin per ml at 37° C. Plasmid DNA was purified from several transformants using a QIAGEN robot according to the manufacturer's instructions and analyzed by ScaI digestion on a 0.8% agarose gel using 0.5×TBE buffer. The correct plasmid was identified by the presence of an approximately 8,755 bp fragment and was designated pRB156 (FIG. 42).

Example 18

Construction of *Bacillus subtilis* MF009

The hasA gene under control of the scBAN promoter was introduced into the pectate lyase gene (pel) locus of *Bacillus subtilis* MF002 to generate *Bacillus subtilis* MF009.

Plasmid pRB156 was digested with SacI. The digested plasmid was then purified using a QIAquick DNA Purification Kit according to the manufacturer's instructions, and finally digested with NotI. The smallest plasmid fragment of approximately 1,377 bp was gel-purified using a QIAquick DNA Gel Extraction Kit from a 0.8% agarose-0.5×TBE gel according to the manufacturer's instructions. The recovered DNA insert was then ligated with the vector DNA described below.

Plasmid pRB162 (Example 16, FIG. 41) was digested with NotI. The digested plasmid was then purified using a QIAquick DNA Purification Kit according to the manufacturer's instructions, and finally digested with SacI. The largest plasmid fragment of approximately 5850 bp was gel-purified using a QIAquick DNA Gel Extraction Kit from a 0.8% agarose-0.5×TBE gel according to the manufacturer's instructions. The recovered vector DNA was then ligated with the DNA insert described above.

The ligation mixture was transformed directly in *Bacillus subtilis* 168Δ4 competent cells. *Bacillus subtilis* chloramphenicol-resistant transformants were selected on TBAB plates supplemented with 5 μg of chloramphenicol per ml at 37° C. To screen for integration of the plasmid by double cross-over at the pel locus, *Bacillus subtilis* primary transformants were patched on TBAB plates supplemented with 6 μg of neomycin per ml and on TBAB plates supplemented with 5 μg of chloramphenicol per ml. Integration of the plasmid by double cross-over at the pel locus does not incorporate the neomycin resistance gene and therefore renders the strain neomycin sensitive. Using this plate screen, chloramphenicol resistant and neomycin sensitive transformants were isolated.

Genomic DNA was isolated from the chloramphenicol resistant and neomycin sensitive *Bacillus subtilis* 168Δ4 transformants using a QIAGEN tip-20 column according to the manufacturer's instructions. This genomic DNA was used to transform competent *Bacillus subtilis* MF002 (Example 15). Transformants were selected on TBAB plates containing 5 μg of chloramphenicol per ml and grown at 37° C. The *Bacillus subtilis* A164Δ5 hasA and tuaD/gtaB integrant was identified by its "wet" phenotype and designated *Bacillus subtilis* MF009.

Example 19

Construction of *Bacillus subtilis* MF010

Plasmid pDG268MCSΔneo/BAN/Sav (U.S. Pat. No. 5,955,310) was digested with NotI. The digested plasmid was then purified using a QIAquick DNA Purification Kit according to the manufacturer's instructions, and finally digested with SfiI. The smallest plasmid fragment of approximately 185 bp was gel-purified using a QIAquick DNA Gel Extraction Kit from a 0.8% agarose-0.5×TBE gel according to the manufacturer's instructions. The recovered DNA insert was then ligated with the vector DNA described below.

Plasmid pRB162 (Example 16, FIG. 41) was digested with NotI. The digested plasmid was then purified using a QIAquick DNA Purification Kit according to the manufacturer's instructions, and finally digested with SfiI. The largest plasmid fragment of approximately 5747 bp was gel-purified using a QIAquick DNA Gel Extraction Kit from a 0.8% agarose-0.5×TBE gel according to the manufacturer's instructions. The recovered vector DNA was then ligated with the DNA insert described above.

The recovered vector and DNA insert were ligated using the Rapid DNA Cloning Kit according to the manufacturer's instructions. The ligation mix was transformed into *E. coli* XLI Blue competent cells. Transformants were selected on 2×YT agar plates supplemented with 100 μg of ampicillin per ml.

Figure 43:
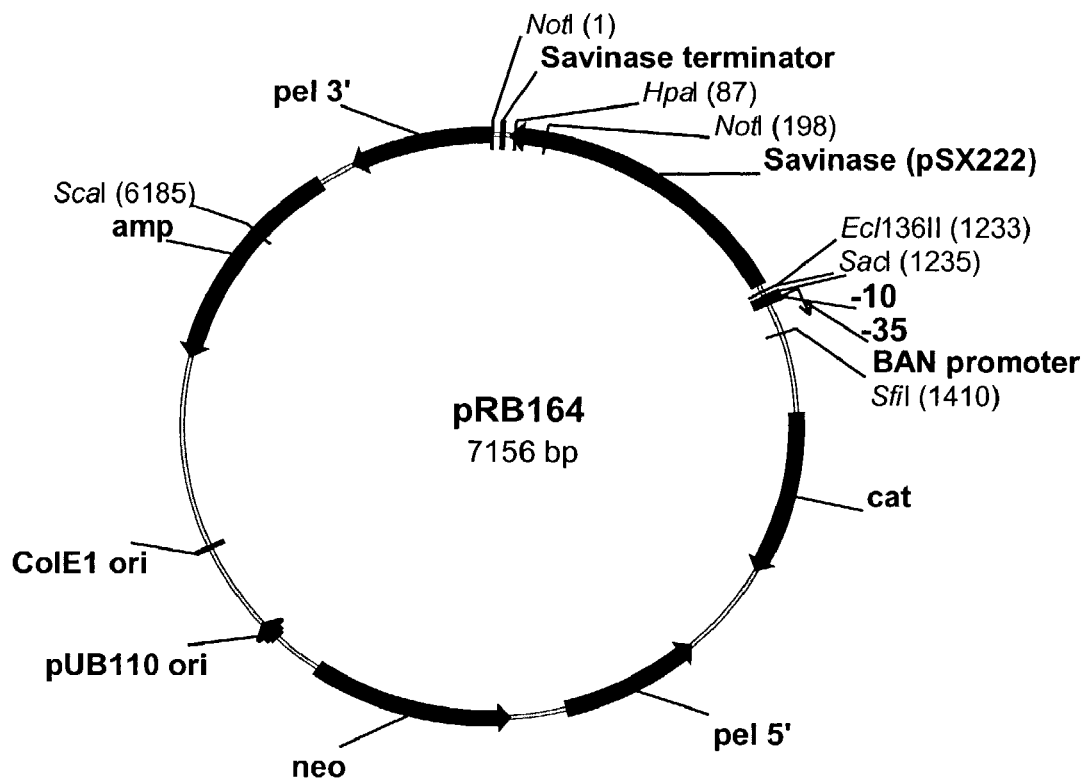
FIG. 43 shows a restriction map of pRB164.

Plasmid DNA was purified from several transformants using a QIAGEN robot according to the manufacturer's instructions and analyzed by BamHI digestion on a 0.8% agarose gel using 0.5×TBE buffer. The correct plasmid was identified by the linearization of the plasmid which provides an approximately 7,156 bp fragment and was designated pRB164 (FIG. 43).

Plasmid pRB156 (Example 17, FIG. 42) was digested with SacI. The digested plasmid was then purified using a QIAquick DNA Purification Kit according to the manufacturer's instructions, and finally digested with NotI. The smallest plasmid fragment of approximately 1377 bp was gel-purified using a QIAquick DNA Gel Extraction Kit from a 0.8% agarose-0.5×TBE gel according to the manufacturer's instructions. The recovered DNA insert was then ligated with the vector DNA described below.

Plasmid pRB164 was digested with NotI. The digested plasmid was then purified using a QIAquick DNA Purification Kit according to the manufacturer's instructions, and finally digested with SacI. The largest plasmid fragment of approximately 5922 bp was gel-purified using a QIAquick DNA Gel Extraction Kit from a 0.8% agarose-0.5×TBE gel according to the manufacturer's instructions. The recovered vector DNA was then ligated with the DNA insert described above.

This ligation mix was transformed directly in *Bacillus subtilis* 168Δ4 competent cells. *Bacillus subtilis* chloramphenicol-resistant transformants were selected on TBAB plates supplemented with 5 μg of chloramphenicol per ml at 37° C. To screen for integration of the plasmid by double cross-over at the amyE locus, *Bacillus subtilis* primary transformants were patched on TBAB plates supplemented with 6 μg of neomycin per ml and on TBAB plates supplemented with 5 μg of chloramphenicol per ml. Integration of the plasmid by double cross-over at the amyE locus does not incorporate the neomycin resistance gene and therefore renders the strain neomycin sensitive. Using this plate screen, chloramphenicol resistant and neomycin sensitive transformants were isolated.

Genomic DNA was isolated from the chloramphenicol resistant and neomycin sensitive *Bacillus subtilis* 168Δ4 transformants using a QIAGEN tip-20 column according to the manufacturer's instructions. This genomic DNA was used to transform competent *Bacillus subtilis* MF002 (Example 15). Transformants were selected on minimal plates containing 5 μg of chloramphenicol per ml and grown at 37° C. for 16 hours. A *Bacillus subtilis* A164Δ5 BAN/hasA and scBAN/ tuaD/gtaB integrant was identified by its "wet" phenotype and designated *Bacillus subtilis* MF010.

Example 20

Fermentations

The ability of the *Bacillus subtilis* strains listed in Table 1 to produce hyaluronic acid was evaluated under various growth conditions.

TABLE 1

| B. subtilis Strain | promoter/gene complement | catΔ | cypXΔ |
|---|---|---|---|
| RB161 | scBAN/hasA/tuaD/gtaB | no | no |
| RB163 | scBAN/hasA/tuaD/gcaD | no | no |
| TH-1 | scBANhasA/hasB/hasC/hasD | no | no |
| RB184 | scBAN/hasA/tuaD | no | no |
| RB187 | scBAN/hasA/tuaD/gtaB | yes | no |
| RB192 | scBAN/hasA/tuaD | yes | no |
| RB194 | scBAN/hasA/tuaD/gtaB | yes | yes |
| RB197 | scBAN/hasA/tuaD/gtaB | yes | yes |
| RB200 | scBAN/hasA/tuaD | yes | yes |
| RB202 | scBAN/hasA/hasB/hasC/hasD | yes | yes |
| MF009 | scBAN/tuaD/gtaB scBAN/hasA | no | no |
| MF010 | scBAN/tuaD/gtaB BAN/hasA | no | no |

The *Bacillus subtilis* strains were fermented in standard small fermenters in a medium composed per liter of 6.5 g of $KH_2PO_4$, 4.5 g of $Na_2HPO_4$, 3.0 g of $(NH_4)_2SO_4$, 2.0 g of $Na_3$-citrate-$2H_2O$, 3.0 g of $MgSO_4.7H_2O$, 6.0 ml of Mikrosoy-2, 0.15 mg of biotin (1 ml of 0.15 mg/ml ethanol), 15.0 g of sucrose, 1.0 ml of SB 2066, 2.0 ml of P2000, 0.5 g of $CaCl_2.2H_2O$. The medium was pH 6.3 to 6.4 (unadjusted) prior to autoclaving. The $CaCl_2.2H_2O$ was added after autoclaving.

The seed medium used was B-3, i.e., Agar-3 without agar, or "S/S-1" medium. The Agar-3 medium was composed per liter of 4.0 g of nutrient broth, 7.5 g of hydrolyzed protein, 3.0 g of yeast extract, 1.0 g of glucose, and 2% agar. The pH was not adjusted; pH before autoclaving was approximately 6.8; after autoclaving approximately pH 7.7.

The sucrose/soy seed flask medium (S/S-1) was composed per liter of 65 g of sucrose, 35 g of soy flour, 2 g of $Na_3$-citrate-$.2H_2O$, 4 g of $KH_2PO_4$, 5 g of $Na_2HPO_4$, and 6 ml of trace elements. The medium was adjusted pH to about 7 with NaOH; after dispensing the medium to flasks, 0.2% vegetable oil was added to suppress foaming. Trace elements was composed per liter of 100 g of citric acid-$H_2O$, 20 g of $FeSO_4.7H_2O$, 5 g of $MnSO_4.H_2O$, 2 g of $CuSO_4.5H_2O$, and 2 g of $ZnCl_2$.

The pH was adjusted to 6.8-7.0 with ammonia before inoculation, and controlled thereafter at pH 7.0±0.2 with ammonia and $H_3PO_4$. The temperature was maintained at 37° C. Agitation was at a maximum of 1300 RPM using two 6-bladed rushton impellers of 6 cm diameter in 3 liter tank with initial volume of 1.5 liters. The aeration had a maximum of 1.5 VVM.

For feed, a simple sucrose solution was used. Feed started at about 4 hours after inoculation, when dissolved oxygen (D.O.) was still being driven down (i.e., before sucrose depletion). The feed rate was ramped linearly from 0 to approximately 6 g sucrose/$L_0$-hr over a 7 hour time span. A lower feed rate, ramped linearly from 0 to approximately 2 g sucrose/$L_0$-hr, was also used in some fermentations.

Viscosity was noticeable by about 10 hours and by 24 hours viscosity was very high, causing the D.O. to bottom-out. End-point viscosity reached 3,220 cP. Cell mass development reached a near maximum (12 to 15 g/liter) by 20 hours. Cells were removed by diluting 1 part culture with 3 parts water, mixing well and centrifuging at about 30,000×g to produce a clear supernatant and cell pellet, which can be washed and dried.

Assays of hyaluronic acid concentration were performed using the ELISA method, based on a hyaluronan binding protein (protein and kits commercially available from Seikagaku America, Falmouth, Mass.).

*Bacillus subtilis* RB 161 and RB163 were cultured in batch and fed-batch fermentations. In the fed-batch processes, the feed rate was varied between cultures of *Bacillus subtilis* strains RB163 and RB161. Assays of hyaluronic acid concentrations were again performed using the ELISA method. The results are provided in Table 2.

TABLE 2

| Strain and Growth Conditions | HA (relative yield) ELISA method |
|---|---|
| RB-161 (hasA/tuaD/gtaB) simple batch | 0.7 ± 0.1 |
| RB-163 (hasA/tuaD/gcaD) fed batch~6 g sucrose/$L_0$-hr | 0.9 ± 0.1 |
| RB161 (hasA/tuaD/gtaB) fed batch~6 g sucrose/$L_0$-hr | 0.9 ± 0.1 |
| RB-163 (hasA/tuaD/gcaD) fed batch~2 g sucrose/$L_0$-hr | 1.0 ± 0..2 |
| RB161 (hasA/tuaD/gtaB) fed batch~2 g sucrose/$L_0$-hr | 1.0 ± 0..1 |

The results of the culture assays for the same strain at a fed batch rate of 2 g/L sucrose/$L_0$-hr compared to 6 g/L sucrose/$L_0$-hr demonstrated that a faster sucrose feed rate did not significantly improve titers.

Figure 44:
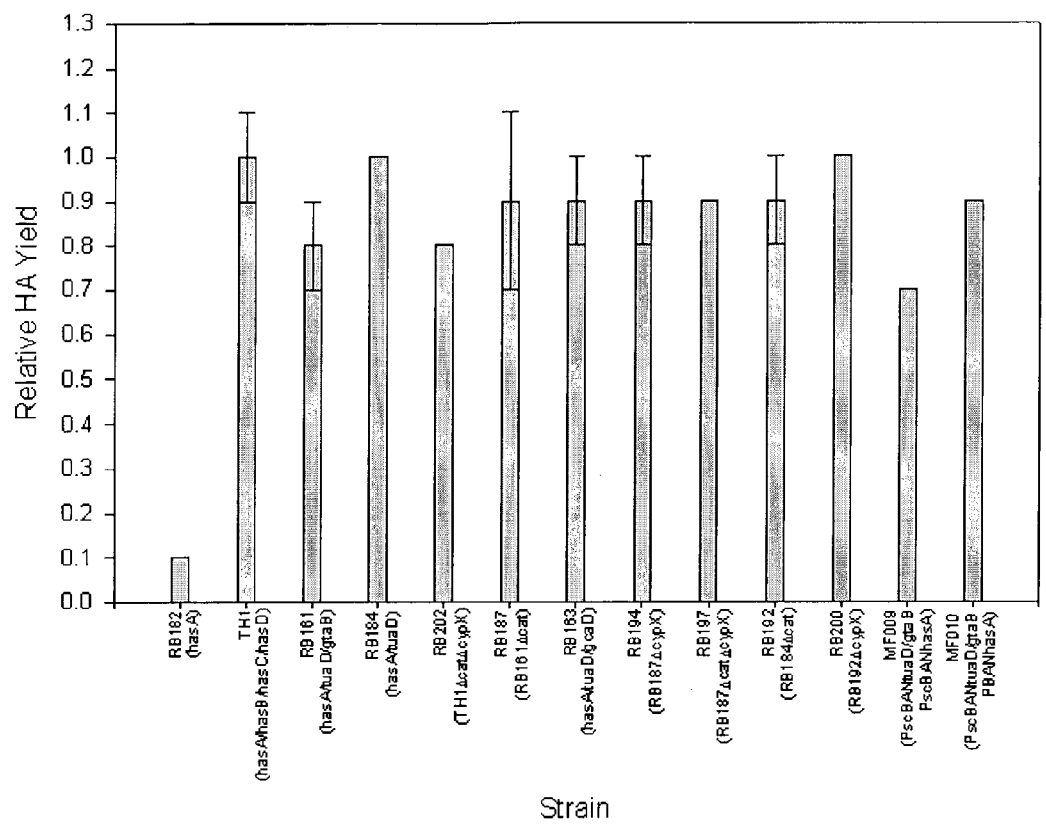
FIG. 44 shows a summary of fermentations of various hyaluronic acid producing *Bacillus subtilis* strains run under fed batch at approximately 2 g sucrose/$L_0$-hr, 37° C.

A summary of the *Bacillus* strains run under same conditions (fed batch at approximately 2 g sucrose/$L_0$-hr, 37° C.) is shown in FIG. 44. In FIG. 44, ± values indicate standard deviation of data from multiple runs under the same conditions. Data without ± values are from single runs. Hyaluronic acid concentrations were determined using the modified carbazole method (Bitter and Muir, 1962, *Anal Biochem.* 4: 330-334).

Figure 45:
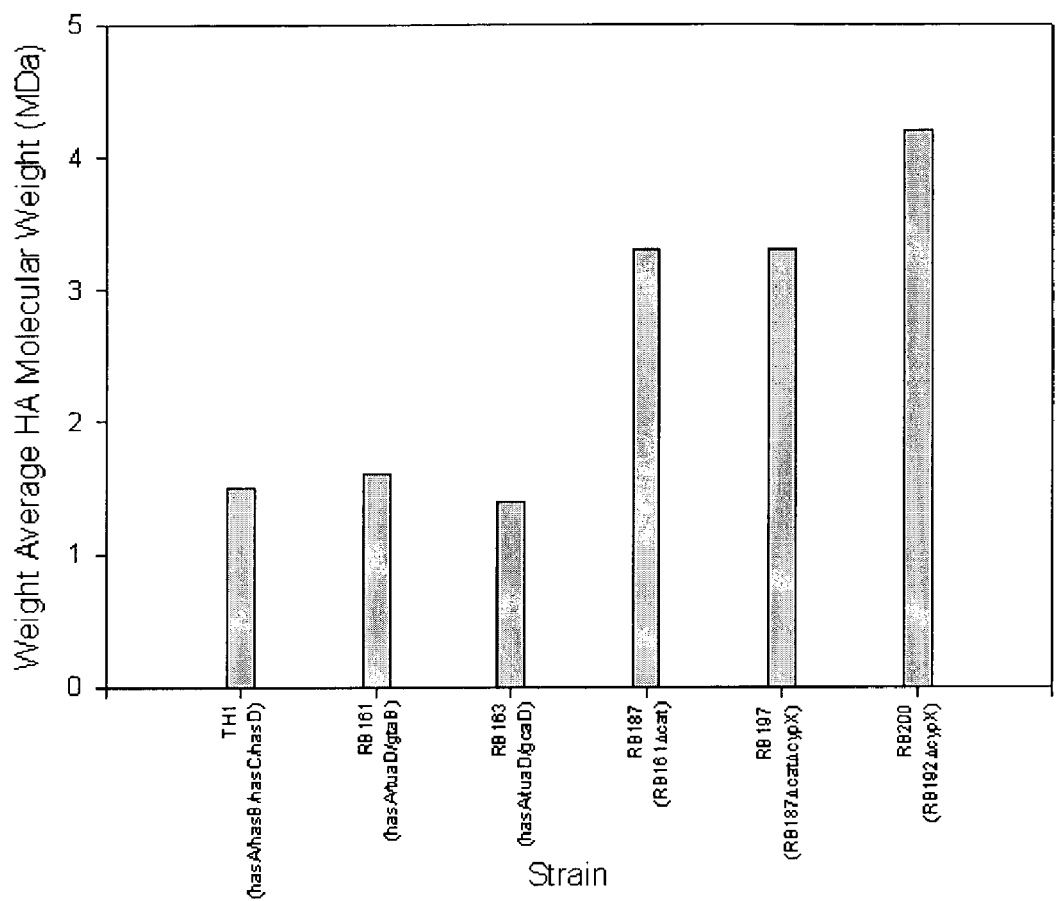
FIG. 45 shows a summary of peak hyaluronic acid weight average molecular weights (MDa) obtained from fermentations of various hyaluronic acid producing *Bacillus subtilis* strains run under fed batch at approximately 2 g sucrose/$L_0$-hr, 37° C.

A summary of peak hyaluronic acid weight average molecular weights (MDa) obtained from fermentation of the recombinant *Bacillus subtilis* strains under the same conditions (fed batch at approximately 2 g sucrose/$L_0$-hr, 37° C.) is shown in FIG. 45. Molecular weights were determined using a GPC MALLS assay. Data was gathered from GPC MALLS assays using the following procedure. GPC-MALLS (gel permeation or size-exclusion) chromatography coupled with multi-angle laser light scattering) is widely used to characterize high molecular weight (MW) polymers. Separation of polymers is achieved by GPC, based on the differential partitioning of molecules of different MW between eluent and resin. The average molecular weight of an individual polymer is determined by MALLS based the differential scattering extent/angle of molecules of different MW. Principles of GPC-MALLS and protocols suited for hyaluronic acid are described by Ueno et al., 1988, *Chem. Pharm. Bull.* 36, 4971-4975; Wyatt, 1993, *Anal. Chim. Acta* 272: 1-40; and Wyatt Technologies, 1999, "Light Scattering University DAWN Course Manual" and "DAWN EOS Manual" Wyatt Technology Corporation, Santa Barbara, Calif.). An Agilent 1100 isocratic HPLC, a Tosoh Biosep G6000 PWxl column for the GPC, and a Wyatt Down EOS for the MALLS were used. An Agilent G1362A refractive index detector was linked downstream from the MALLS for eluate concentration determination. Various commercial hyaluronic acid products with known molecular weights served as standards.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* XL10 Gold kan (pMRT106) | NRRL B-30536 | Dec. 12, 2001 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a hyaluronic acid, comprising:
(a) cultivating a *Bacillus* host cell under conditions suitable for production of the hyaluronic acid, wherein the *Bacillus* host cell comprises an artificial operon comprising a short "consensus" amyQ promoter having the sequence TTGACA for the "−35" region and TATAAT for the "−10" region operably linked to a hyaluronan synthase encoding sequence, a UDP-glucose 6-dehydrogenase encoding sequence, and a UDP-glucose pyrophosphorylase encoding sequence;
wherein the hyaluronan synthase encoding sequence is (i) a nucleic acid sequence encoding a polypeptide comprising SEQ ID NO: 2; or (ii) a nucleic acid sequence which hybridizes under high stringency conditions with SEQ ID NO: 1 or its full length complementary strand;
wherein the UDP-glucose 6-dehydrogenase encoding sequence is (i) a nucleic acid sequence encoding a polypeptide comprising SEQ ID NO: 12; or (ii) a nucleic acid sequence which hybridizes under high stringency conditions with SEQ ID NO: 11 or its full length complementary strand;
wherein the UDP-glucose pyrophosphorylase encoding sequence is (i) a nucleic acid sequence encoding a polypeptide comprising SEQ ID NO: 22; or (ii) a nucleic acid sequence which hybridizes under high stringency conditions with SEQ ID NO: 21 or its full length complementary strand; and
wherein high stringency conditions are defined as prehybridization and hybridization at 42° C. in 5×SSPE, 0.3% SDS, 200 μg/ml sheared and denatured salmon sperm DNA, and 50% formamide, and washing three times each for 15 minutes using 2×SSC, 0.2% SDS preferably at least at 65° C.; and
(b) recovering the hyaluronic acid from the cultivation medium.

2. The method of claim 1, wherein the hyaluronan synthase encoding sequence encodes a polypeptide comprising SEQ ID NO: 2.

3. The method of claim 1, wherein the UDP-glucose 6-dehydrogenase encoding sequence encodes a polypeptide comprising SEQ ID NO: 12.

4. The method of claim 1, wherein the artificial operon further comprises one or more additional genes encoding enzymes in the biosynthesis of a precursor sugar of the hyaluronic acid or the *Bacillus* host cell further comprises one or more nucleic acid constructs comprising one or more additional genes encoding enzymes in the biosynthesis of a precursor sugar of the hyaluronic acid.

5. The method of claim 4, wherein the one or more additional genes encoding enzymes in the biosynthesis of a precursor sugar of the hyaluronic acid are selected from the group consisting of a UDP-N-acetylglucosamine pyrophosphorylase gene, glucose-6-phosphate isomerase gene, hexokinase gene, phosphoglucomutase gene, amidotransferase gene, mutase gene, and acetyl transferase gene.

6. The method of claim 1, wherein the UDP-glucose pyrophosphorylase encoding sequence encodes a polypeptide comprising SEQ ID NO: 22.

7. The method of claim 5, wherein the UDP-N-acetylglucosamine pyrophosphorylase encoding sequence is (a) a nucleic acid sequence encoding a polypeptide comprising SEQ ID NO: 30; or (b) a nucleic acid sequence which hybridizes under high stringency conditions with SEQ ID NO: 29 or its full length complementary strand; wherein high stringency conditions are defined as prehybridization and hybridization at 42° C. in 5×SSPE, 0.3% SDS, 200 μg/ml sheared and denatured salmon sperm DNA, and 50% formamide, and washing three times each for 15 minutes using 2×SSC, 0.2% SDS preferably at least at 65° C.

8. The method of claim 7, wherein the UDP-N-acetylglucosamine pyrophosphorylase encoding sequence encodes a polypeptide comprising SEQ ID NO: 30.

9. The method of claim 5, wherein the glucose-6-phosphate isomerase encoding sequence is (a) a nucleic acid sequence encoding a polypeptide comprising SEQ ID NO: 101; or (b) a nucleic acid sequence which hybridizes under high stringency conditions with SEQ ID NO: 100 or its full length complementary strand; wherein high stringency conditions are defined as prehybridization and hybridization at 42° C. in 5×SSPE, 0.3% SDS, 200 μg/ml sheared and denatured salmon sperm DNA, and 50% formamide, and washing three times each for 15 minutes using 2×SSC, 0.2% SDS preferably at least at 65° C.

10. The method of claim 9, wherein the glucose-6-phosphate isomerase encoding sequence encodes a polypeptide comprising SEQ ID NO: 101.

11. The method of claim 5, wherein the one or more additional genes selected from the group of the UDP-N-acetylglucosamine pyrophosphorylase gene, glucose-6-phosphate isomerase gene, hexokinase gene, phosphoglucomutase gene, amidotransferase gene, mutase gene, and acetyl transferase gene are under the control of the same or a different promoter(s) as the hyaluronan synthase encoding sequence.

12. The method of claim 1, wherein the artificial operon further comprises an mRNA processing/stabilizing sequence located downstream of the short "consensus" amyQ promoter operably linked to the hyaluronan synthase encoding sequence, the UDP-glucose 6-dehydrogenase encoding sequence, and the UDP-glucose pyrophosphorylase encoding sequence and upstream of the hyaluronan synthase encoding sequence, the UDP-glucose 6-dehydrogenase encoding sequence, and the UDP-glucose pyrophosphorylase encoding sequence.

13. The method of claim 1, wherein the artificial operon further comprises a selectable marker gene.

14. The method of claim 1, wherein the *Bacillus* host cell is selected from the group consisting of *Bacillus agaradherens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacil-* lus licheniformis, Bacillus megaterium, Bacillus pumilus, Bacillus stearothermophilus, Bacillus subtilis, and Bacillus thuringiensis.

15. The method of claim 1, wherein the Bacillus host cell is unmarked with a selectable marker.

16. The method of claim 1, wherein the artificial operon is integrated into the chromosome of the Bacillus host cell.

17. The method of claim 1, wherein the Bacillus host cell is a Bacillus licheniformis cell.

18. The method of claim 1, wherein the Bacillus host cell is a Bacillus subtilis cell.

19. The method of claim 7, wherein the UDP-N-acetylglucosamine pyrophosphorylase encoding sequence is a nucleic acid sequence which hybridizes under very high stringency conditions with SEQ ID NO: 29 or its full length complementary strand; wherein very high stringency conditions are defined as prehybridization and hybridization at 42° C. in 5×SSPE, 0.3% SDS, 200 µg/ml sheared and denatured salmon sperm DNA, and 50% formamide, and washing three times each for 15 minutes using 2×SSC, 0.2% SDS preferably at least at 70° C.

20. The method of claim 9, wherein the glucose-6-phosphate isomerase encoding sequence is a nucleic acid sequence which hybridizes under very high stringency conditions with SEQ ID NO: 100 or its full length complementary strand; wherein very high stringency conditions are defined as prehybridization and hybridization at 42° C. in 5×SSPE, 0.3% SDS, 200 µg/ml sheared and denatured salmon sperm DNA, and 50% formamide, and washing three times each for 15 minutes using 2×SSC, 0.2% SDS preferably at least at 70° C.

* * * * *